US009315495B2

(12) United States Patent
Ebright et al.

(10) Patent No.: US 9,315,495 B2
(45) Date of Patent: Apr. 19, 2016

(54) ANTIBACTERIAL AGENTS: ARYL MYXOPYRONIN DERIVATIVES

(71) Applicants: RUTGERS, THE STATE UNIVERSITY OF NEW JERSEY, New Brunswick, NJ (US); PROVID PHARMACEUTICALS INC., Monmouth Junction, NJ (US)

(72) Inventors: Richard H. Ebright, New Brunswick, NJ (US); Yon W. Ebright, New Brunswick, NJ (US); Juan Shen, New Brunswick, NJ (US); James Bacci, Monmouth Junction, NJ (US); Anne-Cecile Hiebel, Monmouth Junction, NJ (US); William Solvibile, Monmouth Junction, NJ (US); Christopher Self, Monmouth Junction, NJ (US); Gary Olson, Monmouth Junction, NJ (US)

(73) Assignees: Rutgers, The State University of New Jersey, New Brunswick, NJ (US); Provid Pharmaceuticals Inc., Monmouth Junction, NJ (US)

( * ) Notice: Subject to any disclaimer, the term of this patent is extended or adjusted under 35 U.S.C. 154(b) by 0 days.

(21) Appl. No.: 14/409,407

(22) PCT Filed: Jun. 19, 2013

(86) PCT No.: PCT/US2013/046655
§ 371 (c)(1),
(2) Date: Dec. 18, 2014

(87) PCT Pub. No.: WO2013/192352
PCT Pub. Date: Dec. 27, 2013

(65) Prior Publication Data
US 2015/0197512 A1 Jul. 16, 2015

Related U.S. Application Data

(60) Provisional application No. 61/661,670, filed on Jun. 19, 2012.

(51) Int. Cl.
| | | |
|---|---|---|
| *C07D 309/30* | (2006.01) |
| *C07D 417/06* | (2006.01) |
| *C07D 309/38* | (2006.01) |
| *C07D 405/06* | (2006.01) |
| *C07D 407/06* | (2006.01) |
| *C07D 407/12* | (2006.01) |
| *C07D 409/06* | (2006.01) |
| *C07D 309/36* | (2006.01) |
| *C07D 405/12* | (2006.01) |

(52) U.S. Cl.
CPC ............ *C07D 417/06* (2013.01); *C07D 309/36* (2013.01); *C07D 309/38* (2013.01); *C07D 405/06* (2013.01); *C07D 405/12* (2013.01); *C07D 407/06* (2013.01); *C07D 407/12* (2013.01); *C07D 409/06* (2013.01)

(58) Field of Classification Search
CPC ...................................................... C07D 309/36
USPC .......................................................... 549/291
See application file for complete search history.

(56) References Cited

U.S. PATENT DOCUMENTS

| 8,114,583 B2 | 2/2012 | Ebright et al. |
| 8,772,332 B2 | 7/2014 | Ebright et al. |
| 2013/0237595 A1 | 9/2013 | Ebright et al. |
| 2013/0289128 A1 | 10/2013 | Ebright et al. |
| 2013/0296421 A1 | 11/2013 | Ebright et al. |
| 2015/0011647 A1 | 1/2015 | Ebright et al. |
| 2015/0031640 A1 | 1/2015 | Ebright et al. |
| 2015/0051275 A1 | 2/2015 | Ebright et al. |

FOREIGN PATENT DOCUMENTS

| WO | WO 2007/094799 | 8/2007 |
| WO | WO 2013/119564 | 8/2013 |
| WO | WO 2013/142812 | 9/2013 |
| WO | WO 2013/192352 | 12/2013 |

OTHER PUBLICATIONS

Lira, Bioorganic & Medicinal Chemistry Letters (2007), 17(24), 6797-6800.*
Lira et al. Bioorganic & Medicinal Chemistry Letters (2007), 17(24), 6797-6800.*
Belogurov et al., "Transcription inactivation through local refolding of the RNA polymerase structure", Nature 457 (7227), 332-335 (2009).
Chopra, "Bacterial RNA polymerase: a promising target for the discovery of new antimicrobial agents", Curr. Opin. Investig. Drugs 8, 600-607 (2007).
Darst, "New inhibitors targeting bacterial RNA polymerase", Trends Biochem. Sci. 29 (4), 159-162 (2004).
Doundoulakis et al., "Myxopyronin B analogs as inhibitors of RNA polymerase, synthesis and biological evaluation", Bioorganic and Medicinal Chemistry Letters, vol. 14. (22), 5667-5672 (2004).
Ho et al., "Structures of RNA polymerase-antibiotic complexes", Curr. Opin. Struct. Biol. 19, 715-723 (2009).
Mukhopadhyay et al., "The RNA Polymerase "Switch Region" is a Target for Inhibitors", Cell 135, 295-307 (2008).
Patent Cooperation Treaty, International Searching Authority, Search Report and Written Opinion for PCT/US2013/046655, 10 pages, Aug. 16, 2013.
Srivastava et al., "New Target for inhibition of bacterial RNA polymerase: switch region", Curr. Opini. Microbiol. 14, 532-563 (2011).
Villain-Guillot et al., "Progress in targeting bacterial transcription", Drug Discov. Today 12 (5/6), 200-208 (2007).

* cited by examiner

Primary Examiner — Nizal Chandrakumar
(74) Attorney, Agent, or Firm — Viksnins Harris & Padys PLLP

(57) ABSTRACT

The invention provides compounds of formula Ia, Ib and Ic: [Formula Ia, Ib, and Ic] and salts thereof, wherein variables are as described in the specification, as well as compositions comprising a compound of formula Ia-Ic, methods of making such compounds, and methods of using such compounds, e.g., as inhibitors of bacterial RNA polymerase and as antibacterial agents.

10 Claims, No Drawings

ANTIBACTERIAL AGENTS: ARYL MYXOPYRONIN DERIVATIVES

CROSS-REFERENCE TO RELATED APPLICATION

This application claims priority from U.S. Provisional Application No. 61/661,670, filed Jun. 19, 2012.

STATEMENT OF GOVERNMENT RIGHTS

The invention was made with government support under AI090837 awarded by the National Institutes of Health. The government has certain rights in the invention.

BACKGROUND OF THE INVENTION

Bacterial infectious diseases kill 100,000 persons each year in the US and 11 million persons each year worldwide, representing nearly a fifth of deaths each year worldwide (Heron et al., *Final Data for* 2006. *National Vital Statistics Reports, Vol.* 57 (Centers for Disease Control and Prevention, Atlanta Ga.) and World Health Organization (2008) *The Global Burden of Disease:* 2004 *Update* (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports,* 122, 160-166; Scott, R. (2009) *The direct medical costs of healthcare-associated infections in U.S. hospitals and benefits of prevention* (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a proven target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* 14, 532-543). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are highly conserved in human RNAP I, RNAP II, and RNAP III (permitting therapeutic selectivity).

The rifamycin antibacterial agents function by binding to and inhibiting bacterial RNAP (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). The rifamycins bind to a site on bacterial RNAP adjacent to the RNAP active center and prevent extension of RNA chains beyond a length of 2-3 nt. The rifamycins are in current clinical use in treatment of both Gram-positive and Gram-negative bacterial infections. The rifamycins are of particular importance in treatment of tuberculosis; the rifamycins are first-line antituberculosis agents and are among the few antituberculosis agents able to kill non-replicating tuberculosis bacteria.

The clinical utility of the rifamycin antibacterial agents is threatened by the existence of bacterial strains resistant to rifamycins (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). Resistance to rifamycins typically involves substitution of residues in or immediately adjacent to the rifamycin binding site on bacterial RNAP—i.e., substitutions that directly decrease binding of rifamycins.

In view of the public-health threat posed by rifamycin-resistant and multidrug-resistant bacterial infections, there is an urgent need for new antibacterial agents that (i) inhibit bacterial RNAP (and thus have the same biochemical effects as rifamycins), but that (ii) inhibit bacterial RNAP through binding sites that do not overlap the rifamycin binding site (and thus do not share cross-resistance with rifamycins.

A new drug target—the "switch region"—within the structure of bacterial RNAP has been identified (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). The switch region is a structural element that mediates conformational changes required for RNAP to bind and retain the DNA template in transcription. The switch region is located at the base of the RNAP active-center cleft and serves as the hinge that mediates opening of the active-center cleft to permit DNA binding and that mediates closing of the active-center cleft to permit DNA retention. The switch region can serve as a binding site for compounds that inhibit bacterial gene expression and kill bacteria. Since the switch region is highly conserved in bacterial species, compounds that bind to the switch region are active against a broad spectrum of bacterial species. Since the switch region does not overlap the rifamycin binding site, compounds that bind to the switch region are not cross-resistant with rifamycins.

It has been shown that the α-pyrone antibiotic myxopyronin (Myx) functions through interactions with the bacterial RNAP switch region (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). Myx binds to the RNAP switch region, traps the RNAP switch region in a single conformational state, and interferes with formation of a catalytically competent transcription initiation complex. Amino acid substitutions within RNAP that confer resistance to Myx occur only within the RNAP switch region. There is no overlap between amino acid substitutions that confer resistance to Myx and amino acid substitutions that confer resistance to rifamycins and, accordingly, there is no cross-resistance between Myx and rifamycins.

A crystal structure of a non-pathogenic bacterial RNAP, *Thermus thermophilus* RNAP, in complex with Myx has been determined, and homology models of pathogenic bacterial RNAP, including *Mycobacterium tuberculosis* RNAP and *Staphylococcus aureus* RNAP, in complex with Myx have been constructed (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). The crystal structure and homology models define interactions between RNAP and Myx and can be used to understand the roles of the "west" and "east" Myx sidechains as well as the Myx α-pyrone core.

SUMMARY OF THE INVENTION

An object of this invention is to provide compounds that have utility as inhibitors of bacterial RNAP.

An object of this invention is to provide compounds that have utility as inhibitors of bacterial growth.

A particular object of this invention is to provide compounds and pharmaceutical compositions that have utility in the treatment of bacterial infection in a mammal.

Accordingly, in one embodiment the invention provides a compound of the invention which is of formula Ia, Ib or Ic:

or a salt thereof, wherein:

W is sulfur, oxygen, or nitrogen;

X, Y, and Z are individually carbon, sulfur, oxygen, or nitrogen, wherein at least two of X, Y, and Z are carbon;

one of $R^1$ and $R^2$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or one of $R^1$ and $R^2$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^1$ and $R^2$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^3$ is absent, or is one of H, $C_1$-$C_2$ alkyl, or halogen-substituted $C_1$-$C_2$ alkyl;

$R^4$ is absent, or is one of H, halogen, $C_1$-$C_2$ alkyl, or halogen-substituted $C_1$-$C_2$ alkyl;

V', W', X', Y', and Z' are individually carbon or nitrogen; wherein at least three of V', W', X', Y', and Z' are carbon;

one of $R^{1'}$ and $R^{2'}$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or one of $R^{1'}$ and $R^{2'}$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^{1'}$ and $R^{2'}$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^{3'}$, $R^{4'}$, and $R^{5'}$ are each independently absent, H, halogen, $C_1$-$C_2$ alkyl, or halogen-substituted $C_1$-$C_2$ alkyl;

W" is sulfur, oxygen, or nitrogen;

U", V", X", Y", and Z" are individually carbon, sulfur, oxygen, or nitrogen, wherein at least three of U", V", X", Y", and Z" are carbon;

one of $R^{1''}$ and $R^{2''}$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or one of $R^{1''}$ and $R^{2''}$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^{1''}$ and $R^{2''}$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;

$R^{3''}$ is absent or is one of H, $C_1$-$C_2$ alkyl, or halogen-substituted $C_1$-$C_2$ alkyl;

$R^{4''}$, $R^{5''}$, and $R^{6''}$ are each independently absent, H, halogen, $C_1$-$C_2$ alkyl, or halogen-substituted $C_1$-$C_2$ alkyl;

$R^5$ and $R^6$ are individually H or methyl;

G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$;

$R^7$ is one of $C_1$-$C_6$ alkyl, —O($C_1$-$C_6$ alkyl), —S($C_1$-$C_6$ alkyl), or —N($R^8$)$_2$;

each $R^8$ is independently one of hydrogen or —$C_1$-$C_6$ alkyl;

$R^9$ is $C_1$-$C_{10}$ alkyl or $C_2$-$C_{10}$ alkenyl, wherein any $C_1$-$C_{10}$ alkyl or $C_2$-$C_{10}$ alkenyl is optionally substituted by at least one of halogen, hydroxy, alkoxy, or $NR^aR^b$;

each $R^a$ is $C_1$-$C_{10}$ alkyl that is optionally substituted by at least one of halogen, hydroxy, or $C_1$-$C_5$ alkoxy; and each $R^b$ is H or $C_1$-$C_{10}$ alkyl that is optionally substituted by at least one of halogen, hydroxy, or $C_1$-$C_5$ alkoxy.

The invention also provides a compound of formula Ia, Ib or Ic, or a pharmaceutically acceptable salt thereof for use in medical treatment.

The invention also provides a compound of formula Ia, Ib or Ic, or a pharmaceutically acceptable salt thereof for use in the prophylaxis or treatment of a bacterial infection.

The invention also provides a composition comprising a compound of formula Ia, Ib or Ic, or a pharmaceutically acceptable salt thereof, and a pharmaceutically acceptable carrier.

The invention also provides the use of a compound of the invention as an inhibitor of a bacterial RNA polymerase.

The invention also provides the use of a compound of the invention as an antibacterial agent.

The invention also provides the use of a compound of the invention as a disinfectant, a sterilant, an antispoilant, an antiseptic, or an antiinfective.

The invention also provides the use of a compound of formula Ia, Ib or Ic, or a pharmaceutically acceptable salt thereof for the preparation of a medicament for prophylaxis or treatment of a bacterial infection in a mammal.

The invention also provides a method of inhibiting a bacterial RNA polymerase, comprising contacting a bacterial RNA polymerase with a compound of the invention.

The invention also provides a method of treating a bacterial infection in a mammal, comprising administering to the mammal a therapeutically effective amount of a compound of formula Ia, Ib or Ic, or a pharmaceutically acceptable salt thereof.

DETAILED DESCRIPTION OF THE INVENTION

Definitions

The following definitions are used, unless otherwise indicated.

The term "halo" means fluoro, chloro, bromo, or iodo.

The term "alkyl" used alone or as part of a larger moiety, includes both straight and branched chains. For example, $C_1$-$C_{10}$ alkyl includes both straight and branched chained alkyl groups having from one to ten carbon atoms. The term alkyl also includes cycloalkyl groups (e.g. cyclopropyl, cyclobutyl, cyclopently, cyclohexyl, cycloheptyl, and cyclooctyl), as well as (cycloalkyl)alkyl groups (e.g. 3-cyclohexylpropyl, cyclopentylmethyl, 2-cyclohexylethyl, and 2-cyclopropylethyl).

The term "alkenyl" used alone or as part of a larger moiety, includes an alkyl that has one or more double bonds. For example, $C_2$-$C_{10}$ alkenyl includes both straight and branched chained groups having from two to ten carbon atoms and one or more (e.g. 1, 2, or 3) double bonds, as well as (cycloalkyl) alkyl groups having one or more double bonds in the cycloalkyl portion or in the alkyl portion of the (cycloalkyl) alkyl.

The term "alkoxy" used alone or as part of a larger moiety is a group alkyl-O—, wherein alkyl has any of the values defined herein.

The term "aryl" denotes a phenyl radical or an ortho-fused bicyclic carbocyclic radical having about nine to ten ring atoms in which at least one ring is aromatic. For example, aryl can be phenyl, indenyl, or naphthyl.

The term "heteroaryl" encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X). For example heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "heterocycle" or "heterocyclyl" ring as used herein refers to a ring that has at least one atom other than carbon in the ring, wherein the atom is selected from the group consisting of oxygen, nitrogen and sulfur. The ring can be saturated, partially unsaturated, or aromatic. The term includes single (e.g., monocyclic) saturated, partially unsaturated, and aromatic rings (e.g., 3, 4, 5, 6 or 7-membered rings) from about 1 to 6 carbon atoms and from about 1 to 4 heteroatoms selected from the group consisting of oxygen, nitrogen and sulfur in the ring. In one embodiment the term includes 5-6 membered saturated, partially unsaturated, and aromatic heterocycles that include 1-5 carbon atoms and 1-4 heteroatoms.

A combination of substituents or variables is permissible only if such a combination results in a stable or chemically feasible compound. The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents.

Unless otherwise stated, structures depicted herein are also meant to include all stereochemical forms of the structure (i.e., the R and S configurations for each asymmetric center). Therefore, single stereochemical isomers, as well as enantiomeric and diastereomeric mixtures, of the present compounds are within the scope of the invention. Similarly, E- and Z-isomers, or mixtures thereof, of olefins within the structures also are within the scope of the invention.

Unless otherwise stated, structures depicted herein also are meant to include compounds that differ only by the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, p-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Antibacterial Agents

The invention provides new compositions of matter that highly potently inhibit bacterial RNA polymerase and inhibit bacterial growth. Certain compounds of this invention exhibit potencies higher than the potencies of the natural products myxopyronin A and B and of other known analogs of myxopyronin A and B.

Compounds of this invention are anticipated to have applications in analysis of RNA polymerase structure and function, control of bacterial gene expression, control of bacterial growth, antibacterial chemistry, antibacterial therapy, and drug discovery.

This invention provides novel compounds that contain alterations of the Myx "west" sidechain that, it is believed, and is shown by Example, have one or more of the following advantages relative to the Myx native "west" side chain: (1) improvement of interactions with the bacterial-RNAP Myx binding site and an adjacent hydrophobic pocket, (2) increased potency of inhibition of bacterial RNAP, (3) increased potency of antibacterial activity, (4) broadened spectrum of antibacterial activity, and (5) decreased serum protein binding.

Said compounds contain an "east" sidechain that, it is believed, may form most or all of the same hydrogen-bonded interactions with the bacterial-RNAP Myx binding site that are formed by the Myx native "east" sidechain.

The compounds of this invention have utility as RNAP inhibitors.

The compounds of this invention have utility as antibacterial agents.

In one embodiment the invention provides a compound of formula Ia', Ib' or Ic':

Ia'

Ib'

Ic' or a salt thereof, wherein:
W is sulfur, oxygen, or nitrogen;
X, Y, and Z are individually carbon, sulfur, oxygen, or nitrogen, wherein at least two of X, Y, and Z are carbon;
one of $R^1$ and $R^2$ is $C_1$-$C_8$ alkyl or $C_1$-$C_8$ alkoxy optionally substituted by at least one of halogen, hydroxy, alkoxy, or furanyl; and the other of $R^1$ and $R^2$ is absent or is one of H, halogen, or $C_1$-$C_8$ alkyl or $C_1$-$C_8$ alkoxy optionally substituted by at least one of halogen, hydroxy, or alkoxy;
$R^3$ is absent, or is one of H, $C_1$-$C_2$ alkyl, or halogen-substituted $C_1$-$C_2$ alkyl;
$R^4$ is absent, or is one of H, halogen, $C_1$-$C_2$ alkyl, or halogen-substituted $C_1$-$C_2$ alkyl;
V', W', X', Y', and Z' are individually carbon or nitrogen; wherein at least four of V', W', X', Y', and Z' are carbon;
one of $R^{1'}$ and $R^{2'}$ is $C_1$-$C_8$ alkyl or $C_1$-$C_8$ alkoxy optionally substituted by at least one of halogen, hydroxy, or alkoxy, or furanyl; and the other of $R^{1'}$ and $R^{2'}$ is absent, or is one of H, halogen, or $C_1$-$C_8$ alkyl or $C_1$-$C_8$ alkoxy optionally substituted by at least one of halogen, hydroxy, or alkoxy;

$R^{3'}$, $R^{4'}$, and $R^{5'}$ each is absent, or each of $R^{3'}$, $R^{4'}$, and $R^{5'}$ is H, halogen, $C_1$-$C_2$ alkyl, or W" is sulfur, oxygen, or nitrogen;

U", V", X", Y", and Z" are individually carbon, sulfur, oxygen, or nitrogen, wherein at least three of U", V", X", Y", and Z" are carbon;

one of $R^{1''}$ and $R^{2''}$ is $C_1$-$C_8$ alkyl or $C_1$-$C_8$ alkoxy optionally substituted by at least one of halogen, hydroxy, or alkoxy, or furanyl; and the other of $R^{1''}$ and $R^{2''}$ is absent, or is one of H, halogen, or $C_1$-$C_8$ alkyl or $C_1$-$C_8$ alkoxy optionally substituted by at least one of halogen, hydroxy, or alkoxy;

$R^{3''}$ is absent or is one of H, $C_1$-$C_2$ alkyl, or halogen-substituted $C_1$-$C_2$ alkyl;

$R^{4''}$, $R^{5''}$, and $R^{6''}$ each is absent, or each of $R^{4''}$, $R^{5''}$, and $R^{6''}$ is H, halogen, $C_1$-$C_2$ alkyl, or halogen-substituted $C_1$-$C_2$ alkyl; and $R^5$ and $R^6$ are individually H or methyl;

G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$;

$R^7$ is one of $C_1$-$C_6$ alkyl, —O($C_1$-$C_6$ alkyl), —S($C_1$-$C_6$ alkyl), or —N($R^8$)$_2$; and each $R^8$ is independently one of hydrogen or —$C_1$-$C_6$ alkyl.

In each of the above general structural formulae—(Ia), (Ib), and (Ic)—$R^6$ may be H or methyl. When $R^5$ is methyl, it will be attached to chiral carbon. With respect to this chiral center, compounds of general structural formula (I) may exist as the R configuration, as the S configuration, or as a mixture of R and S stereoisomers.

One specific embodiment relates to a compound of general structural formula (Ia), (Ib), or (Ic) where $R^6$ is methyl and where the compound is a mixture of the R and S stereoisomers.

Another specific embodiment relates to a compound of general structural formula (Ia), (Ib), or (Ic) where $R^6$ is methyl and where the compound is predominantly the R stereoisomer, preferably at least 90% of the R isomer.

Certain embodiments of the invention also provide methods for preparation of a compound according to general structural formula (Ia), (Ib), or (Ic).

Certain embodiments of the invention also provide an assay for inhibition of a RNA polymerase comprising contacting a bacterial RNA polymerase with a compound according to general structural formula (Ia), (Ib), or (Ic).

Certain embodiments of the invention also provide an assay for antibacterial activity comprising contacting a bacterial RNA polymerase with a compound according to general structural formula (Ia), (Ib), or (Ic).

Certain embodiments of the invention also provide the use of a compound according to general structural formula (Ia), (Ib), or (Ic) as an inhibitor of a bacterial RNA polymerase.

Certain embodiments of the invention also provide the use of a compound according to general structural formula (Ia), (Ib), or (Ic) as an antibacterial agent.

Certain embodiments of the invention also provide the use of a compound according to general structural formula (Ia), (Ib), or (Ic) as one of a disinfectant, a sterilant, an antispoilant, an antiseptic, or an antiinfective.

Compound Synthesis

Compounds of general structural formulae (Ia), (Ib), and (Ic) may be prepared by the synthetic Schemes 1-5 shown below, and by reference to analogous chemistry known in the art as well as synthetic examples presented herein. Useful literature references are those that describe the synthesis of other alpha-pyrone compounds. See Lira, R. et al., (2007) Bioorg. Med. Chem. Letters 17, 6797-6800; Doundoulakis, T. et al. (2004), Bioorg. Med. Chem. Letters 14, 5667-5672; Xiang, A. X. et al. (2006), Heterocycles 68, 1099-1103; Wardenga, G., (2007) Enwicklung eines synthetischen Zugangs zu potentiellen Antibiotika auf Basis der Naturstoffs Corallopyronin A. Thesis, (Gottfried Wilhelm Leibniz Universität, Hannover, Germany); and U.S. Pat. Nos. 6,239,291; 6,191,288, and 6,022,983.

Schemes 1-5 show general routes for preparing certain compounds of general structural formulae (Ia), (Ib), and (Ic). The schemes are illustrated for compounds where $R^5$ is —H, $R^6$ is —CH$_3$, and G is —CH=CH—NHC(O)—CH$_3$. One skilled in the art will understand how the general scheme may be modified in various ways to obtain other compounds of general structural formulae (Ia), (Ib), and (Ic). Furthermore, one skilled in the art will appreciate that compounds 1a-6 and 8-20 in Schemes 1-5 are useful intermediates for obtaining further compounds of general structural formula (Ia), (Ib), and (Ic) by methods that are well-known in the art.

In Schemes 1-5, a crossed-double-bond symbol denotes an unspecified double-bond configuration (i.e., a mixture of E configuration and Z configuration).

Schemes 1, 2, 3, 4, and 5 correspond to Methods A, B, C, D, and E, respectively. Method C is a preferred method of preparation, providing a substantial improvement in efficiency over Methods A and B and over other known methods of preparation of Myx derivatives. Method D also is a preferred method of preparation, offering compatibility with a wider range of aldehyde building blocks, including both aryl and alkyl aldehyde building blocks. Method E also is a preferred method of preparation, offering compatibility with a wider range of aldehyde building blocks, including both aryl and alkyl aldehyde building blocks, and offering a generally cleaner reaction profile, which may prove beneficial for larger-scale preparation of Myx derivatives.

Scheme 1: General Scheme for Preparing Certain Compounds of Formulae Ia-Ic: Method A

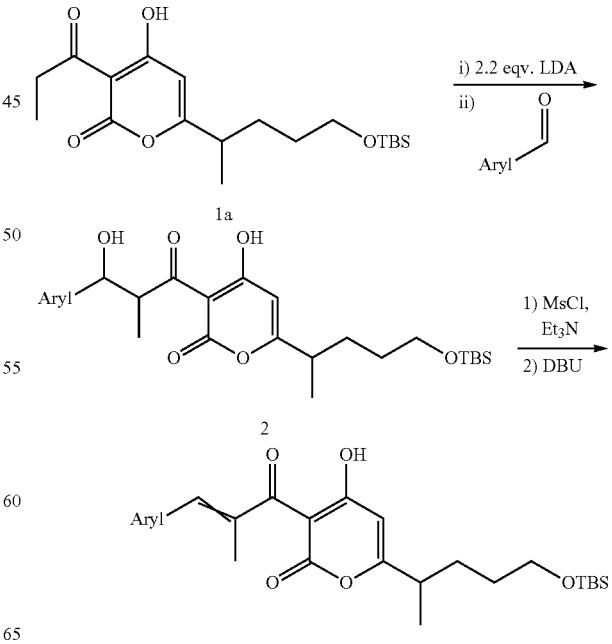

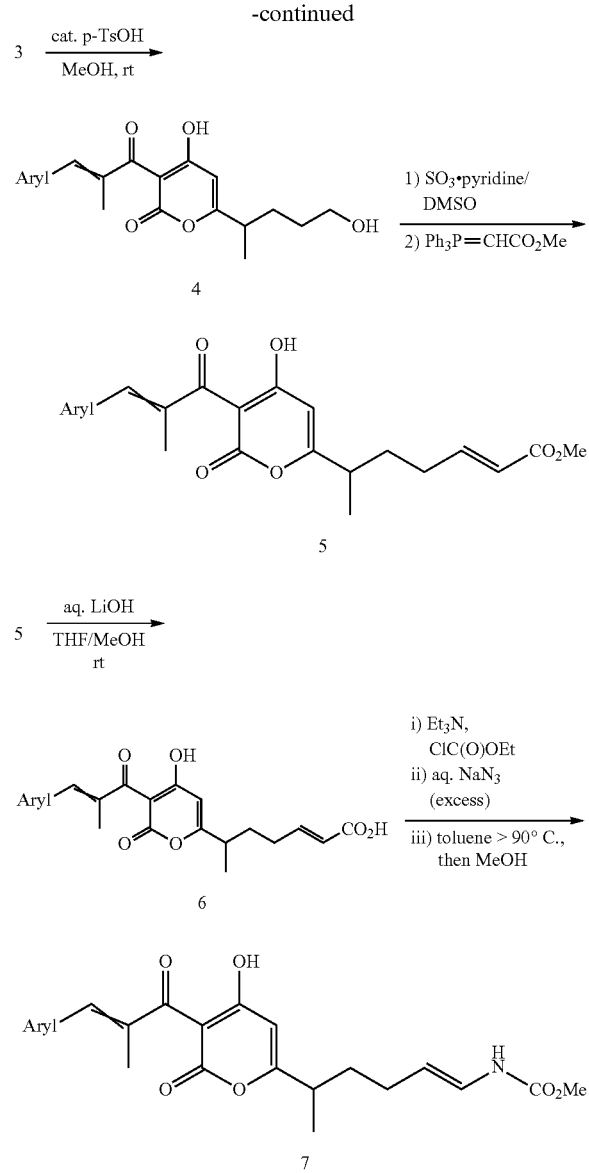

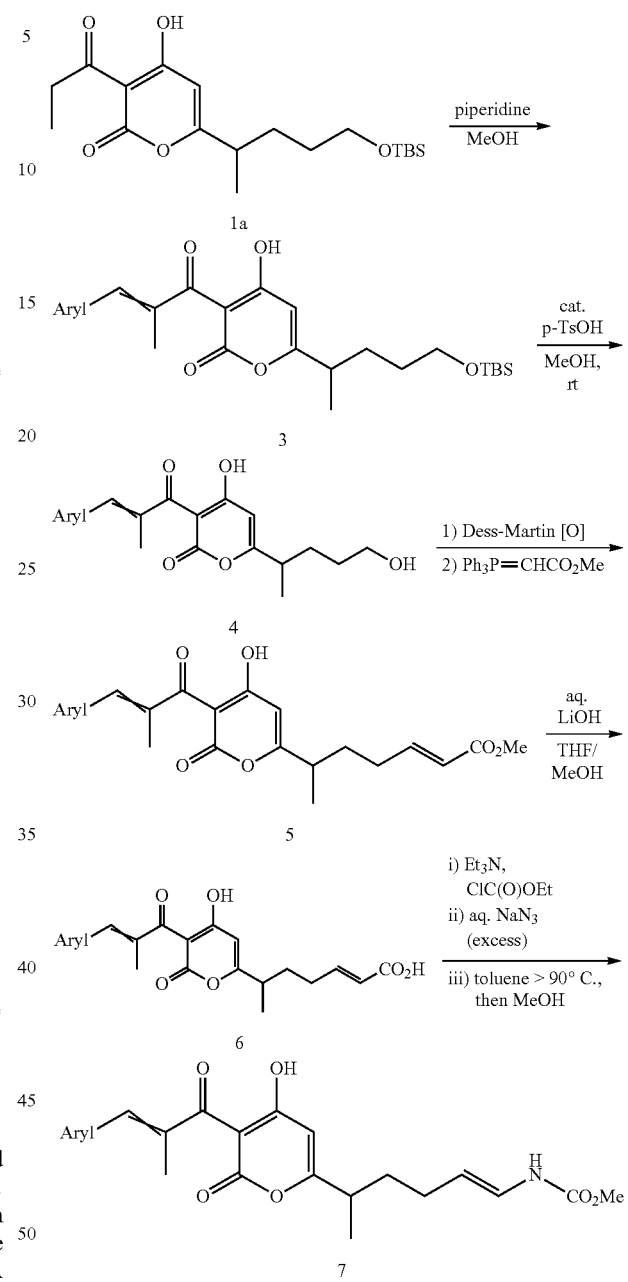

Scheme 1 exemplifies Method A. Compounds are prepared starting from the pyrone 1a (see: Panek, et. al. *J. Org. Chem.* 1998, 63, 2401). Referring to Scheme 1, an aldol reaction between the pyrone 1a and an appropriate aryl aldehyde yields the hydroxy ketone 2 as a mixture of diastereomers. A two-step sequence comprising mesylation of the beta-hydroxyl group and DBU-mediated elimination yields the enone 3. Removal of the TBS protecting group of enone 3 using catalytic p-tosic acid in the presence of methanol at room temperature yields the alcohol 4. Oxidation of 4 with sulfur trioxide•pyridine in the presence of dimethylsulfoxide yields the corresponding aldehyde, which is converted to the methyl ester 5 by Wittig olefination with methyl(triphenylphosphoranylidene)acetate. Hydrolysis of the methyl ester 5 with aqueous lithium hydroxide in tetrahydrofuran/methanol yields the acid 6, which is subjected to a Curtius rearrangement sequence involving activation of the carboxylic acid with ethyl chloroformate, substitution with azide anion, thermal rearrangement to the isocyanate, and trapping with methanol, to yield the aryl Myx derivative 7.

Scheme 2 exemplifies Method B. Introduction of the aryl group is accomplished by direct piperidine-catalyzed aldol condensation of the appropriate aryl aldehyde and the pyrone 1a to yield the enone 3 (see: Tobinaga, et. al. *Chem. Pharm. Bull.* 1980, 28, 3013). Aldol condensation (rather than addition/elimination as in Method A) provides the requisite enones in one step (rather than in three). The enone 3 is elaborated to the aryl Myx derivative 7 in a manner analogous to in Method A, with the principal difference being that Dess-Martin periodinane is used in place of sulfur trioxide•pyridine/dimethylsulfoxide. Treatment of the enone 3 with p-tosic acid in methanol yields the alcohol 4, which is subjected to oxidation/Wittig olefination to yield the methyl ester 5. Hydrolysis with aqueous lithium hydroxide in tetrahydrofuran/methanol yields the acid 6, which is transformed to the aryl Myx derivative 7 by a Curtius rearrangement sequence.

Scheme 3: General Scheme for Preparing Certain Compounds of Formulae Ia-Ic: Method C

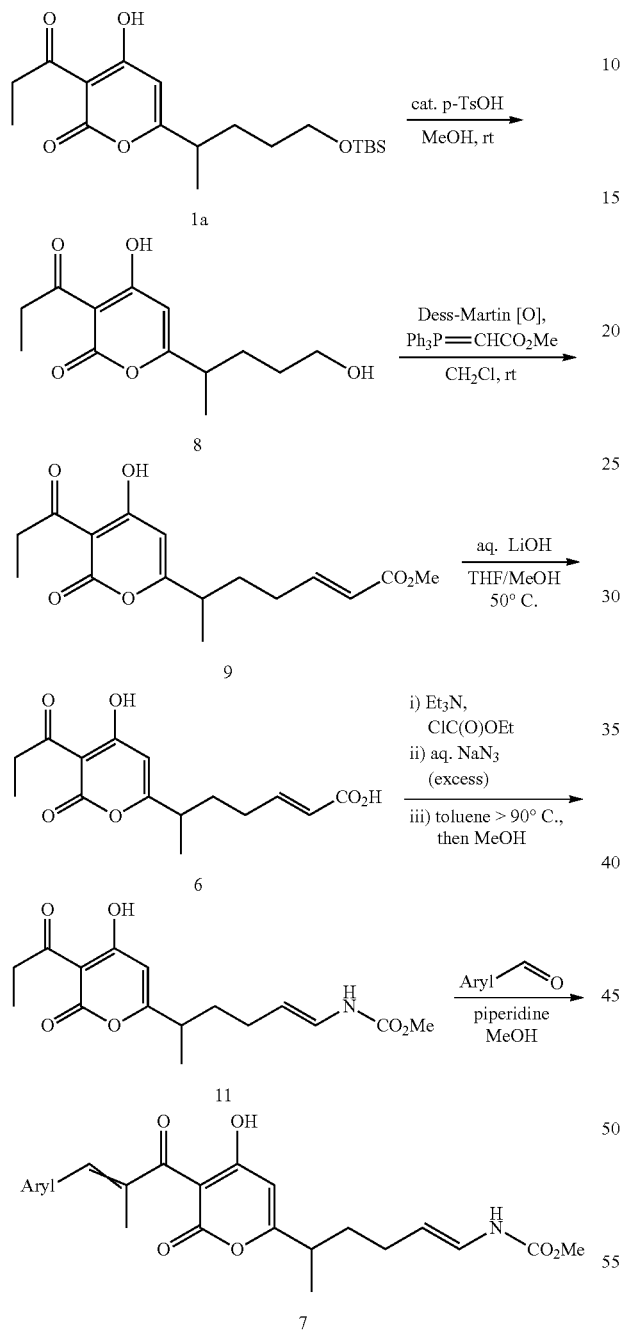

Method C provides a substantial improvement in efficiency over Method A, Method B, and other known methods of preparation of Myx derivatives. For a typical aryl Myx derivative 7, Method C allows the preparation of milligram quantities in hours starting from a similar weight of an enecarbamate 11. In contrast, using Method A, Method B, and other known methods of preparation of Myx derivatives, the synthesis of a typical aryl Myx derivative 7 requires days to weeks and typically requires 10 to 50 times the amount of the starting pyrone 1a.

Scheme 4: General Scheme for Preparing Certain Compounds of Formulae Ia-Ic: Method D

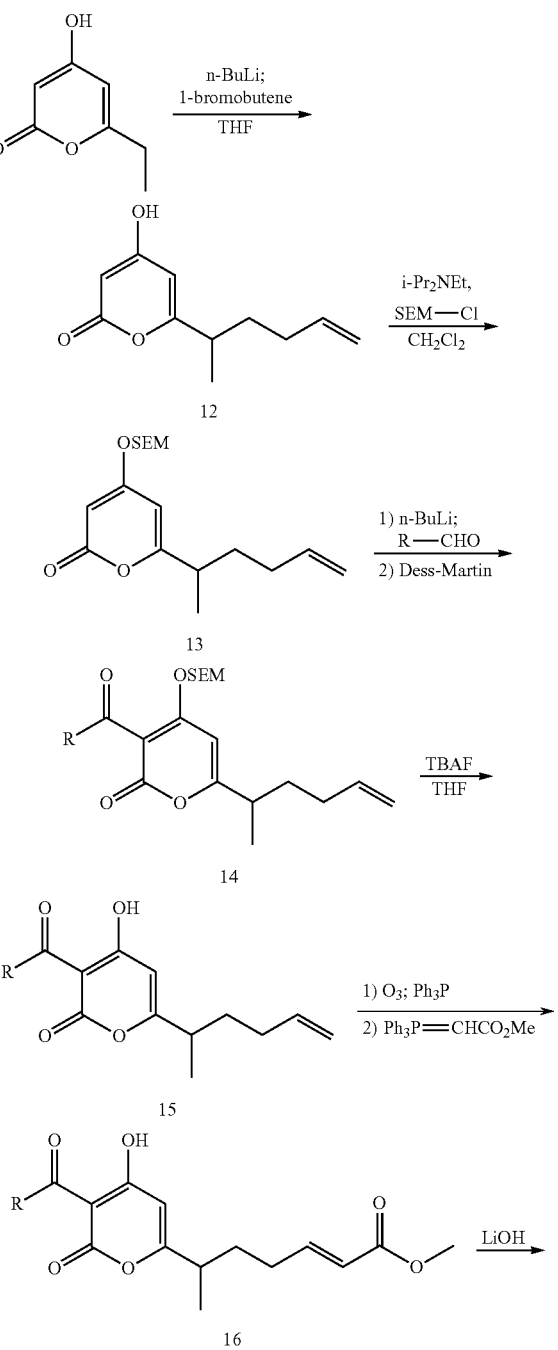

Scheme 3 exemplifies Method C. The pyrone 1a is treated with p-tosic acid in methanol to yield the alcohol 8, which is transformed to the methyl ester 9 by one-pot oxidation/Wittig olefination. Hydrolysis with aqueous lithium hydroxide in tetrahydrofuran/methanol yields the acid 10. Curtius rearrangement yields the enecarbamate 11. Heating of the enecarbamate 11 and the appropriate aryl aldehyde in the presence of piperidine yields the aryl Myx derivative 7.

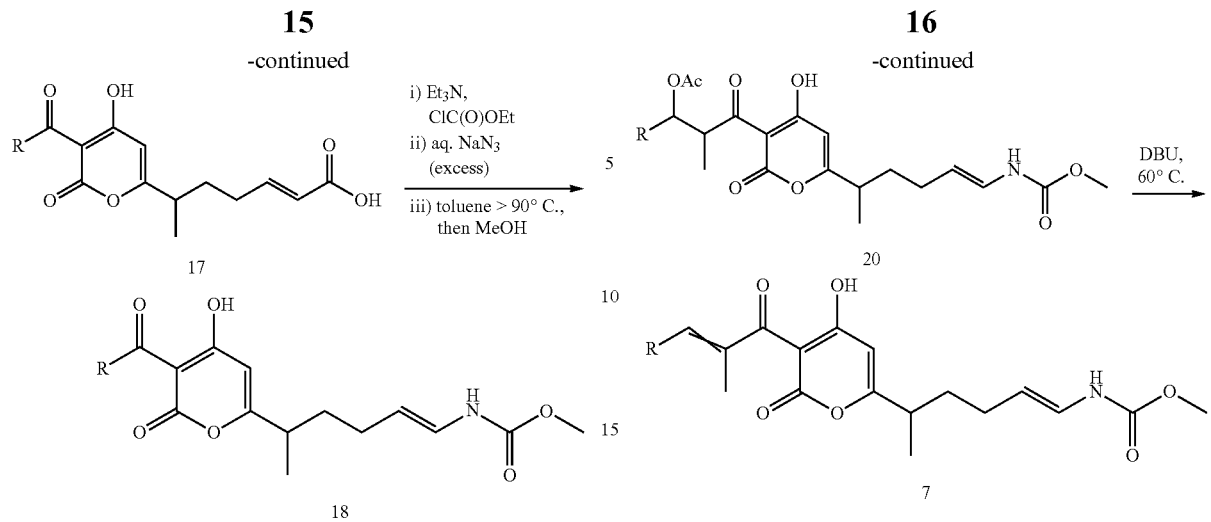

Scheme 4 exemplifies Method D. The starting pyrone (unsubstituted at the 3-position) is alkylated with 1-bromobutene to yield pyrone 12, which then is protected with SEM, yielding pyrone 13. Addition of an appropriate aldehyde building block then is accomplished using a modification of the procedure of Wardenga (Wardenga, G., (2007) Enwicklung eines synthetischen Zugangs zu potentiellen Antibiotika auf Basis der Naturstoffs Corallopyronin A. Thesis. Gottfried Wilhelm Leibniz Universität, Hannover, Germany), and oxidation of the intermediate alcohol is accomplished using the Dess-Martin periodinane or other appropriate reagent, yielding pyrone 14. The SEM protecting group is removed using tetrabutylammonium fluoride, yielding pyrone 15. Ozonolysis and treatment of the resulting aldehyde with the appropriate Wittig reagent provides methyl ester 16, which is transformed to aryl Myx derivative 7 via hydrolysis and Curtius rearrangement.

Method D allows for the use of alkyl aldehyde building blocks as well as aryl aldehyde building blocks. Method D also allows for the preparation of Myx derivatives that do not contain an enone functionality directly appended to the pyrone at the 3-position.

Scheme 5: General Scheme for Preparing Certain Compounds of Formulae Ia-Ic: Method E

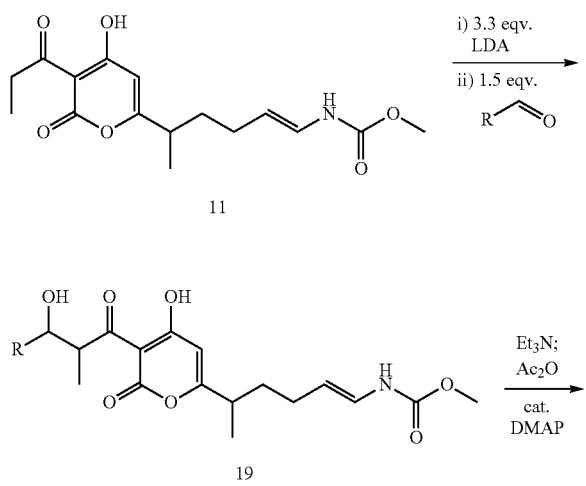

Scheme 5 exemplifies Method E. Enecarbamate 11 is deprotonated with a strong base, such as lithium diisopropylamide, and is treated with the appropriate aldehyde building block, yielding alcohol 19. The alcohol is transformed to an appropriate leaving group, such as acetate, yielding pyrone 20, which is treated with a base, such as 1,8-diazabicyclo[5.4.0]undec-7-ene (DBU), to induce elimination and provide aryl Myx derivative 7.

Method E allows for the use of alkyl aldehyde building blocks as well as aryl aldehyde building blocks.

Method E also allows for the use of aldehyde building blocks that are not usable in Method C, such as aldehydes with α-protons and other aldehydes that are otherwise unstable to piperidine.

Method E also potentially allows for the incorporation of electrophiles other than aldehydes, such as halides.

Under any of the above schemes 1-5, compounds of general structural formulae (Ia), (Ib), and (Ic) typically are obtained as mixtures of E and Z isomers at the enone double bond.

The E and Z isomers can be separated using HPLC. However, following the separation of isomers, under certain circumstances, the separated isomers regenerate mixtures of isomers.

The E and Z isomers are distinguishable by $^1$H NMR spectroscopy, most notably in the 6-8 ppm region. The chemical shift of the beta-hydrogen for the E isomer is higher than the corresponding hydrogen for the Z isomer, as is characteristic of these types of systems (see Pretsch, E.; Bühlmann, P.; Affolter, C. *Structure Determination of Organic Compounds*, 3$^{rd}$ ed.; Springer-Verlag: Berlin, 2000).

The E isomer typically exhibits higher structural similarity than the Z isomer to the structure of Myx and typically exhibits higher structural complementarity to the structure of the Myx binding site within the RNAP switch region. Therefore, it is believed that the E isomer typically exhibits higher RNAP-inhibitory and antibacterial activities than the Z isomer.

Administration of Pharmaceutical Compositions

The compounds of Formula Ia-Ic may be formulated as pharmaceutical compositions and administered to a mammalian host, such as a human patient in a variety of forms adapted to the chosen route of administration (i.e., orally or parenterally, by intravenous, intramuscular, topical or subcutaneous routes).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 125 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations; such as multiple inhalations from an insufflator or by application of a plurality of drops into the eye.

The following illustrate representative preferred pharmaceutical dosage forms, containing a compound of formula I, or a pharmaceutically acceptable salt thereof, ('Compound X'), for therapeutic or prophylactic use in humans:

a) A formulation comprising from about 0.25 mg/ml to about 5 mg/ml of Compound X, about 0% to about 20% dimethylacetamide, and about 0% to about 10% Cremophor EL;

b) A formulation comprising from about 0.5 mg/ml to about 4 mg/ml of Compound X, about 2% to about 10% dimethylacetamide, and about 0% to about 8% Cremophor EL;

c) A formulation comprising about 3 mg/ml of Compound X, about 5% dimethylacetamide, and about 4% Cremophor EL.

The invention will now be illustrated by the following non-limiting Examples.

EXAMPLES

Example Compounds

APY15

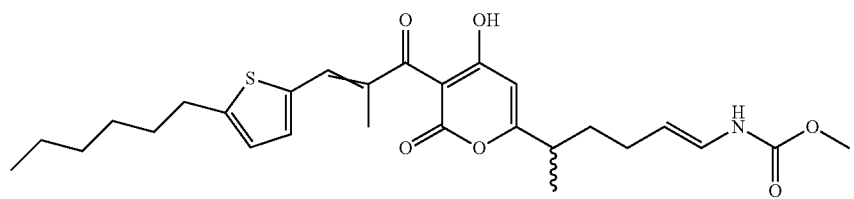

APY16

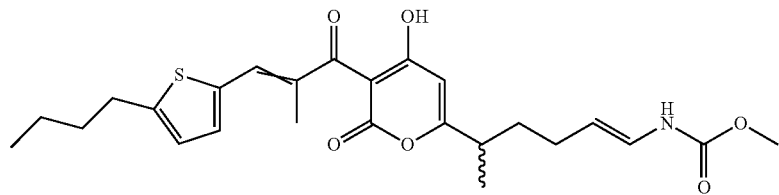

APY17

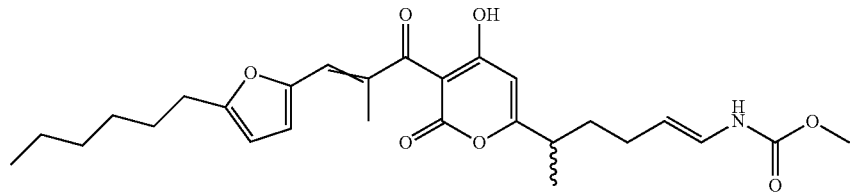

APY18

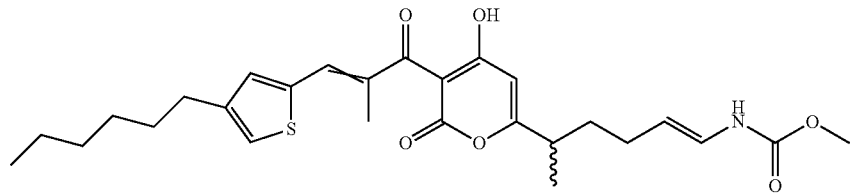

APY19

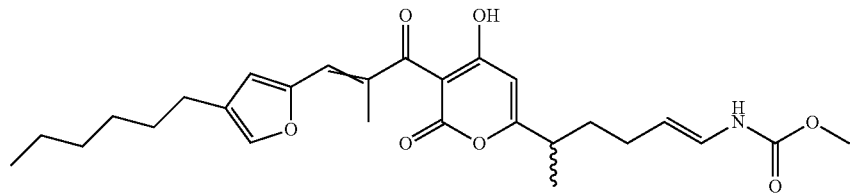

APY20
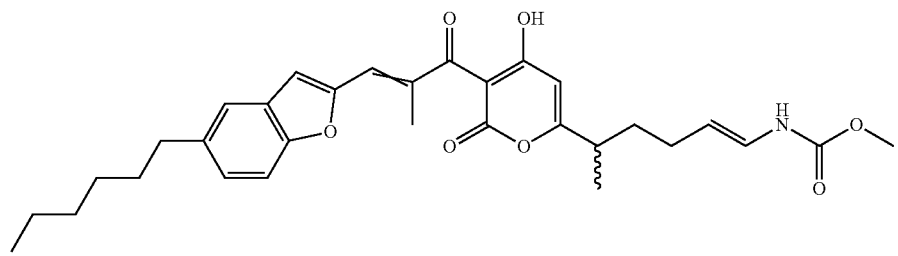
APY21
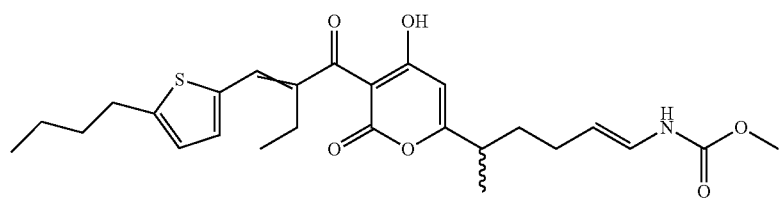
APY25
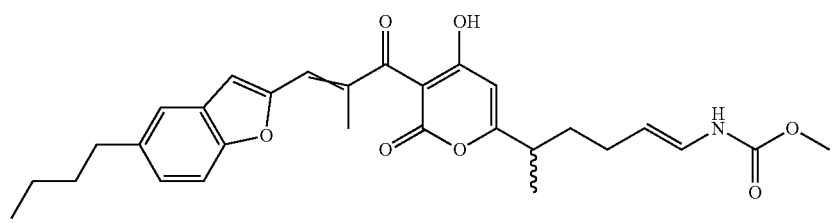
APY26
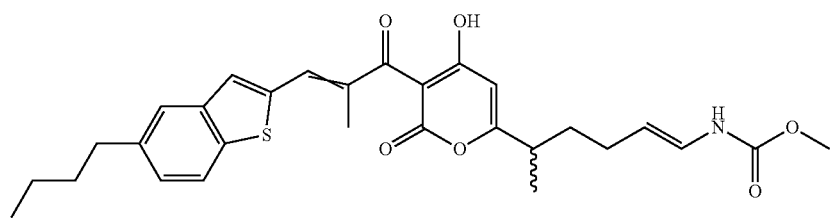
APY27
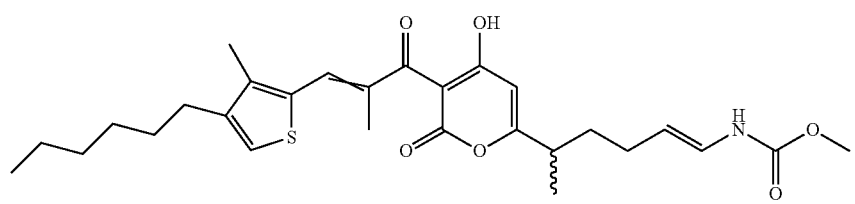
APY28
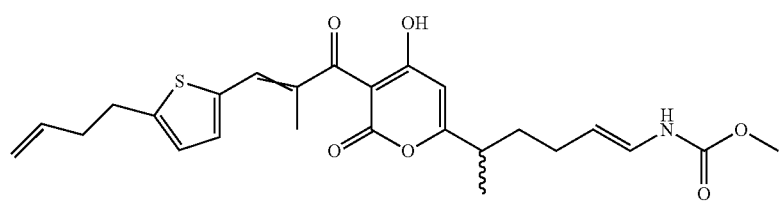
APY29
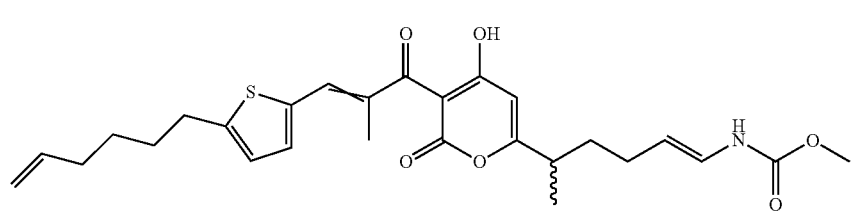

-continued
APY31
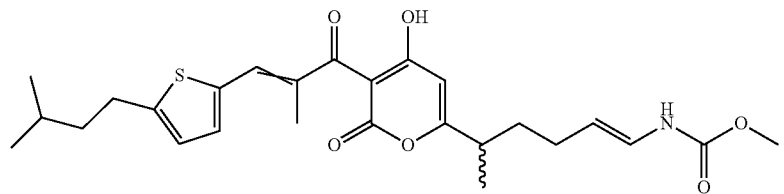
APY32
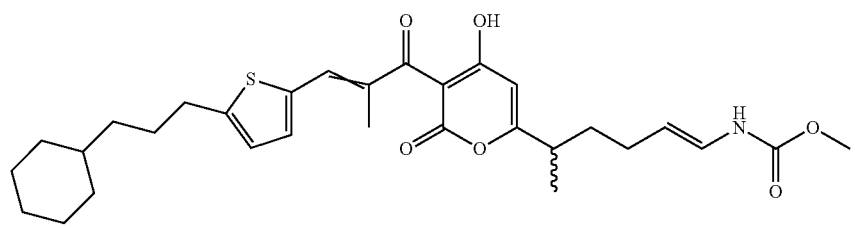
APY33
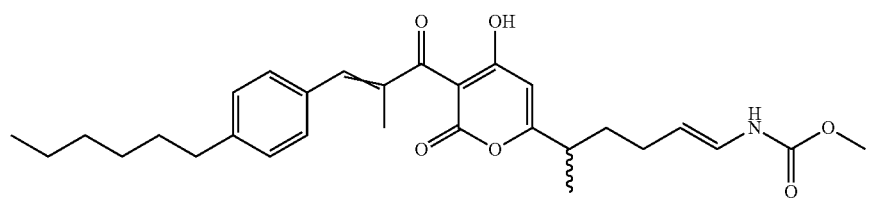
APY34
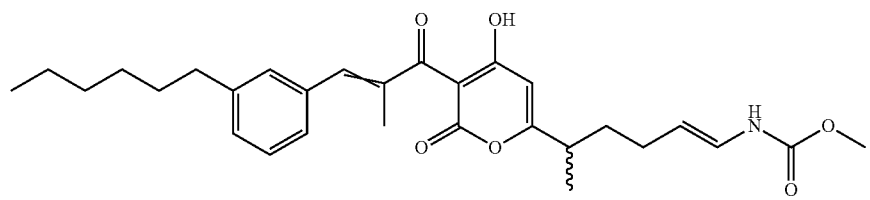
APY36
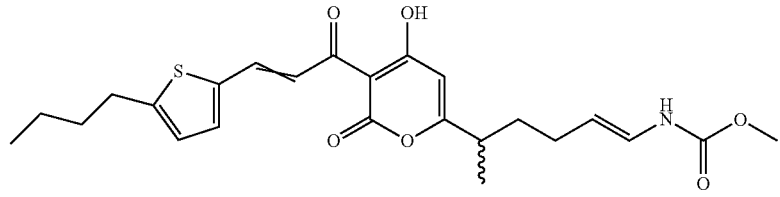
APY37
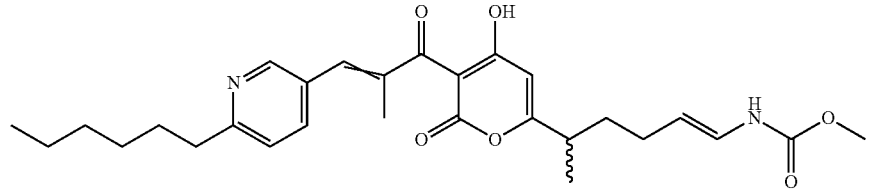
APY39
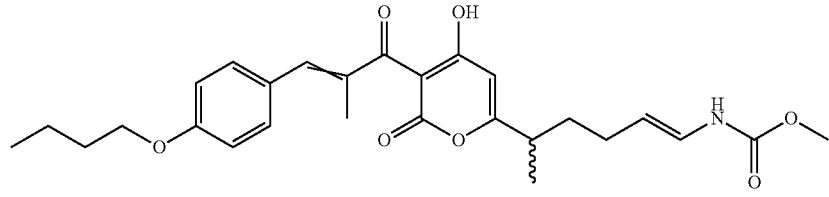

-continued
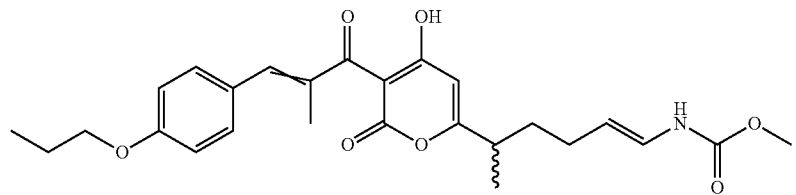
APY40
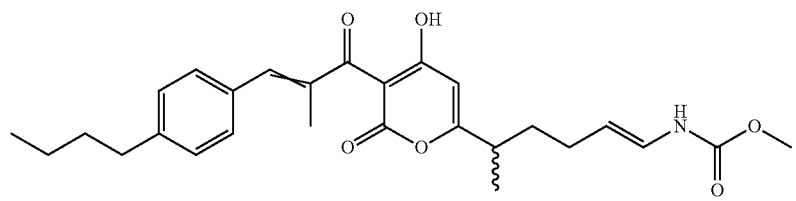
APY41
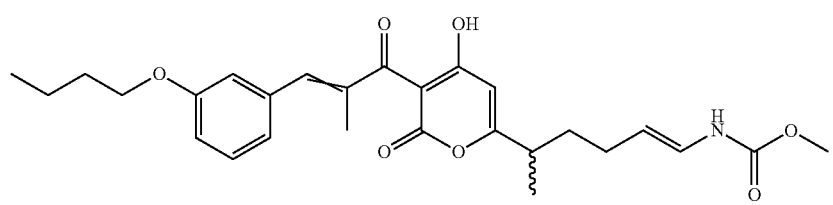
APY42
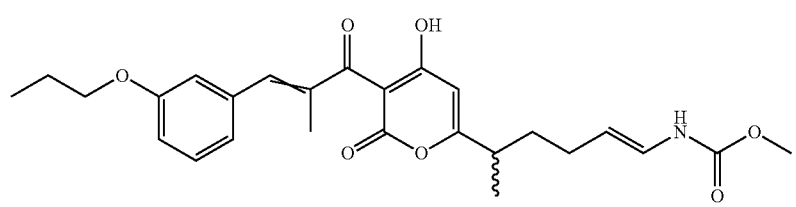
APY43
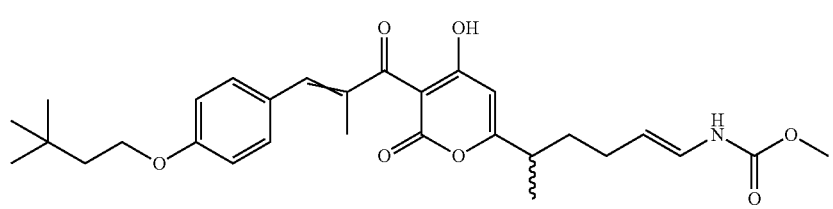
APY48
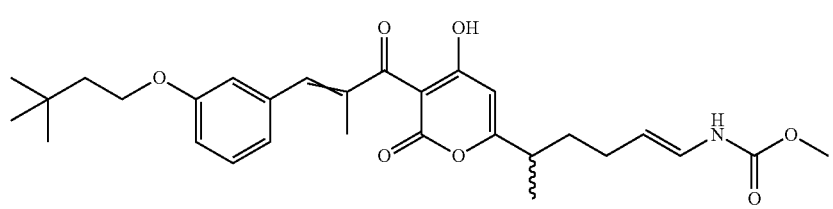
APY49
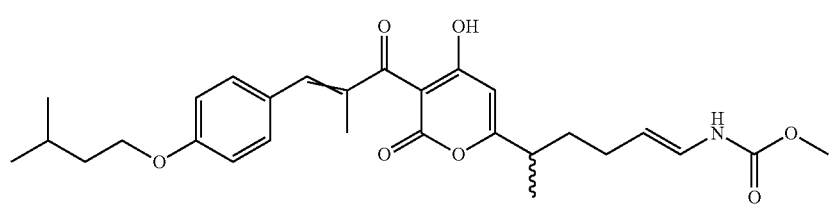
APY50

APY51
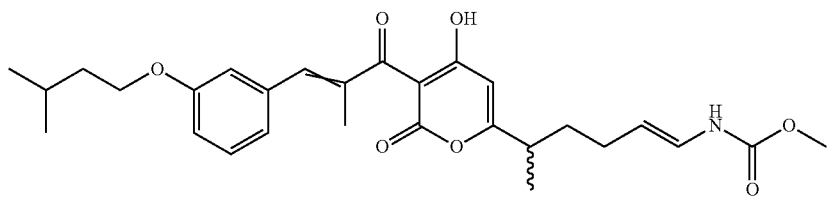
APY52
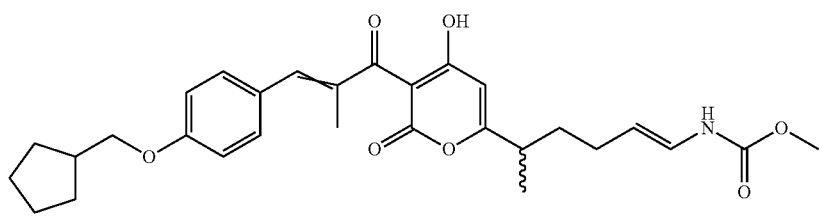
APY53
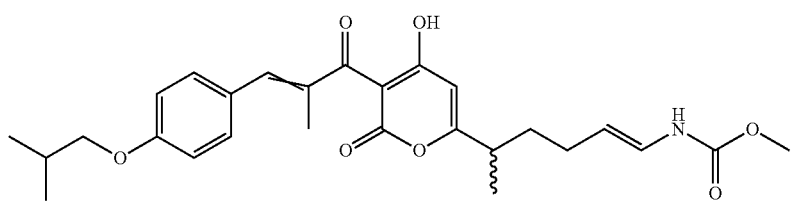
APY54
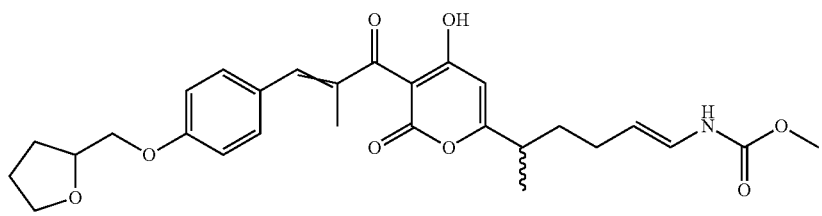
APY55
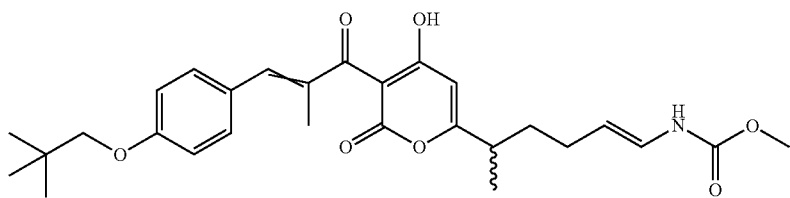
APY56
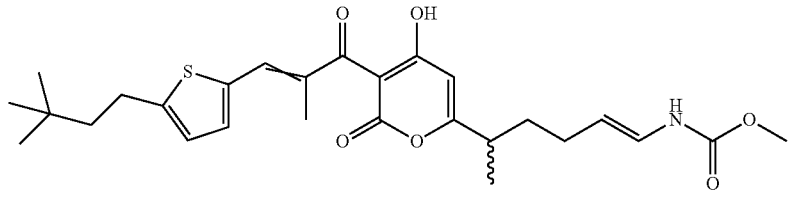
APY57
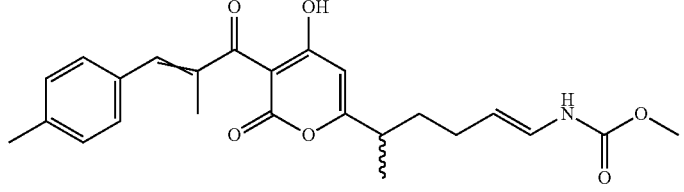

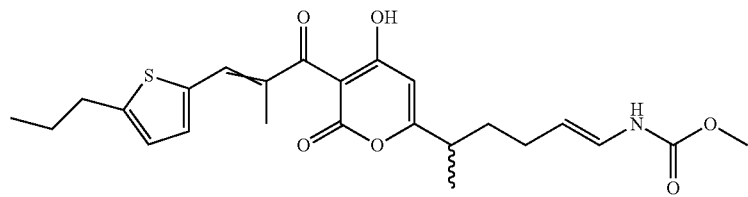
APY58
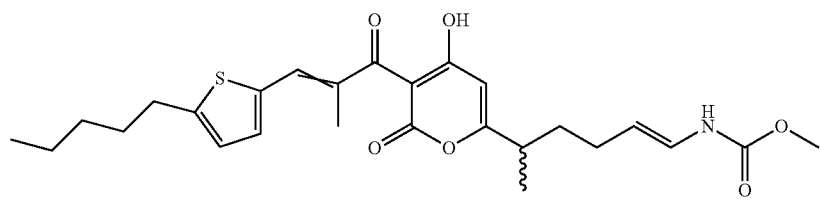
APY59
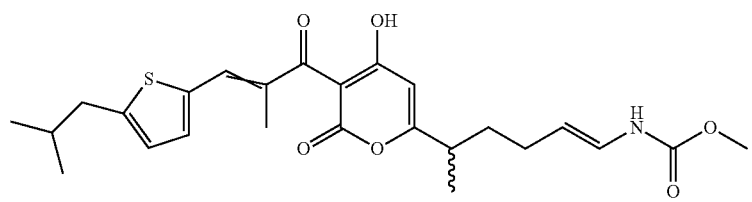
APY60
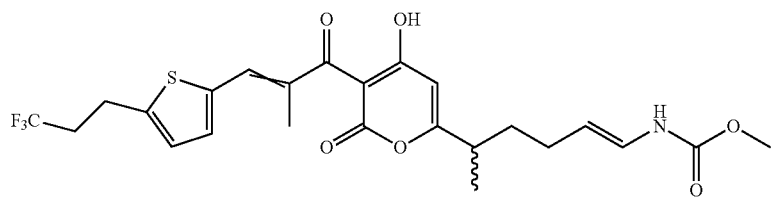
APY61
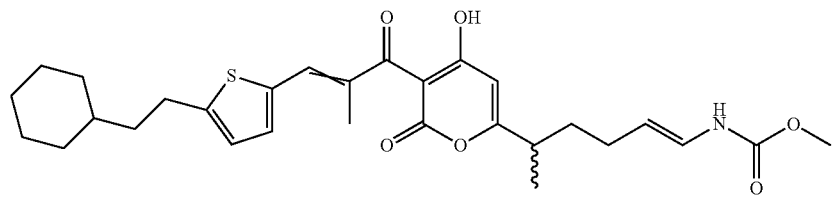
APY62
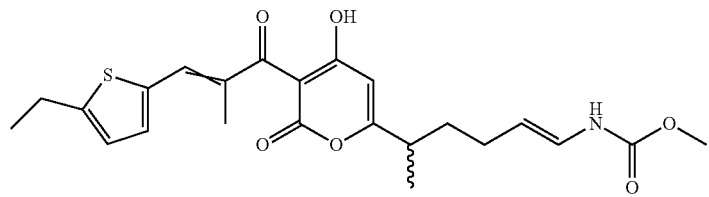
APY64
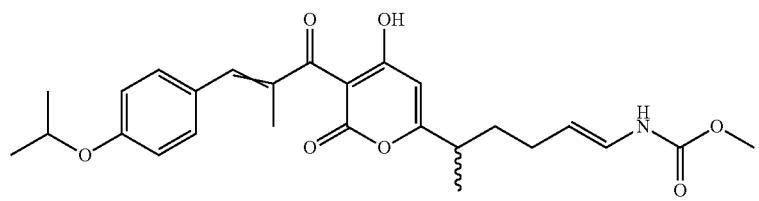
APY66

-continued
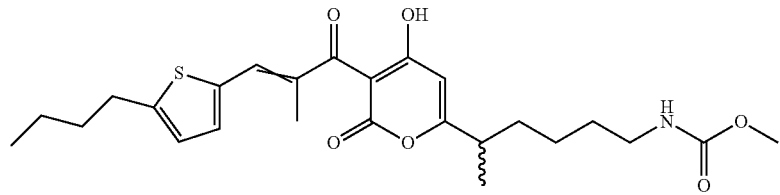
APY67
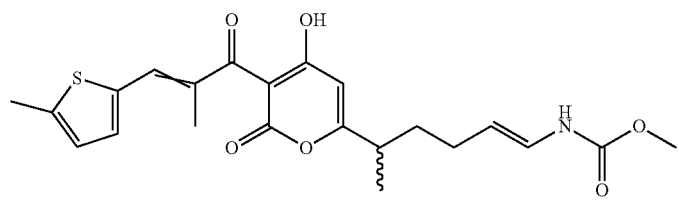
APY68
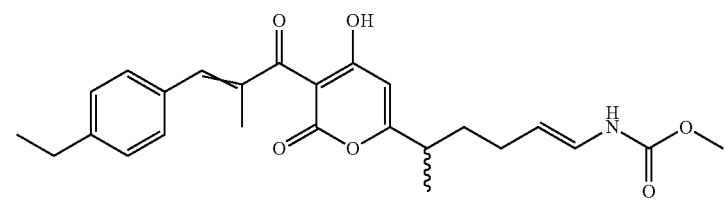
APY70
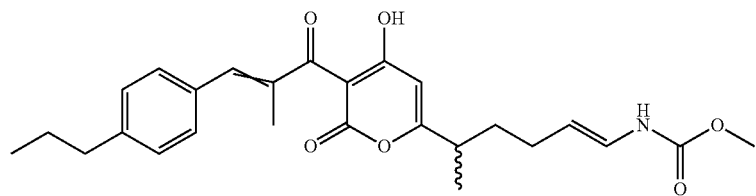
APY71
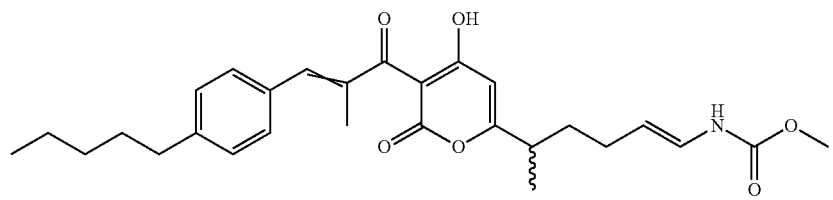
APY72
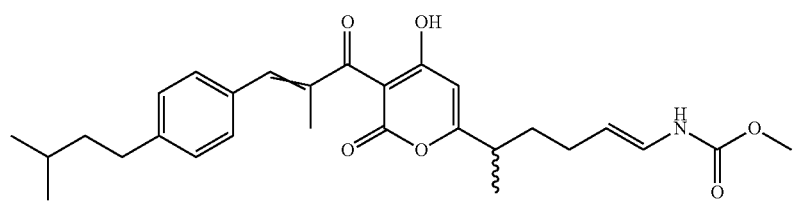
APY73
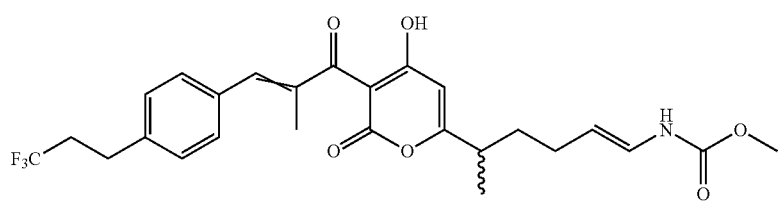
APY74

APY75
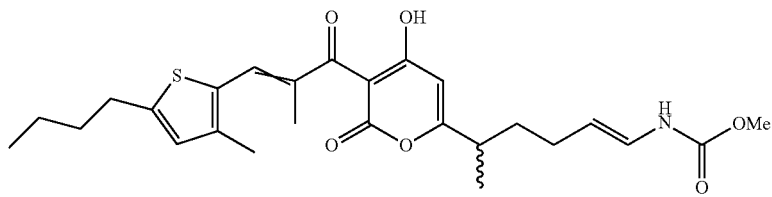
APY76
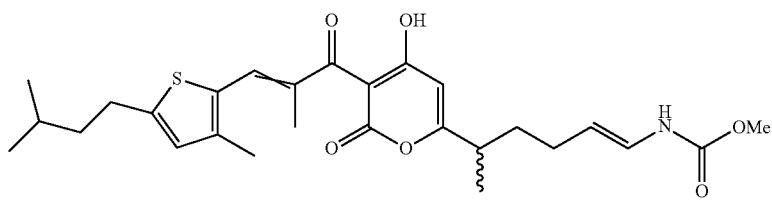
APY81
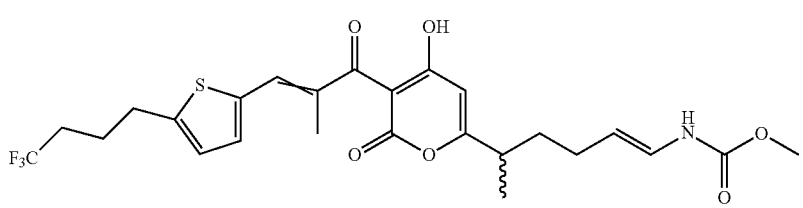
APY82
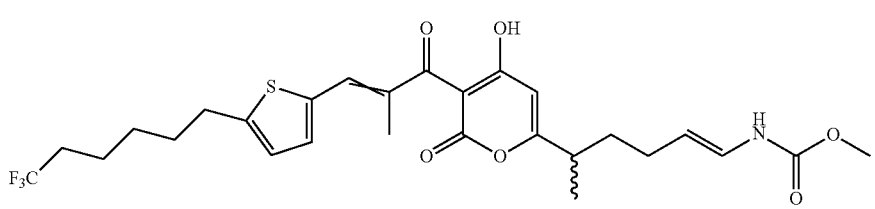
APY84
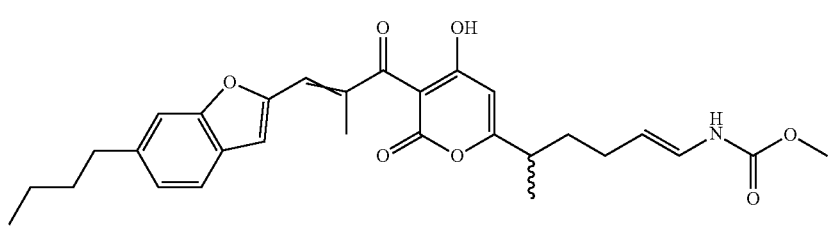
APY86
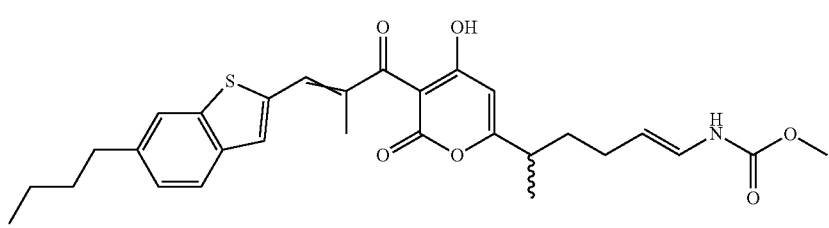
APY87
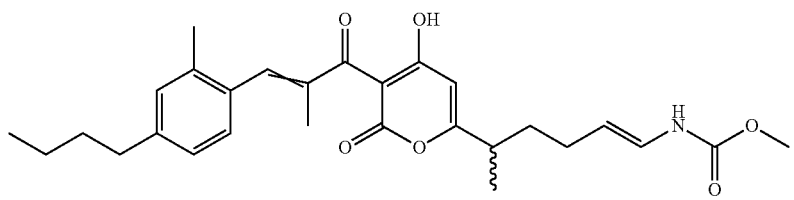

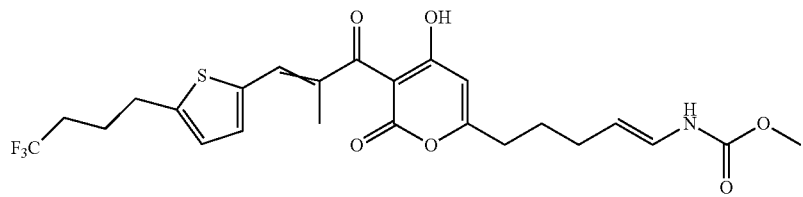
APY90
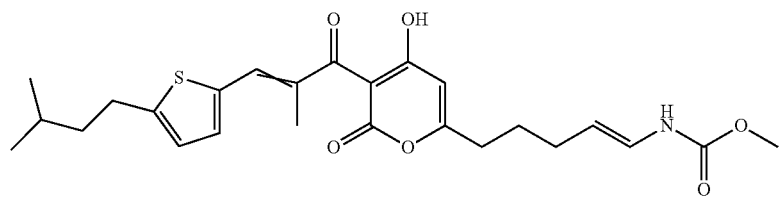
APY91
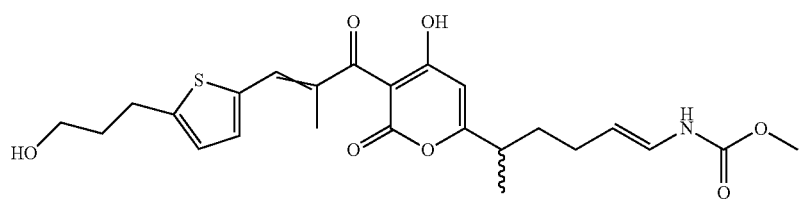
APY94
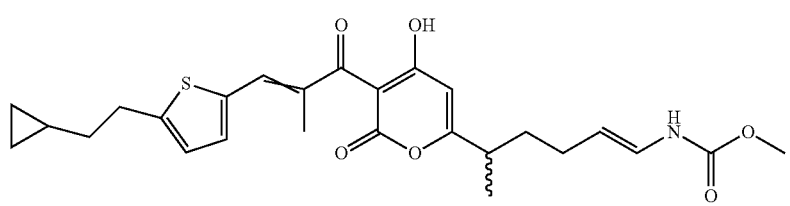
APY95
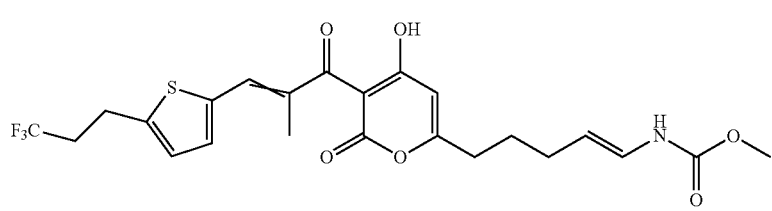
APY96
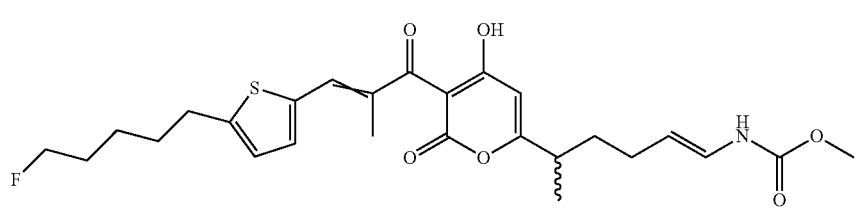
APY97
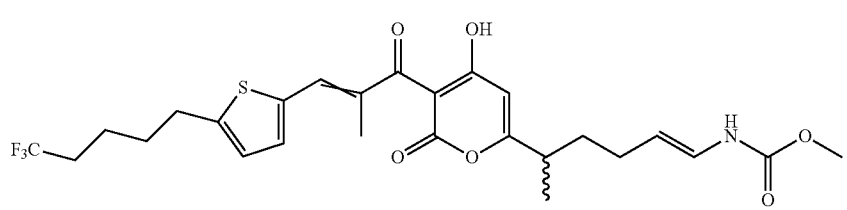
APY98

-continued
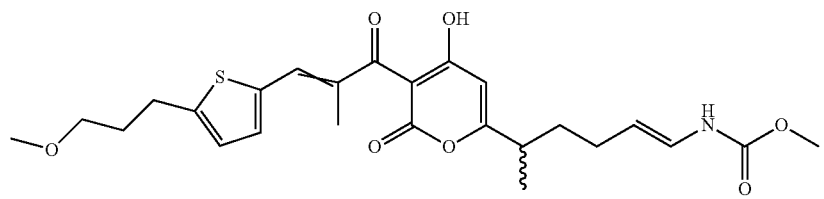
APY100
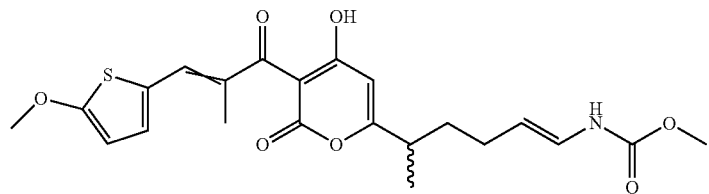
APY101
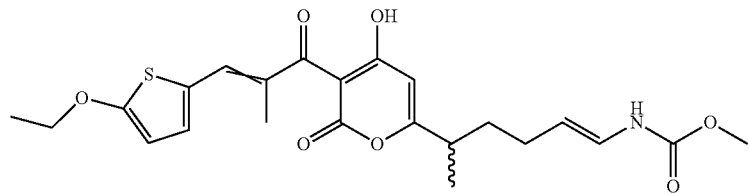
APY102
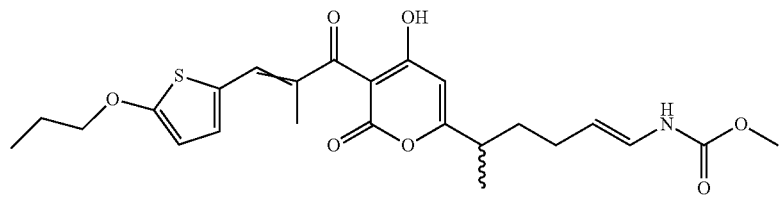
APY103
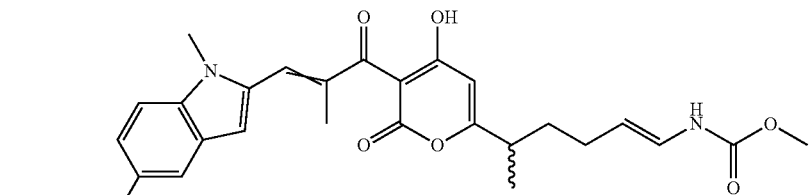
APY104
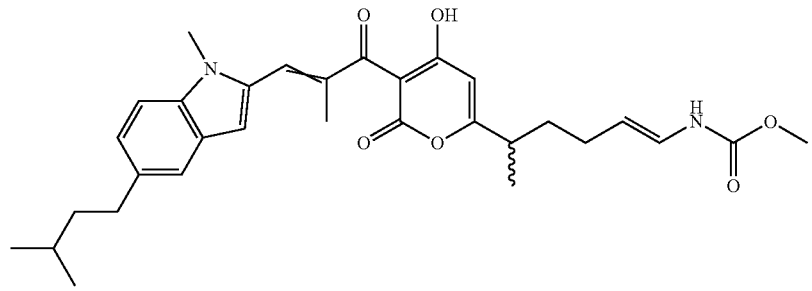
APY105
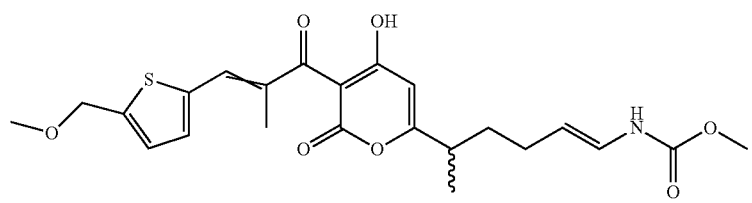
APY106

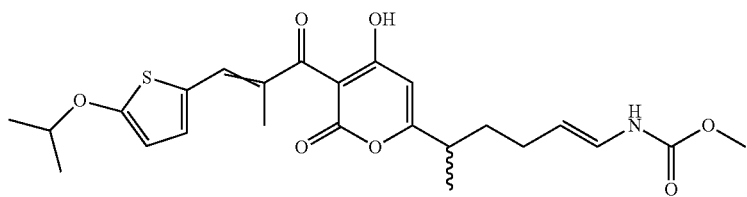
APY107
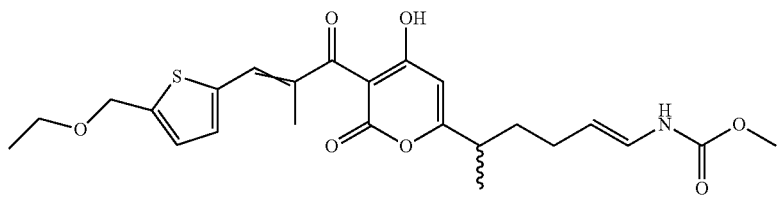
APY108
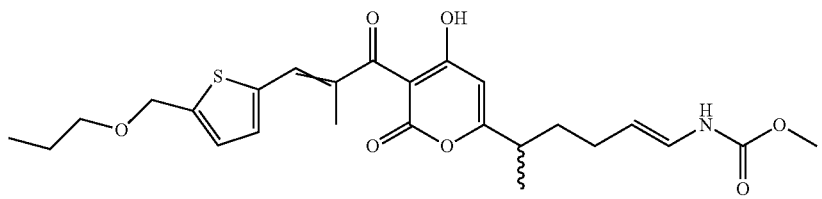
APY109
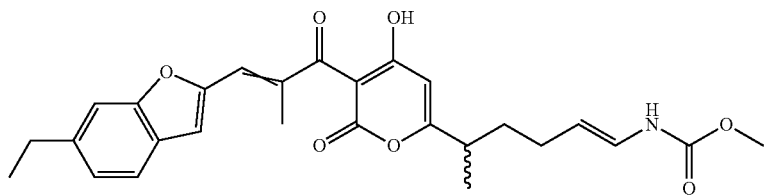
APY110
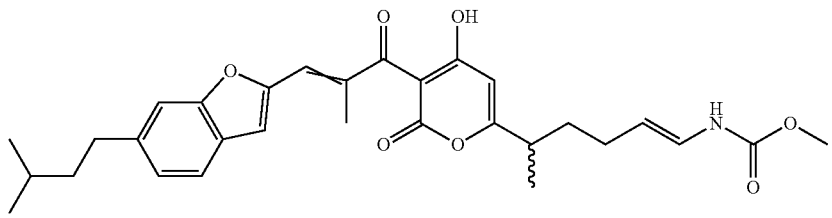
APY111
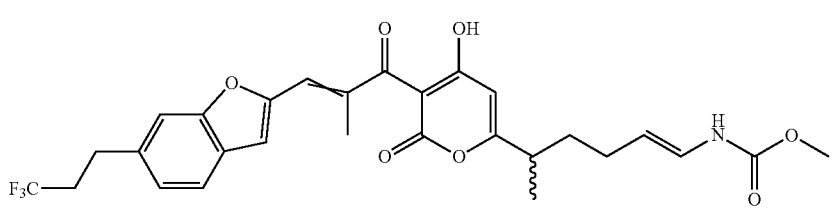
APY112
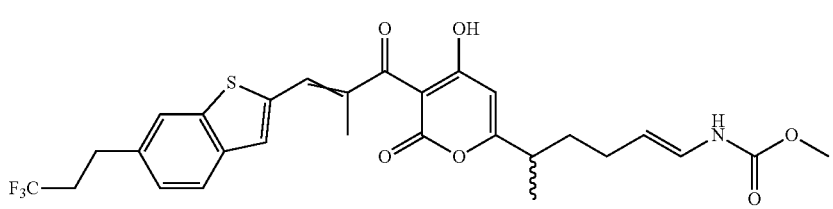
APY114

APY116
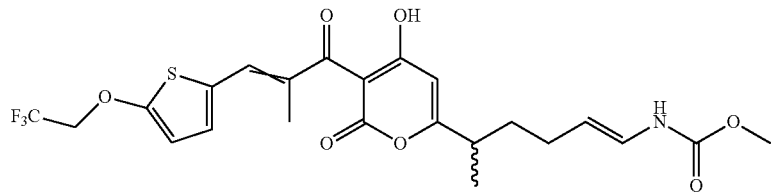
APY117
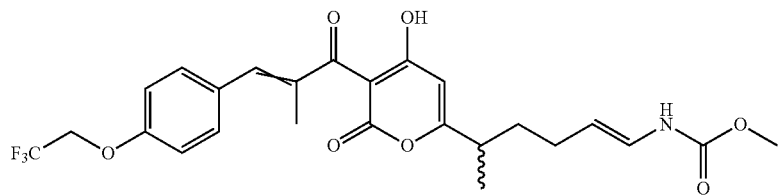
APY119
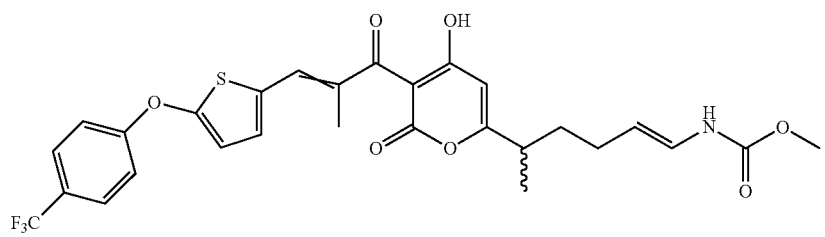
APY120
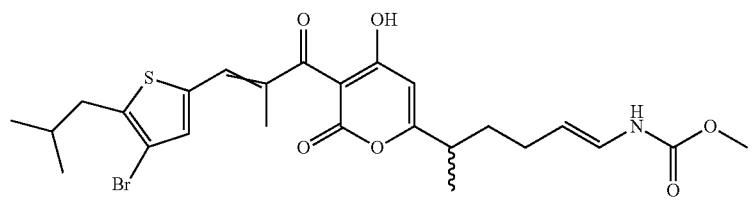
APY121
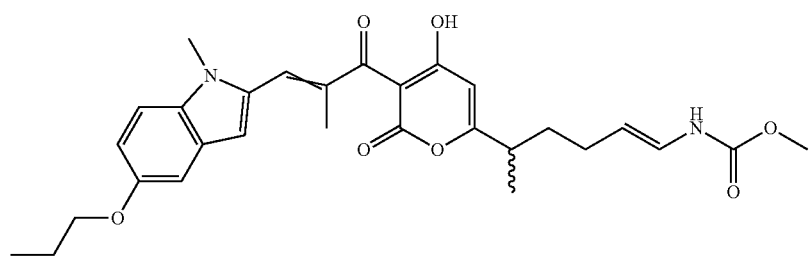
APY122
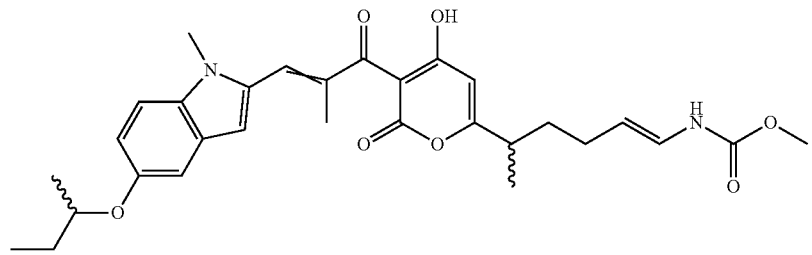

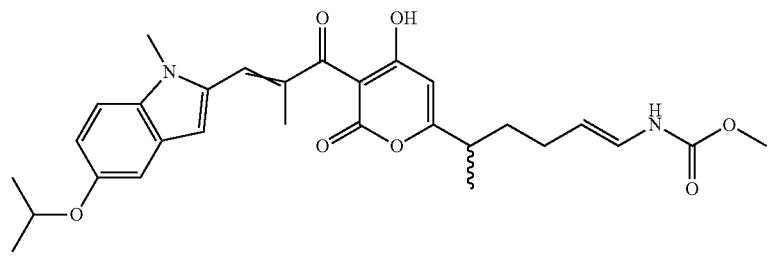
APY123
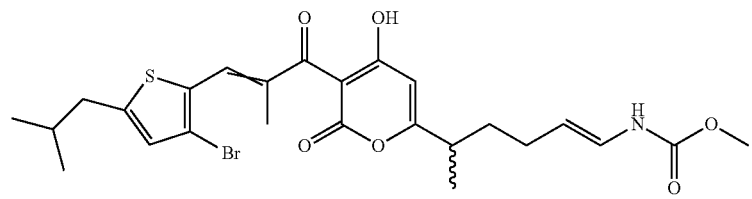
APY124
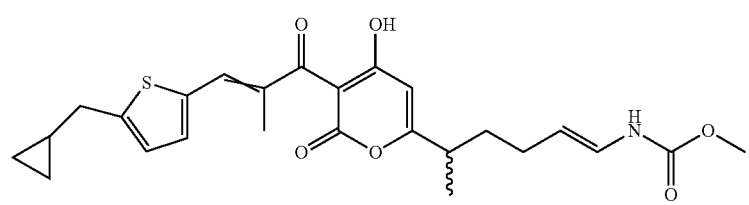
APY125
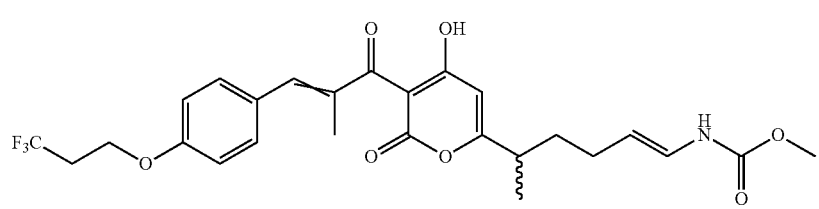
APY126
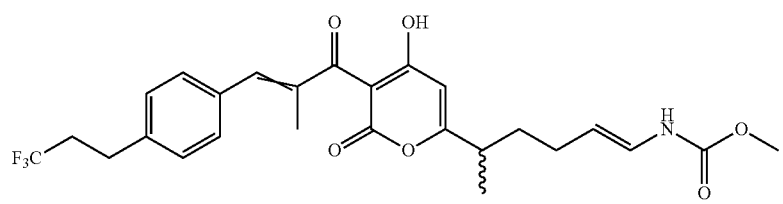
APY127
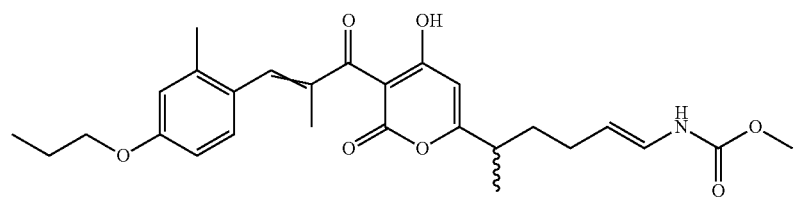
APY128
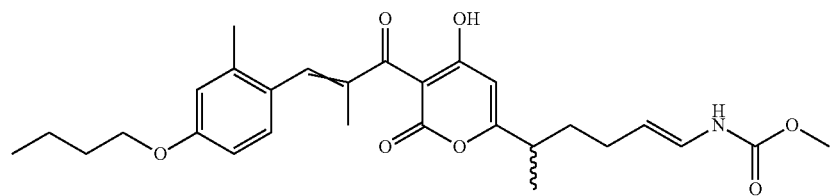
APY129

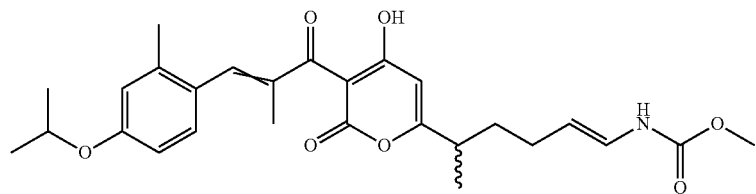
APY130
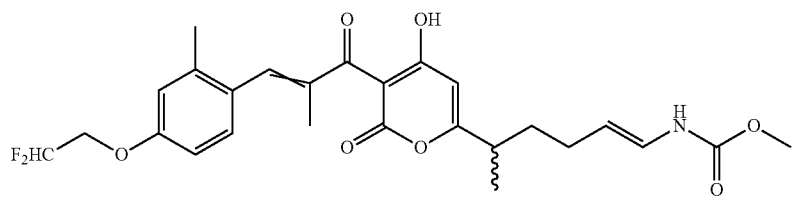
APY131
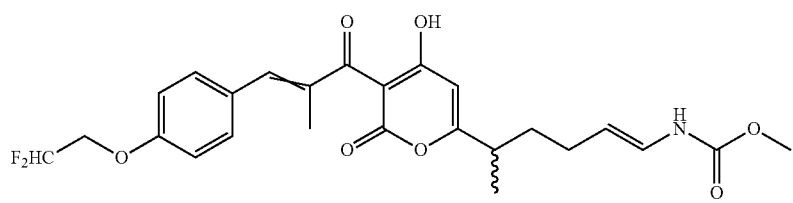
APY132
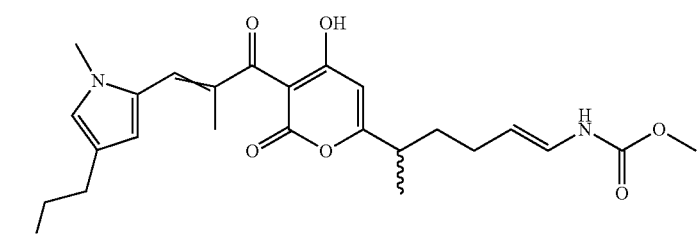
APY135
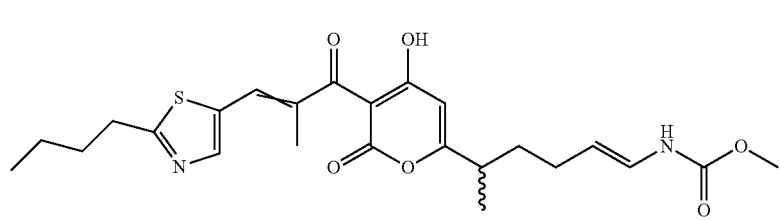
APY136
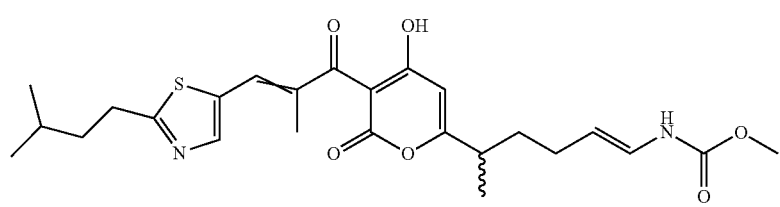
APY137
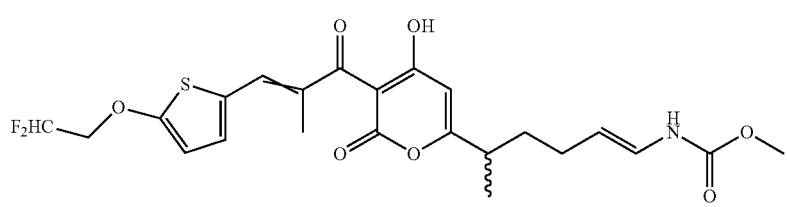
APY138

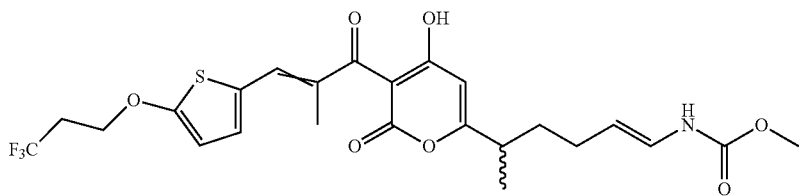

APY139

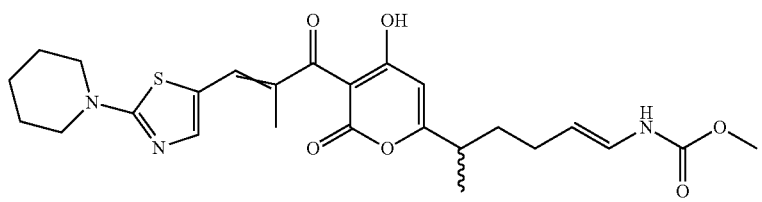

APY142

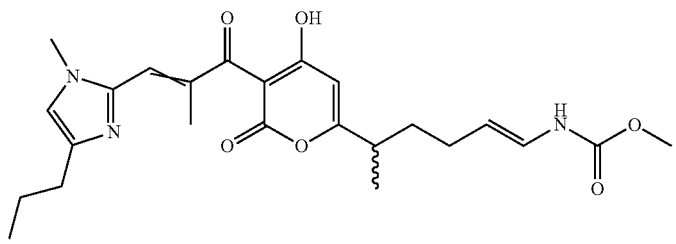

APY143

Example 1

APY15 Prepared by Method A

Example 1.1

Method A, Aldol Addition: Hydroxy Ketone 2a (aryl=5-hexyl-2-thiophenyl)

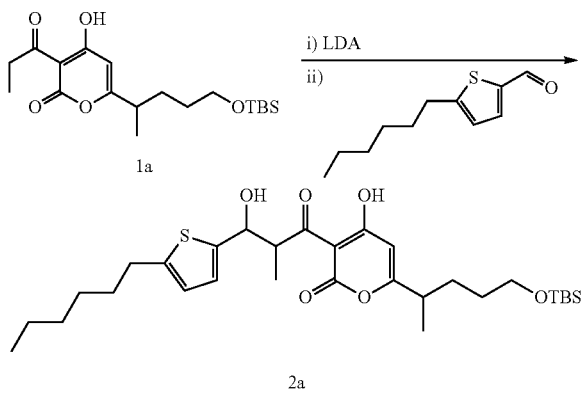

n-Butyllithium (1.43 mL, 2.5 M in hexanes) was added dropwise to a solution of diisopropyl amine (379 mg, 3.74 mmol) in anhydrous tetrahydrofuran (8 mL) at −78° C. under argon. The resulting solution was allowed to warm to 0° C. over 30 minutes before being re-cooled to −78° C. Pyrone 1a (prepared as in Panek, et. al. *J. Org. Chem.* 1998, 63, 2401; 600 mg, 1.63 mmol) was added dropwise as a solution in anhydrous tetrahydrofuran (4 mL) over 10 minutes. After stirring for 2 h at −78° C., the reaction mixture was treated with a solution of 5-hexyl-2-formylthiophene (639 mg, 3.26 mmol) in anhydrous tetrahydrofuran (4 mL). Stirring was continued at −78° C. for 1 h, before the reaction mixture was quenched at this temperature with saturated aqueous ammonium chloride (20 mL). Organics were extracted with ethyl acetate (3×25 mL), dried over magnesium sulfate, filtered, and concentrated. The residue was purified by chromatography on silica gel with gradient elution (5→20% ethyl acetate/hexanes) to give hydroxy ketone 2a where aryl=5-hexyl-2-thiophenyl (642 mg, 80%) as a yellow oil containing a mixture of syn and anti diastereomers: LRMS (ES$^+$) m/z [M+H]. found 565 (Exact mass=564.29). Used without further characterization.

Example 1.2

Method A, Dehydration: Enone 3a
(aryl=5-hexyl-2-thiophenyl)

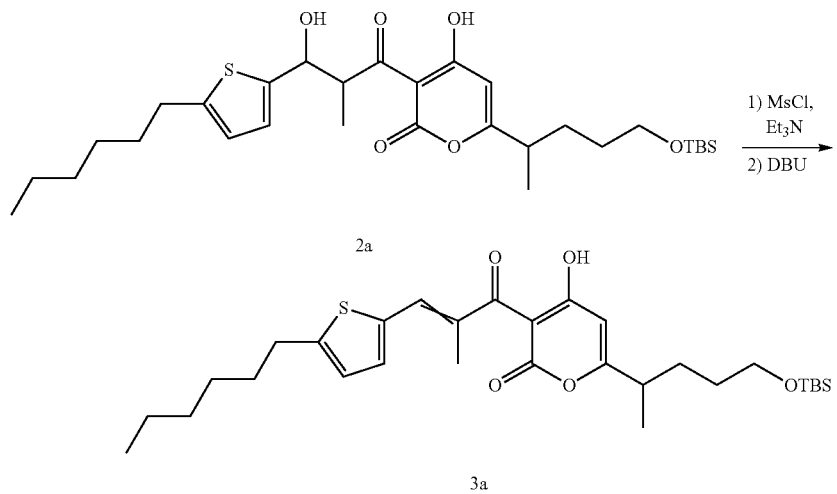

A solution of hydroxy ketone 2a (Example 1.1; 508 mg, 0.90 mmol) and triethylamine (273 mg, 2.7 mmol) in 9 mL of anhydrous dichloromethane was flushed with argon and cooled to 0° C. Methanesulfonyl chloride (206 mg, 1.80 mmol) was added dropwise and the resulting solution was allowed to warm to room temperature over 30 minutes before quenching with saturated sodium bicarbonate (aq.). The mixture was acidified with 0.1 N hydrochloric acid. Organics were extracted with dichloromethane (3×15 mL), dried with magnesium sulfate, filtered and concentrated. The resulting crude mesylate was dissolved in tetrahydrofuran (9 mL), treated with 1,8-diazabicycloundec-7-ene (411 mg, 2.70 mmol) and stirred at room temperature overnight. The reaction mixture was acidified by addition of 0.1 N hydrochloric acid, and organics were extracted with ethyl acetate (3×15 mL). The combined extracts were washed with water (2×15 mL) and brine (15 mL), dried over magnesium sulfate, filtered and concentrated. The crude residue was purified by chromatography on silica gel (20% ethyl acetate in hexanes) to afford enone 3a (348 mg, 71%) as a yellow oil: LRMS (ES$^+$) m/z [M+H]. found 547 (Exact mass=546.28). Used without further characterization.

Example 1.3

Method A, OTBS Deprotection: Alcohol 4a
(aryl=5-hexyl-2-thiophenyl)

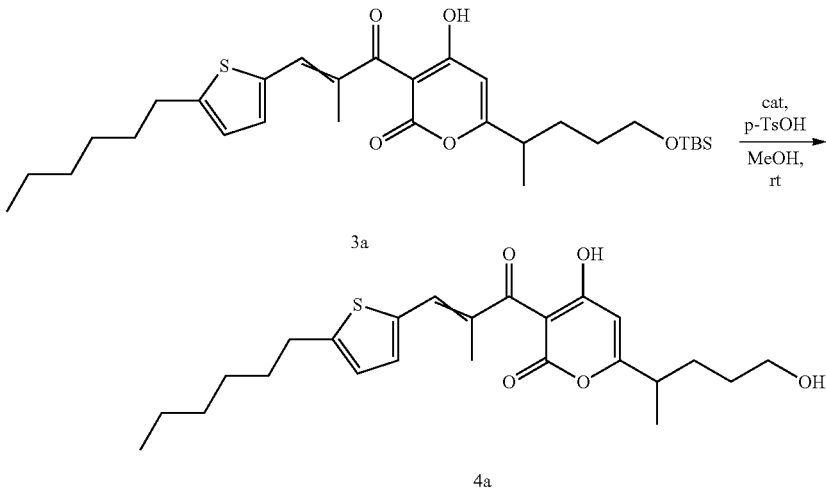

A solution of enone 3a (Example 1.2; 429 mg, 0.78 mmol) and p-tosic acid monohydrate (12 mg, 0.06 mmol) in 4:1 methanol/dichloromethane (25 mL) was stirred at room temperature for 1 h. The reaction mixture was poured into ethyl acetate (50 mL) and washed with water (2×50 mL) and brine (50 mL). The organic layer was dried over magnesium sulfate, filtered and concentrated. The crude product was purified by chromatography on silica gel (33% ethyl acetate in hexanes) to give alcohol 4a (167 mg, 49%) as a clear oil: LRMS (ES$^+$) m/z [M+H]. found 433 (Exact mass=432.20). Used without further characterization.

Example 1.4

Method A, Oxidation/Olefination: Methyl Ester 5a (aryl=5-hexyl-2-thiophenyl)

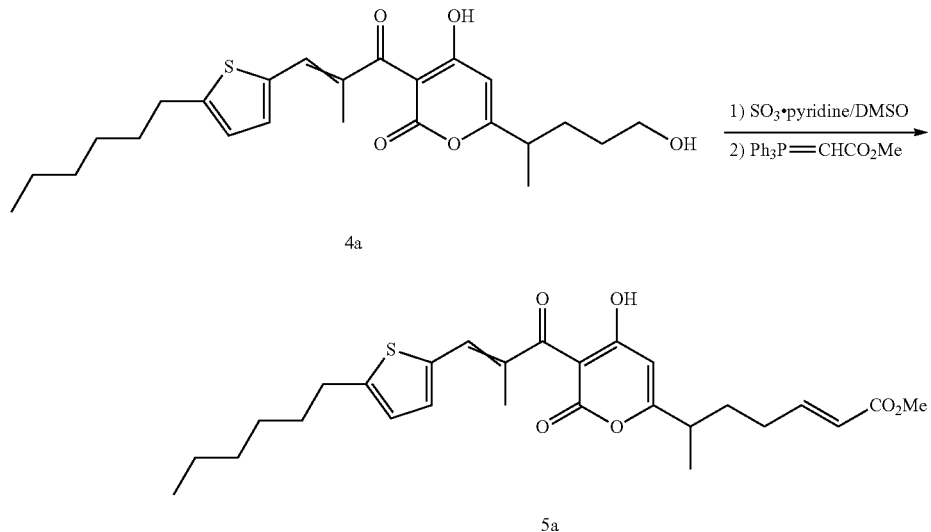

Sulfur trioxide•pyridine (126 mg, 0.79 mmol) was added portionwise over 1 minute to a 0° C. solution of alcohol 4a (Example 1.3; 143 mg, 0.39 mmol), triethylamine (120 mg, 1.18 mmol) and dimethyl sulfoxide (92 mg, 1.18 mmol) in anhydrous dichloromethane (4 mL). The resulting mixture was allowed to warm to room temperature over 30 minutes with vigorous stirring before being poured into 0.1 N hydrochloric acid (20 mL). Organics were extracted with ether (3×20 mL). The combined extracts were washed with 0.1 N hydrochloric acid, water, and brine (20 mL each), dried over magnesium sulfate, filtered and concentrated. The crude aldehyde was dissolved in dichloromethane (4 mL) and treated dropwise with a solution of methyl(triphenylphosphoranylidene) acetate (223 mg, 0.67 mmol) in dichloromethane (4 mL) at room temperature. After stirring at room temperature overnight, the reaction mixture was concentrated and purified by chromatography on silica gel (33% ethyl acetate in hexanes) to afford methyl ester 5a (109 mg, 67%) as a white solid: LRMS (ES$^+$) m/z [M+H]. found 487 (Exact mass=486.21). Used without further characterization.

Example 1.5

Method A, Hydrolysis: Acid 6a (aryl=5-hexyl-2-thiophenyl)

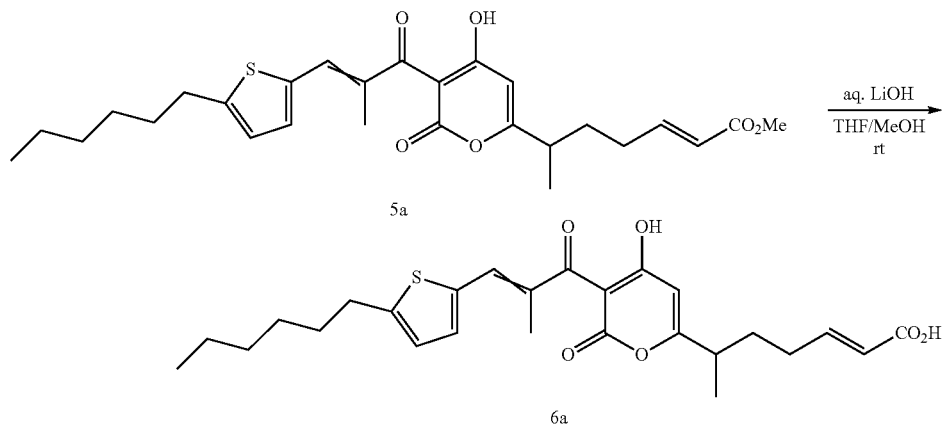

A solution of methyl ester 5a (Example 1.4; 108 mg, 0.22 mmol) in 5:1 tetrahydrofuran/methanol (12 mL) at room temperature was treated with lithium hydroxide (2.22 mL, 1 M in water). The resulting solution was stirred at room temperature for 24 h. Organic solvents were removed in vacuo and the aqueous residue poured into 1 N hydrochloric acid (20 mL). Organics were extracted with ethyl acetate (3×25 mL), dried with magnesium sulfate, filtered and concentrated. The crude product was purified by chromatography on silica gel (5% methanol in dichloromethane+0.5% acetic acid) to give acid 6a (55 mg, 50%) as a white solid: LRMS (ES$^+$) m/z [M+H]. found 473 (Exact mass=472.19). Used without further characterization.

Example 1.6

Method A, Curtius Rearrangement Sequence: APY15

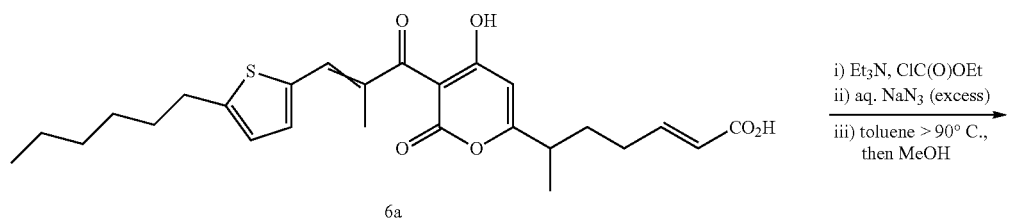

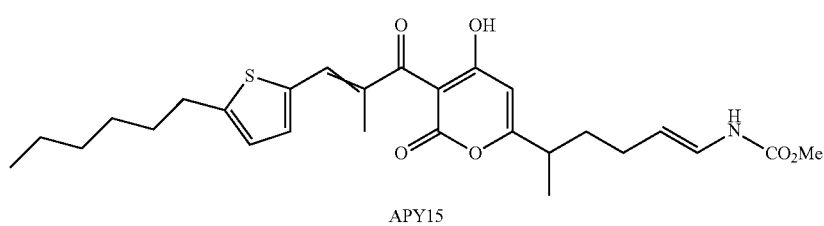

A solution of acid 6a (Example 1.5; 45 mg, 0.095 mmol) in anhydrous acetone (3 mL) at 0° C. under argon was treated with diisopropylethylamine (58 mg, 0.448 mmol), followed by dropwise addition of ethyl chloroformate (44 mg, 0.409 mmol). After stirring the mixture for 1.5 h at 0° C., a solution of sodium azide (30 mg, 0.457 mmol) in water (0.54 mL) was added and the resulting slurry was stirred vigorously at 0° C. for 1 h, before being poured into 0.1 N hydrochloric acid (15 mL). Organics were extracted with ether (3×15 mL) and toluene (5 mL) was added. The ether was removed in vacuo and the residual toluene solution azeotroped with more toluene (3×15 mL) but never concentrated to below 5 mL. After the final round of azeotropic drying, the 5 mL of remaining toluene solution was transferred to a pressure-relief reaction vial, flushed with argon, sealed and heated in a 120° C. bath for 20 minutes. The vial was removed from the heating bath, allowed to cool enough such that it was safe to open, and 2 mL of anhydrous methanol was added. The vial was re-sealed and heated in a 100-120° C. bath for an additional 20 minutes. The vial was removed from the heating bath, cooled to room temperature and the contents concentrated. The crude product was purified by chromatography on silica gel (50% ethyl acetate in hexanes+0.5% acetic acid) to give APY15 (9 mg, 19%) as an off-white oily solid containing a mixture of E and Z isomers (8:1): $^1$H NMR (E isomer, 500 MHz, CDCl$_3$, 298 K) δ 15.9 (s, 1H), 7.24 (s, 1H), 7.10 (d, 1H), 6.79 (d, 1H), 6.51-6.41 (m, 1H), 6.22 (br d, 1H), 5.95 (s, 1H), 4.99-4.91 (m, 1H), 3.71 (s, 3H), 2.84 (t, 2H), 2.60 (q, 1H), 2.21 (d, 3H), 2.08-1.98 (m, 2H), 1.85-1.56 (m, 4H), 1.41-1.29 (m, 6H), 1.25 (d, 3H), 0.89 (t, 3H); LRMS (ES$^+$) m/z [M+H]. found 502 (Exact mass=501.22).

Example 2

APY16 Prepared by Method A

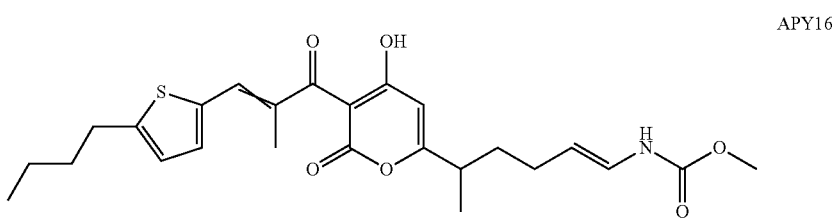 [SMILES: CCCCc1ccc(C=C(C)C(=O)c2c(O)cc(C(C)CC/C=C/NC(=O)OC)oc2=O)s1]

The compound was synthesized as in Example 1, using 5-butyl-2-formylthiophene (457 mg, 2.71 mmol) in place of 5-hexyl-2-formylthiophene to give APY16 (7 mg) as an off-white solid containing a mixture of E and Z isomers (12:1): $^1$H NMR (E isomer, 500 MHz, CDCl$_3$, 298 K) δ 15.9 (s, 1H), 7.23 (s, 1H), 7.10 (s, 1H), 6.79 (d, 1H), 6.49-6.42 (m, 1H), 6.25-6.22 (m, 1H), 5.95 (s, 1H), 5.00-4.91 (m, 1H), 3.71 (s, 3H), 2.85 (t, 2H), 2.60 (q, 1H), 2.21 (d, 3H), 2.07-1.99 (m, 2H), 1.84-1.76 (m, 1H), 1.69 (quintet, 2H), 1.59-1.54 (m, 1H), 1.40 (sextet, 2H), 1.25 (d, 3H), 0.94 (t, 3H); LRMS (ES$^+$) m/z [M+H]. found 474 (Exact mass=473.19).

Example 3

APY17 Prepared by Method A

Example 3.1

5-hexyl-2-formylfuran

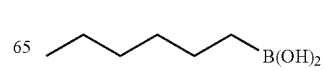

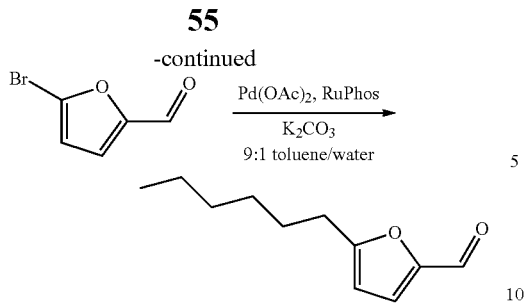

According to the method of Molander, et. al. (*J. Org. Chem.* 2009, 74, 3636), a suspension of 5-bromo-2-formylfuran (695 mg, 3.97 mmol), hexylboronic acid (775 mg, 5.96 mmol), potassium carbonate (1.65 g, 11.91 mmol), palladium (II) acetate (18 mg, 0.079 mmol) and RuPhos (74 mg, 0.16 mmol) in 9:1 toluene/water (22 mL) in a pressure-relief vial under argon was heated in a 120° C. bath for 18 h. After cooling to room temperature, the tion mixture was diluted with water (25 mL) and organics extracted with ether (3×50 mL), dried with magnesium sulfate, filtered, and concentrated. The crude product was purified by chromatography on silica gel (10% ethyl acetate in hexanes) to give 5-hexyl-2-formylfuran (665 mg, 93%) as a clear oil. Used without further characterization.

Example 3.2

APY17

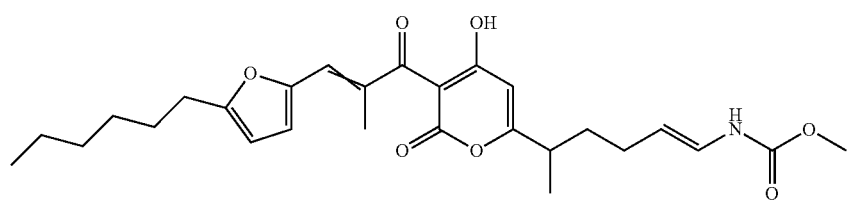

The compound was synthesized as in Example 1, using 5-hexyl-2-formylfuran (Example 3.1; 489 mg, 2.71 mmol) in place of 5-hexyl-2-formylthiophene to give APY17 (18.5 mg) as an off-white solid containing a mixture of E and Z isomers (5:1): $^1$H NMR (E isomer, 500 MHz, CDCl$_3$, 298 K) δ 15.9 (br s, 1H), 6.89 (s, 1H), 6.54 (d, 1H), 6.49-6.43 (m, 1H), 6.29-6.25 (m, 1H), 6.11 (d, 1H), 5.95 (s, 1H), 4.97-4.90 (m, 1H), 3.70 (s, 3H), 2.65 (t, 2H), 2.60 (q, 1H), 2.22 (d, 3H), 2.08-1.97 (m, 2H), 1.84-1.77 (m, 1H), 1.69-1.63 (m, 2H), 1.59-1.53 (m, 1H), 1.35-1.28 (m, 6H), 1.25 (d, 3H), 0.89 (t, 3H); LRMS (ES$^+$) m/z [M+H]. found 486 (Exact mass=485.24).

Example 4

APY18 Prepared by Method A

Example 4.1

4-hexyl-2-formylthiophene

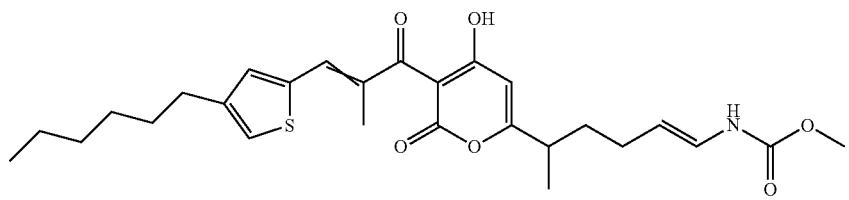

The compound was synthesized as in Example 3.1, using 4-bromo-2-formylthiophene (781 mg, 3.68 mmol) in place of 5-bromo-2-formylfuran to give 4-hexyl-2-formylthiophene (710 mg, 98%). Used without further characterization.

APY17

Example 4.2

APY18

APY18

The compound was synthesized as in Example 1, using 4-hexyl-2-formylthiophene (Example 4.2; 533 mg, 2.71 mmol) in place of 5-hexyl-2-formylthiophene to give APY18 (62 mg) as an off-white solid containing a mixture of E and Z isomers (12:1): $^1$H NMR (E isomer, 500 MHz, CDCl$_3$, 298 K) δ 15.9 (br s, 1H), 7.21 (s, 1H), 7.10 (s, 2H), 6.49-6.43 (m, 1H), 6.26-6.22 (m, 1H), 5.96 (s, 1H), 4.98-4.91 (m, 1H), 3.71 (s, 3H), 2.63-2.58 (m, 3H), 2.22 (d, 3H), 2.08-1.99 (m, 2H), Example 5

APY20 Prepared by Method A

Example 5.1

5-hexyl-2-formylbenzofuran

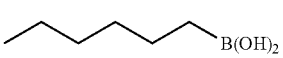

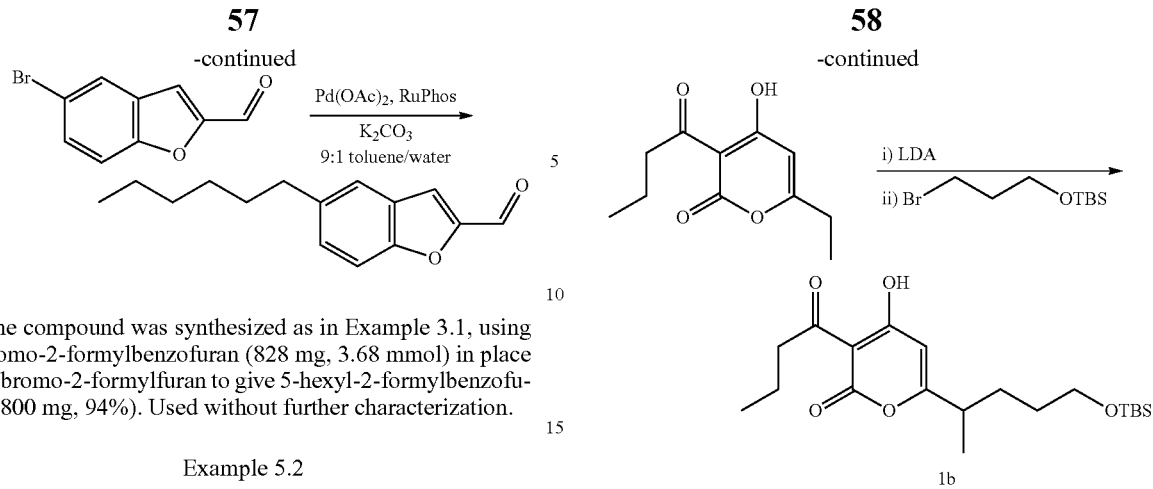

The compound was synthesized as in Example 3.1, using 5-bromo-2-formylbenzofuran (828 mg, 3.68 mmol) in place of 5-bromo-2-formylfuran to give 5-hexyl-2-formylbenzofuran (800 mg, 94%). Used without further characterization.

Example 5.2

APY20

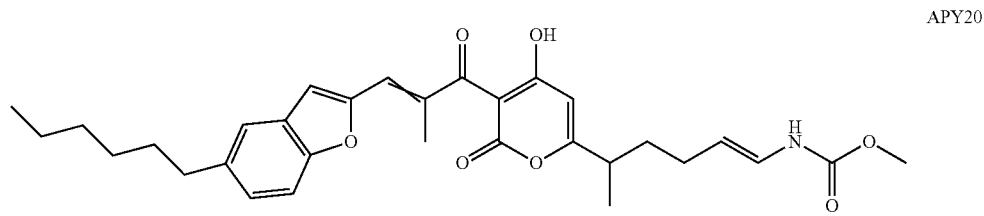 [SMILES: CCCCCCc1ccc2oc(C=C(C)C(=O)c3c(O)cc(C(C)CC/C=C/NC(=O)OC)oc3=O)cc2c1]

The compound was synthesized as in Example 1, using 5-hexyl-2-formylbenzofuran (Example 5.1; 625 mg, 2.71 mmol) in place of 5-hexyl-2-formylthiophene to give APY20 (60 mg) as an off-white solid containing a mixture of E and Z isomers (3.5:1): $^1$H NMR (E isomer, 500 MHz, CDCl$_3$, 298 K) δ 15.8 (br s, 1H), 7.37 (d, 2H), 7.14 (dd, 1H), 6.86-6.85 (m, 2H), 6.49-6.41 (m, 1H), 6.34-6.25 (m, 1H), 5.98 (s, 1H), 4.97-4.90 (m, 1H), 3.70 (s, 3H), 2.68 (t, 2H), 2.61 (q, 2H), 2.38 (d, 3H), 2.07-1.96 (m, 2H), 1.85-1.76 (m, 1H), 1.68-1.61 (m, 2H), 1.60-1.54 (m, 1H), 1.36-1.27 (m, 6H), 1.25 (d, 3H), 0.88 (t, 3H); LRMS (ES) m/z [M+H]. found 536 (Exact mass=535.26).

Example 6

APY21 Prepared by Method B

Example 6.1

Pyrone 1b

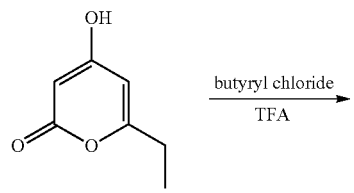

According to the method of Douglas and Money (see: *Can. J. Chem.* 1968, 46, 695), 4-hydroxy-6-ethyl-2-pyrone (see: Hsung, et. al. *Synthesis* 2007, 749; 1.24 g, 8.85 mmol) was dissolved in trifluoroacetic acid (4 mL) in a pressure-safe vessel. Butyryl chloride (1.0 mL, 9.73 mmol) was added and the solution flushed with argon. The vessel was sealed and stirred in a 90° C. heating bath overnight. After cooling to room temperature, the solution was poured onto powdered sodium bicarbonate (9 g) before water (80 mL) was added carefully. Organics were extracted from the aqueous slurry with dichloromethane (3×80 mL), dried with magnesium sulfate, filtered, and concentrated. The crude product was purified by chromatography on silica gel with gradient elution (10→20% ether in hexanes) to afford 3-butyryl-6-ethyl-4-hydroxy-2-pyrone (1.20 g, 65%) as an oily solid. Used without further characterization.

A solution of diisopropylamine (1.91 mL, 13.53 mmol) in anhydrous tetrahydrofuran (3 mL) under argon at −30° C. was treated dropwise with n-butyllithium (5.2 mL, 2.5 M in hexanes). The resulting solution was stirred 15 minutes at −20 to −30° C. In a separate flask, hexamethylphosphoramide (2 mL) and 3-butyryl-6-ethyl-4-hydroxy-2-pyrone (862 mg, 4.10 mmol) were combined and azeotroped to dryness with benzene (3×25 mL) before being dissolved in anhydrous tetrahydrofuran (5 mL). To the LDA solution at −78° C. was added dropwise over 10 minutes the solution of hexamethylphosphoramide and pyrone 7a. The resulting mixture was stirred at −78° C. for 1 h before (3-bromopropoxy)-t-butyldimethylsilane (1.04 mL, 4.51 mmol) was added dropwise over 1 minute. The reaction mixture was stirred at −78° C. for 3 h before being quenched with saturated ammonium chloride (50 mL in water). The pH of the resulting slurry was adjusted to 1-2 by careful addition of concentrated hydrochloric acid. Organics were extracted with ether (3×75 mL), dried with magnesium sulfate, filtered, and concentrated. The resulting crude oil was purified by chromatography on silica gel with gradient elution (3→8% ethyl acetate in hexanes) to provide pyrone 1b (1.01 g, 64%) as a clear, viscous oil: LRMS (ES$^+$) m/z [M+H]. found 383 (Exact mass=382.22). Used without further characterization.

Example 6.2

Method B, Aldol Condensation: Enone 3b

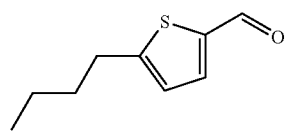

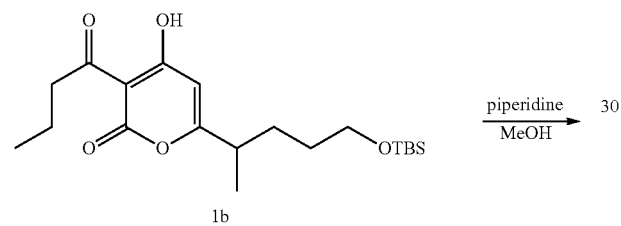

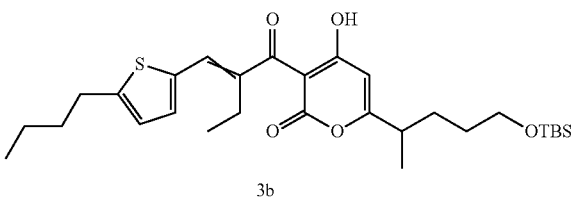

3b

A solution of pyrone 1b (Example 6.1; 227 mg, 0.59 mmol) and 5-butyl-2-formylthiophene (150 mg, 0.89 mmol) in methanol (3 mL) was treated with piperidine (26 mg, 0.31 mmol) and heated to 60° C. in a sealed vial. After 30 minutes, the temperature was increased to 80° C. for 2 h, then increased again to 90° C. for another 2 h. The reaction mixture was allowed to cool to room temperature and concentrated. The product was purified by chromatography on silica gel with gradient elution (5→15% ethyl acetate in hexanes+1% acetic acid) to give enone 3b (116 mg, 37%) as a pale yellow oil: LRMS (ES$^+$) m/z [M+H]. found 533 (Exact mass=532.27). Used without further characterization.

Example 6.3

Method B, OTBS Deprotection: Alcohol 4b

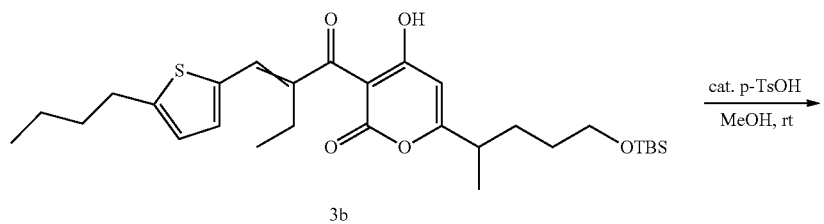

3b

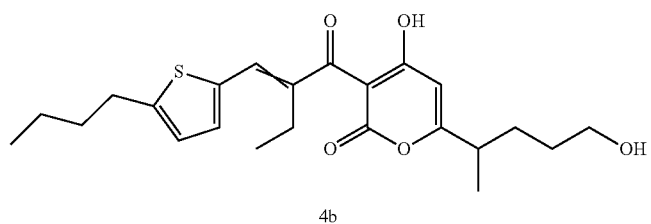

4b

A solution of enone 3b (Example 6.2; 116 mg, 0.22 mmol) in 4:1 methanol/dichloromethane (3 mL) was treated with p-tosic acid monohydrate (4.1 mg, 0.02 mmol) and stirred at room temperature for 1 h. The reaction mixture was poured into water (20 mL) and organics were extracted with ethyl acetate (3×20 mL), dried with magnesium sulfate, filtered and concentrated. The product was purified by chromatography on silica gel with gradient elution (5→10% isopropanol in hexanes+1% acetic acid) to afford alcohol 4b (86 mg, 93%) as a pale yellow viscous oil: LRMS (ES$^+$) m/z [M+H]. found 419 (Exact mass=418.18). Used without further characterization.

Example 6.4

Method B, Oxidation/Olefination: Methyl Ester 5b

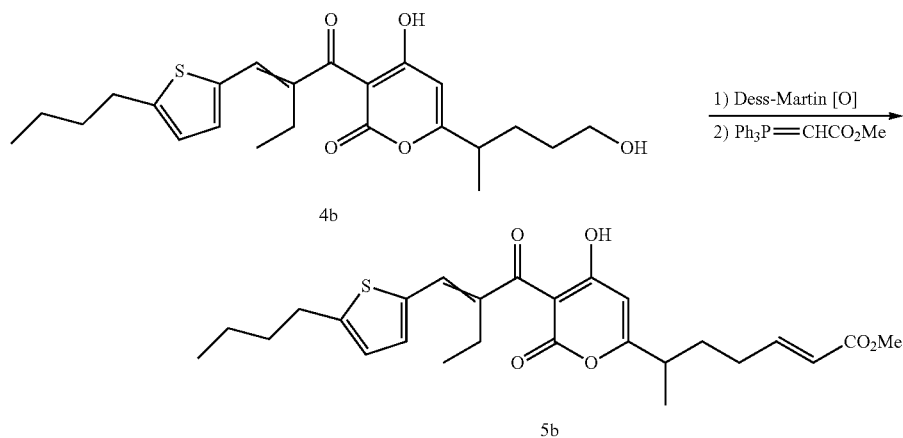

A solution of alcohol 4b (Example 6.3; 86 mg, 0.21 mmol) in dichloromethane (1.5 mL) was treated with the Dess-Martin periodinane (130 mg, 0.31 mmol). The resulting slurry was stirred vigorously for 16 h at room temperature before being poured into water (20 mL). Organics were extracted with ether (3×25 mL), dried over magnesium sulfate, filtered and concentrated. The crude aldehyde was dissolved in anhydrous dichloromethane (1 mL) and treated with methyl(triphenylphosphoranylidene) acetate (137 mg, 0.41 mmol). The resulting solution was stirred at room temperature for 1 h before being concentrated. The product was purified by chromatography on silica gel with gradient elution (5→7% ethyl acetate in hexanes+1% acetic acid) to give methyl ester 5b (82 mg, 83%) as an oily solid: LRMS (ES) m/z [M+H]. found 473 (Exact mass=472.19). Used without further characterization.

Example 6.5

Method B, Hydrolysis: Acid 6b

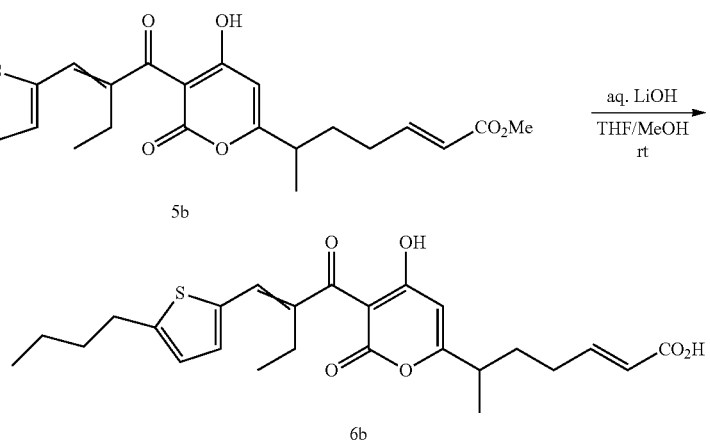

A solution of methyl ester 5b (Example 6.4; 82 mg, 0.17 mmol) in 1:1 tetrahydrofuran/methanol (6 mL) was treated with lithium hydroxide (1.74 mL, 1 M in water). After stirring at room temperature for 18 h, organic solvents were removed in vacuo and the remaining aqueous slurry poured into 1 N hydrochloric acid (25 mL). Organics were extracted with ethyl acetate (3×25 mL), dried over magnesium sulfate, filtered and concentrated. The crude product was purified by chromatography on silica gel (20% ethyl acetate in hexanes+1% acetic acid) to afford acid 6b (31 mg, 40%) as an off-white solid: LRMS (ES) m/z [M+H]. found 459 (Exact mass=458.18). Used without further characterization.

Example 6.6

Method B, Curtius Rearrangement Sequence: APY21

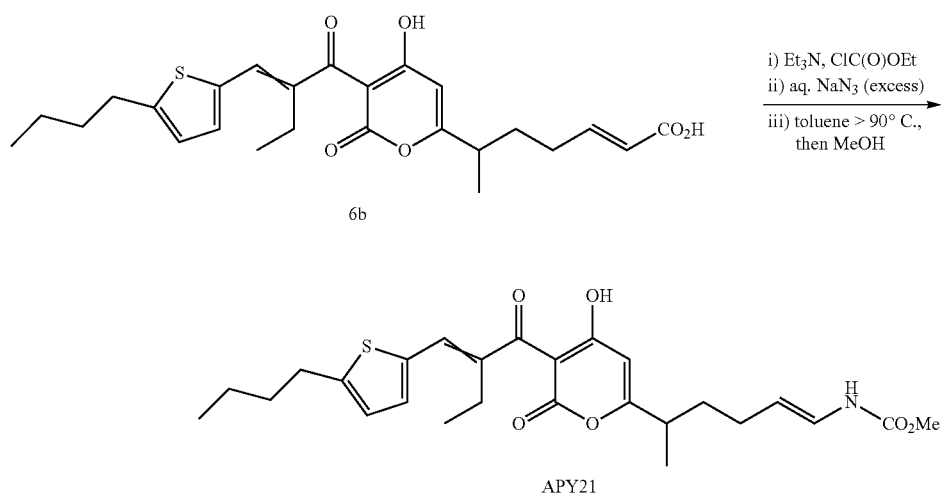 [SMILES: CCCCc1ccc(C=C(CC)C(=O)c2c(O)cc(C(C)CC/C=C/C(=O)O)oc2=O)s1 ; "6b" ; CCCCc1ccc(C=C(CC)C(=O)c2c(O)cc(C(C)CC/C=C/NC(=O)OC)oc2=O)s1 ; "APY21"]

A solution of acid 6b (Example 6.5; 31 mg, 0.068 mmol) and triethylamine (0.05 mL, 0.34 mmol) in anhydrous acetone (1.4 mL) under argon at 0° C. was treated with ethyl chloroformate (19 µL, 0.20 mmol). After stirring at 0° C. for 1 h, sodium azide (44 mg, 0.68 mmol) was added as a solution in 0.5 mL water. The reaction mixture was allowed to warm to room temperature over 1 h with vigorous stirring and poured into water (20 mL). The pH of the mixture was adjusted to approximately 2 by careful addition of 1 N hydrochloric acid. Organics were extracted with ethyl acetate (3×20 mL), dried over magnesium sulfate, filtered and concentrated to a volume of ca. 1 mL. Trace water was removed by benzene azeotrope (3×15 mL), while never fully concentrating the solution. The crude azide solution (ca. 1 mL) was diluted with anhydrous toluene (4 mL), transferred to a pressure-relief reaction vial, flushed with argon, sealed and heated in a 110° C. bath for 25 minutes. The vial was removed from the heating bath, allowed to cool enough such that it was safe to open, and 3 mL of anhydrous methanol was added. The vial was re-sealed and placed in a 75° C. heating bath for 30 minutes. The vial was removed from the heating bath, allowed to cool to room temperature and the contents concentrated. The crude product was purified by RP-HPLC on a PrincetonSPHER-60 $C_{18}$ column (60 Å-10µ, 250×30 mm) at a flow rate of 30 mL/min with a linear gradient of 80→100% acetonitrile/water+1% acetic acid over 20 minutes to give APY21 (11 mg, 30%) as a pale glassy solid which is a mixture of E and Z isomers (2.5:1): $^1$H NMR for E isomer (500 MHz, CDCl$_3$, 298 K) δ 7.02 (d, 1H), 6.98 (s, 1H), 6.74 (d, 1H), 6.51-6.43 (m, 1H), 6.25-6.17 (m, 1H), 5.95 (s, 1H), 4.99-4.88 (m, 1H), 3.71 (s, 3H), 2.83 (t, 2H), 2.78 (q, 2H), 2.64-2.55 (m, 1H), 2.10-1.97 (m, 2H), 1.86-1.74 (m, 1H), 1.71-1.64 (m, 2H), 1.60-1.51 (m, 1H), 1.45-1.36 (m, 2H), 1.25 (d, 3H), 1.15 (t, 3H), 0.94 (t, 3H); LRMS (ES$^+$) m/z [M+H]. found 488 (Exact mass=487.20).

Example 7

APY25 Prepared by Method B

Example 7.1

5-butyl-2-formylbenzofuran

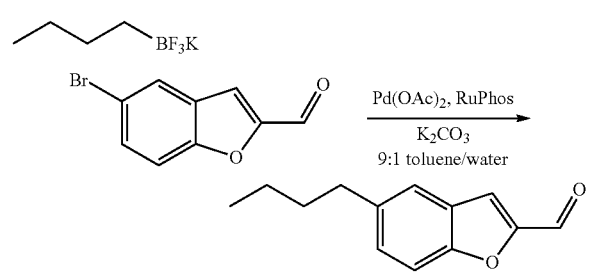

The compound was synthesized as in Example 3.1, using 5-bromo-2-formylbenzofuran (500 mg, 2.22 mmol) in place of 5-bromo-2-formylfuran and potassium butyltrifluoroborate (546 mg, 3.33 mmol) in place of hexylboronic acid to give 5-butyl-2-formylbenzofuran (402 mg, 90%). Used without further characterization.

Example 7.2

APY25

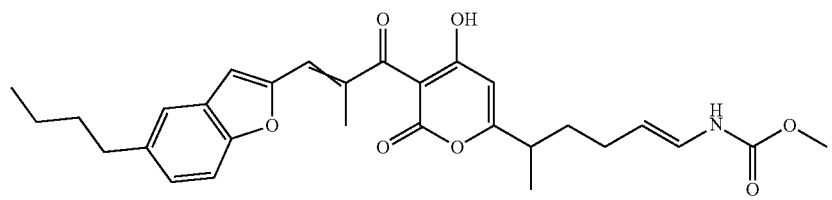

APY25

The compound was synthesized as in Example 6, using 5-butyl-2-formylbenzofuran (Example 7.1; 402 mg, 1.99 mmol) in place of 5-butyl-2-formylthiophene and pyrone 1a (488 mg, 1.33 mmol) in place of pyrone 1b to give APY25 (51 mg) as an off-white solid containing a mixture of E and Z isomers (2.7:1): $^1$H NMR (E isomer, 500 MHz, CDCl$_3$, 298 K) δ 15.8 (br s, 1H), 7.39-7.37 (m, 2H), 7.14 (dd, 1H), 6.86-6.85 (m, 2H), 6.48-6.44 (m, 1H), 6.24-6.20 (m, 1H), 5.98 (s, 1H), 4.96-4.91 (m, 1H), 3.71 (s, 3H), 2.69 (t, 2H), 2.64-2.59 (m, 1H), 2.38 (d, 3H), 2.06-1.97 (m, 2H), 1.85-1.78 (m, 1H), 1.66-1.56 (m, 3H), 1.41-1.35 (m, 2H), 1.26 (d, 3H), 0.94 (t, 3H); LRMS (ES$^+$) m/z [M+H]. found 508 (Exact mass=507.23).

Example 8.1

4-hexyl-3-methyl-2-formylthiophene

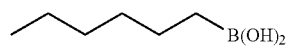

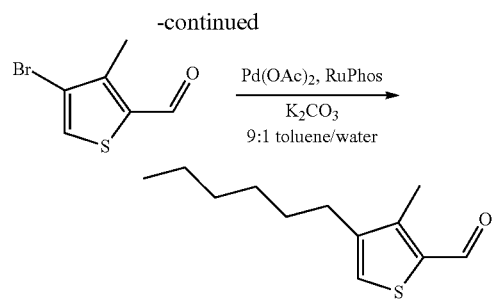

The compound was synthesized as in Example 3.1, using 4-bromo-3-methyl-2-formylthiophene (252 mg, 1.23 mmol) in place of 5-bromo-2-formylfuran to give 4-hexyl-3-methyl-2-formylthiophene (239 mg, 92%). Used without further characterization.

Example 8.2

APY27

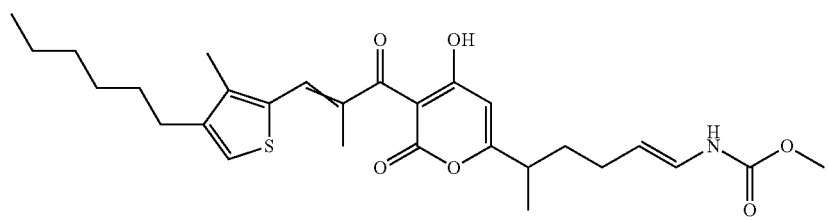

APY27

The compound was synthesized as in Example 6, using 4-butyl-3-methyl-2-formylthiophene (Example 8.1; 239 mg, 1.14 mmol) in place of 5-butyl-2-formylthiophene to give APY27 (6.7 mg) as an off-white solid containing a mixture of E and Z isomers (10:1): $^1$H NMR (E isomer, 500 MHz, CDCl$_3$, 298 K) δ 7.38 (s, 1H), 7.12 (s, 1H), 6.51-6.44 (m, 1H), 6.26-6.22 (m, 1H), 5.96 (s, 1H), 4.96-4.92 (m, 1H), 3.71 (s, 1H), 2.61 (q, 1H), 2.52 (t, 2H), 2.23 (s, 6H), 2.06-2.01 (m, 2H), 1.82-1.79 (m, 1H), 1.60-1.54 (m, 3H), 1.40-1.29 (m, 6H), 1.28-1.25 (m, 3H), 0.89 (t, 3H); LRMS (ES$^+$) m/z [M+H]. found 516 (Exact mass=515.23).

Example 9

APY19 Prepared by Method C

Example 9.1

Method C, OTBS Deprotection: Alcohol 8a

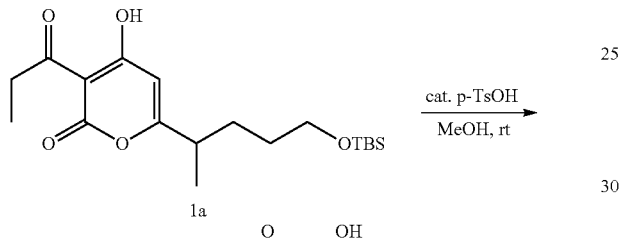

A solution of pyrone 1a (prepared as in: Panek, et. al. *J. Org. Chem.* 1998, 63, 2401; 2.8 g, 7.6 mmol) in methanol (40 mL) was treated with p-tosic acid monohydrate (145 mg, 0.76 mmol). The resulting solution was stirred for 1.5 h at room temperature before the solvents were evaporated. The crude product was purified by chromatography on silica gel with gradient elution (8→30% ethyl acetate in hexanes+1% acetic acid) to afford alcohol 8a (1.95 g, quant.) as a glassy solid: LRMS (ES) m/z [M+H]. found 255 (Exact mass=254.12). Used without further characterization.

Example 9.2

Method C, Oxidation/Olefination: Methyl Ester 9a

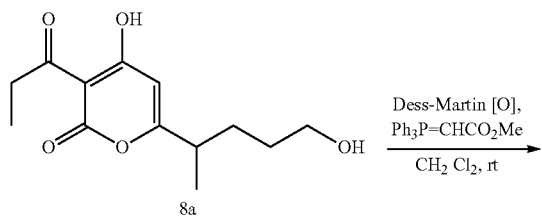

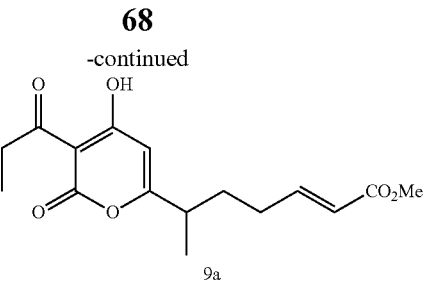

Alcohol 8a (Example 9.1; 1.75 g, 6.88 mmol) was dissolved in dichloromethane (16 mL) and treated with the Dess-Martin periodinane (3.80 g, 8.95 mmol). The resulting slurry was stirred vigorously at room temperature for 30 minutes before methyl(triphenylphosphoranylidene) acetate (4.72 g, 14.1 mmol) was added. After stirring vigorously at room temperature for an additional 16 h, solids were filtered and washed with ether, and the filtrate concentrated. The crude product was purified by chromatography on silica gel with gradient elution (8→15% ethyl acetate in hexanes+0.5% acetic acid) to give methyl ester 9a (1.82 g, 86%) as an oily solid. LRMS (ES) m/z [M+H]. found 309 (Exact mass=308.13). Used without further characterization.

Example 9.3

Method C, Hydrolysis: Acid 10a

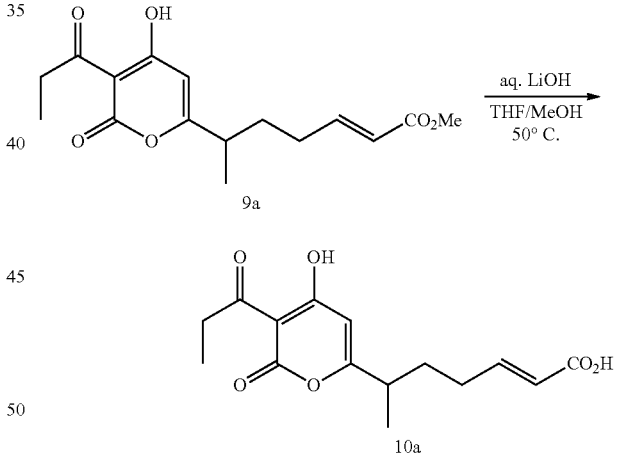

A solution of methyl ester 9a (Example 9.2; 1.82 g, 5.90 mmol) in tetrahydrofuran (60 mL) was treated with lithium hydroxide (60 mL, 1 M in water). The resulting biphasic mixture was heated to 50° C. and then titrated with methanol (1.2 mL) until homogeneous. The resulting solution was stirred at 50° C. for 2 h. Organic solvents were evaporated and the aqueous residue poured into 1 N hydrochloric acid (100 mL). Organics were extracted with ethyl acetate (2×100 mL), washed with brine (100 mL), dried over magnesium sulfate, filtered and concentrated to give acid 10a (1.74 g, crude) as an oily white solid: LRMS (ES) m/z [M+H]. found 295 (Exact mass=294.11). Used without further characterization.

Example 9.4

Method C, Curtius Rearrangement Sequence: Enecarbamate 11a

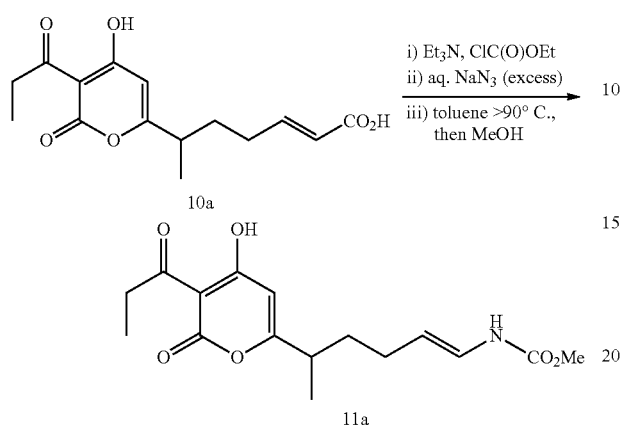

A solution of crude acid 10a (Example 9.3; 1.74 g, 5.90 mmol) and triethylamine (4.1 mL, 29.51 mmol) in anhydrous acetone (87 mL) at −30° C. under argon was treated dropwise with ethyl chloroformate (0.68 mL, 7.38 mmol). After stirring at −30 to −10° C. for 2 h, sodium azide (1.92 g, 29.51 mmol) was added as a solution in 35 mL water. The reaction mixture was stirred vigorously at −30 to −10° C. for 1 h and poured into 0.1 N hydrochloric acid (200 mL). Organics were extracted with ether (2×200 mL), dried over magnesium sulfate, filtered and concentrated to a volume of ca. 10 mL. Excess water was removed by toluene azeotrope (three cycles) and the mixture finally concentrated to a volume of ca. 10 mL. The crude azide solution was added dropwise to rapidly refluxing anhydrous toluene (100 mL), and the resulting solution was stirred at reflux for 30 minutes. Methanol (20 mL) was added and the reaction mixture was stirred at rapid reflux for an additional 20 minutes. After cooling to room temperature, the reaction mixture was concentrated and purified by chromatography on silica gel with gradient elution (15→30% ethyl acetate in hexanes+0.5% acetic acid) to yield enecarbamate 11a (851 mg, 45%) as an off-white solid: $^1$H NMR (500 MHz, CDCl$_3$, 298 K) δ 6.45 (m, 1H), 6.30 (m, 1H), 5.91 (s, 1H), 4.93 (m, 1H), 3.70 (s, 3H), 3.10 (q, 2H), 2.63-2.53 (m, 1H), 2.07-1.94 (m, 2H), 1.78 (ddt, 1H), 1.55 (ddt, 1H), 1.23 (d, 3H), 1.15 (t, 3H); LRMS (ES) m/z [M+H]. found 324 (Exact mass=323.14).

Example 9.5

4-hexyl-2-formylfuran

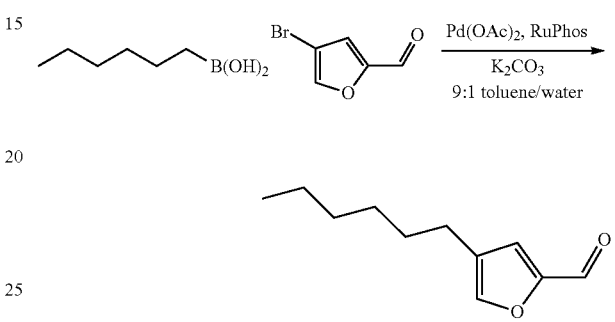

The compound was prepared as in Example 3.1 using 4-bromo-2-formylfuran (58 mg, 0.33 mmol) in place of 5-bromo-2-formylfuran to give 4-hexyl-2-formylfuran (41.6 mg, 69%). Used without further characterization.

Example 9.6

APY19

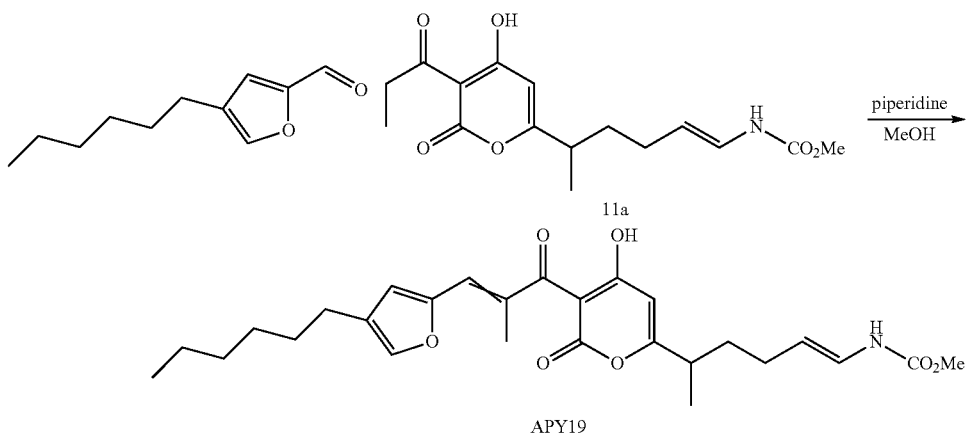

A solution of 4-hexyl-2-formylfuran (Example 9.5; 18.4 mg, 0.10 mmol), enecarbamate 11a (22 mg, 0.068 mmol) and piperidine (26 mg, 0.31 mmol) in methanol (0.8 mL) was heated to 75° C. in a sealed vial under argon for 2 h. The reaction mixture was allowed to cool to room temperature, poured into ethyl acetate (20 mL), and washed with 0.2 N hydrochloric acid (2×10 mL). The acidic washes were extracted with ethyl acetate (20 mL) and the two organic phases were combined, washed with brine (20 mL), dried with magnesium sulfate, filtered, and concentrated. The crude product was purified by RP-HPLC on a PrincetonSPHER-60 C$_{18}$ column (60 Å-10μ, 250×30 mm) at a flow rate of 30 mL/min with a linear gradient of 80→90% acetonitrile/water+1% acetic acid over 20 minutes to give APY19 (15.2 mg, 31%) as an off-white solid containing a mixture of E and Z isomers (5:1): $^1$H NMR (E isomer, 500 MHz, CDCl$_3$, 298 K) δ 7.29 (s, 1H), 6.83 (d, 1H), 6.50-6.44 (m, 2H), 6.28-6.24 (m, 1H), 5.95 (s, 1H), 4.97-4.91 (m, 1H), 3.70 (s, 3H), 2.63-2.56 (m, 1H), 2.41 (t, 2H), 2.22 (d, 3H), 2.07-1.99 (m, 2H), 1.84-1.76 (m, 1H), 1.59-1.52 (m, 3H), 1.36-1.27 (m, 6H), 1.25 (d, 3H), 0.89 (t, 3H); LRMS (ES$^+$) m/z [M+H]. found 486 (Exact mass=485.24).

Example 10

APY26 Prepared by Method C

Example 10.1

5-butyl-2-formylbenzothiophene

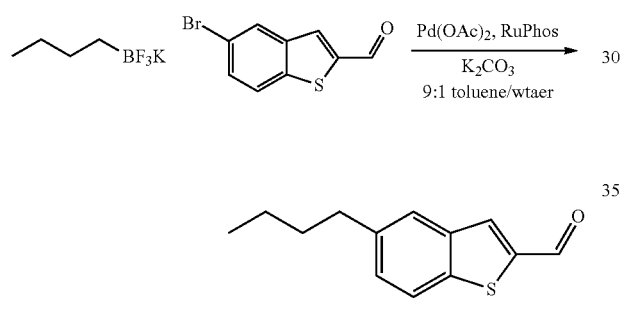

The compound was prepared as in Example 3.1 using 5-bromo-2-formylbenzothiophene (241 mg, 1.0 mmol) in place of 5-bromo-2-formylfuran and potassium butyltrifluoroborate (246 mg, 1.5 mmol) in place of hexylboronic acid to give 5-butyl-2-formylbenzothiophene (185 mg, 85%). Used without further characterization.

Example 10.2

APY26

The compound was synthesized as in Example 9.6, using 5-butyl-2-formylbenzothiophene (Example 10.1; 38 mg, 0.17 mmol) in place of 4-hexyl-2-formylfuran to give APY26 (32 mg) as an off-white solid containing a mixture of E and Z isomers (3:1): $^1$H NMR (E isomer, 500 MHz, CDCl$_3$, 298 K) δ 7.73 (d, 1H), 7.59 (s, 1H), 7.40 (s, 1H), 7.36 (s, 1H), 7.21 (s, 1H), 6.48-6.45 (m, 1H), 6.24-6.21 (m, 1H), 5.98 (s, 1H), 4.96-4.93 (m, 1H), 3.71 (s, 3H), 2.72 (t, 2H), 2.62 (q, 1H), 2.32 (d, 3H), 2.08-1.98 (m, 2H), 1.85-1.77 (m, 1H), 1.68-1.62 (m, 2H), 1.61-1.55 (m, 1H), 1.42-1.33 (m, 2H), 1.26 (d, 3H), 0.94 (t, 3H); LRMS (ES$^+$) m/z [M+H]. found 524 (Exact mass=523.20).

Example 11

APY28 Prepared by Method C

Example 11.1

5-(3-butenyl)-2-formylthiophene

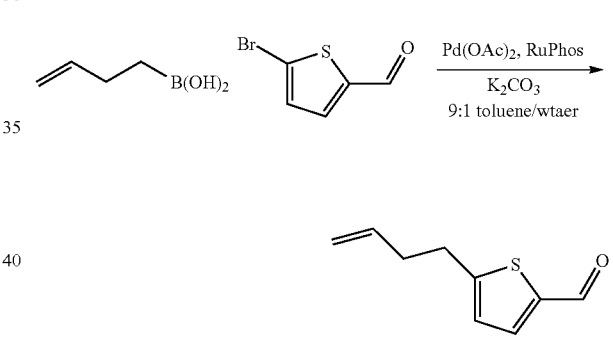

The compound was synthesized as in Example 3.1 using 5-bromo-2-formylthiophene (191 mg, 1.0 mmol) in place of 5-bromo-2-formylfuran and 3-butenylboronic acid (150 mg, 1.5 mmol) in place of hexylboronic acid to give 5-(3-butenyl)-2-formylthiophene (91 mg, 55%). Used without further characterization.

APY26

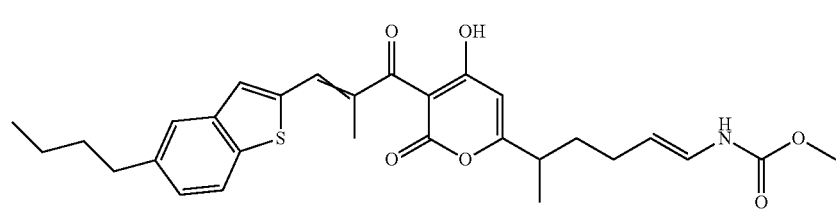

Example 11.2

APY28

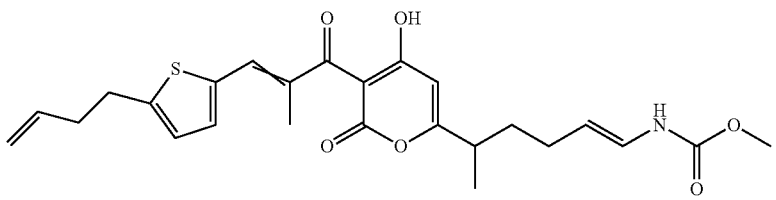

The compound was synthesized as in Example 9.6, using 5-(3-butenyl)-2-formylthiophene (Example 11.1; 17 mg, 0.10 mmol) in place of 4-hexyl-2-formylfuran to give APY28 (1.1 mg) as an off-white solid containing a mixture of E and Z isomers (4:1): $^1$H NMR (E isomer, 500 MHz, CDCl$_3$, 298 K) δ 7.22 (s, 1H), 7.10 (d, 1H), 6.81 (d, 1H), 6.50-6.43 (m, 1H), 6.22-6.18 (m, 1H), 5.96 (s, 1H), 5.89-5.83 (m, 1H), 5.11-5.06 (m, 1H), 5.04-5.01 (m, 1H), 4.98-4.92 (m, 1H), 3.71 (s, 3H), 2.95 (t, 2H), 2.60 (q, 1H), 2.46 (q, 2H), 2.21 (d, 3H), 2.08-1.99 (m, 2H), 1.85-1.77 (m, 1H), 1.61-1.50 (m, 1H), 1.25 (d, 3H); LRMS (ES$^+$) m/z [M+H]. found 472 (Exact mass=471.17).

Example 12

APY29 Prepared by Method C

Example 12.1

5-(5-hexenyl)-2-formylthiophene

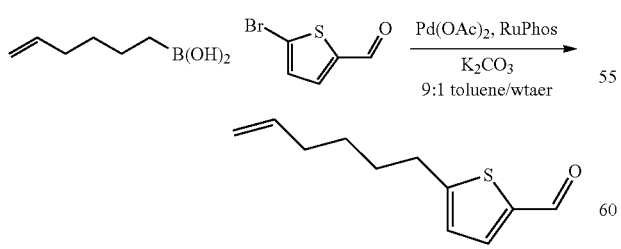

The compound was synthesized as in Example 3.1 using 5-hexenylboronic acid (192 mg, 1.5 mmol) in place of hexylboronic acid to give 5-(5-hexenyl)-2-formylthiophene (91 mg, 55%). Used without further characterization.

Example 12.2

APY29

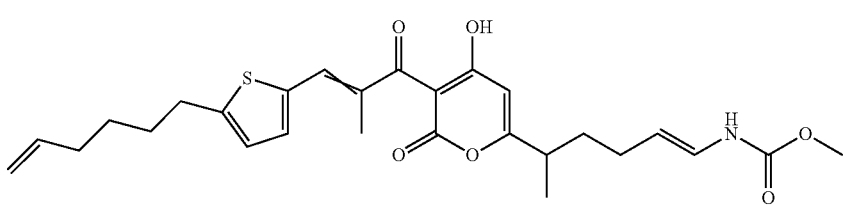

The compound was synthesized as in Example 9.6, using 5-(5-hexenyl)-2-formylthiophene (Example 12.1; 20 mg, 0.10 mmol) in place of 4-hexyl-2-formylfuran to give APY29 (1.8 mg) as an off-white solid containing a mixture of E and Z isomers (10:1): $^1$H NMR (E isomer, 500 MHz, CDCl$_3$, 298 K) δ 7.23 (s, 1H), 7.10 (d, 1H), 6.79 (d, 1H), 6.48-6.47 (m, 1H), 6.21-6.19 (m, 1H), 5.95 (s, 1H), 5.83-5.77 (m, 1H), 5.04-4.99 (m, 1H), 4.97-4.94 (m, 2H), 3.71 (s, 3H), 2.86 (t, 2H), 2.60 (q, 1H), 2.21 (d, 3H), 2.12-2.00 (m, 4H), 1.85-1.69 (m, 4H), 1.48-1.43 (m, 2H), 1.26 (d, 3H); LRMS (ES$^+$) m/z [M+H]$^+$. found 500 (Exact mass=499.20).

Example 13

APY31 Prepared by Method C

Example 13.1

5-isopentyl-2-formylthiophene

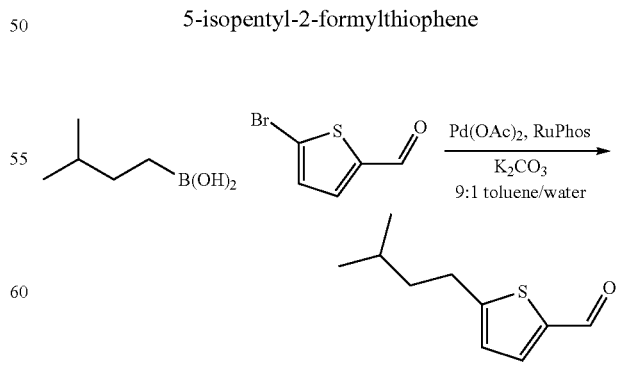

The compound was synthesized as in Example 3.1 using isopentylboronic acid (174 mg, 1.5 mmol) in place of hexylboronic acid to give 5-isopentyl-2-formylthiophene (166 mg, 91%). Used without further characterization.

Example 13.2

APY31

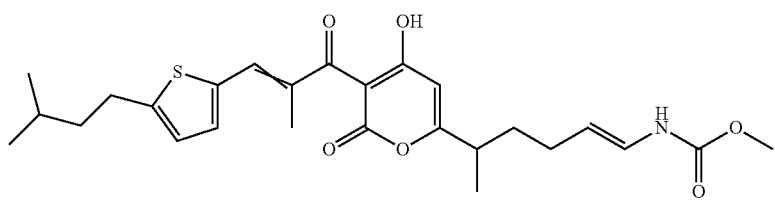

APY31

The compound was synthesized as in Example 9.6, using 5-isopentyl-2-formylthiophene (Example 13.1; 19 mg, 0.10 mmol) in place of 4-hexyl-2-formylfuran to give APY31 (1.7 mg) as an off-white solid containing a mixture of E and Z isomers (8:1): $^1$H NMR (E isomer, 500 MHz, CDCl$_3$, 298 K) δ 15.9 (br s, 1H), 7.23 (s, 1H), 7.10 (d, 1H), 6.79 (d, 1H), 6.50-6.44 (m, 1H), 6.22-6.18 (m, 1H), 5.95 (s, 1H), 4.97-4.92 (m, 1H), 3.71 (s, 3H), 2.85 (t, 2H), 2.60 (q, 1H), 2.21 (s, 3H), 2.08-1.99 (m, 2H), 1.83-1.77 (m, 1H), 1.67-1.50 (m, 4H), 1.25 (d, 3H), 0.94 (d, 6H); LRMS (ES$^+$) m/z [M+H]$^+$. found 488 (Exact mass=487.20).

Example 14

APY32 Prepared by Method C

Example 14.1

5-(3-cyclohexylpropyl)-2-formylthiophene

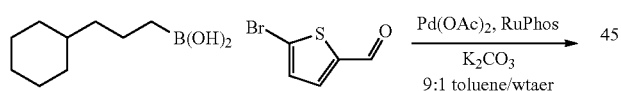

-continued

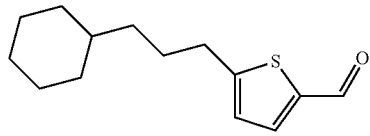

The compound was synthesized as in Example 3.1 using 3-cyclohexylpropylboronic acid (255 mg, 1.5 mmol) in place of hexylboronic acid to give 5-(3-cyclohexylpropyl)-2-formylthiophene (230 mg, 97%). Used without further characterization.

Example 14.2

APY32

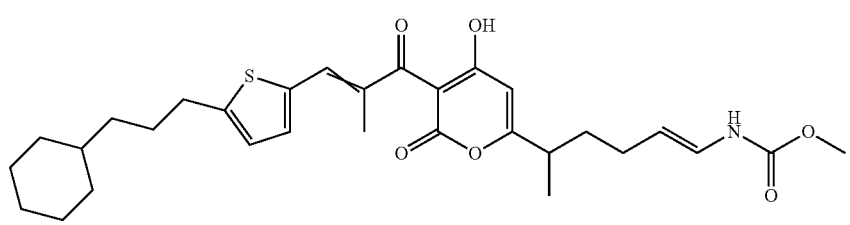

APY32

The compound was synthesized as in Example 9.6, using 5-(3-cyclohexylpropyl)-2-formylthiophene (Example 14.1; 24 mg, 0.10 mmol) in place of 4-hexyl-2-formylfuran to give APY32 (1.7 mg) as an off-white solid containing a mixture of E and Z isomers (12:1): $^1$H NMR (E isomer, 500 MHz, CDCl$_3$, 298 K) δ 15.9 (br s, 1H), 7.24 (s, 1H), 7.10 (d, 1H), 6.79 (d, 1H), 6.50-6.42 (m, 1H), 6.23-6.17 (m, 1H), 5.95 (s, 1H), 4.98-4.91 (m, 1H), 3.71 (s, 3H), 2.82 (t, 2H), 2.60 (q, 1H), 2.21 (d, 3H), 2.07-1.99 (m, 2H), 1.85-1.77 (m, 1H), 1.73-1.66 (m, 5H), 1.60-1.54 (m, 4H), 1.27-1.12 (m, 8H), 0.88 (m, 2H); LRMS (ES$^+$) m/z [M+H]$^+$. found 542 (Exact mass=541.25).

Example 15

APY33 Prepared by Method C

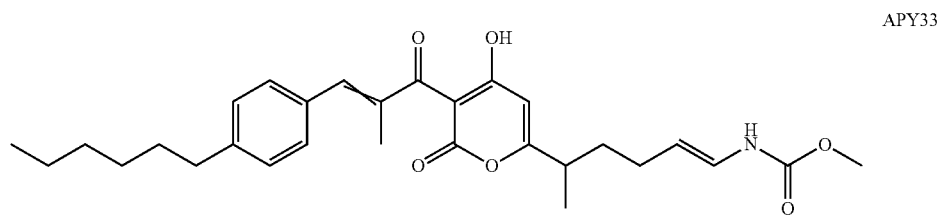 [SMILES: CCCCCCc1ccc(C=C(C)C(=O)c2c(O)cc(C(C)CC/C=C/NC(=O)OC)oc2=O)cc1]

APY33

The compound was synthesized as in Example 9.6, using 4-hexylbenzaldehyde (15 mg, 0.08 mmol) in place of 4-hexyl-2-formylfuran to give APY33 (3 mg) as an off-white solid containing a mixture of E and Z isomers (2.3:1): $^1$H NMR (E isomer, 500 MHz, CDCl$_3$, 298 K) δ 16.0 (br s, 1H), 7.37 (d, 2H), 7.19 (d, 2H), 6.88 (s, 1H), 6.48-6.44 (m, 1H), 6.22-6.18 (m, 1H), 5.96 (s, 1H), 4.96-4.91 (m, 1H), 3.71 (s, 3H), 2.64-2.58 (m, 3H), 2.19 (d, 3H), 2.07-1.97 (m, 2H), 1.83-1.78 (m, 1H), 1.64-1.58 (m, 3H), 1.35-1.28 (m, 6H), 1.25 (d, 3H), 0.90-0.86 (m, 3H); LRMS (ES) m/z [M+H]$^+$. found 496 (Exact mass=495.26).

Example 16

APY32 Prepared by Method C

Example 16.1

3-hexylbenzaldehyde

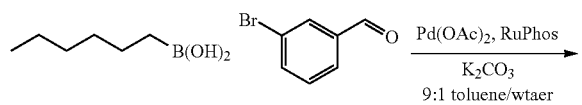

-continued

The compound was synthesized as in Example 3.1 using 3-bromobenzaldehyde (1.0 g, 5.4 mmol) in place of 5-bromo-2-formylfuran to give 3-hexylbenzaldehyde (1.02 g, quant.). Used without further characterization.

Example 16.2

APY34

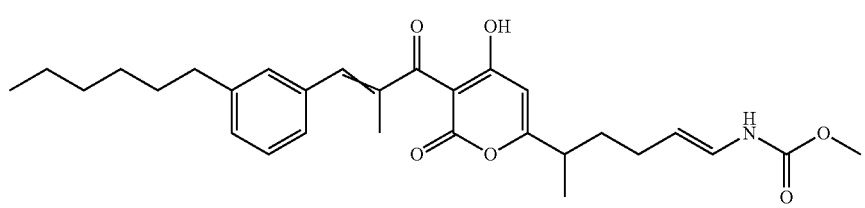

APY34

The compound was synthesized as in Example 9.6, using 3-hexylbenzaldehyde (Example 16.1; 17 mg, 0.09 mmol) in place of 4-hexyl-2-formylfuran to give APY34 (6.5 mg) as an off-white solid containing a mixture of E and Z isomers (2.3:1): $^1$H NMR (E isomer, 500 MHz, CDCl$_3$, 298 K) δ 15.9 (br s, 1H), 7.30-7.25 (m, 2H), 7.13-7.10 (m, 1H), 6.98-6.95 (m, 1H), 6.86 (s, 1H), 6.48-6.44 (m, 1H), 6.23-6.19 (m, 1H), 5.97 (s, 1H), 4.96-4.91 (m, 1H), 3.71 (s, 3H), 2.64-2.59 (m, 3H), 2.18 (d, 3H), 2.07-2.00 (m, 2H), 1.84-1.77 (m, 1H), 1.64-1.58 (m, 2H), 1.52-1.48 (m, 1H), 1.35-1.28 (m, 6H), 1.26 (d, 3H), 0.90-0.86 (m, 3H); LRMS (ES) m/z [M+H]$^+$. found 496 (Exact mass=495.26).

Example 17

APY36 Prepared by Method C

Example 17.1

3-Acetyl-6-ethyl-4-hydroxy-2-pyrone

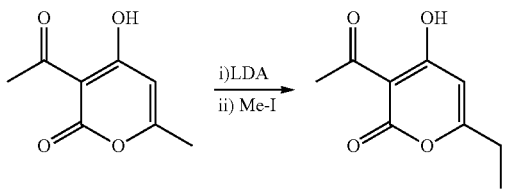

A solution of diisopropylamine (2.6 mL, 18.1 mmol) in anhydrous tetrahydrofuran (5 mL) under argon at −40° C. was treated dropwise with n-butyllithium (7.0 mL, 2.5 M in hexanes). The resulting solution was allowed to warm to −10° C. over 15 minutes. In a separate flask, hexamethylphosphoramide (2 mL) and 3-acetyl-6-methyl-4-hydroxy-2-pyrone (923 mg, 5.49 mmol) were combined and azeotroped to dryness with benzene (3×25 mL) before being dissolved in anhydrous tetrahydrofuran (5 mL). To the LDA solution at −78° C. was added dropwise over 5 minutes the solution of hexamethylphosphoramide and 3-acetyl-6-methyl-4-hydroxy-2-pyrone. The reaction mixture became a solid red/orange mass after the addition was complete and was kept at −78° C. for 40 minutes before methyl iodide (0.38 mL, 6.04 mmol) was added in a single portion. The reaction flask was removed from the cooling bath and swirled vigorously by hand as it warmed to room temperature over 20 minutes. Over this time the solid mass dissipated and became a coarse precipitate. The reaction mixture was poured into 30 mL 1 N hydrochloric acid and organics were extracted with ethyl acetate (3×25 mL). The combined organic extracts were washed with 5% aqueous sodium bisulfite and brine (30 mL each), dried over magnesium sulfate, filtered, and concentrated. The crude product was purified by chromatography on silica gel (10% ethyl acetate in hexanes+1% acetic acid) to afford 3-acetyl-6-ethyl-4-hydroxy-2-pyrone (471 mg, 47%) as a white solid: LRMS (ES$^+$) m/z [M+H]$^+$. found 183 (Exact mass=182.06). Used without further characterization.

Example 17.2

Pyrone 1c

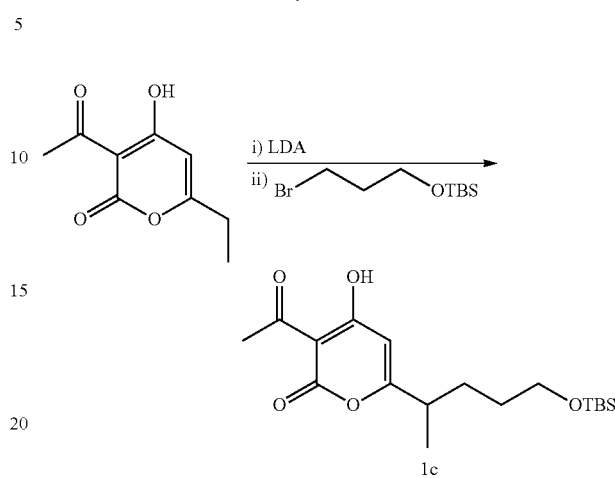

A solution of diisopropylamine (1.2 mL, 8.52 mmol) in anhydrous tetrahydrofuran (4 mL) under argon at −40° C. was treated dropwise with n-butyllithium (3.5 mL, 2.5 M in hexanes). The resulting solution was allowed to warm to −10° C. over 20 minutes. In a separate flask, hexamethylphosphoramide (2 mL) and 3-acetyl-6-ethyl-4-hydroxy-2-pyrone (Example 17.1; 470 mg, 2.58 mmol) were combined and azeotroped to dryness with benzene (3×25 mL) before being dissolved in anhydrous tetrahydrofuran (4 mL). To the LDA solution at −78° C. was added dropwise over 5 minutes the solution of hexamethylphosphoramide and 3-acetyl-6-ethyl-4-hydroxy-2-pyrone. The resulting solution was stirred at −78° C. for 1 h before (3-bromopropoxy)-t-butyldimethylsilane (0.66 mL, 2.84 mmol) was added dropwise over 5 minutes. The resulting solution was stirred at −78° C. for 3 h. The reaction mixture was poured into saturated aqueous ammonium chloride (50 mL) and the pH of the resulting mixture was adjusted to 1-2 by addition of 1 N hydrochloric acid (20 mL). Organics were extracted with ether (3×65 mL), dried over magnesium sulfate, filtered, and concentrated. The crude product was purified by chromatography on silica gel (5% ethyl acetate in hexanes+1% acetic acid) to give pyrone 1c (559 mg, 61%) as an oily solid: LRMS (ES$^+$) m/z [M+H]$^+$. found 355 (Exact mass=354.19). Used without further characterization.

Example 17.3

Method C, OTBS Deprotection: Alcohol 8b

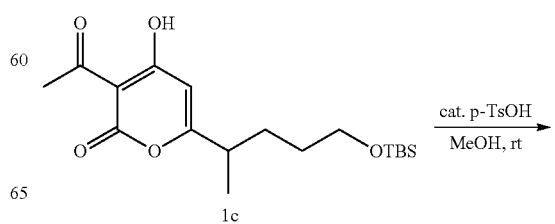

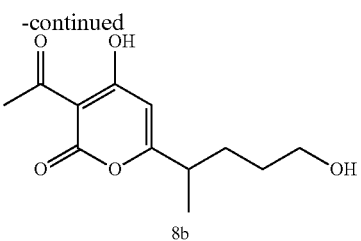

A solution of pyrone 1c (Example 17.2; 279 mg, 0.79 mmol) in 9:1 methanol/dichloromethane (8 mL) was treated with p-tosic acid monohydrate (15 mg, 0.08 mmol). The resulting solution was stirred for 30 minutes at room temperature before being poured into water (50 mL). Organics were extracted with ethyl acetate (3×40 mL), dried over magnesium sulfate, filtered, and concentrated to afford alcohol 8b (190 mg, crude) as a glassy solid: LRMS (ES$^+$) m/z [M+H]. found 241 (Exact mass=240.10). Used without further purification or characterization.

Example 17.4

Method C, Oxidation/Olefination: Methyl Ester 9b

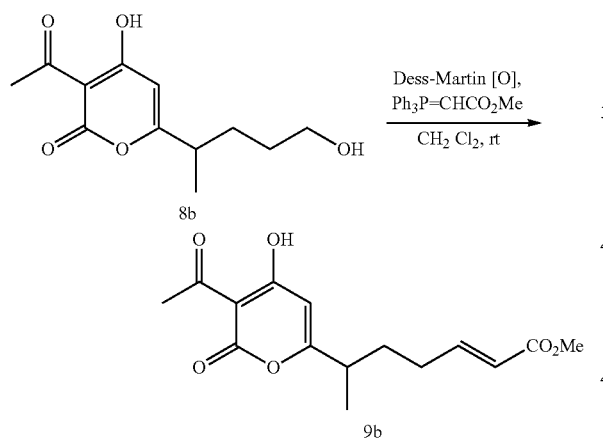

Alcohol 8b (Example 17.3; 190 mg, 0.79 mmol) was dissolved in dichloromethane (2 mL) and treated with the Dess-Martin periodinane (503 mg, 1.19 mmol). The resulting slurry was stirred vigorously at room temperature for 30 minutes before methyl(triphenylphosphoranylidene) acetate (528 mg, 1.58 mmol) was added. After stirring vigorously at room temperature for an additional 1 h, the reaction mixture was poured into 0.2 N hydrochloric acid (40 mL). Organics were extracted with ether (3×40 mL), dried over magnesium sulfate, filtered, and concentrated. The crude product was purified by chromatography on silica gel (10% isopropanol in hexanes+1% acetic acid) to give a mixture of methyl ester 9b and 2-iodobenzoic acid (a by-product from the oxidation) as an oily solid (309 mg): LRMS (ES$^+$) m/z [M+H]. found 295 (Exact mass=294.11). Used without further purification or characterization.

Example 17.5

Method C, Hydrolysis: Acid 10b

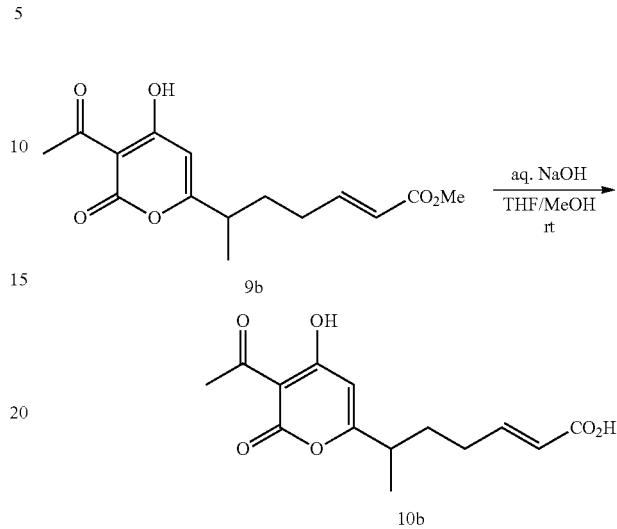

A mixture of methyl ester 9b and 2-iodobenzoic acid (Example 17.4; 309 mg) was dissolved in tetrahydrofuran (6 mL) and treated with sodium hydroxide (3.95 mL, 2 N in water). Methanol (ca. 4 mL) was added and the resulting solution was stirred at room temperature overnight. Organic solvents were evaporated and the resulting aqueous slurry poured into 1 N hydrochloric acid (30 mL). Organics were extracted with ethyl acetate (3×30 mL), dried over magnesium sulfate, filtered, and concentrated. The crude product was purified by chromatography on silica gel with gradient elution (15→20% ethyl acetate in hexanes+1% acetic acid) to afford acid 10b (70 mg, 32% over 3 steps): LRMS (ES$^+$) m/z [M+H]. found 281 (Exact mass=280.09). Used without further characterization.

Example 17.6

Method C, Curtius Rearrangement Sequence: Enecarbamate 11b

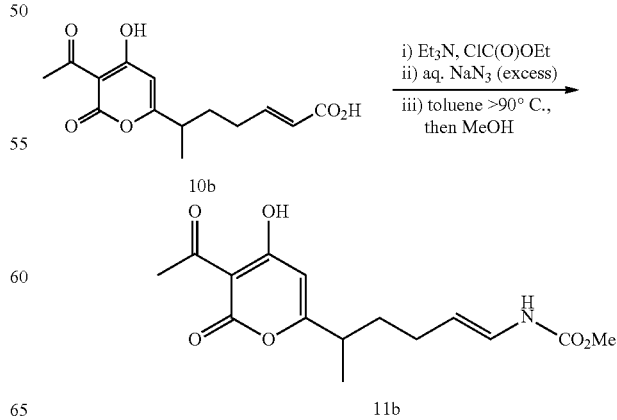

A solution of acid 10b (Example 17.5; 70 mg, 0.25 mmol) and triethylamine (0.17 mL, 1.25 mmol) in anhydrous acetone (6 mL) at −20° C. under argon was treated dropwise with ethyl chloroformate (29 μL, 0.31 mmol). After stirring at −10 to 0° C. for 1.5 h, sodium azide (163 mg, 2.5 mmol) was added as a solution in 3 mL water. The reaction mixture was stirred vigorously at 0° C. for 1 h, warmed to room temperature, and poured into 0.1 N hydrochloric acid (20 mL). Organics were extracted with ether (2×20 mL), dried over magnesium sulfate, filtered and concentrated to a volume of ca. 1 mL Trace water was removed by benzene azeotrope (3×15 mL), while never fully concentrating the solution. The crude azide solution (ca. 1 mL) was diluted with anhydrous toluene (4 mL), transferred to a pressure-relief reaction vial, flushed with argon, sealed and heated in a 115° C. bath for 30 minutes. The vial was removed from the heating bath, allowed to cool enough such that it was safe to open, and 3 mL of anhydrous methanol was added. The vial was re-sealed and placed in a 110° C. heating bath for 30 minutes. The vial was removed from the heating bath, allowed to cool to room temperature and the contents concentrated. The crude product was purified by chromatography on silica gel with gradient elution (20→30% ethyl acetate in hexanes+1% acetic acid) to yield enecarbamate 11b (49 mg, 63%) as an off-white solid: LRMS (ES) m/z [M+H]. found 310 (Exact mass=309.12). Used without further characterization.

Example 17.7

APY36 Prepared by Method C

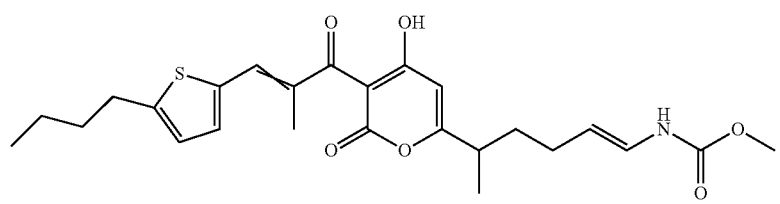

APY36

The compound was synthesized as in Example 9.6, using enecarbamate 11 b (Example 17.6; 49 mg, 0.16 mmol) in place of enecarbamate 11a and 5-butyl-2-formylthiophene (40 mg, 0.24 mmol) in place of 4-hexyl-2-formylfuran to give APY36 (15.4 mg) as an off-white solid containing a mixture of E and Z isomers (3.7:1): $^1$H NMR (E isomer, 500 MHz, CDCl$_3$, 298 K) δ 8.03 (d, 1H), 7.98 (d, 1H), 7.24 (d, 1H), 6.78 (d, 1H), 6.49-6.44 (m, 1H), 6.26-6.23 (m, 1H), 5.91 (s, 1H), 4.96-4.91 (m, 1H), 3.70 (s, 3H), 2.84 (t, 2H), 2.58 (q, 1H), 2.03 (m, 2H), 1.83-1.74 (m, 1H), 1.73-1.65 (m, 2H), 1.59-1.52 (m, 1H), 1.44-1.36 (m, 2H), 1.24 (d, 3H), 0.94 (t, 3H); LRMS (ES) m/z [M+H]. found 460 (Exact mass=459.17).

Example 18

APY37 Prepared by Method C

Example 18.1

6-hexylnicotinaldehyde

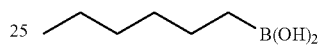

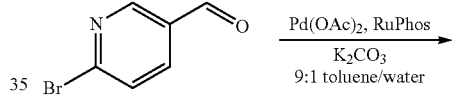

-continued

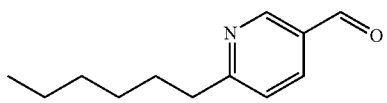

The compound was synthesized as in Example 3.1 using 6-bromonicotinaldehyde (200 mg, 1.08 mmol) in place of 5-bromo-2-formylfuran to give 6-hexylnicotinaldehyde (20 mg, 10%). Used without further characterization.

Example 18.2

APY37

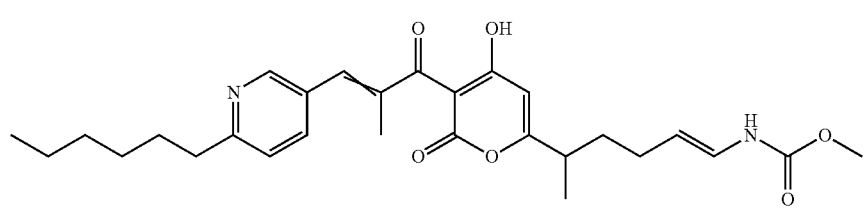

The compound was synthesized as in Example 9.6, using 6-hexylnicotinaldehyde (Example 18.1; 11 mg, 0.06 mmol) in place of 4-hexyl-2-formylfuran to give APY37 (0.8 mg) as an off-white solid containing a mixture of E and Z isomers (2:1): $^1$H NMR (E isomer, 500 MHz, CDCl$_3$, 298 K) δ 15.7 (br s, 1H), 8.73 (s, 1H), 7.92-7.85 (m, 1H), 7.37-7.31 (m, 1H), 6.69 (s, 1H), 6.51-6.42 (m, 1H), 6.23-6.17 (m, 1H), 6.00 (s, 1H), 4.96-4.84 (m, 1H), 3.71 (s, 3H), 2.95-2.89 (m, 2H), 2.88-2.82 (m, 1H), 2.20 (d, 3H), 2.08-1.99 (m, 2H), 1.76-1.53 (m, 4H), 1.34-1.30 (m, 6H), 1.27-1.25 (m, 3H), 0.90-0.86 (m, 3H); LRMS (ES$^+$) m/z [M+H]$^+$. found 497 (Exact mass=496.26).

(m, 1H), 5.96 (s, 1H), 4.96-4.91 (m, 1H), 3.99 (t, 2H), 3.71 (s, 3H), 2.60 (q, 1H), 2.19 (d, 3H), 2.07-1.99 (m, 2H), 1.84-1.75 (m 3H), 1.60-1.48 (m, 3H), 1.25 (d, 3H), 0.98 (t, 3H); LRMS (ES$^+$) m/z [M+H]$^+$. found 484 (Exact mass=483.23).

Example 19

APY39 Prepared by Method C

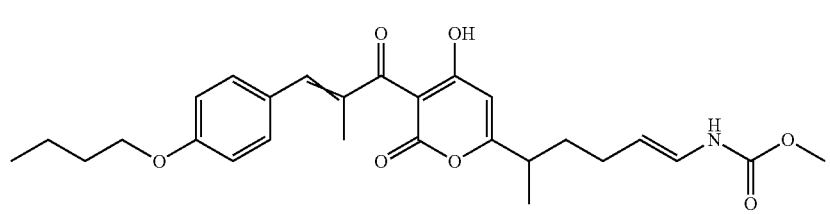

The compound was synthesized as in Example 9.6, using 4-butoxybenzaldehyde (13 mg, 0.07 mmol) in place of 4-hexyl-2-formylfuran to give APY39 (9.1 mg) as an off-white solid containing a mixture of E and Z isomers (4:1): $^1$H NMR (E isomer, 500 MHz, CDCl$_3$, 298 K) δ 16.0 (s, 1H), 7.41 (d, 2H), 6.92-6.89 (m, 3H), 6.49-6.43 (m, 1H), 6.22-6.19

Example 20

APY40 Prepared by Method C

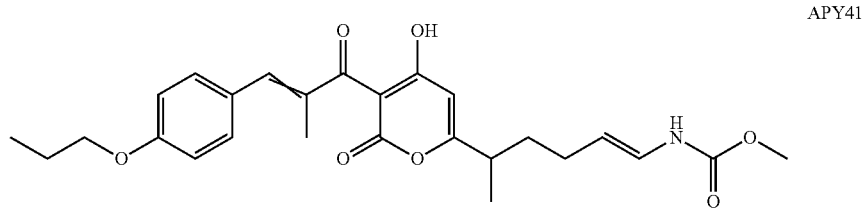 [SMILES: CCCOc1ccc(C=C(C)C(=O)c2c(O)cc(C(C)CC/C=C/NC(=O)OC)oc2=O)cc1]

The compound was synthesized as in Example 9.6, using 4-propoxybenzaldehyde (9 mg, 0.06 mmol) in place of 4-hexyl-2-formylfuran to give APY40 (6.3 mg) as an off-white solid containing a mixture of E and Z isomers (4:1): $^1$H NMR (E isomer, 500 MHz, CDCl₃, 298 K) δ 16.0 (br s, 1H), 7.41 (d, 2H), 6.92-6.89 (m, 3H), 6.49-6.43 (m, 1H), 6.22-6.19 (m, 1H), 5.96 (s, 1H), 4.96-4.92 (m, 1H), 3.95 (t, 2H), 3.71 (s, 3H), 2.60 (q, 1H), 2.19 (d, 3 H), 2.06-2.01 (m, 2H), 1.86-1.77 (m, 2H), 1.59-1.53 (m, 2H), 1.25 (d, 3H), 1.04 (t, 3H); LRMS (ES⁺) m/z [M+H]⁺. found 470 (Exact mass=469.21).

Example 21

APY41 Prepared by Method C

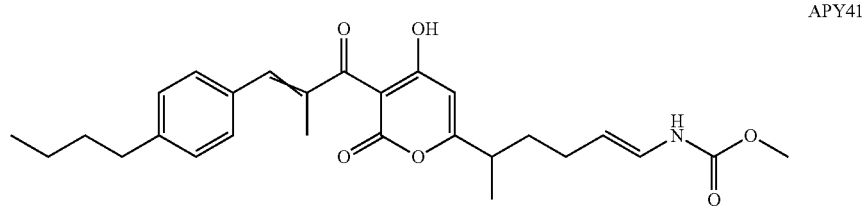 [SMILES: CCCCc1ccc(C=C(C)C(=O)c2c(O)cc(C(C)CC/C=C/NC(=O)OC)oc2=O)cc1]

The compound was synthesized as in Example 9.6, using 4-butylbenzaldehyde (20 µL, 0.11 mmol) in place of 4-hexyl-2-formylfuran to give APY41 (10.5 mg) as an off-white solid containing a mixture of E and Z isomers (4:1): ¹H NMR (E isomer, 500 MHz, CDCl₃, 298 K) δ 7.37 (d, 2H), 7.19 (d, 2H), 6.87 (s, 1H), 6.49-6.44 (m, 2H), 6.25-6.22 (m, 1H), 5.96 (s, 1H), 4.96-4.91 (m, 1H), 3.71 (s, 3H), 2.67-2.58 (m, 3H), 2.19 (d, 3H), 2.05-1.96 (m, 2H), 1.84-1.76 (m, 1H), 1.64-1.49 (m, 3H), 1.41-1.34 (m, 2H), 1.25 (d, 3H), 0.93 (t, 3H); LRMS (ES⁺) m/z [M+H]⁺. found 468 (Exact mass=467.23).

Example 22

APY42 Prepared by Method C

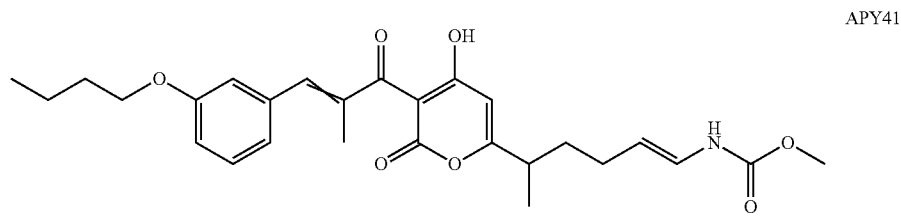 [SMILES: CCCCOc1cccc(C=C(C)C(=O)c2c(O)cc(C(C)CC/C=C/NC(=O)OC)oc2=O)c1]

The compound was synthesized as in Example 9.6, using 3-butoxybenzaldehyde (10 mg, 0.06 mmol) in place of 4-hexyl-2-formylfuran to give APY42 (5.5 mg) as an off-white solid containing a mixture of E and Z isomers (3:1): ¹H NMR (E isomer, 500 MHz, CDCl₃, 298 K) δ 15.9 (br s, 1H), 7.29 (d, 1H), 7.01 (d, 1H), 6.97 (s, 1H), 6.84 (dd, 1H), 6.82 (s, 1H), 6.48-6.45 (m, 1H), 6.23-6.19 (m, 1H), 5.97 (s, 1H), 4.97-4.87 (m, 1H), 3.93 (t, 2H), 3.71 (s, 3H), 2.61 (q, 1H), 2.18 (d, 3H), 2.06-1.99 (m, 2H), 1.83-1.69 (m, 4H), 1.53-1.48 (m, 3H), 1.25 (d, 3H), 0.98 (t, 3H); LRMS (ES⁺) m/z [M+H]⁺. found 484 (Exact mass=483.23).

Example 23

APY43 Prepared by Method C

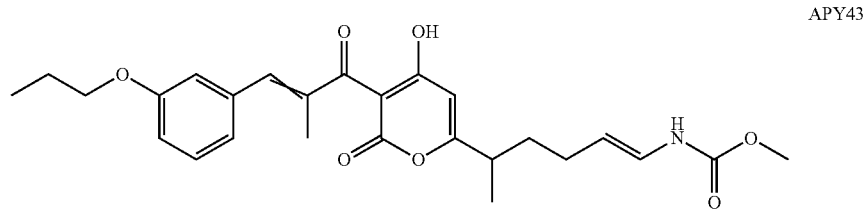 [SMILES: CCCOc1cccc(C=C(C)C(=O)c2c(O)cc(C(C)CC/C=C/NC(=O)OC)oc2=O)c1]

The compound was synthesized as in Example 9.6, using 3-propoxybenzaldehyde (9 mg, 0.04 mmol) in place of 4-hexyl-2-formylfuran to give APY43 (6.6 mg) as an off-white solid containing a mixture of E and Z isomers (3:1): $^1$H NMR (E isomer, 500 MHz, CDCl$_3$, 298 K) δ 15.9 (br s, 1H), 7.28 (d, 1H), 7.01 (d, 1H), 6.97 (s, 1H), 6.86-6.84 (m, 1H), 6.82 (s, 1H), 6.47-6.45 (m, 1H), 6.22-6.19 (m, 1H), 5.97 (s, 1H), 4.96-4.93 (m, 1H), 3.93 (t, 2H), 3.71 (s, 3H), 2.61 (q, 1H), 2.18 (d, 3H), 2.06-1.99 (m, 2H), 1.84-1.57 (m, 4H), 1.25 (d, 3H), 1.04 (t, 3H); LRMS (ES$^+$) m/z [M+H]$^+$. found 470 (Exact mass=469.21).

Example 24

APY48 Prepared by Method C

Example 24.1

4-(3,3-dimethylbutoxyl)benzaldehyde

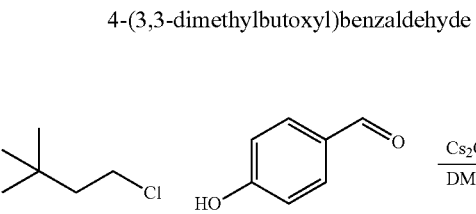

A suspension of 4-hydroxybenzaldehyde (200 mg, 1.64 mmol), 1-chloro-3,3-dimethylbutane (395 mg, 1.97 mmol), sodium iodide (24 mg, 0.16 mmol), and cesium carbonate (800 mg, 2.46 mmol) in anhydrous dimethylformamide (5 mL) was stirred at 80° C. overnight. After cooling to room temperature, solids were filtered and washed with ether. The filtrate was washed with 2 N sodium hydroxide (2×20 mL), water (20 mL), and brine (20 mL), dried over magnesium sulfate, filtered, and concentrated to give 4-(3,3-dimethylbutoxyl)benzaldehyde (262 mg, 78% crude) as a pale yellow oil that was used without further purification or characterization.

Example 24.2

APY48

The compound was synthesized as in Example 9.6, using 4-(3,3-dimethylbutoxyl)benzaldehyde (Example 24.1; 11 mg, 0.06 mmol) in place of 4-hexyl-2-formylfuran to give APY48 (1.7 mg) as an oily solid containing a mixture of E and Z isomers (5:1): $^1$H NMR (E isomer, 500 MHz, CDCl$_3$, 298 K) δ 16.0 (br s, 1H), 7.42 (d, 2H), 6.92-6.89 (m, 3H), 6.47-6.42 (m, 1H), 6.21-6.18 (m, 1H), 5.96 (s, 1H), 4.96-4.93 (m, 1H), 4.05 (t, 2H), 3.71 (s, 3H), 2.61 (q, 1H), 2.20 (d, 3H), 2.07-1.99 (m, 2H), 1.84-1.77 (m, 1H), 1.74 (t, 2H), 1.61-1.55 (m, 1H), 1.25 (d, 3H), 1.00 (s, 9H); LRMS (ES$^+$) m/z [M+H]$^+$. found 512 (Exact mass=511.26).

Example 25

APY49 Prepared by Method C

Example 25.1

3-(3,3-dimethylbutoxyl)benzaldehyde

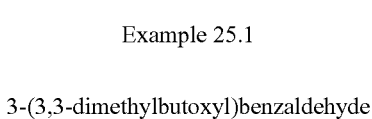

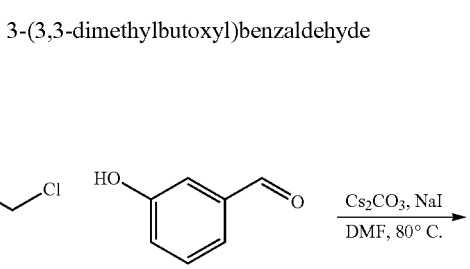

The compound was synthesized as in Example 24.1, using 3-hydroxybenzaldehyde (200 mg, 1.64 mmol) in place of 4-hydroxybenzaldehyde to give 3-(3,3-dimethylbutoxyl)benzaldehyde (224 mg, 66% crude) as a pale yellow oil that was used without further purification or characterization.

APY48

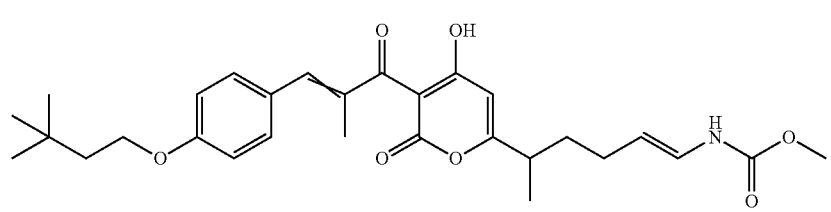

Example 25.2

APY49

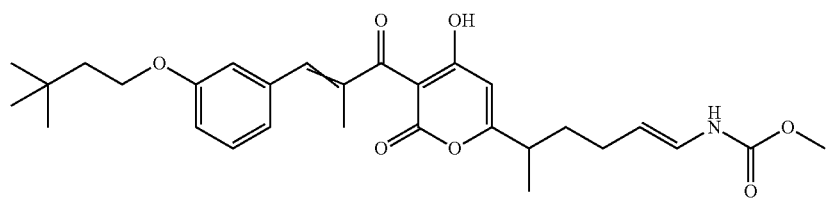

The compound was synthesized as in Example 9.6, using 3-(3,3-dimethylbutoxyl)benzaldehyde (Example 25.1; 11 mg, 0.06 mmol) in place of 4-hexyl-2-formylfuran to give APY49 (8.8 mg) as an oily solid containing a mixture of E and Z isomers (2.7:1): $^1$H NMR (E isomer, 500 MHz, CDCl$_3$, 298 K) δ 15.9 (br s, 1H), 7.29 (d, 1H), 7.02 (d, 1H), 6.96 (s, 1H), 6.84 (dd, 1H), 6.82 (s, 1H), 6.50-6.43 (m, 1H), 6.23-6.19 (m, 1H), 5.97 (s, 1H), 4.96-4.90 (m, 1H), 4.03 (t, 2H), 3.71 (s, 3H), 2.61 (q, 1H), 2.18 (d, 3H), 2.07-1.99 (m, 2H), 1.84-1.77 (m, 1H), 1.73 (t, 2H), 1.61-1.57 (m, 2H), 1.25 (d, 3H), 0.99 (s, 9H); LRMS (ES$^+$) m/z [M+H]$^+$. found 512 (Exact mass=511.26).

Example 26

APY50 Prepared by Method C

Example 26.1

4-(isopentyloxy)benzaldehyde

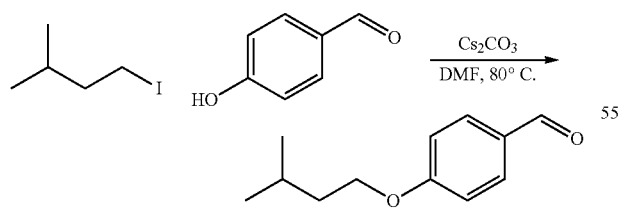

The compound was synthesized as in Example 24.1, using 4-hydroxybenzaldehyde (200 mg, 1.64 mmol) and 1-iodo-3-methylbutane (649 mg, 1.97 mmol) in place of 1-chloro-3,3-dimethylbutane (no sodium iodide was used) to give 4-(isopentyloxy)benzaldehyde (292 mg, quant. crude) as a dark yellow oil that was used without further purification or characterization.

Example 26.2

APY50

APY49

APY50

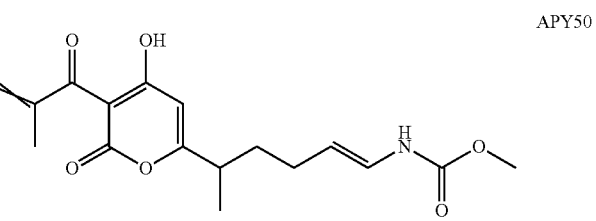

The compound was synthesized as in Example 9.6, using 4-(isopentyloxy)benzaldehyde (Example 26.1; 11 mg, 0.06 mmol) in place of 4-hexyl-2-formylfuran to give APY50 (3.9 mg) as an oily solid containing a mixture of E and Z isomers (4.5:1): $^1$H NMR (E isomer, 500 MHz, CDCl$_3$, 298 K) δ 16.0 (br s, 1H), 7.41 (d, 2H), 6.92-6.90 (m, 3H), 6.50-6.42 (m, 1H), 6.22-6.18 (m, 1H), 5.96 (s, 1H), 4.96-4.93 (m, 1H), 4.02 (t, 2H), 3.71 (br s, 3H), 2.61 (q, 1H), 2.20 (d, 3H), 2.08-1.99 (m, 2H), 1.87-1.78 (m, 2H), 1.71-1.67 (m, 3H), 1.25 (d, 3H), 0.97 (d, 6H); LRMS (ES$^+$) m/z [M+H]$^+$. found 498 (Exact mass=497.58).

Example 27

APY51 Prepared by Method C

Example 27.1

3-(isopentyloxy)benzaldehyde

The compound was synthesized as in Example 24.1, using 3-hydroxybenzaldehyde (200 mg, 1.64 mmol) in place of 4-hydroxybenzaldehyde and 1-iodo-3-methylbutane (649 mg, 1.97 mmol) in place of 1-chloro-3,3-dimethylbutane (no sodium iodide was used) to give 3-(isopentyloxy)benzaldehyde (292 mg, quant. crude) as a dark yellow oil that was used without further purification or characterization.

Example 27.2

APY51

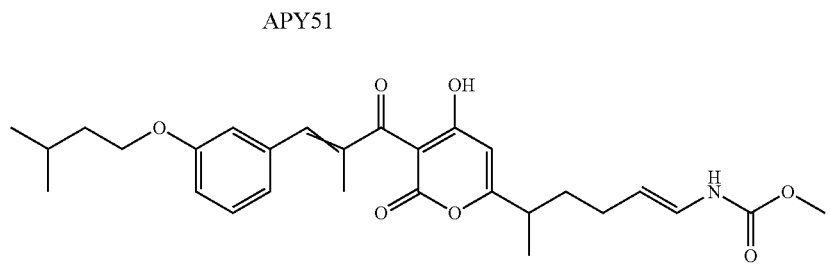

The compound was synthesized as in Example 9.6, using 3-(isopentyloxy)benzaldehyde (Example 27.1; 11 mg, 0.06 mmol) in place of 4-hexyl-2-formylfuran to give APY51 (4.8 mg) as an oily solid containing a mixture of E and Z isomers (2.6:1): $^1$H NMR (E isomer, 500 MHz, CDCl$_3$, 298 K) δ 15.9 (br s, 1H), 7.28 (d, 1H), 7.02 (d, 1H), 6.96 (br s, 1H), 6.84 (dd, 1H), 6.82 (s, 1H), 6.50-6.42 (m, 1H), 6.25-6.18 (m, 1H), 5.97 (s, 1H), 4.98-4.87 (m, 1H), 3.99 (t, 2H), 3.71 (br s, 3H), 2.61 (q, 1H), 2.18 (d, 3 H), 2.07-1.99 (m, 2H), 1.88-1.80 (m, 2H), 1.69 (t, 2H), 1.60-1.50 (1H), 1.25 (d, 3H), 0.96 (d, 6H); LRMS (ES$^+$) m/z [M+H]$^+$. found 498 (Exact mass=497.58).

Example 28

APY52 Prepared by Method C

Example 28.1

4-(cyclopentylmethoxy)benzaldehyde

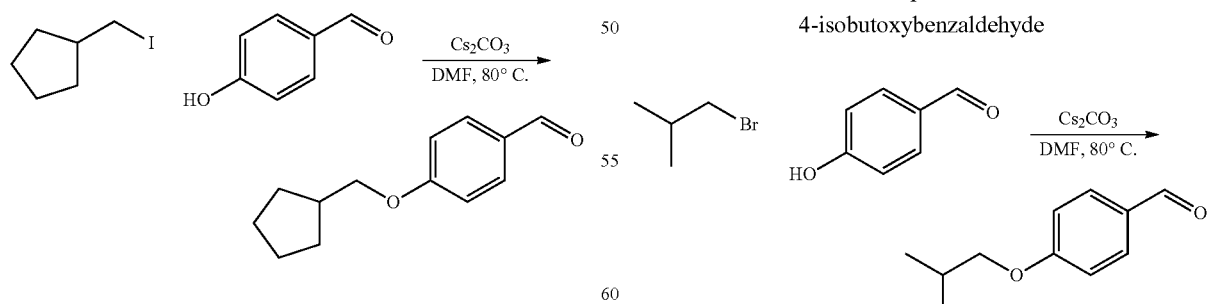

The compound was synthesized as in Example 24.1, using 4-hydroxybenzaldehyde (200 mg, 1.64 mmol) and 1-iodo-3-methylmethylcyclopentane (344 mg, 0.98 mmol) in place of 1-chloro-3,3-dimethylbutane (no sodium iodide was used) to give 4-(cyclopentylmethoxy)benzaldehyde (102 mg, 50% crude) as a yellow oil that was used without further purification or characterization.

Example 28.2

APY52

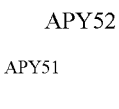

APY52

The compound was synthesized as in Example 9.6, using 4-(cyclopentylmethoxy)benzaldehyde (Example 28.1; 14 mg, 0.07 mmol) in place of 4-hexyl-2-formylfuran to give APY52 (3.6 mg) as an oily solid containing a mixture of E and Z isomers (4:1): $^1$H NMR (E isomer, 500 MHz, CDCl$_3$, 298 K) δ 16.0 (br s, 1H), 7.41 (d, 2H), 6.92-6.89 (m, 3H), 6.47-6.43 (m, 1H), 6.22-6.19 (m, 1H), 5.96 (s, 1H), 4.96-4.93 (m, 1H), 3.6 (d, 2H), 3.71 (br s, 3H), 2.61 (q, 1H), 2.37 (pentet, 1H), 2.19 (d, 3H), 2.07-1.98 (m, 2H), 1.88-1.77 (m, 3H), 1.67-1.57 (m, 4H), 1.40-1.33 (m, 3H), 1.25 (d, 3H); LRMS (ES$^+$) m/z [M+H]$^+$. found 510 (Exact mass=509.59).

Example 29

APY53 Prepared by Method C

Example 29.1

4-isobutoxybenzaldehyde

The compound was synthesized as in Example 24.1, using 4-hydroxybenzaldehyde (200 mg, 1.64 mmol) and isobutyl bromide (449 mg, 1.97 mmol) in place of 1-chloro-3,3-dimethylbutane (no sodium iodide was used) to give 4-isobutoxybenzaldehyde (294 mg, quant. crude) as a yellow oil that was used without further purification or characterization.

Example 29.2

APY53

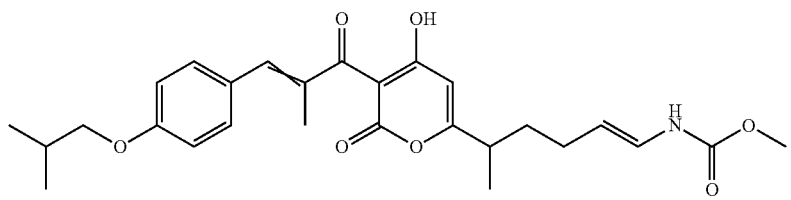

The compound was synthesized as in Example 9.6, using 4-isobutoxybenzaldehyde (Example 29.1; 12 mg, 0.07 mmol) in place of 4-hexyl-2-formylfuran to give APY53 (6.9 mg) as an oily solid containing a mixture of E and Z isomers (5:1): $^1$H NMR (E isomer, 500 MHz, CDCl$_3$, 298 K) δ 16.0 (br s, 1H), 7.41 (d, 2H), 6.92-6.89 (m, 3H), 6.47-6.43 (m, 1H), 6.22-6.21 (m, 1H), 5.96 (s, 1H), 4.98-4.89 (m, 1H), 3.75 (d, 2H), 3.71 (br s, 3H), 2.61 (q, 1H), 2.19 (d, 3H), 2.07-1.96 (m, 3H), 1.84-1.76 (m, 1H), 1.60-1.57 (m, 1H), 1.25 (d, 3H), 1.03 (d, 6H); LRMS (ES) m/z [M+H]$^+$. found 484 (Exact mass=483.55).

Example 30

APY54 Prepared by Method C

Example 30.1

4-((tetrahydrofuran-2-yl)methoxy)benzaldehyde

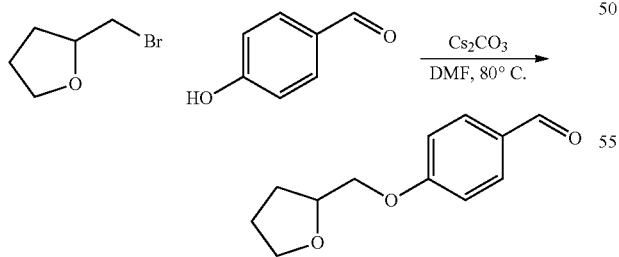

The compound was synthesized as in Example 24.1, using 4-hydroxybenzaldehyde (200 mg, 1.64 mmol) and 2-(bromomethyl)tetrahydrofuran (541 mg, 1.97 mmol) in place of 1-chloro-3,3-dimethylbutane (no sodium iodide was used) to give 4-((tetrahydrofuran-2-yl)methoxy)benzaldehyde (338 mg, quant. crude) as a yellow oil that was used without further purification or characterization.

Example 30.2

APY54

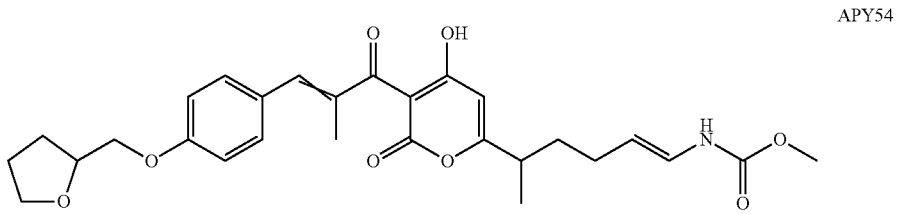 [SMILES: COC(=O)N/C=C/CCC(C)c1cc(O)c(C(=O)C(C)=Cc2ccc(OCC3CCCC3)cc2)c(=O)o1]

The compound was synthesized as in Example 9.6, using 4-((tetrahydrofuran-2-yl)methoxy)benzaldehyde (Example 30.1; 14 mg, 0.07 mmol) in place of 4-hexyl-2-formylfuran to give APY54 (6.6 mg) as an oily solid containing a mixture of E and Z isomers (3:1): $^1$H NMR (E isomer, 500 MHz, CDCl$_3$, 298 K) δ 16.0 (br s, 1H), 7.41 (d, 2H), 6.94 (d, 2H), 6.89 (s, 1H), 6.47-6.43 (m, 1H), 6.23-6.20 (m, 1H), 5.96 (s, 1H), 4.96-4.91 (m, 1H), 4.31-4.26 (m, 1H), 4.01-3.97 (m, 2H), 3.97-3.92 (m, 1H), 3.86-3.80 (m, 1H), 3.71 (br s, 3H), 2.60 (q, 1H), 2.19 (d, 3H), 2.09-2.00 (m, 2H), 1.99-1.90 (m, 2H), 1.84-1.74 (m, 3H), 1.58-1.53 (m, 1H), 1.25 (d, 3H); LRMS (ES$^+$) m/z [M+H]$^+$. found 512 (Exact mass=511.56).

Example 31

APY55 Prepared by Method C

Example 31.1

4-(neopentyloxy)benzaldehyde

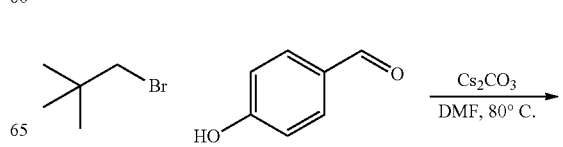

-continued

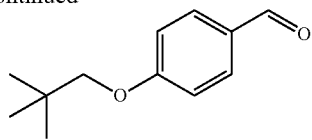

The compound was synthesized as in Example 24.1, using 4-hydroxybenzaldehyde (200 mg, 1.64 mmol) and neopentyl bromide (495 mg, 1.97 mmol) in place of 1-chloro-3,3-dimethylbutane (no sodium iodide was used) to give 4-(neopentyloxy)benzaldehyde (315 mg, quant. crude) as a yellow oil that was used without further purification or characterization.

Example 31.2

APY55

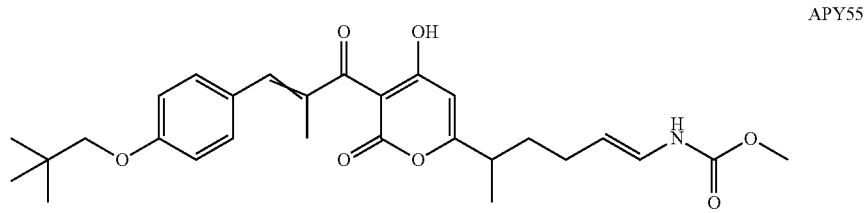

The compound was synthesized as in Example 9.6, using 4-(neopentyloxy)benzaldehyde (Example 31.1; 13 mg, 0.07 mmol) in place of 4-hexyl-2-formylfuran to give APY55 (6.8 mg) as an oily solid containing a mixture of E and Z isomers (4:1): $^1$H NMR (E isomer, 500 MHz, CDCl$_3$, 298 K) δ 16.0 (br s, 1H), 7.41 (d, 2H), 6.92-6.90 (m, 3H), 6.49-6.43 (m, 1H), 6.25-6.20 (m, 1H), 5.96 (s, 1H), 4.96-4.91 (m, 1H), 3.71 (br s, 3H), 3.62 (s, 2H), 2.60 (q, 1H), 2.19 (d, 3H), 2.07-1.97 (m, 2H), 1.84-1.78 (m, 1H), 1.55-1.50 (m, 1H), 1.25 (d, 3H), 0.99 (s, 9H); LRMS (ES$^+$) m/z [M+H]$^+$. found 498 (Exact mass=497.58).

Example 32

APY56 Prepared by Method C

Example 32.1

5-(3,3-dimethylbutyl)thiophene-2-carbaldehyde

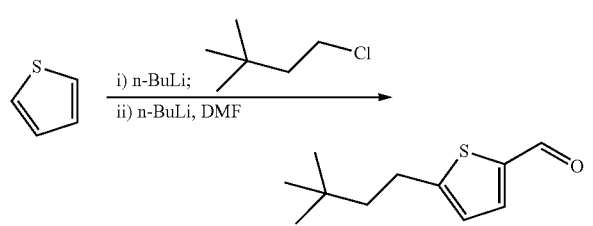

To a solution of thiophene (300 mg, 3.57 mmol) in anhydrous 10% hexamethylphosphoramide in tetrahydrofuran (33 mL) under argon at –78° C. was added n-butyllithium (1.57 mL, 2.5 M in hexanes) dropwise. After stirring at –78° C. for 1 hour, 1-chloro-3,3-dimethylbutane (430 mg, 3.57 mmol) was added dropwise and the resulting solution allowed to warm to room temperature over 3 hours. The reaction mixture was re-cooled to –78° C., a second portion of n-butyllithium (1.78 mL, 4.46 mmol) was added dropwise over 5 minutes and the mixture was stirred for 1 hour at –78° C. before anhydrous dimethylformamide (1.38 mL, 17.8 mmol) was added dropwise and the resulting mixture allowed to warm to room temperature. The reaction mixture was poured into 1 N hydrochloric acid (150 mL) and organics were extracted with ether (3×100 mL), dried with magnesium sulfate, filtered and concentrated. The residue was purified by flash chromatography on silica gel with gradient elution (5%→20% ethyl acetate in hexanes) to give 5-(3,3-dimethylbutyl)thiophene-2-carbaldehyde (130 mg, 19%). Used without further characterization.

Example 32.2

APY56

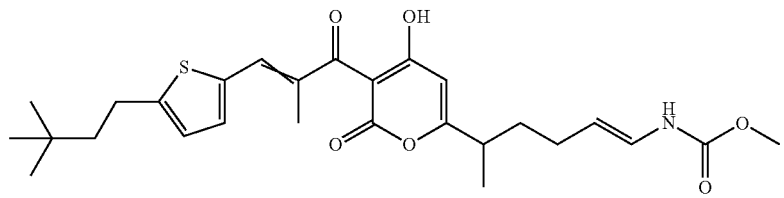

The compound was synthesized as in Example 9.6, using 5-(3,3-dimethylbutyl)thiophene-2-carbaldehyde (Example 32.1; 14 mg, 0.07 mmol) in place of 4-hexyl-2-formylfuran to give APY56 (5.6 mg) as an oily solid containing a mixture of E and Z isomers (>10:1): $^{1}$H NMR (E isomer, 500 MHz, CDCl$_3$, 298 K) δ 7.24 (s, 1H), 7.10 (d, 1H), 6.80 (d, 1H), 6.51-6.42 (m, 1H), 6.24-6.17 (m, 1H), 5.95 (s, 1H), 4.99-4.91 (m, 1H), 3.71 (br s, 3H), 2.85-2.79 (m, 2H), 2.60 (q, 1H), 2.21 (d, 3H), 2.08-2.00 (m, 2H), 1.85-1.77 (m, 1H), 1.65-1.59 (m, 2H), 1.59-1.52 (m, 1H), 1.25 (d, 3H), 1.00 (s, 9H); LRMS (ES$^+$) m/z [M+H]$^+$. found 502 (Exact mass=501.22).

Example 33

APY57 Prepared by Method C

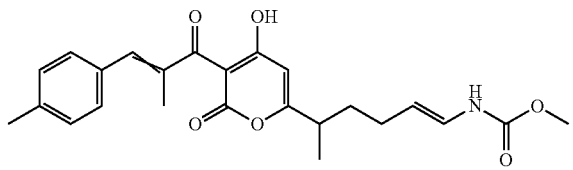

APY57

The compound was synthesized as in Example 9.6 using 4-methylbenzaldehyde (9 mg, 0.07 mmol) in place of 4-hexyl-2-formylfuran to APY57 (2.9 mg) as an oily solid containing a mixture of E and Z isomers (3.5:1): $^{1}$H NMR (E isomer, 500 MHz, CDCl$_3$, 298 K) δ 7.35 (d, 2H), 7.19 (d, 2H), 6.87 (s, 1H), 6.51-6.42 (m, 1H), 6.25-6.18 (m, 1H), 5.97 (s, 1H), 4.99-4.90 (m, 1H), 3.71 (s, 3H), 2.61 (q, 1H), 2.37 (s, 3H), 2.19 (d, 3H), 2.07-1.98 (m, 2H), 1.85-1.76 (m, 1H), 1.61-1.52 (m, 1H), 1.25 (d, 3H); LRMS (ES$^+$) m/z [M+H]$^+$. found 426 (Exact mass=425.18).

Example 34

APY58 Prepared by Method C

Example 34.1

5-propylthiophene-2-carbaldehyde

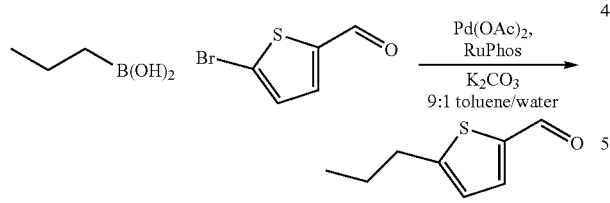

The compound was synthesized as in Example 3.1 using 5-bromothiophene-2-carbaldehyde (250 mg, 1.31 mmol) in place of 5-bromo-2-formylfuran and propylboronic acid (190 mg, 2.16 mmol) in place of hexylboronic acid to give 5-propylthiophene-2-carbaldehyde (58 mg, 29%). Used without further characterization.

Example 34.2

APY58

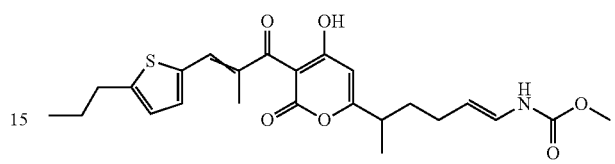

APY58

The compound was synthesized as in Example 9.6, using 5-propylthiophene-2-carbaldehyde (Example 34.1; 11 mg, 0.07 mmol) in place of 4-hexyl-2-formylfuran to give APY58 (3.6 mg) as an oily solid containing a mixture of E and Z isomers (3:1): $^{1}$H NMR (E isomer, 500 MHz, CDCl$_3$, 298 K) δ 7.24 (s, 1H), 7.11 (d, 1H), 6.79 (d, 1H), 6.51-6.41 (m, 1H), 6.25-6.19 (m, 1H), 5.95 (s, 1H), 4.99-4.90 (m, 1H), 3.71 (s, 3H), 2.83 (t, 2H), 2.60 (q, 1H), 2.21 (d, 3H), 2.07-1.99 (m, 2H), 1.85-1.77 (m, 1H), 1.60-1.53 (m, 3H), 1.25 (d, 3H), 0.99 (t, 3H); LRMS (ES) m/z [M+H]$^+$. found 460 (Exact mass=459.17).

Example 35

APY59 Prepared by Method C

Example 35.1

5-pentylthiophene-2-carbaldehyde

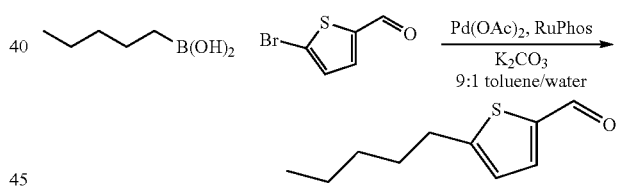

The compound was synthesized as in Example 3.1 using 5-bromothiophene-2-carbaldehyde (250 mg, 1.31 mmol) in place of 5-bromo-2-formylfuran and pentylboronic acid (250 mg, 2.16 mmol) in place of hexylboronic acid to give 5-pentylthiophene-2-carbaldehyde (161 mg, 67%). Used without further characterization.

Example 35.2

APY59

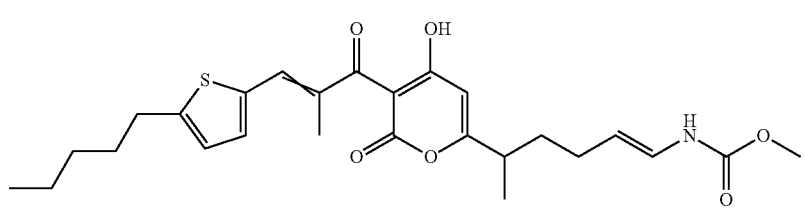

APY59

The compound was synthesized as in Example 9.6, using 5-pentylthiophene-2-carbaldehyde (Example 35.1; 13 mg, 0.07 mmol) in place of 4-hexyl-2-formylfuran to give APY59 (3.1 mg) as an oily solid containing a mixture of E and Z isomers (2:1): $^1$H NMR (E isomer, 500 MHz, CDCl$_3$, 298 K) δ 7.24 (s, 1H), 7.10 (d, 1H), 6.79 (d, 1H), 6.51-6.42 (m, 1H), 6.25-6.18 (m, 1H), 5.95 (s, 1H), 4.99-4.91 (m, 1H), 3.71 (s, 3H), 2.84 (t, 2H), 2.60 (q, 1H), 2.21 (d, 3H), 2.08-1.99 (m, 2H), 1.85-1.77 (m, 1H), 1.65-1.57 (m, 3H), 1.38-1.34 (m, 4H), 1.25 (d, 3H), 0.91 (t, 3H); LRMS (ES) m/z [M+H]$^+$. found 488 (Exact mass=487.61).

Example 36

APY60 Prepared by Method C

Example 36.1

5-isobutylthiophene-2-carbaldehyde

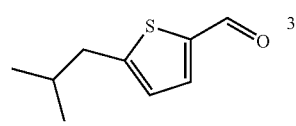

The compound was synthesized as in Example 3.1 using 5-bromothiophene-2-carbaldehyde (250 mg, 1.31 mmol) in place of 5-bromo-2-formylfuran and 5-isobutylboronic acid (220 mg, 2.16 mmol) in place of hexylboronic acid to give 5-isobutylthiophene-2-carbaldehyde (168 mg, 76%). Used without further characterization.

Example 36.2

APY60

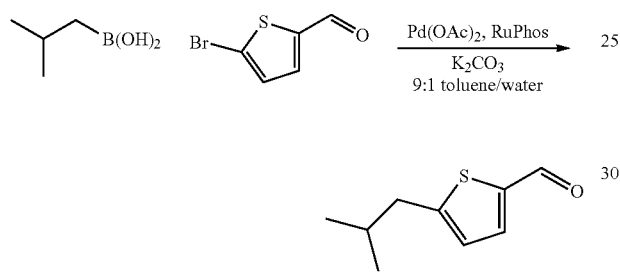

The compound was synthesized as in Example 9.6, using 5-isobutylthiophene-2-carbaldehyde (Example 36.1; 12 mg, 0.07 mmol) in place of 4-hexyl-2-formylfuran to give APY60 (2.8 mg) as an oily solid containing a mixture of E and Z isomers (>10:1): $^1$H NMR (E isomer, 500 MHz, CDCl$_3$, 298 K) δ 7.24 (s, 1H), 7.11 (d, 1H), 6.77 (d, 1H), 6.51-6.42 (m, 1H), 6.25-6.19 (m, 1H), 5.96 (s, 1H), 4.99-4.91 (m, 1H), 3.71 (s, 3H), 2.71 (d, 2H), 2.61 (q, 1H), 2.21 (d, 3H), 2.08-2.00 (m, 2H), 1.97-1.89 (m, 1H), 1.85-1.77 (m, 1H), 1.60-1.56 (m, 1H), 1.25 (d, 3H), 0.96 (d, 6H); LRMS (ES$^+$) m/z [M+H]$^+$. found 474 (Exact mass=473.19).

Example 37

APY61 Prepared by Method C

Example 37.1

5-(3,3,3-trifluoropropyl)thiophene-2-carbaldehyde

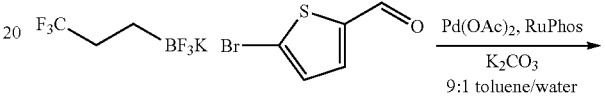

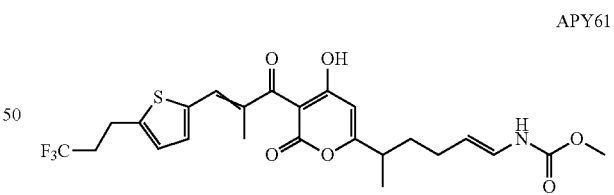

The compound was synthesized as in Example 3.1 using 5-bromothiophene-2-carbaldehyde (250 mg, 1.31 mmol) in place of 5-bromo-2-formylfuran and 3,3,3-trifluoropropyltrifluoroborate (440 mg, 2.16 mmol) in place of hexylboronic acid to give 5-(3,3,3-trifluoropropyl)thiophene-2-carbaldehyde (244 mg, 90%). Used without further characterization.

Example 37.2

APY61

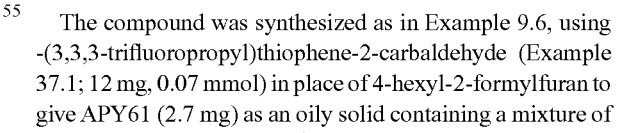

The compound was synthesized as in Example 9.6, using -(3,3,3-trifluoropropyl)thiophene-2-carbaldehyde (Example 37.1; 12 mg, 0.07 mmol) in place of 4-hexyl-2-formylfuran to give APY61 (2.7 mg) as an oily solid containing a mixture of E and Z isomers (>10:1): $^1$H NMR (E isomer, 500 MHz, CDCl$_3$, 298 K) δ 7.17 (s, 1H), 7.11 (d, 1H), 6.85 (d, 1H), 6.51-6.42 (m, 1H), 6.25-6.19 (m, 1H), 5.96 (s, 1H), 4.99-4.91 (m, 1H), 3.71 (s, 3H), 3.16-3.10 (m, 2H), 2.61 (q, 1H), 2.55-2.44 (m, 2H), 2.21 (d, 3H), 2.08-2.00 (m, 2H), 1.84-1.76 (m, 1H), 1.60-1.56 (m, 1H), 1.25 (d, 3H); LRMS (ES$^+$) m/z [M+H]$^+$. found 514 (Exact mass=513.14).

Example 38

APY62 Prepared by Method C

Example 38.1

5-(2-cyclohexylethyl)thiophene-2-carbaldehyde

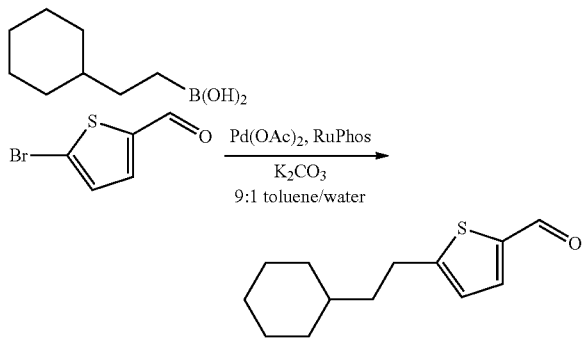

The compound was synthesized as in Example 3.1 using 5-bromothiophene-2-carbaldehyde (250 mg, 1.31 mmol) in place of 5-bromo-2-formylfuran and 2-cyclohexylethylboronic acid (337 mg, 2.16 mmol) in place of hexylboronic acid to give 5-(2-cyclohexylethyl)thiophene-2-carbaldehyde (168 mg, 58%). Used without further characterization.

Example 38.2

APY62

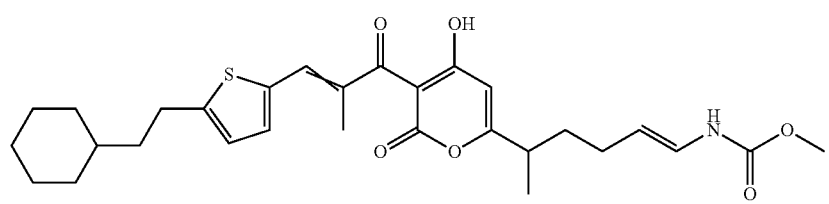

The compound was synthesized as in Example 9.6, using 5-(2-cyclohexylethyl)thiophene-2-carbaldehyde (Example 38.1; 16 mg, 0.07 mmol) in place of 4-hexyl-2-formylfuran to give APY62 (7.0 mg) as an oily solid containing a mixture of E and Z isomers (3.5:1): $^1$H NMR (E isomer, 500 MHz, CDCl$_3$, 298 K) δ 7.24 (s, 1H), 7.10 (d, 1H), 6.79 (d, 1H), 6.51-6.41 (m, 1H), 6.26-6.20 (m, 1H), 5.95 (s, 1H), 4.99-4.91 (m, 1H), 3.71 (s, 3H), 2.86 (t, 2H), 2.60 (q, 1H), 2.21 (d, 3H), 2.07-2.00 (m, 2H), 1.86-1.77 (m, 1H), 1.76-1.52 (m, 8H), 1.35-1.12 (m, 5H), 0.99-0.84 (m, 4H); LRMS (ES$^+$) m/z [M+H]$^+$. found 528 (Exact mass=527.23).

Example 39

APY64 Prepared by Method C

Example 39.1

5-ethylthiophene-2-carbaldehyde

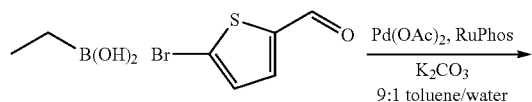

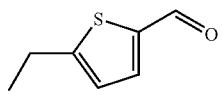

The compound was synthesized as in Example 3.1 using 5-bromothiophene-2-carbaldehyde (250 mg, 1.31 mmol) in place of 5-bromo-2-formylfuran and ethylboronic acid (160 mg, 2.16 mmol) in place of hexylboronic acid to give 5-ethylthiophene-2-carbaldehyde (93 mg, 51%). Used without further characterization.

Example 39.2

APY64

APY64

The compound was synthesized as in Example 9.6, using ethylthiophene-2-carbaldehyde (Example 39.1; 10 mg, 0.07 mmol) in place of 4-hexyl-2-formylfuran to give APY64 (7.0 mg) as an oily solid containing a mixture of E and Z isomers (>10:1): $^1$H NMR (E isomer, 500 MHz, CDCl$_3$, 298 K) δ 7.24 (s, 1H), 7.11 (d, 1H), 6.81 (d, 1H), 6.50-6.41 (m, 1H), 6.25-6.19 (m, 1H), 5.95 (s, 1H), 4.99-4.90 (m, 1H), 3.71 (s, 3H), 2.89 (q, 2H), 2.60 (q, 1H), 2.21 (d, 3H), 2.07-1.98 (m, 2H), 1.86-1.77 (m, 1H), 1.60-1.52 (m, 1H), 1.34 (t, 3H), 1.25 (d, 3H); LRMS (ES$^+$) m/z [M+H]$^+$. found 446 (Exact mass=445.16).

Example 40

APY66 Prepared by Method C

Example 40.1

4-isopropoxybenzaldehyde

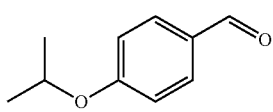

The compound was synthesized as in Example 24.1, using 2-iodopropane (557 mg, 1.97 mmol) in place of 1-chloro-3,3-dimethylbutane (no sodium iodide was used) to give 4-isopropoxybenzaldehyde (177 mg, 66% crude) as a pale yellow oil that was used without further purification or characterization.

Example 40.2

APY66

APY66

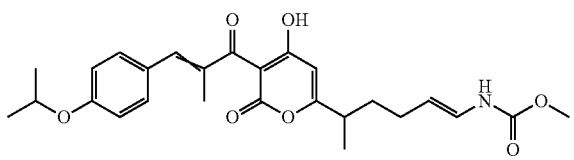

The compound was synthesized as in Example 9.6, using 4-isopropoxybenzaldehyde (Example 40.1; 12 mg, 0.07 mmol) in place of 4-hexyl-2-formylfuran to give APY66 (7.4 mg) as an oily solid containing a mixture of E and Z isomers (4.5:1): $^1$H NMR (E isomer, 500 MHz, CDCl$_3$, 298 K) δ 7.41 (d, 2H), 6.92-6.86 (m, 3H), 6.50-6.41 (m, 1H), 6.27-6.19 (m, 1H), 5.96 (s, 1H), 4.99-4.88 (m, 1H), 4.58 (septet, 1H), 3.71 (s, 3H), 2.60 (q, 1H), 2.19 (d, 3H), 2.07-1.97 (m, 2H), 1.85-1.77 (m, 1H), 1.60-1.53 (m, 1H), 1.35 (d, 6H), 1.23 (d, 3H); LRMS (ES$^+$) m/z [M+H]$^+$. found 470 (Exact mass=469.21).

Example 41

APY67 Prepared by Method C

Example 41.1

Methyl 5-(4-hydroxy-2-oxo-3-propionyl-2H-pyran-6-yl)hexylcarbamate

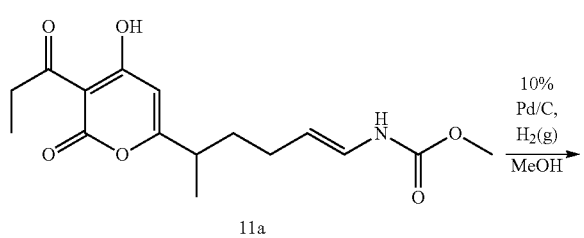

A suspension of enecarbamate 11a (76 mg, 0.24 mmol) and 10% Pd/C (6 mg) in methanol (5 mL) was flushed three times with hydrogen gas and stirred vigorously under balloon pressure of hydrogen at room temperature for 1 h. The suspension was filtered through Celite and the filtrate concentrated and purified by chromatography on silica gel (30% ethyl acetate in hexanes+1% acetic acid) to give methyl 5-(4-hydroxy-2-oxo-3-propionyl-2H-pyran-6-yl)hexylcarbamate (33 mg, 43%) as a yellow oil that was used without further characterization.

Example 41.2

APY67

APY67

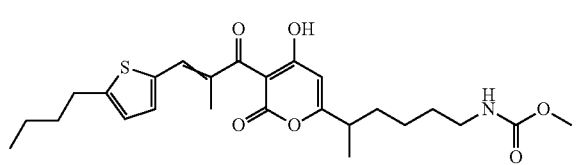

The compound was synthesized as in Example 9.6, using 5-butylthiophenecarbaldehyde in place of 4-hexyl-2-formylfuran and methyl 5-(4-hydroxy-2-oxo-3-propionyl-2H-pyran-6-yl)hexylcarbamate in place of enecarbamate 11a to give APY67 (6.9 mg) as an oil containing a mixture of E and Z isomers (>10:1): $^1$H NMR (E isomer, 500 MHz, CDCl$_3$) δ 7.24 (s, 1H), 7.10 (d, 1H), 6.79 (d, 1H), 5.94 (s, 1H), 4.66 (br s, 1H), 3.66 (s, 3H), 3.21-3.13 (m, 2H), 2.85 (t, 2H), 2.58 (q, 1H), 2.21 (d, 3H), 1.73-1.65 (m, 3H), 1.57-1.49 (m, 4H), 1.45-1.36 (m, 3H), 1.25 (d, 3H), 0.94 (t, 3H); LRMS (ES$^+$) m/z [M+H]$^+$. found 476 (Exact mass=475.20).

Example 42

APY69 Prepared by Method C

APY69

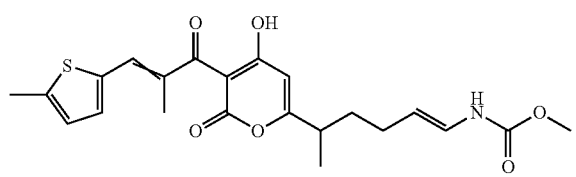

The compound was synthesized as in Example 9.6, using methylthiophene-2-carbaldehyde (9 mg, 0.07 mmol) in place of 4-hexyl-2-formylfuran to give APY69 (4.0 mg) as an oily solid containing a mixture of E and Z isomers (>10:1): $^1$H NMR (E isomer, 500 MHz, CDCl₃, 298 K) δ 7.22 (s, 1H), 7.09 (d, 1H), 6.77 (d, 1H), 6.50-6.40 (m, 1H), 6.26-6.18 (m, 1H), 5.95 (s, 1H), 4.99-4.90 (m, 1H), 3.71 (s, 3H), 2.60 (q, 1H), 2.54 (s, 3H), 2.20 (d, 3H), 2.07-1.99 (m, 2H), 1.85-1.76 (m, 1H), 1.61-1.52 (m, 1H), 1.25 (d, 3H); LRMS (ES⁺) m/z [M+H]⁺. found 432 (Exact mass=431.14).

Example 43

APY70 Prepared by Method C

Example 43.1

4-ethylbenzaldehyde

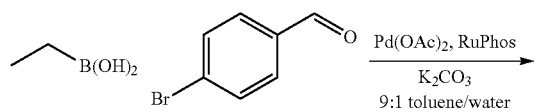

The compound was synthesized as in Example 3.1 using 4-bromobenzaldehyde (250 mg, 1.35 mmol) in place of 5-bromo-2-formylfuran and ethylboronic acid (165 mg, 2.23 mmol) in place of hexylboronic acid to give 4-ethylbenzaldehyde (93 mg, 51%). Used without further characterization.

Example 43.2

APY70

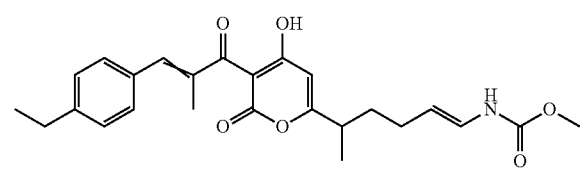

The compound was synthesized as in Example 9.6, using 4-ethylbenzaldehyde (Example 43.1; 10 mg, 0.07 mmol) in place of 4-hexyl-2-formylfuran to give APY70 (3.0 mg) as an oily solid containing a mixture of E and Z isomers (4:1): ¹H NMR (E isomer, 500 MHz, CDCl₃, 298 K) δ 7.38 (d, 2H), 7.22 (d, 2H), 6.88 (s, 1H), 6.51-6.43 (m, 1H), 6.25-6.18 (m, 1H), 5.96 (s, 1H), 4.98-4.88 (m, 1H), 3.71 (s, 3H), 2.67 (q, 2H), 2.60 (q, 1H), 2.19 (d, 3H), 2.09-1.97 (m, 2H), 1.85-1.76 (m, 1H), 1.62-1.54 (m, 1H), 1.27-1.24 (m, 6H); LRMS (ES⁺) m/z [M+H]⁺. found 440 (Exact mass=439.20).

Example 44

APY71 Prepared by Method C

Example 44.1

4-propylbenzaldehyde

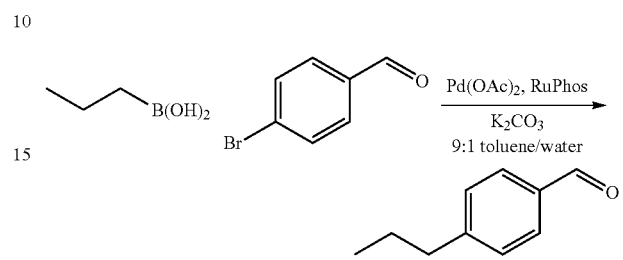

The compound was synthesized as in Example 3.1 using 4-bromobenzaldehyde (250 mg, 1.35 mmol) in place of 5-bromo-2-formylfuran and propylboronic acid (196 mg, 2.23 mmol) in place of hexylboronic acid to give 4-propylbenzaldehyde (58 mg, 29%). Used without further characterization.

Example 44.2

APY71

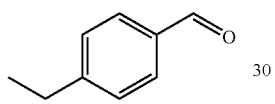

The compound was synthesized as in Example 9.6, using 4-propylbenzaldehyde (Example 44.1; 10 mg, 0.07 mmol) in place of 4-hexyl-2-formylfuran to give APY71 (3.0 mg) as an oily solid containing a mixture of E and Z isomers (4:1): ¹H NMR (E isomer, 500 MHz, CDCl₃, 298 K) δ 7.37 (d, 2H), 7.19 (d, 2H), 6.88 (s, 1H), 6.51-6.43 (m, 1H), 6.25-6.18 (m, 1H), 5.96 (s, 1H), 4.98-4.88 (m, 1H), 3.71 (s, 3H), 2.66-2.57 (m, 3H), 2.19 (d, 3H), 2.09-1.97 (m, 2H), 1.85-1.76 (m, 1H), 1.68-1.56 (m, 3H), 1.25 (d, 3H), 0.95 (t, 3H); LRMS (ES⁺) m/z [M+H]⁺. found 454 (Exact mass=453.22).

Example 45

APY72 Prepared by Method C

Example 45.1

4-pentylbenzaldehyde

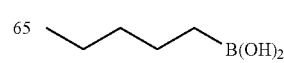

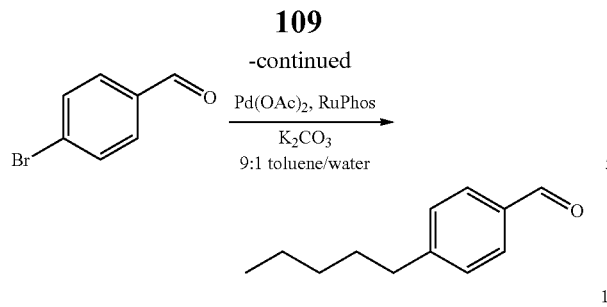

The compound was synthesized as in Example 3.1 using 4-bromobenzaldehyde (250 mg, 1.35 mmol) in place of 5-bromo-2-formylfuran and pentylboronic acid (259 mg, 2.23 mmol) in place of hexylboronic acid to give 4-pentylbenzaldehyde (161 mg, 68%). Used without further characterization.

Example 45.2

APY72

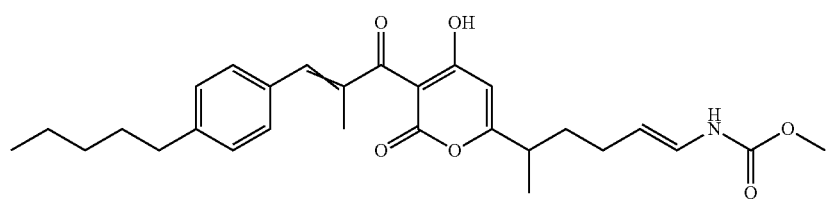

The compound was synthesized as in Example 9.6, using 4-pentylbenzaldehyde (Example 45.1; 10 mg, 0.07 mmol) in place of 4-hexyl-2-formylfuran to give APY72 (5.0 mg) as an oily solid containing a mixture of E and Z isomers (2:1): $^1$H NMR (E isomer, 500 MHz, CDCl$_3$, 298 K) δ 7.38 (d, 2H), 7.20 (d, 2H), 6.88 (s, 1H), 6.51-6.41 (m, 1H), 6.25-6.18 (m, 1H), 5.96 (s, 1H), 4.98-4.88 (m, 1H), 3.71 (s, 3H), 2.66-2.58 (m, 3H), 2.20 (d, 3H), 2.09-1.97 (m, 2H), 1.85-1.76 (m, 1H), 1.67-1.59 (m, 3H), 1.37-1.21 (m, 7H), 0.90 (t, 3H); LRMS (ES$^+$) m/z [M+H]$^+$. found 482 (Exact mass=481.25).

Example 46

APY73 Prepared by Method C

Example 46.1

4-isopentylbenzaldehyde

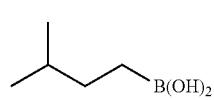

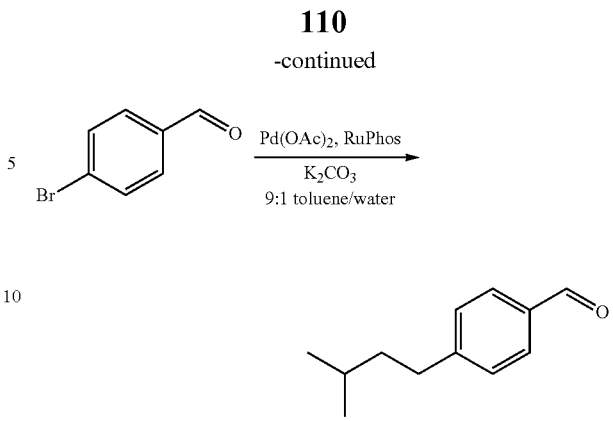

The compound was synthesized as in Example 3.1 using 4-bromobenzaldehyde (250 mg, 1.35 mmol) in place of 5-bromo-2-formylfuran and 4-isopentylboronic acid (259 mg, 2.23 mmol) in place of hexylboronic acid to give 4-isopentylbenzaldehyde (168 mg, 71%). Used without further characterization.

Example 46.2

APY73

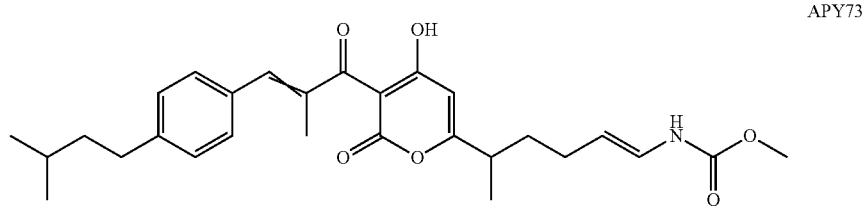 [SMILES: COC(=O)N/C=C/CCC(C)c1cc(O)c(C(=O)C(C)=Cc2ccc(OCC(C)C)cc2)c(=O)o1]

The compound was synthesized as in Example 9.6, using 4-isopentylbenzaldehyde (Example 46.1; 10 mg, 0.07 mmol) in place of 4-hexyl-2-formylfuran to give APY73 (4.0 mg) as an oily solid containing a mixture of E and Z isomers (2:1): $^1$H NMR (E isomer, 500 MHz, CDCl$_3$, 298 K) δ 7.37 (d, 2H), 7.20 (d, 2H), 6.87 (s, 1H), 6.51-6.41 (m, 1H), 6.25-6.18 (m, 1H), 5.96 (s, 1H), 4.98-4.88 (m, 1H), 3.71 (s, 3H), 2.66-2.58 (m, 3H), 2.19 (d, 3 H), 2.09-1.97 (m, 2H), 1.85-1.76 (m, 1H), 1.67-1.59 (m, 2H), 1.55-1.48 (m, 2H), 1.25 (d, 3H), 0.94 (d, 6H); LRMS (ES$^+$) m/z [M+H]$^+$. found 482 (Exact mass=481.25).

Example 47

APY74 Prepared by Method C

Example 47.1

4-(3,3,3-trifluoropropyl)benzaldehyde

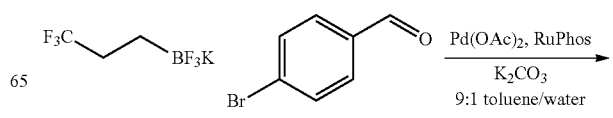

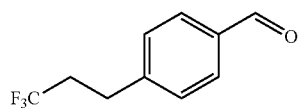

The compound was synthesized as in Example 3.1 using 4-bromobenzaldehyde (250 mg, 1.35 mmol) in place of 5-bromo-2-formylfuran and 3,3,3-trifluoropropyltrifluoroborate (455 mg, 2.23 mmol) in place of hexylboronic acid to give 4-(3,3,3-trifluoropropyl)benzaldehyde (244 mg, 89%). Used without further characterization.

Example 47.2

APY74

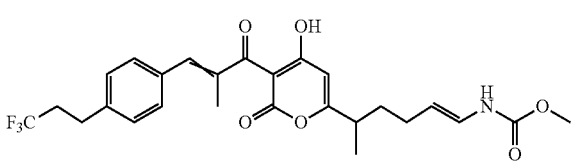

The compound was synthesized as in Example 9.6, using 4-(3,3,3-trifluoropropyl)benzaldehyde (Example 47.1; 10 mg, 0.07 mmol) in place of 4-hexyl-2-formylfuran to give APY74 (4.0 mg) as an oily solid containing a mixture of E and Z isomers (2:1): $^1$H NMR (E isomer, 500 MHz, CDCl$_3$, 298 K) δ 7.40 (d, 2H), 7.22 (d, 2H), 6.83 (s, 1H), 6.50-6.42 (m, 1H), 6.25-6.18 (m, 1H), 5.97 (s, 1H), 4.98-4.88 (m, 1H), 3.71 (s, 3H), 2.91-2.86 (m, 2H), 2.61 (q, 1H), 2.46-2.37 (m, 2H), 2.19 (d, 3H), 2.09-1.97 (m, 2H), 1.85-1.76 (m, 1H), 1.64-1.54 (m, 1H), 1.25 (d, 3H); LRMS (ES$^+$) m/z [M+H]$^+$. found 508 (Exact mass=507.19).

Example 48

APY75 Prepared by Method C

Example 48.1

2-formyl-3-methyl-5-butylthiophene

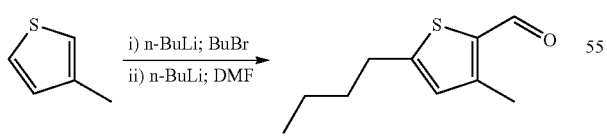

The compound was synthesized as in Example 32.1, using 3-methylthiophene (0.26 mL, 2.74 mmol) in place of thiophene and n-butylbromide (0.31 mL, 2.88 mmol) in place of 1-chloro-3,3-dimethylbutane to give 2-formyl-3-methyl-5-butylthiophene (337 mg, 67%, contaminated with ca. 17% 2-formyl-4-methyl-5-butylthiophene). Used without further characterization.

Example 48.2

APY75

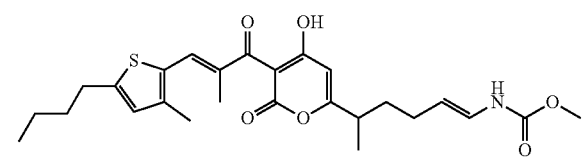

The compound was synthesized as in Example 9.6, using 2-formyl-3-methyl-5-butylthiophene (Example 48.1; 13 mg, 0.084 mmol) in place of 4-hexyl-2-formylfuran to give APY75 (4.2 mg) as an oily solid containing a mixture of regioisomers (3-methyl vs. 4-methyl), each of which is an E/Z mixture that is >19:1 in favor of the E isomer: $^1$H NMR (3-methyl isomer, 500 MHz, CDCl$_3$, 298 K) δ 7.36 (s, 1H), 6.64 (s, 1H), 6.51-6.39 (m, 1H), 6.27-6.19 (m, 1H), 5.95 (s, 1H), 4.99-4.90 (m, 1H), 3.71 (s, 3H), 2.80 (t, 2H), 2.60 (q, 1H), 2.28 (s, 3H), 2.20 (s, 3H), 2.09-2.04 (m, 2H), 1.84-1.77 (m, 1H), 1.68-1.62 (m, 3H), 1.42-1.37 (m, 2H), 1.25 (d, 3H), 0.94 (t, 3H); LRMS (ES$^+$) m/z [M+H]$^+$. found 488 (Exact mass=487.20).

Example 49

APY76 Prepared by Method C

Example 49.1

2-formyl-3-methyl-5-isopentylthiophene

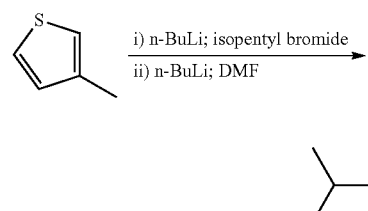 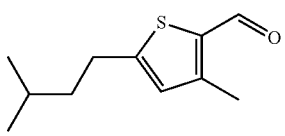

The compound was synthesized as in Example 32.1, using 3-methylthiophene (0.26 mL, 2.74 mmol) in place of thiophene and isopentyl iodide (0.38 mL, 2.88 mmol) in place of 1-chloro-3,3-dimethylbutane to give 2-formyl-3-methyl-5-isopentylthiophene (371 mg, 69%, contaminated with ca. 20% 2-formyl-4-methyl-5-isopentylthiophene). Used without further characterization.

Example 49.2

APY76

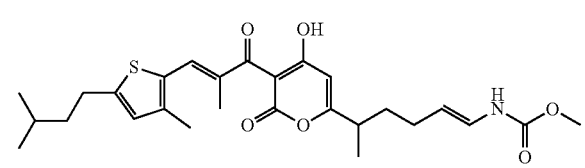

The compound was synthesized as in Example 9.6, using 2-formyl-3-methyl-5-isopentylthiophene (Example 49.1; 16.5 mg, 0.084 mmol) in place of 4-hexyl-2-formylfuran to give APY76 (3.4 mg) as an oily solid containing a mixture of regioisomers (3-methyl vs 4-methyl), each of which is an E/Z mixture that is >19:1 in favor of the E isomer: $^1$H NMR (3-methyl isomer, 500 MHz, CDCl$_3$, 298 K) δ 7.36 (s, 1H), 6.64 (s, 1H), 6.50-6.41 (m, 1H), 6.25-6.19 (m, 1H), 5.95 (s, 1H), 2.81 (t, 2H), 2.61 (q, 1H), 2.28 (s, 3H), 2.21 (s, 3H), 2.07-1.99 (m, 2H), 1.84-1.77 (m, 1H), 1.68-1.59 (m, 4H), 1.25 (d, 3H), 0.94 (d, 6H); LRMS (ES$^+$) m/z [M+H]$^+$. found 502 (Exact mass=501.22).

Example 50

APY81 Prepared by Method C

Example 50.1

5-(4,4,4-trifluorobutyl)thiophene-2-carbaldehyde

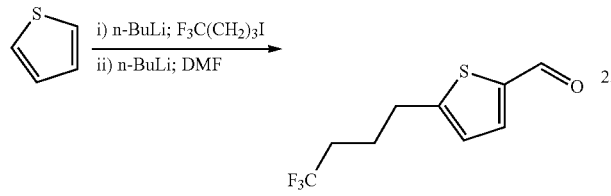

The compound was synthesized as in Example 32.1, using 1,1,1-trifluoro-4-iodobutane (850 mg, 3.57 mmol) in place of 1-chloro-3,3-dimethylbutane to give 5-(4,4,4-trifluorobutyl)thiophene-2-carbaldehyde (167 mg, 21%). Used without further characterization.

Example 50.2

APY81

The compound was synthesized as in Example 9.6, using 5-(4,4,4-trifluorobutyl)thiophene-2-carbaldehyde (Example 50.1; 24 mg, 0.11 mmol) in place of 4-hexyl-2-formylfuran to give APY81 (8.9 mg) as an oily solid containing a mixture of E and Z isomers (11:1): $^1$H NMR (E isomer, 500 MHz, CDCl$_3$, 298 K) δ 15.87 (br s, 1H), 7.19 (s, 1H), 7.11 (d, 1H), 6.82 (d, 1H), 6.51-6.41 (m, 1H), 6.28-6.19 (m, 1H), 5.96 (s, 1H), 3.71 (s, 3H), 2.94 (t, 2H), 2.61 (q, 1H), 2.22 (d, 3H), 2.19-2.08 (m, 2H), 2.06-2.00 (m, 3H), 1.86-1.75 (1H), 1.63-1.52 (2H), 1.25 (d, 3H); LRMS (ES$^+$) m/z [M+H]$^+$. found 528 (Exact mass=527.16).

Example 51

APY82 Prepared by Method C

Example 51.1

5-(6,6,6-trifluorohexyl)thiophene-2-carbaldehyde

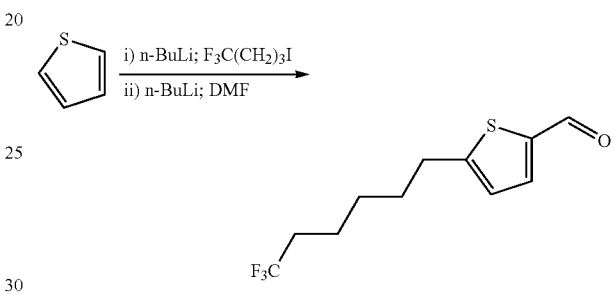

The compound was synthesized as in Example 32.1, using 1,1,1-trifluoro-6-iodohexane (529 mg, 2.38 mmol) in place of 1-chloro-3,3-dimethylbutane to give 5-(6,6,6-trifluorohexyl)thiophene-2-carbaldehyde (197 mg, 33%). Used without further characterization.

Example 51.2

APY82

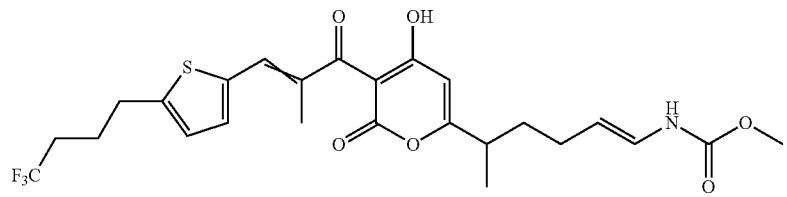

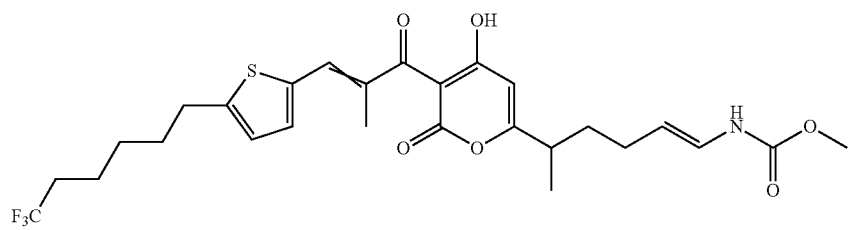

The compound was synthesized as in Example 9.6, using 5-(6,6,6-trifluorohexyl)thiophene-2-carbaldehyde (Example 51.1; 27 mg, 0.11 mmol) in place of 4-hexyl-2-formylfuran to give APY82 (4.2 mg) as an oily solid containing a mixture of E and Z isomers: LRMS (ES+) m/z [M+H]+. found 556 (Exact mass=555.19).

Example 52

APY84 Prepared by Method C

Example 52.1

6-butylbenzofuran-2-carbaldehyde

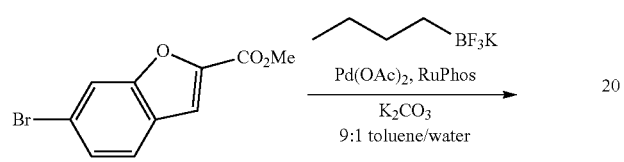

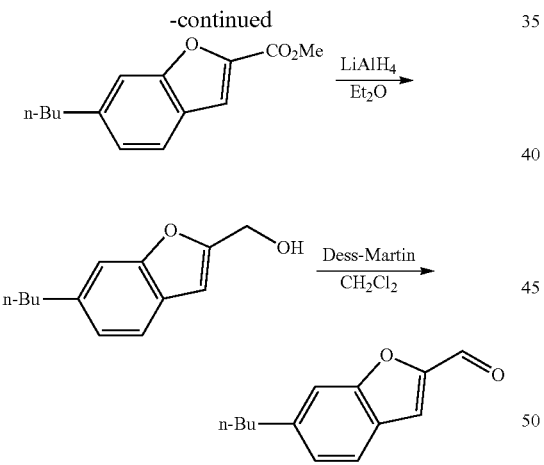

Methyl-6-butylbenzofuran-2-carboxylate was synthesized as in Example 3.1 using methyl-6-bromobenzofuran-2-carboxylate (195 mg, 0.76 mmol) in place of 5-bromo-2-formylfuran and potassium butyltrifluoroborate (188 mg, 1.15 mmol) in place of hexylboronic acid to give methyl-6-butylbenzofuran-2-carboxylate (118 mg, 67%). Used without further characterization.

Methyl-6-butylbenzofuran-2-carboxylate (118 mg, 0.51 mmol) was dissolved in 2 mL of anhydrous ether, flushed with argon and cooled to 0° C. Powdered lithium aluminum hydride (21 mg, 0.56 mmol) was added and the resulting suspension stirred vigorously for 2 h at 0° C. The mixture was poured into 25 mL of 1 N hydrochloric acid and extracted with ether (3×20 mL). The combined ether extracts were dried over magnesium sulfate, filtered and concentrated. The crude mixture was subjected to chromatography on silica gel with gradient elution (5-20% ethyl acetate in hexanes) to give (6-butylbenzofuran-2-yl)methanol (85 mg, 82%) as an oil. Used without further characterization.

To a solution of (6-butylbenzofuran-2-yl)methanol (85 mg, 0.42 mmol) in 1.5 mL dichloromethane at room temperature was added Dess-Martin periodinane (247 mg, 0.58 mmol). The resulting suspension was stirred vigorously for 2 h at room temperature, poured into 20 mL saturated sodium bicarbonate and extracted with dichloromethane (3×15 mL). The combined dichloromethane extracts were dried over magnesium sulfate, filtered and concentrated. The crude mixture was subjected to chromatography on silica gel (5% ethyl acetate in hexanes) to give 6-butylbenzofuran-2-carbaldehyde (81 mg, 96%) as an oil. Used without further characterization.

Example 52.2

APY84

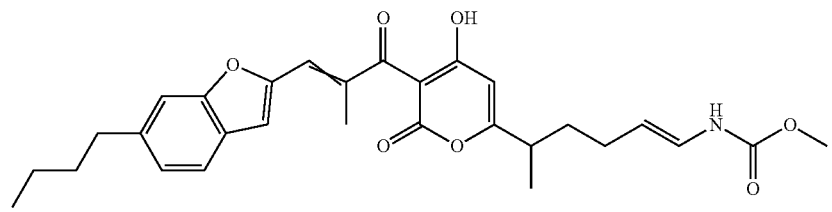

APY84

The compound was synthesized as in Example 9.6, using 6-butylbenzofuran-2-carbaldehyde (Example 52.1; 81 mg, 0.40 mmol) in place of 4-hexyl-2-formylfuran to give APY84 (8.5 mg) as an oily solid containing a mixture of E and Z isomers (6:1): $^1$H NMR (E isomer, 500 MHz, CDCl$_3$, 298 K) δ 7.47 (d, 1H), 7.30 (s, 1H), 7.07 (dd, 1H), 6.87 (s, 2H), 6.51-6.43 (m, 1H), 6.28-6.22 (m, 1H), 5.98 (s, 1H), 4.99-4.91 (m, 1H), 3.71 (s, 3H), 2.73 (t, 2H), 2.66-2.60 (m, 1H), 2.38 (d, 2H), 2.09-1.98 (m, 2H), 1.85-1.77 (m, 1H), 1.69-1.62 (m, 2H), 1.42-1.34 (m, 2H), 1.24 (d, 3H), 0.94 (t, 3H); LRMS (ES+) m/z [M+H]+. found 508 (Exact mass=507.23).

Example 53

APY86 Prepared by Method C

Example 53.1

6-butylbenzothiophene-2-carbaldehyde

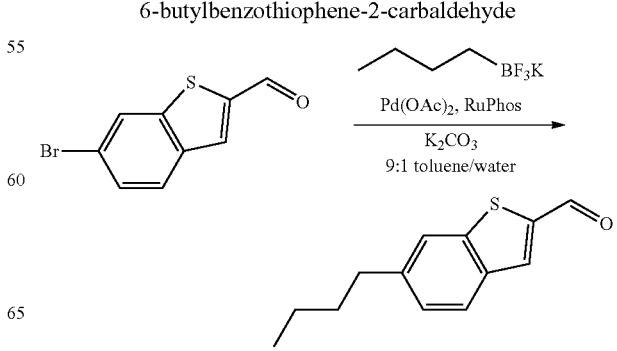

117

The compound was synthesized as in Example 3.1 using 6-bromobenzothiophene-2-carbaldehyde (110 mg, 0.46 mmol) in place of 5-bromo-2-formylfuran and potassium butyltrifluoroborate (113 mg, 0.69 mmol) in place of hexylboronic acid to give 6-butylbenzothiophene-2-carbaldehyde (86 mg, 78%). Used without further characterization.

Example 53.2

APY86

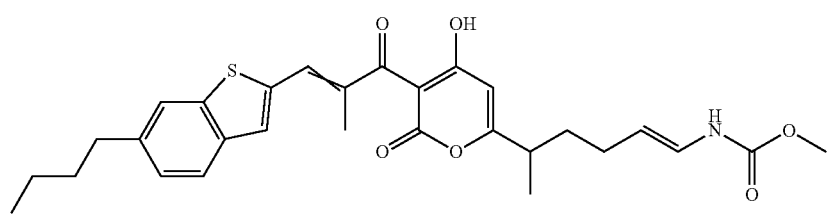

APY86

The compound was synthesized as in Example 9.6, using 6-butylbenzofuran-2-carbaldehyde (Example 53.1; 28 mg, 0.13 mmol) in place of 4-hexyl-2-formylfuran to give APY86 (6.0 mg) as an oily solid containing a mixture of E and Z isomers (6:1): $^1$H NMR (E isomer, 500 MHz, CDCl$_3$, 298 K) δ 7.69 (d, 1H), 7.63 (s, 1H), 7.42 (s, 1H), 7.22 (s, 1H), 7.20 (dd, 1H), 6.52-6.44 (m, 1H), 6.26-6.19 (m, 1H), 5.98 (s, 1H), 4.99-4.91 (m, 1H), 3.71 (s, 3H), 2.73 (t, 2H), 2.64-2.60 (m, 1H), 2.33 (d, 3H), 2.11-1.97 (m, 2H), 1.86-1.76 (m, 1H), 1.66-1.62 (m, 3H), 1.61-1.52 (m, 4H), 1.41-1.35 (m, 2H), 1.26 (d, 3H), 0.94 (t, 3H); LRMS (ES) m/z [M+H]$^+$. found 524 (Exact mass=523.20).

Example 54

APY87 Prepared by Method C

Example 54.1

2-methyl-4-butylbenzaldehyde

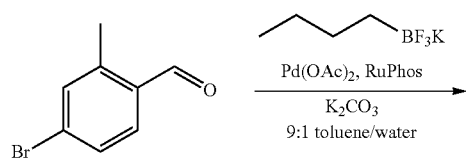

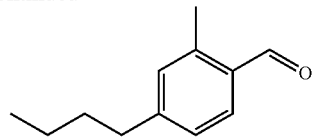

The compound was synthesized as in Example 3.1 using 2-methyl-4-bromobenzaldehyde (113 mg, 0.57 mmol) in place of 5-bromo-2-formylfuran and potassium butyltrifluoroborate (113 mg, 0.69 mmol) in place of hexylboronic acid to give 2-methyl-4-butylbenzaldehyde (34 mg, 35%). Used without further characterization.

Example 54.2

APY87

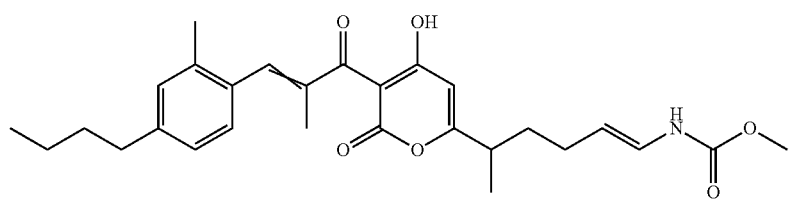

APY87

The compound was synthesized as in Example 9.6, using 2-methyl-4-butylbenzaldehyde (Example 54.1; 34 mg, 0.19 mmol) in place of 4-hexyl-2-formylfuran to give APY87 (2.9 mg) as an oily solid containing a mixture of E and Z isomers (11:1): $^1$H NMR (E isomer, 500 MHz, CDCl$_3$, 298 K) δ 7.24 (s, 1H), 7.02 (s, 2H), 6.88 (s, 1H), 6.51-6.43 (m, 1H), 6.24-6.17 (m, 1H), 5.97 (s, 1H), 4.98-4.86 (m, 1H), 3.71 (s, 3H), 2.60-2.55 (m, 1H), 2.35 (t, 2H), 2.29 (s, 3H), 2.03 (d, 3H), 1.85-1.75 (m, 1H), 1.67-1.46 (m, 5H), 1.30-1.24 (m, 2H), 0.93 (t, 3H), 0.88 (t, 3H); LRMS (ES) m/z [M+H]$^+$. found 482 (Exact mass=481.25).

Example 55

APY90 Prepared by Method C

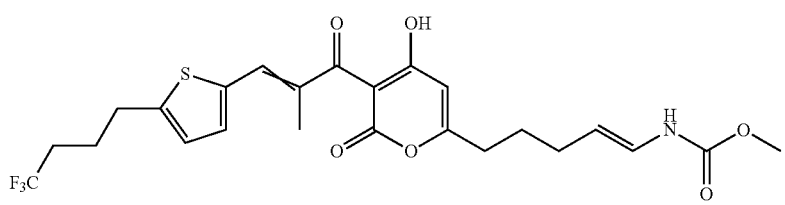

APY90

The compound was synthesized as in Example 9.6, using 5-(4,4,4-trifluorobutyl)thiophene-2-carbaldehyde (Example 50.1; 24 mg, 0.11 mmol) in place of 4-hexyl-2-formylfuran and methyl (E)-(5-(4-hydroxy-2-oxo-3-propionyl-2H-pyran-6-yl)pent-1-en-1-yl)carbamate (20 mg, 0.06 mmol) in place of enecarbamate 11a to give APY90 (4.0 mg) as an oily solid containing a mixture of E and Z isomers (13:1): $^1$H NMR (E isomer, 500 MHz, CDCl$_3$, 298 K) δ 7.20 (s, 1H), 7.11 (d, 1H), 6.82 (d, 1H), 6.53-6.46 (m, 1H), 6.29-6.22, (m, 1H), 5.97 (s, 1H), 5.01-4.90 (m, 1H), 3.72 (s, 3H), 2.94 (t, 2H), 2.50 (t, 2H), 2.21 (d, 3H), 2.19-2.05 (m, 4H), 2.02-1.94 (m, 2H), 1.80-1.71 (m, 2H); LRMS (ES) m/z [M+H]$^+$. found 514 (Exact mass=513.14).

Example 56

APY91 Prepared by Method C

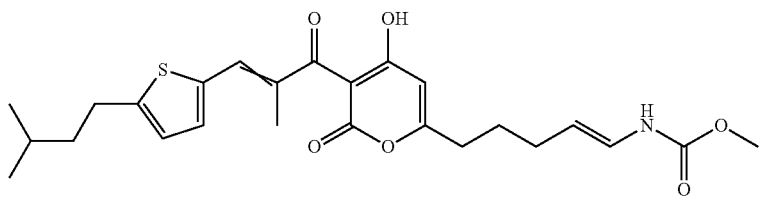

APY91

The compound was synthesized as in Example 9.6, using 5-isopentylthiophene-2-carbaldehyde (Example 13.1; 19 mg, 0.11 mmol) in place of 4-hexyl-2-formylfuran and methyl (E)-(5-(4-hydroxy-2-oxo-3-propionyl-2H-pyran-6-yl)pent-1-en-1-yl)carbamate (20 mg, 0.06 mmol) in place of enecarbamate 11a to give APY91 (3.0 mg) as an oily solid containing a mixture of E and Z isomers: LRMS (ES) m/z [M+H]$^+$. found 474 (Exact mass=473.19).

Example 57

APY94 Prepared by Method C

Example 57.1

5-(3-hydroxypropyl)thiophene-2-carbaldehyde

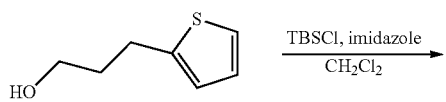

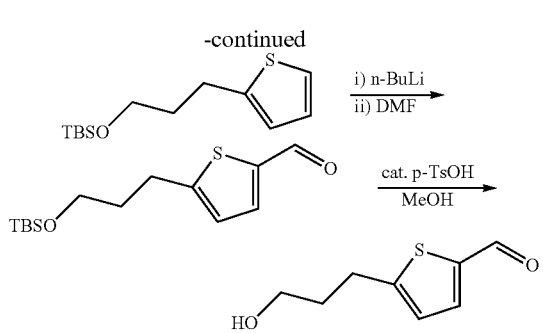

To a solution of 3-(thiophene-2-yl)propanol (500 mg, 3.52 mmol) and imidazole (288 mg, 4.22 mmol) in 9 mL anhydrous dichloromethane was added TBS-Cl (584 mg, 3.87 mmol). The resulting mixture was stirred at room temperature for 30 minutes and poured into 50 mL water. Organics were extracted with ether (2×40 mL), dried over magnesium sulfate, filtered and concentrated. The crude oil was subjected to chromatography on silica gel with gradient elution (1-2% ethyl acetate in hexanes) to give tert-butyldimethyl(3-(thiophen-2-yl)propoxy)silane (787 mg, 87%). Used without further characterization.

To a solution of tert-butyldimethyl(3-(thiophen-2-yl)propoxy)silane (787 mg, 3.07 mmol) in 15 mL 9:1 tetrahydrofuran/hexamethylphosphoramide under argon at −78° C. was added n-butyllithium (1.35 mL, 2.5 M in hexanes) dropwise over 5 minutes. The resulting solution was stirred at −78° C. for 1 h. Dimethylformamide (1.18 mL, 15.35 mmol) was added dropwise and the reaction mixture was allowed to warm to room temperature before being poured into 100 mL of 1 N hydrochloric acid. Organics were extracted with ether (2×75 m), dried over magnesium sulfate, filtered and concentrated to give crude 5-(3-((t-butyldimethylsilyl)oxy)propyl)thiophene-2-carbaldehyde. Used without further purification.

To a solution of crude 5-(3-((t-butyldimethylsilyl)oxy)propyl)thiophene-2-carbaldehyde (ca. 871 mg, 3.06 mmol) in 32 mL of 9:1 methanol/water was added p-tosic acid monohydrate (58 mg, 0.31 mmol). The resulting mixture was stirred at room temperature for 45 minutes and poured into 100 mL water. Organics were extracted with ethyl acetate (2×75 mL) and ether (75 mL), dried over magnesium sulfate, filtered and concentrated. The crude residue was subjected to chromatography on silica gel with gradient elution (20-50% ethyl acetate in hexanes) to give 5-(3-hydroxypropyl)thiophene-2-carbaldehyde (360 mg, 69%).

Example 57.2

APY94

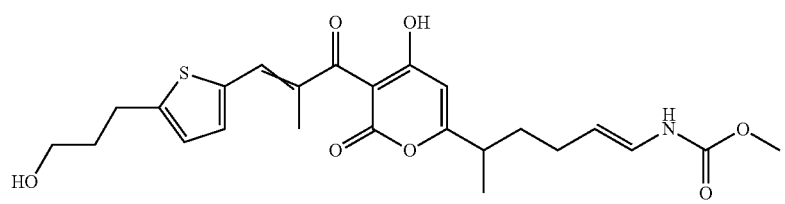

The compound was synthesized as in Example 9.6, using 5-(3-hydroxypropyl)thiophene-2-carbaldehyde (Example 58.1; 15.3 mg, 0.09 mmol) in place of 4-hexyl-2-formylfuran to give APY94 (6.6 mg) as an oily solid containing a mixture of E and Z isomers (10:1): $^1$H NMR (E isomer, 500 MHz, CDCl$_3$, 298 K) δ 7.21 (s, 1H), 7.11 (d, 1H), 6.82 (d, 1H), 6.51-6.42 (m, 1H), 6.27-6.20 (m, 1H), 5.96 (s, 1H), 4.99-4.89 (m, 1H), 3.74-3.71 (m, 5H), 2.97 (t, 2H), 2.63-2.60 (m, 1H), 2.22 (d, 3H), 2.08-1.97 (m, 3H), 1.85-1.76 (m, 1H), 1.63-1.53 (m, 2H), 1.25 (d, 3H); LRMS (ES) m/z [M+H]$^+$. found 476 (Exact mass=475.17).

Example 58

APY95 Prepared by Method C

Example 58.1

5-(2-cyclopropylethyl)thiophene-2-carbaldehyde

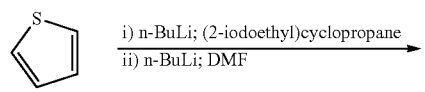

i) n-BuLi; (2-iodoethyl)cyclopropane
ii) n-BuLi; DMF

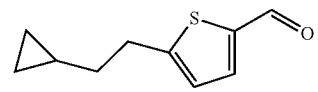

The compound was synthesized as in Example 32.1, using (2-iodoethyl)cyclopropane (323 mg, 1.64 mmol) in place of

APY94

1-chloro-3,3-dimethylbutane to give 5-(2-cyclopropylethyl)thiophene-2-carbaldehyde (142 mg, 50%). Used without further characterization.

Example 58.2

APY95

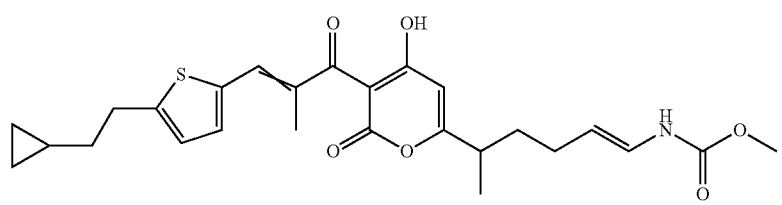

APY95

The compound was synthesized as in Example 9.6, using 5-(3-hydroxypropyl)thiophene-2-carbaldehyde (Example 59.1; 18.4 mg, 0.102 mmol) in place of 4-hexyl-2-formylfuran to give APY95 (7.7 mg) as an oily solid containing a mixture of E and Z isomers: LRMS (ES$^+$) m/z [M+H]$^+$. found 486 (Exact mass=485.19).

Example 59

APY96 Prepared by Method C

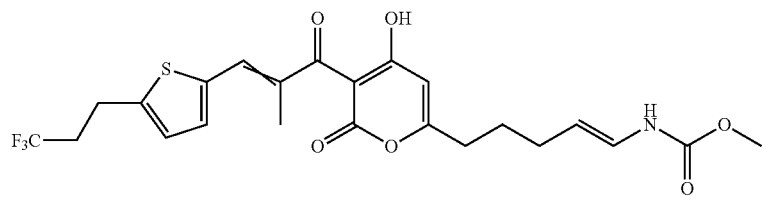
APY96

The compound was synthesized as in Example 9.6, using -(3,3,3-trifluoropropyl)thiophene-2-carbaldehyde (Example 37.1; 33 mg, 0.16 mmol) in place of 4-hexyl-2-formylfuran and methyl (E)-(5-(4-hydroxy-2-oxo-3-propionyl-2H-pyran-6-yl)pent-1-en-1-yl)carbamate (30 mg, 0.10 mmol) in place of enecarbamate 11a to give APY96 (5.0 mg) as an oily solid containing a mixture of E and Z isomers: LRMS (ES+) m/z [M+H]+. found 500 (Exact mass=499.13).

Example 60

APY97 Prepared by Method C

Example 60.1

5-(5-fluoropentyl)thiophene-2-carbaldehyde

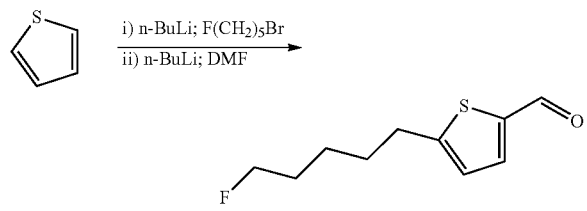

The compound was synthesized as in Example 32.1, using 1-bromo-5-fluoropentane (323 mg, 1.64 mmol) in place of 1-chloro-3,3-dimethylbutane to give 5-(5-fluoropentyl)thiophene-2-carbaldehyde (36 mg, 11%). Used without further characterization.

Example 60.2

APY97

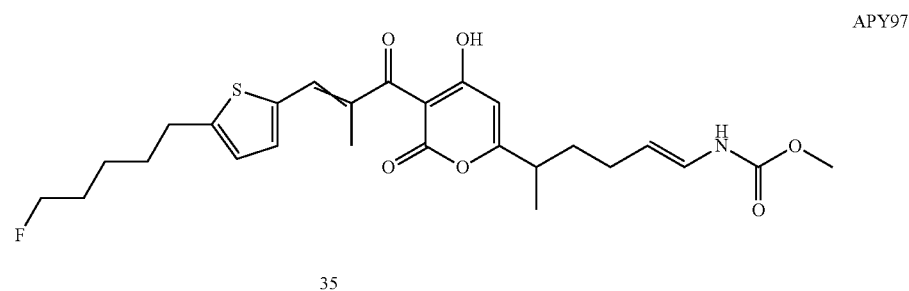
APY97

The compound was synthesized as in Example 9.6, using 5-(5-fluoropentyl)thiophene-2-carbaldehyde (Example 61.1; 22 mg, 0.11 mmol) in place of 4-hexyl-2-formylfuran to give APY97 (8.0 mg) as an oily solid containing a mixture of E and Z isomers: LRMS (ES+) m/z [M+H]+. found 506 (Exact mass=505.19).

Example 61

APY98 Prepared by Method C

Example 61.1

5-(5,5,5-trifluoropentyl)thiophene-2-carbaldehyde

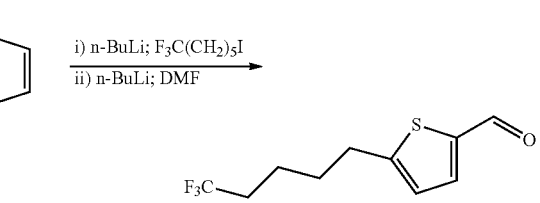

The compound was synthesized as in Example 32.1, using 1-iodo-5,5,5-trifluoropentane (1.05 g, 4.16 mmol) in place of 1-chloro-3,3-dimethylbutane to give 5-(5,5,5-trifluoropentyl)thiophene-2-carbaldehyde (157 mg, 16%). Used without further characterization.

Example 61.2

APY98

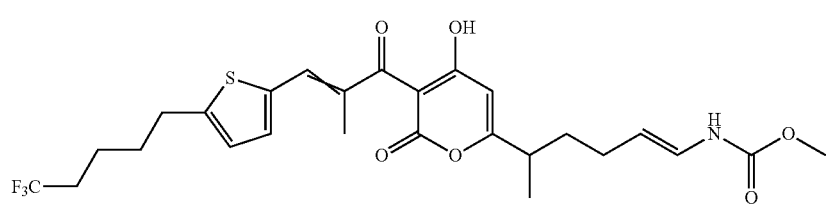
APY98

The compound was synthesized as in Example 9.6, using 5-(5,5,5-trifluoropentyl)thiophene-2-carbaldehyde (Example 62.1; 27 mg, 0.11 mmol) in place of 4-hexyl-2-formylfuran to give APY98 (7.0 mg) as an oily solid containing a mixture of E and Z isomers: LRMS (ES$^+$) m/z [M+H]$^+$. found 506 (Exact mass=541.58).

Example 62

APY100 Prepared by Method C

Example 62.1

5-(3-methoxypropyl)thiophene-2-carbaldehyde

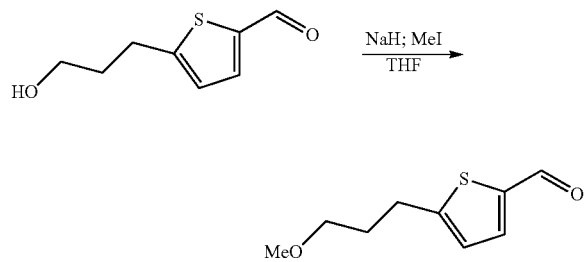

To a solution of 5-(3-hydroxypropyl)thiophene-2-carbaldehyde (Example 58.1; 70 mg, 0.41 mmol) in 1 mL anhydrous tetrahydrofuran under argon at room temperature was added hexanes-rinsed sodium hydride (17 mg of 60% dispersion in oil, 0.45 mmol) as a slurry in 1 mL anhydrous tetrahydrofuran. The resulting suspension was stirred for 15 minutes at room temperature. Methyl iodide (35 μL, 0.57 mmol) was added and the resulting mixture stirred for 2 h at room temperature. The reaction mixture was poured into 30 mL of 0.2 N hydrochloric acid. Organics were extracted with ether (2×30 mL), washed with 5% sodium bisulfite solution, dried over magnesium sulfate, filtered and concentrated. The crude residue was subjected to chromatography on silica gel with gradient elution (8-12% ethyl acetate in hexanes) to give 5-(3-methoxypropyl)thiophene-2-carbaldehyde (17 mg, 23%) as an oil. Used without further characterization.

Example 62.2

APY100

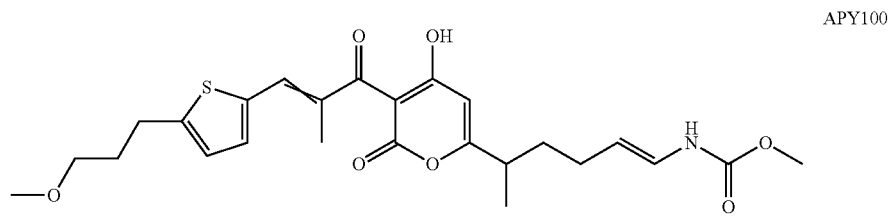
APY100

The compound was synthesized as in Example 9.6, using 5-(3-methoxypropyl)thiophene-2-carbaldehyde (Example 63.1; 17 mg, 0.09 mmol) in place of 4-hexyl-2-formylfuran to give APY100 (7.6 mg) as an oily solid containing a mixture of E and Z isomers: LRMS (ES⁺) m/z [M+H]⁺. found 490 (Exact mass=489.18).

Example 63

APY101 Prepared by Method C

Example 63.1

5-methoxy-2-thiophenecarbaldehyde

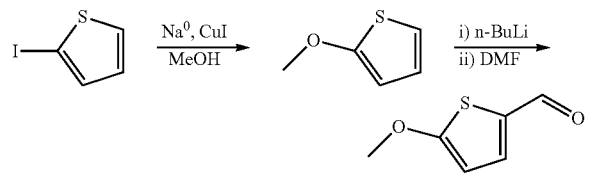

To 3.5 mL anhydrous methanol under argon at 0° C. was added sodium metal (121 mg, 5.26 mmol). The resulting mixture was stirred vigorously until all the sodium metal was consumed, at which point the mixture was removed from the cooling bath. Copper(I) iodide (67 mg, 0.35 mmol) and 2-iodothiophene (736 mg, 3.50 mmol) were added and the resulting suspension heated to 70° C. and stirred vigorously for 6 h. After cooling to room temperature, 7 mL of 0.5 M aqueous potassium cyanide solution was added and the resulting mixture stirred for 15 minutes. Organics were extracted with ether (3×15 mL), dried over magnesium sulfate, filtered and concentrated. The residue was subjected to chromatography on silica gel (100% hexanes) to give 2-methoxythiophene (79 mg, 20%). Used without further characterization.

To a solution of 2-methoxythiophene (79 mg, 0.69 mmol) in 3.5 mL of 9:1 tetrahydrofuran/hexamethylphosphoramide under argon at −78° C. was added n-butyllithium (0.30 mL, 2.5 M in hexanes) dropwise. After stirring at −78° C. for 20 minutes, dimethylformamide (0.27 mL, 3.5 mmol) was added in a single portion and the reaction mixture allowed to warm to room temperature while stirring, before being poured into 25 mL of 1 N hydrochloric acid. Organics were extracted with ether (2×25 mL), dried over magnesium sulfate, filtered and concentrated. The crude residue was subjected to chromatography on silica gel with gradient elution (10-12% ethyl acetate in hexanes) to give 5-methoxy-2-thiophenecarbaldehyde (71 mg, 72%). Used without further characterization.

Example 63.2

APY101

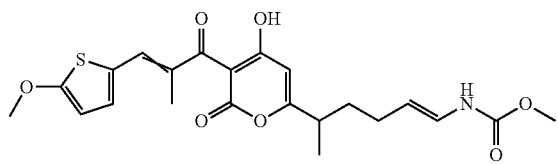

APY101

The compound was synthesized as in Example 9.6, using 5-methoxy-2-thiophenecarbaldehyde (Example 64.1; 19 mg, 0.14 mmol) in place of 4-hexyl-2-formylfuran to give APY101 (2.6 mg) as an oily solid containing a mixture of E and Z isomers (3:1): ¹H NMR (E isomer, 500 MHz, CDCl₃, 298 K) δ 7.21 (s, 1H), 6.99 (d, 1H), 6.51-6.42 (m, 1H), 6.26 (d, 1H), 6.24-6.18 (m, 1H), 5.95 (s, 1H), 4.99-4.91 (m, 1H), 3.95 (s, 3H), 3.71 (s, 3 H), 2.59 (quintet, 1H), 2.17 (d, 3H), 2.10-2.01 (m, 2H), 1.86-1.75 (m, 1H), 1.61-1.52 (m, 1H), 1.25 (t, 3H); LRMS (ES⁺) m/z [M+H]⁺. found 448 (Exact mass=447.14).

Example 64

APY102 Prepared by Method C

Example 64.1

5-ethoxy-2-thiophenecarbaldehyde

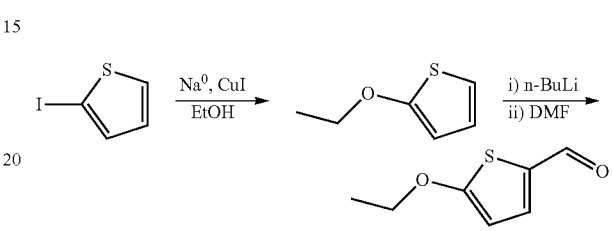

To 8.5 mL absolute ethanol under argon at room temperature was added sodium metal (292 mg, 12.69 mmol). The resulting mixture was stirred vigorously until all the sodium metal was consumed. Copper(I) iodide (322 mg, 1.69 mmol) and 2-iodothiophene (1.78 g, 8.46 mmol) were added and the resulting suspension heated to 75° C. and stirred vigorously for 16 h. After cooling to room temperature, 17 mL of 0.5 M aqueous potassium cyanide solution was added and the resulting mixture stirred for 15 minutes. Water (10 mL) was added and organics were extracted with hexanes (3×35 mL), washed with water (2×20 mL), dried over magnesium sulfate, filtered and concentrated. The residue was subjected to chromatography on silica gel (100% hexanes) to give 2-ethoxythiophene (355 mg, 33%). Used without further characterization.

To a solution of 2-ethoxythiophene (355 mg, 2.77 mmol) in 14 mL of 9:1 tetrahydrofuran/hexamethylphosphoramide under argon at −78° C. was added n-butyllithium (1.22 mL, 2.5 M in hexanes) dropwise over 5 minutes. After stirring at −78° C. for 20 minutes, dimethylformamide (1.07 mL, 13.9 mmol) was added in a single portion and the reaction mixture allowed to warm to room temperature while stirring, before being poured into 60 mL of 1 N hydrochloric acid. Organics were extracted with 1:1 ether/hexanes (2×75 mL), washed with 1 N hydrochloric acid (2×40 mL), water (40 mL) and brine, dried over magnesium sulfate, filtered and concentrated. The crude residue was subjected to chromatography on silica gel with gradient elution (5-7% ethyl acetate in hexanes) to give 5-ethoxy-2-thiophenecarbaldehyde (216 mg, 49%). Used without further characterization.

Example 64.2

APY102

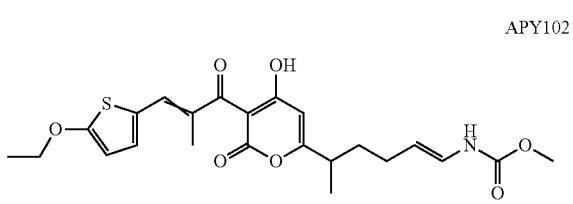 [SMILES: CCOc1ccc(C=C(C)C(=O)c2c(O)cc(C(C)CC/C=C/NC(=O)OC)oc2=O)s1]

APY102

The compound was synthesized as in Example 9.6, using 5-ethoxy-2-thiophenecarbaldehyde (Example 65.1; 28 mg, 0.176 mmol) in place of 4-hexyl-2-formylfuran to give APY102 (7.3 mg) as an oily solid containing a mixture of E and Z isomers: LRMS (ES$^+$) m/z [M+H]$^+$. found 462 (Exact mass=461.15).

Example 65

APY103 Prepared by Method C

Example 65.1

5-propoxy-2-thiophenecarbaldehyde

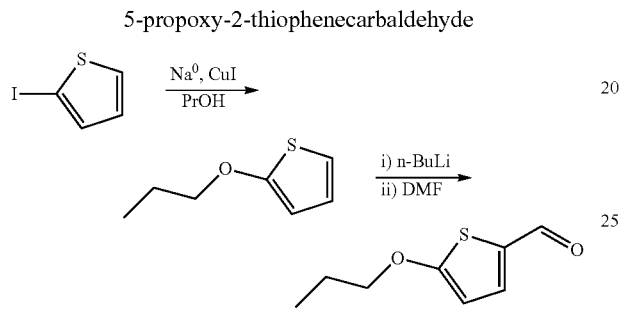

The compound was synthesized as in Example 65.1, using anhydrous n-propanol (8.5 mL) in place of ethanol to give 5-propoxy-2-thiophenecarbaldehyde (290 mg, 20% over two steps).

Example 65.2

APY103

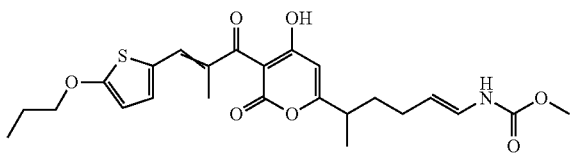

The compound was synthesized as in Example 9.6, using 5-propoxy-2-thiophenecarbaldehyde (Example 66.1; 32 mg, 0.186 mmol) in place of 4-hexyl-2-formylfuran to give APY103 (6.6 mg) as an oily solid containing a mixture of E and Z isomers: LRMS (ES$^+$) m/z [M+H]$^+$. found 476 (Exact mass=475.17).

Example 66

APY104 Prepared by Method C

Example 66.1

5-butyl-1-methyl-1H-indole-2-carbaldehyde

5-Butyl-1H-indole-2-carbaldehyde was synthesized as in Example 3.1 using 5-bromo-1H-indole-2-carbaldehyde (300 mg, 1.34 mmol) in place of 5-bromo-2-formylfuran and potassium butyltrifluoroborate (352 mg, 2.21 mmol) in place of hexylboronic acid to give 5-butyl-1H-indole-2-carbaldehyde (75 mg, 28%). Used without further characterization.

To a solution of 5-butyl-1H-indole-2-carbaldehyde (75 mg, 0.37 mmol) and methyl iodide (57 mg, 0.40 mmol) in 0.75 mL dimethylformamide was added potassium carbonate (57 mg, 0.41 mmol). The resulting suspension was stirred vigorously at 150° C. in a sealed vial under argon for 1 h. Solids were filtered and the liquor concentrated before being subjected to chromatography on silica gel (40% ethyl acetate in hexanes) to give 5-butyl-1-methyl-1H-indole-2-carbaldehyde (15 mg, 18%).

Example 66.2

APY104

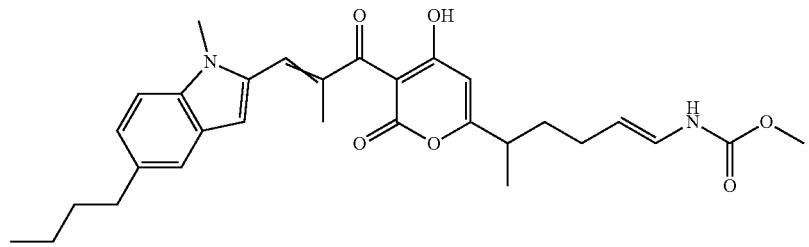

The compound was synthesized as in Example 9.6, using 5-butyl-1-methyl-1H-indole-2-carbaldehyde (Example 67.1; 15 mg, 0.08 mmol) in place of 4-hexyl-2-formylfuran to give APY104 (3.0 mg) as a white solid containing a mixture of E and Z isomers: LRMS (ES⁺) m/z [M+H]⁺. found 521 (Exact mass=520.26).

Example 67

APY105 Prepared by Method C

Example 67.1

5-isopentyl-1-methyl-1H-indole-2-carbaldehyde

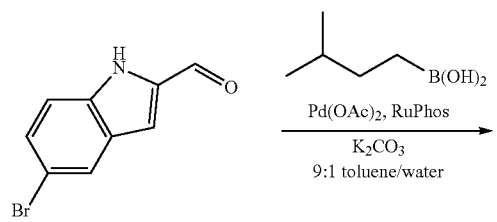

5-Isopentyl-1H-indole-2-carbaldehyde was synthesized as in Example 3.1 using 5-bromo-1H-indole-2-carbaldehyde (300 mg, 1.34 mmol) in place of 5-bromo-2-formylfuran and isopentylboronic acid (256 mg, 2.21 mmol) in place of hexylboronic acid to give 5-isopentyl-1H-indole-2-carbaldehyde (107 mg, 37%). Used without further characterization.

To a solution of 5-isopentyl-1H-indole-2-carbaldehyde (100 mg, 0.46 mmol) and methyl iodide (71 mg, 0.50 mmol) in 0.93 mL dimethylformamide was added potassium carbonate (71 mg, 0.51 mmol). The resulting suspension was stirred vigorously at 150° C. in a sealed vial under argon for 1 h. Solids were filtered and the liquor concentrated before being subjected to chromatography on silica gel (40% ethyl acetate in hexanes) to give 5-isopentyl-1-methyl-1H-indole-2-carbaldehyde (16 mg, 15%).

Example 67.2

APY105

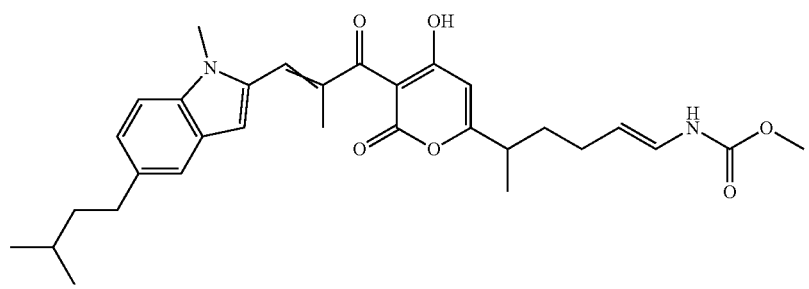

-continued

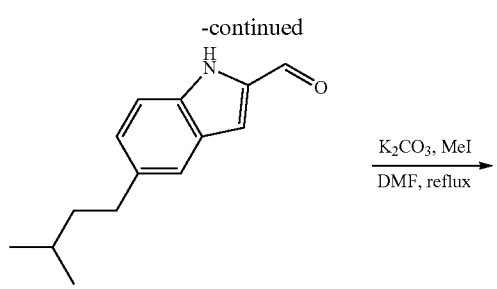

The compound was synthesized as in Example 9.6, using 5-isopentyl-1-methyl-1H-indole-2-carbaldehyde (Example 68.1; 15 mg, 0.08 mmol) in place of 4-hexyl-2-formylfuran to give APY105 (2.0 mg) as a white solid containing a mixture of E and Z isomers: LRMS (ES⁺) m/z [M+H]⁺. found 535 (Exact mass=534.27).

Example 68

APY106 Prepared by Method C

Example 68.1

5-(methoxymethyl)thiophene-2-carbaldehyde

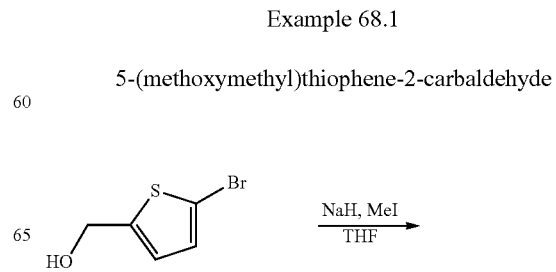

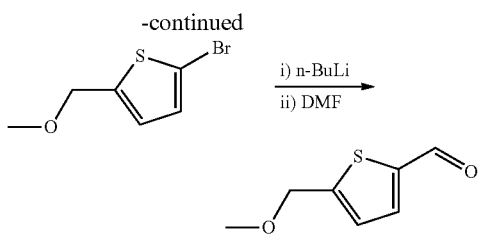

To a solution of (5-bromothiophen-2-yl)methanol (460 mg, 2.38 mmol) in 5 mL anhydrous tetrahydrofuran at room temperature was added carefully hexanes-washed sodium hydride (60% in oil, 143 mg, 3.57 mmol). After stirring at room temperature for 30 minutes, methyl iodide (0.3 mL, 4.76 mmol) was added in a single portion and the reaction mixture stirred for 16 h at room temperature. The reaction mixture was poured into 20 mL of 0.2 N hydrochloric acid. Organics were extracted with 1:1 ether/hexanes (3×25 mL), washed with 30 mL each of 5% aqueous sodium bisulfite solution and brine, dried over magnesium sulfate, filtered and concentrated. The crude residue was subjected to chromatography on silica gel with gradient elution (2-3% ethyl acetate in hexanes) to give 2-bromo-5-(methoxymethyl)thiophene (439 mg, 89%) as an oil. Used without further characterization.

To a solution of 2-bromo-5-(methoxymethyl)thiophene (439 mg, 2.12 mmol) in 6 mL of 9:1 tetrahydrofuran/hexamethylphosphoramide under argon at −78° C. was added n-butyllithium (0.93 mL, 2.5 M in hexanes) dropwise. After stirring for 2 minutes at −78° C., dimethylformamide (0.82 mL, 10.6 mmol) was added in a single portion and the reaction mixture was allowed to warm to room temperature before being poured into 30 mL of 1 N hydrochloric acid. Organics were extracted with 1:1 ether/hexanes (3×30 mL), washed with water (2×30 mL, brine (30 mL), dried over magnesium sulfate, filtered and concentrated. The crude residue was subjected to chromatography on silica gel with gradient elution (5-20% ethyl acetate in hexanes) to give 5-(methoxymethyl)thiophene-2-carbaldehyde (103 mg, 31%) as an oil. Used without further characterization.

Example 68.2

APY106

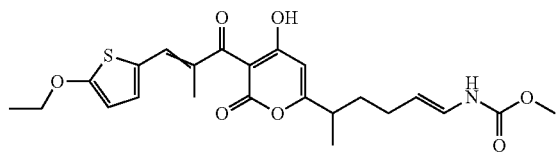

APY106

The compound was synthesized as in Example 9.6, using 5-(methoxymethyl)thiophene-2-carbaldehyde (Example 69.1; 16 mg, 0.102 mmol) in place of 4-hexyl-2-formylfuran to give APY106 (8.6 mg) as a white solid containing a mixture of E and Z isomers: LRMS (ES$^+$) m/z [M+H]$^+$. found 462 (Exact mass=461.15).

Example 69

APY107 Prepared by Method C

Example 69.1

5-isopropoxythiophene-2-carbaldehyde

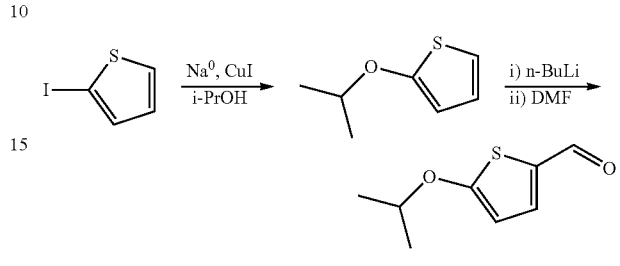

To a mixture of 10 mL anhydrous isopropanol and 5 mL anhydrous tetrahydrofuran under argon at room temperature was added sodium metal (350 mg, 15.22 mmol). The resulting mixture was stirred vigorously at 35° C. until all the sodium metal was consumed (ca. 20 minutes). Copper(I) iodide (386 mg, 2.03 mmol) and 2-iodothiophene (2.13 g, 10.14 mmol) were added and the resulting suspension heated to 90° C. and stirred vigorously for 16 h. After cooling to room temperature, 20 mL of 0.5 M potassium cyanide aqueous solution was added and the resulting mixture stirred for 30 minutes. Organics were extracted with hexanes (2×75 mL), washed with water (3×50 mL) and brine (50 mL), dried over magnesium sulfate, filtered and concentrated. The residue was subjected to chromatography on silica gel (100% hexanes) to give 2-isopropoxythiophene (250 mg, 16%). Used without further characterization.

To a solution of 2-isopropoxythiophene (250 mg, 1.76 mmol) in 9 mL of 9:1 tetrahydrofuran/hexamethylphosphoramide under argon at −78° C. was added n-butyllithium (0.77 mL, 2.5 M in hexanes) dropwise. After stirring at −78° C. for 20 minutes, dimethylformamide (0.68 mL, 8.80 mmol) was added in a single portion and the reaction mixture allowed to warm to room temperature while stirring, before being poured into 30 mL of 1 N hydrochloric acid. Organics were extracted with 1:1 ether/hexanes (2×35 mL), washed with 1 N hydrochloric acid (2×20 mL), water (20 mL) and brine, dried over magnesium sulfate, filtered and concentrated. The crude residue was subjected to chromatography on silica gel (7% ethyl acetate in hexanes) to give 5-isopropoxy-2-thiophenecarbaldehyde (108 mg, 36%). Used without further characterization.

Example 69.2

APY107

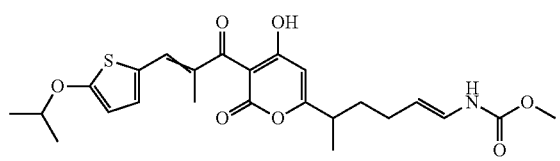

APY107

The compound was synthesized as in Example 9.6, using 5-isopropoxy-2-thiophenecarbaldehyde (Example 70.1; 24 mg, 0.14 mmol) in place of 4-hexyl-2-formylfuran to give APY107 (5.8 mg) as an oily solid containing a mixture of E and Z isomers: LRMS (ES+) m/z [M+H]+. found 476 (Exact mass=475.17).

Example 70

APY108 Prepared by Method C

Example 70.1

5-(ethoxymethyl)thiophene-2-carbaldehyde

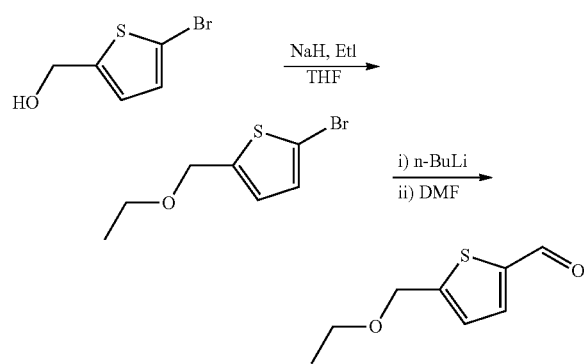

2-Bromo-5-(ethoxymethyl)thiophene was synthesized as in Example 69.1, using ethyl iodide (0.38 mL, 4.76 mmol) in place of methyl iodide to give 2-bromo-5-(ethoxymethyl) thiophene (430 mg, 82%) as an oil. Used without further characterization.

2-Bromo-5-(ethoxymethyl)thiophene-2-carbaldehyde was synthesized as in Example 69.1 to give 5-(ethoxymethyl) thiophene-2-carbaldehyde (101 mg, 32%) as an oil.

Example 70.2

APY108

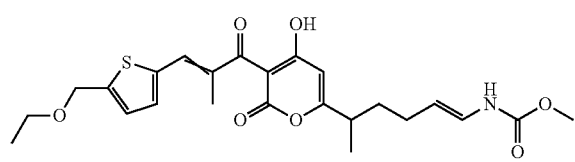

The compound was synthesized as in Example 9.6, using 5-(ethoxymethyl)thiophene-2-carbaldehyde (Example 71.1; 13.4 mg, 0.08 mmol) in place of 4-hexyl-2-formylfuran to give APY108 (12.4 mg) as an oily solid containing a mixture of E and Z isomers: LRMS (ES+) m/z [M+H]+. found 476 (Exact mass=475.17).

Example 71

APY109 Prepared by Method C

Example 71.1

5-(propoxymethyl)thiophene-2-carbaldehyde

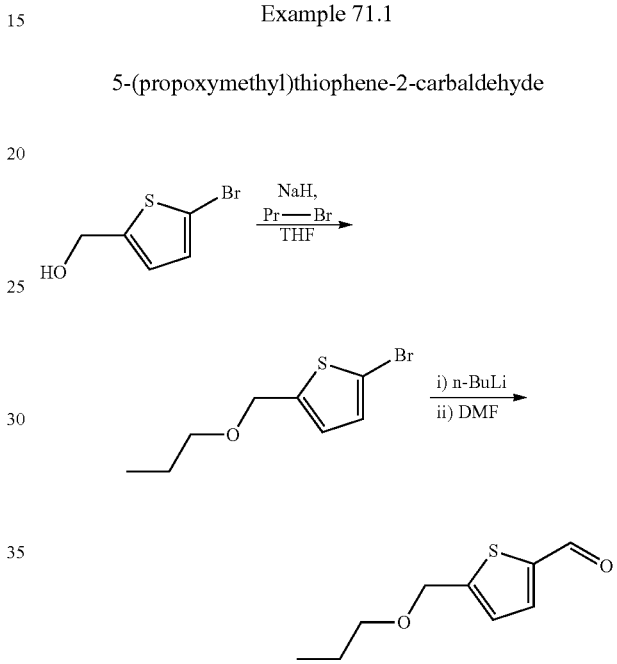

2-Bromo-5-(propoxymethyl)thiophene was synthesized as in Example 69.1, using propyl bromide (0.43 mL, 4.76 mmol) in place of methyl iodide to give 2-bromo-5-(propoxymethyl) thiophene (157 mg, 28%) as an oil. Used without further characterization.

2-Bromo-5-(propoxymethyl)thiophene-2-carbaldehyde was synthesized as in Example 69.1 to give 5-(propoxymethyl)thiophene-2-carbaldehyde (13 mg, 11%) as an oil.

Example 71.2

APY109

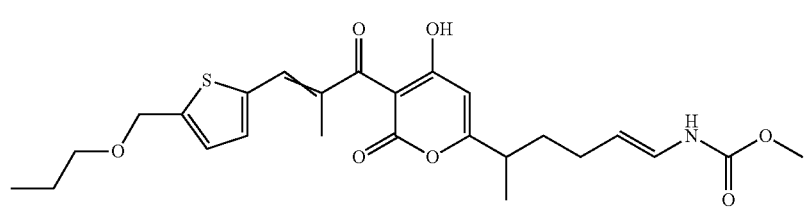

The compound was synthesized as in Example 9.6, using 5-(propoxymethyl)thiophene-2-carbaldehyde (Example 72.1; 13 mg, 0.071 mmol) in place of 4-hexyl-2-formylfuran to give APY109 (11.1 mg) as an oily solid containing a mixture of E and Z isomers: LRMS (ES⁺) m/z [M+H]⁺. found 490 (Exact mass=489.18).

Example 72

APY110 Prepared by Method C

Example 72.1

6-ethylbenzofuran-2-carbaldehyde

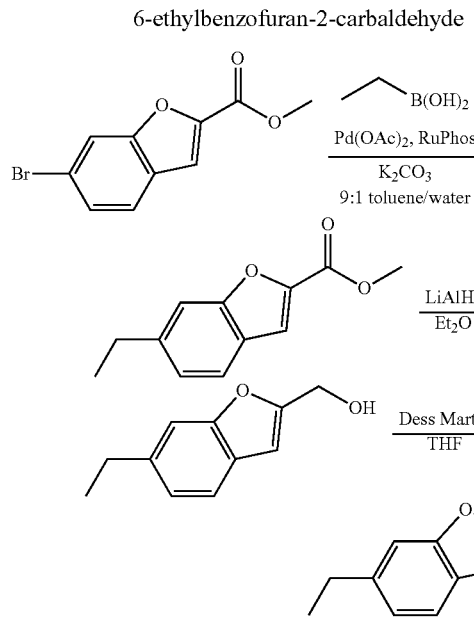

Methyl-6-ethylbenzofuran-2-carboxylate (71 mg, 96%) was synthesized as in Example 52.1, using ethylboronic acid (64 mg, 0.86 mmol) in place of potassium butyltrifluoroborate. Used without further characterization.

(6-Ethylbenzofuran-2-yl)methanol (61 mg, 91%) was synthesized as in Example 52.1, using methyl-6-ethylbenzofuran-2-carboxylate (71 mg, 0.35 mmol) in place of methyl-6-butylbenzofuran-2-carboxylate. Used without further characterization.

6-Ethylbenzofuran-2-carbaldehyde (51 mg, 86%) was synthesized as in Example 52.1, using (6-ethylbenzofuran-2-yl)methanol (61 mg, 0.34 mmol) in place of (6-butylbenzofuran-2-yl)methanol. Used without further characterization.

Example 72.2

APY110

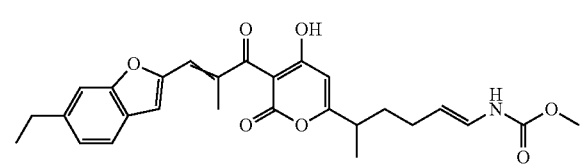

The compound was synthesized as in Example 9.6, using 6-ethylbenzofuran-2-carbaldehyde (Example 73.1; 13 mg, 0.08 mmol) in place of 4-hexyl-2-formylfuran to give APY110 (9.0 mg) as an oily solid containing a mixture of E and Z isomers: LRMS (ES⁺) m/z [M+H]⁺. found 480 (Exact mass=479.19).

Example 73

APY111 Prepared by Method C

Example 73.1

6-isopentylbenzofuran-2-carbaldehyde

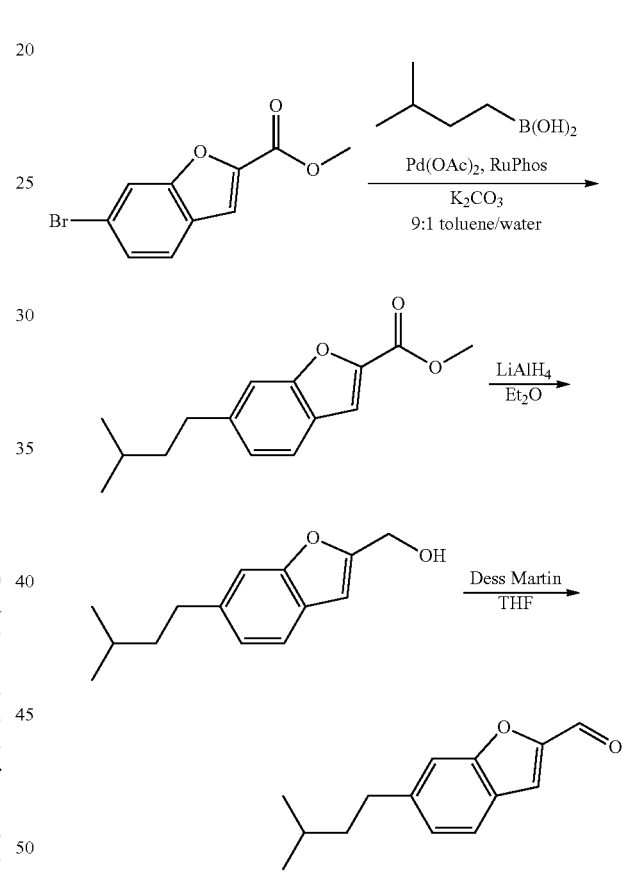

Methyl-6-isopentylbenzofuran-2-carboxylate (68 mg, 82%) was synthesized as in Example 52.1, using isopentylboronic acid (100 mg, 0.86 mmol) in place of potassium butyltrifluoroborate. Used without further characterization.

(6-isopentylbenzofuran-2-yl)methanol (63 mg, 98%) was synthesized as in Example 52.1, using methyl-6-isopentylbenzofuran-2-carboxylate (68 mg, 0.28 mmol) in place of methyl-6-butylbenzofuran-2-carboxylate. Used without further characterization.

6-Isopentylbenzofuran-2-carbaldehyde (51 mg, 81%) was synthesized as in Example 52.1, using (6-isopentylbenzofuran-2-yl)methanol (63 mg, 0.31 mmol) in place of (6-butylbenzofuran-2-yl)methanol. Used without further characterization.

Example 73.2

APY111

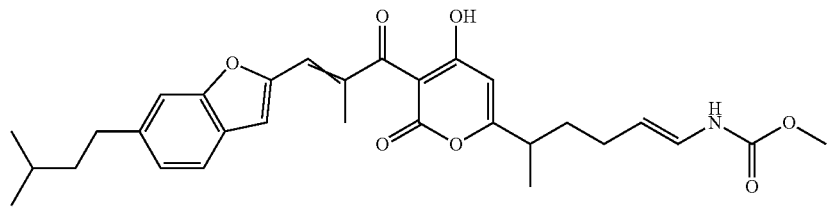

APY111

The compound was synthesized as in Example 9.6, using 6-isopentylbenzofuran-2-carbaldehyde (Example 74.1; 17 mg, 0.08 mmol) in place of 4-hexyl-2-formylfuran to give APY111 (8.0 mg) as an oily solid containing a mixture of E and Z isomers: LRMS (ES⁺) m/z [M+H]⁺. found 522 (Exact mass=521.24).

Example 74

APY112 Prepared by Method C

Example 74.1

6-(3,3,3-trifluoropropyl)benzofuran-2-carbaldehyde

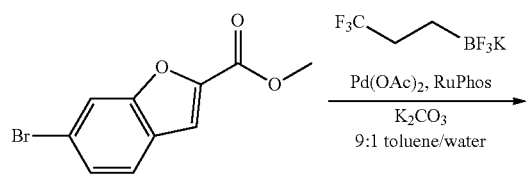

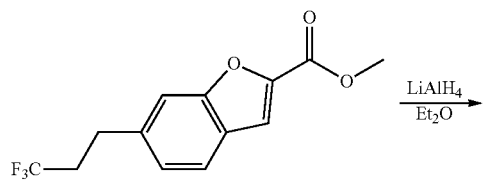

-continued

Methyl-6-(3,3,3-trifluoropropyl)benzofuran-2-carboxylate (112 mg, 79%) was synthesized as in Example 52.1, using potassium (3,3,3-trifluoropropyl)trifluoroborate (175 mg, 0.86 mmol) in place of potassium butyltrifluoroborate. Used without further characterization.

(6-(3,3,3-trifluoropropyl)benzofuran-2-yl)methanol (69 mg, 91%) was synthesized as in Example 52.1, using methyl-6-(3,3,3-trifluoropropyl)benzofuran-2-carboxylate (77 mg, 0.32 mmol) in place of methyl-6-butylbenzofuran-2-carboxylate. Used without further characterization.

6-(3,3,3-trifluoropropyl)benzofuran-2-carbaldehyde (56 mg, 74%) was synthesized as in Example 52.1, using (6-(3,3,3-trifluoropropyl)benzofuran-2-yl)methanol (77 mg, 0.32 mmol) in place of (6-butylbenzofuran-2-yl)methanol. Used without further characterization.

Example 74.2

APY112

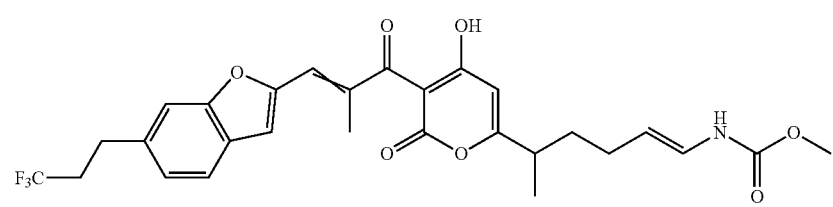

APY112

The compound was synthesized as in Example 9.6, using 6-(3,3,3-trifluoropropyl)benzofuran-2-carbaldehyde (Example 75.1; 17 mg, 0.08 mmol) in place of 4-hexyl-2-formylfuran to give APY112 (4.0 mg) as an oily solid containing a mixture of E and Z isomers: LRMS (ES⁺) m/z [M+H]⁺. found 548 (Exact mass=547.18).

Example 75

APY114 Prepared by Method C

Example 75.1

6-(3,3,3-trifluoropropyl)benzothiophene-2-carbaldehyde

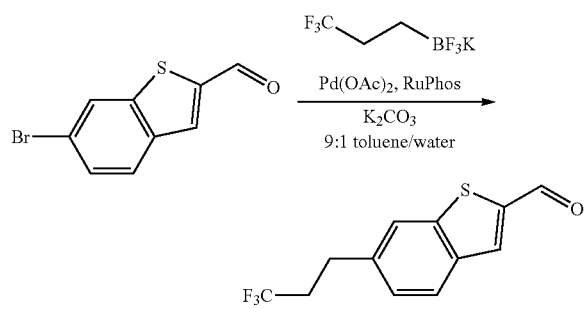

The compound was synthesized as in Example 3.1 using 6-bromobenzothiophene-2-carbaldehyde (50 mg, 0.21 mmol) in place of 5-bromo-2-formylfuran and potassium (3,3,3-trifluoro)propyltrifluoroborate (63 mg, 0.31 mmol) in place of hexylboronic acid to give 6-(3,3,3-trifluoropropyl)benzothiophene-2-carbaldehyde (43 mg, 80%). Used without further characterization.

Example 75.2

APY114

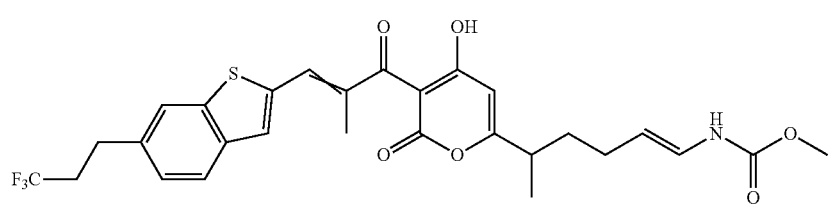

The compound was synthesized as in Example 9.6, using 6-(3,3,3-trifluoropropyl)benzothiophene-2-carbaldehyde (Example 77.1; 19 mg, 0.08 mmol) in place of 4-hexyl-2-formylfuran to give APY114 (5.0 mg) as an oily solid containing a mixture of E and Z isomers: LRMS (ES⁺) m/z [M+H]⁺. found 564 (Exact mass=563.16).

Example 76

APY116 Prepared by Method C

Example 76.1

5-(2,2,2-trifluoroethoxy)thiophene-2-carbaldehyde

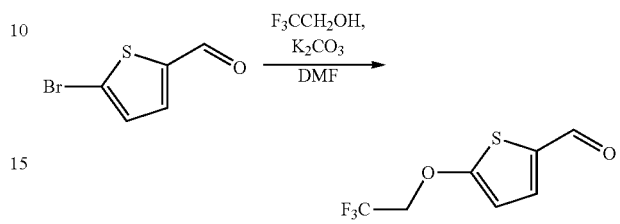

To a solution of 5-bromothiophene-2-carbaldehyde (909 mg, 4.76 mmol) and trifluoroethanol (0.69 mL, 9.52 mmol) in 10 mL dimethylformamide was added potassium carbonate (1.38 g, 10.00 mmol). The resulting suspension was stirred at 100° C. for 20 h before being cooled to room temperature and poured into 50 mL water. Organics were extracted with ether (3×50 mL), washed with water and brine (50 mL each), dried over magnesium sulfate, filtered and concentrated. The crude residue was subjected to chromatography on silica gel with gradient elution (10-20% ethyl acetate in hexanes) to give 5-(2,2,2-trifluoroethoxyl)thiophene-2-carbaldehyde (664 mg, 66%) as an off-white solid. Used without further characterization.

Example 76.2

APY116

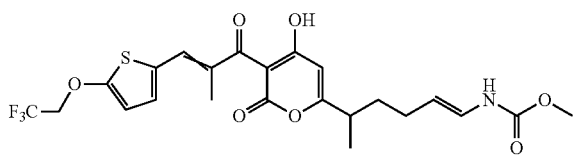

The compound was synthesized as in Example 9.6, using 5-(2,2,2-trifluoroethoxyl)thiophene-2-carbaldehyde (Example 78.1; 49 mg, 0.23 mmol) in place of 4-hexyl-2-formylfuran and isopropanol in place of methanol to give APY116 (5.8 mg) as an oily solid containing a mixture of E and Z isomers: LRMS (ES⁺) m/z [M+H]⁺. found 516 (Exact mass=515.12).

Example 77

APY117 Prepared by Method C

Example 77.1

4-(2,2,2-trifluoroethoxyl)benzaldehyde

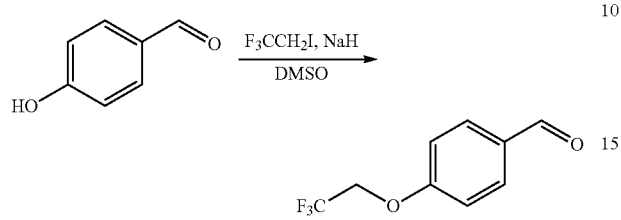

To sodium hydride (60% in oil, 240 mg, 6.0 mmol) 0° C. was added 2 mL anhydrous dimethylsulfoxide. The resulting suspension was stirred for 15 minutes at 0° C. 4-Hydroxybenzaldehyde (610 mg, 5.0 mmol) was added dropwise as a solution in 2 mL dimethylsulfoxide and the resulting mixture stirred for 30 minutes at 0° C. Trifluoroethyl iodide (1.5 mL, 15.24 mmol) was added and the reaction mixture was heated to 55° C. for 24 h. The reaction mixture was cooled to room temperature and poured into water. Organics were extracted with ether (3×50 mL), dried with magnesium sulfate, filtered and concentrated. The crude residue was subjected to chromatography on silica gel (20% ethyl acetate in hexanes) to give 4-(2,2,2-trifluoroethoxyl)benzaldehyde (250 mg, 24%) as an oil. Used without further characterization.

Example 77.2

APY117

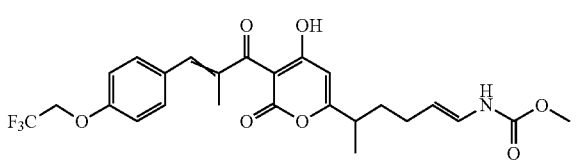

The compound was synthesized as in Example 9.6, using 4-(2,2,2-trifluoroethoxyl)benzaldehyde (Example 79.1; 15 mg, 0.075 mmol) in place of 4-hexyl-2-formylfuran to give APY117 (7.0 mg) as an oily solid containing a mixture of E and Z isomers: LRMS (ES) m/z [M+H]$^+$. found 510 (Exact mass=509.17).

Example 78

APY119 Prepared by Method C

Example 78.1

5-(4-(trifluoromethyl)phenoxy)thiophene-2-carbaldehyde

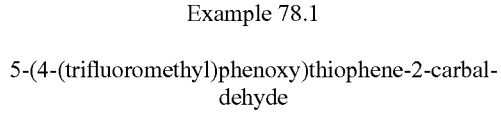

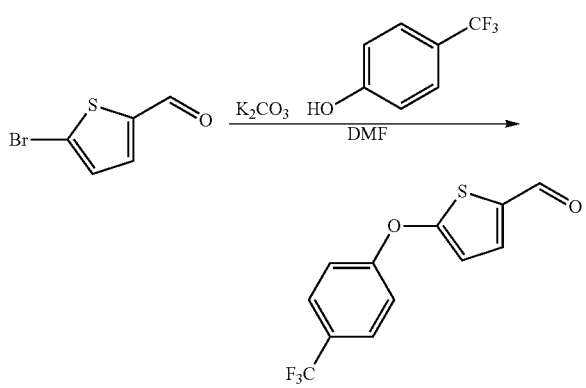

To a solution of 5-bromothiophene-2-carbaldehyde (0.12 mL, 1.0 mmol) and 4-trifluoromethylphenol (195 mg, 1.20 mmol) in 3 mL dimethylformamide was added potassium carbonate (276 mg, 2.00 mmol). The resulting suspension was stirred at 100° C. for 68 h before being cooled to room temperature and poured into 20 mL 0.2 N hydrochloric acid. Organics were extracted with ether (3×25 mL), washed with 2 N NaOH (2×30 mL), 0.2 N hydrochloric acid and brine (30 mL each), dried over magnesium sulfate, filtered and concentrated. The crude residue was subjected to chromatography on silica gel with gradient elution (5-10% ethyl acetate in hexanes+2% triethylamine) to give 5-(4-(trifluoromethyl)phenoxy)thiophene-2-carbaldehyde (79 mg, 29%) as an off-white solid. Used without further characterization.

Example 78.2

APY119

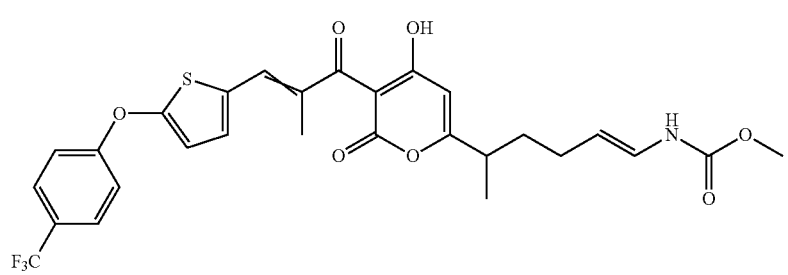

The compound was synthesized as in Example 9.6, using 5-(2,2,2-trifluoroethoxyl)thiophene-2-carbaldehyde (Example 80.1; 30 mg, 0.11 mmol) in place of 4-hexyl-2-formylfuran and isopropanol in place of methanol to give APY119 (10.1 mg) as an oily solid containing a mixture of E and Z isomers: LRMS (ES) m/z [M+H]$^+$. found 578 (Exact mass=577.14).

Example 79

APY120 Prepared by Method C

Example 79.1

4-bromo-5-isobutylthiophene-2-carbaldehyde

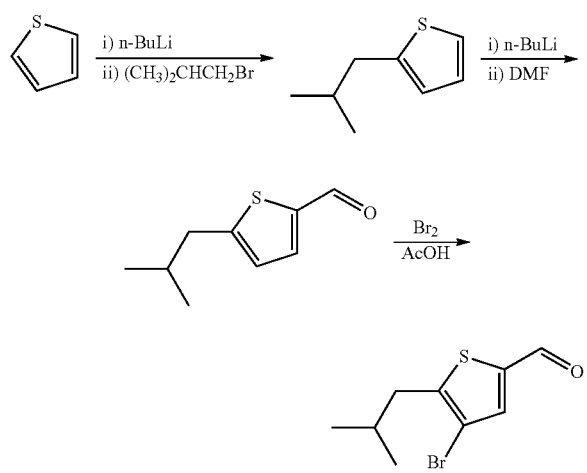

To a solution of thiophene (1.12 mL, 14.26 mmol) in 35 mL of 9:1 tetrahydrofuran/hexamethylphosphoramide under argon at −78° C. was added n-butyllithium (6.28 mL, 2.5 M in hexanes) and the resulting solution stirred at −78° C. for 20 minutes. Isobutylbromide (1.63 mL, 15.00 mmol) was added dropwise and the resulting solution stirred while warming to room temperature over 2 h before being poured into 100 mL 1 N hydrochloric acid. Organics were extracted with hexanes (3×100 mL), washed with 0.1 N hydrochloric acid (3×50 mL), water and brine (50 mL each), dried with magnesium sulfate, filtered and concentrated to give crude 2-isobutylthiophene. Used without further purification or characterization.

5-Isobutylthiophene-2-carbaldehyde (192 mg, 16% over two steps) was synthesized as in Example 70.1, using 2-isobutylthiophene in place of 2-isopropoxythiophene.

To a solution of 5-isobutylthiophene-2-carbaldehyde (192 mg, 1.14 mmol) in 3 mL acetic acid at room temperature was added bromine (0.07 mL, 1.36 mmol). The resulting solution was stirred at room temperature in the dark for 48 h before being poured into 35 mL saturated sodium bicarbonate. Organics were extracted with ether (2×30 mL), dried with magnesium sulfate, filtered and concentrated. The crude residue was subjected to chromatography on silica gel (5% ethyl acetate in hexanes) to give 4-bromo-5-isobutylthiophene-2-carbaldehyde (147 mg, 52%). Used without further purification or characterization.

Example 79.2

APY120

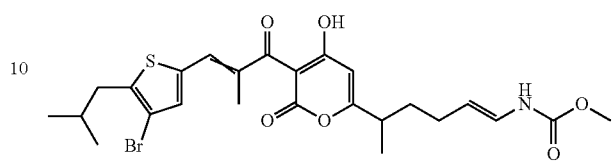

The compound was synthesized as in Example 9.6, using 4-bromo-5-isobutylthiophene-2-carbaldehyde (Example 81.1; 16.7 mg, 0.068 mmol) in place of 4-hexyl-2-formylfuran and isopropanol in place of methanol to give APY120 (6.7 mg) as an oily solid containing a mixture of E and Z isomers: LRMS (ES$^+$) m/z [M+H]$^+$. found 552 (Exact mass=551.10).

Example 80

APY121 Prepared by Method C

Example 80.1

1-methyl-5-propoxy-1H-indole-2-carbaldehyde

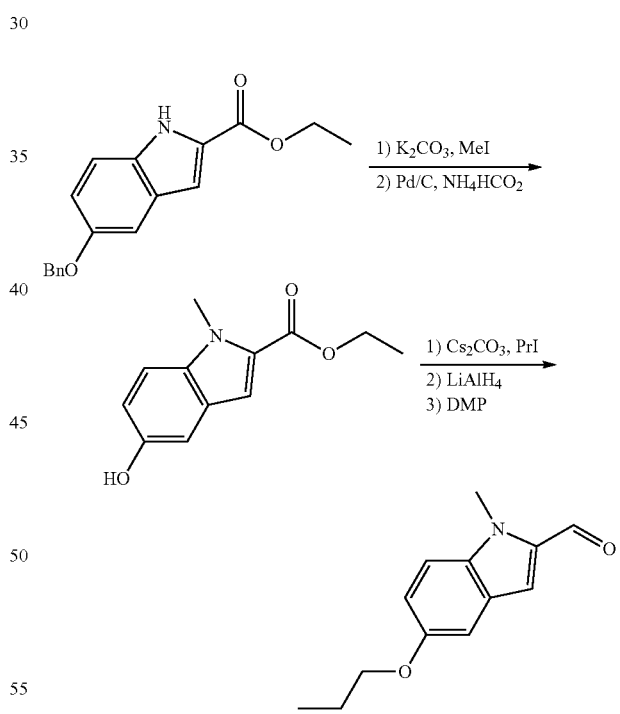

To a solution of ethyl 5-(benzyloxy)-1H-indole-2-carboxylate (5.00 g, 16.93 mmol) and methyl iodide (1.14 mL, 18.28) in 17 mL dimethylformamide was added potassium carbonate (2.57 g, 18.62 mmol). The resulting suspension was stirred for 2 h at 150° C. in a sealed reaction vessel. Solids were filtered and the liquor concentrated to give crude ethyl 5-(benzyloxy)-1-methyl-1H-indole-2-carboxylate. Used without further purification or characterization.

A mixture of crude ethyl 5-(benzyloxy)-1-methyl-1H-indole-2-carboxylate (1.07 g, 3.46 mmol), 10% palladium on carbon (500 mg, 0.47 mmol) and ammonium formate (1.09 g, 17.29 mmol) in 50 mL ethanol was sparged with argon three times and heated at reflux for 1 h. The mixture was cooled, diluted with 100 mL ethanol and filtered through Celite, washed with ethanol and concentrated to give ethyl 5-hydroxy-1-methyl-1H-indole-2-carboxylate (1.82 g, 49% over two steps).

A mixture of ethyl 5-hydroxy-1-methyl-1H-indole-2-carboxylate (103 mg, 0.47 mmol), propyl iodide (141 mg, 0.56 mmol) and cesium carbonate (230 mg, 0.70 mmol) in 1 mL dimethylformamide was stirred vigorously at 100° C. in a sealed vessel for 16 h. After cooling to room temperature, solids were filtered and the liquor concentrated. The crude residue was subjected to chromatography on silica gel with gradient elution (20-40% ethyl acetate in hexanes) to give ethyl 1-methyl-5-propoxy-1H-indole-2-carboxylate (96 mg, 55%). Used without further characterization.

1-Methyl-5-propoxy-1H-indole-2-carbaldehyde (60 mg, 75% over two steps) was synthesized by the same reduction/oxidation sequence as in Example 52.1, using ethyl 1-methyl-5-propoxy-1H-indole-2-carboxylate (96 mg, 0.37 mmol) in place of methyl-6-butylbenzofuran-2-carboxylate, and (1-methyl-5-propoxy-1H-indol-2-yl)methanol (60 mg, 0.27 mmol) in place of (6-butylbenzofuran-2-yl)methanol.

Example 80.2

APY121

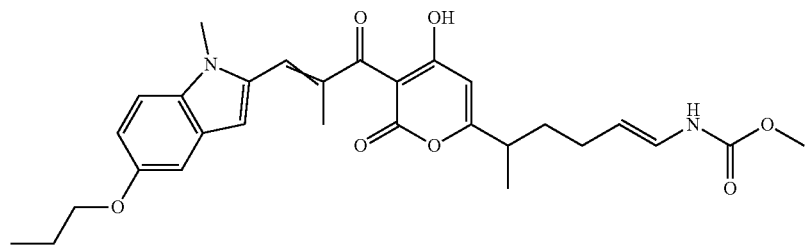

The compound was synthesized as in Example 9.6, using 1-methyl-5-propoxy-1H-indole-2-carbaldehyde (Example 82.1; 13 mg, 0.06 mmol) in place of 4-hexyl-2-formylfuran to give APY121 (1.5 mg) as an off-white solid containing a mixture of E and Z isomers: LRMS (ES) m/z [M+H]$^+$. found 523 (Exact mass=522.24).

Example 81

APY122 Prepared by Method C

Example 81.1

5-(sec-butoxy)-1-methyl-1H-indole-2-carbaldehyde

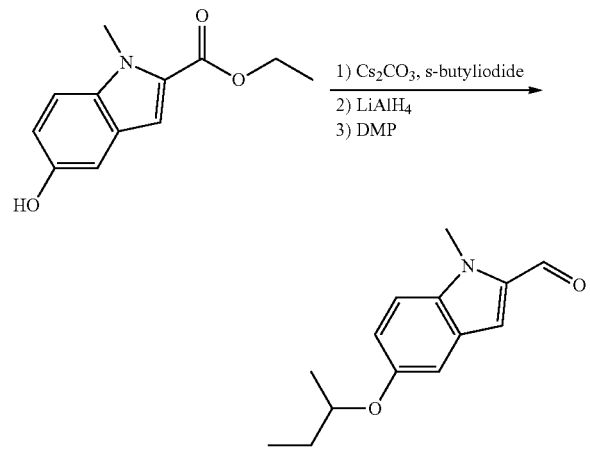

The compound was synthesized by the same sequence of alkylation, reduction and oxidation as in Example 82.1 to give 5-(sec-butoxy)-1-methyl-1H-indole-2-carbaldehyde (49 mg, 40% over three steps). Used without further characterization.

Example 81.2

APY122

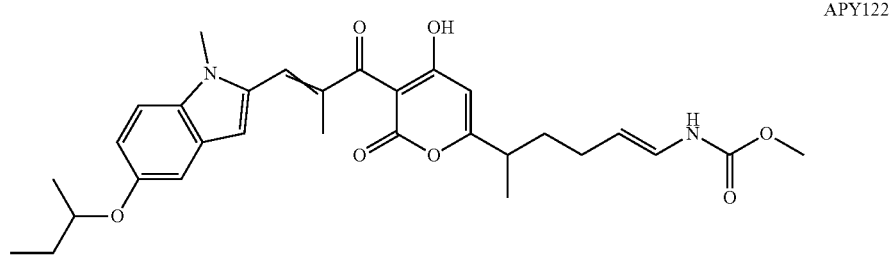 [SMILES: CCC(C)Oc1ccc2c(c1)cc(C=C(C)C(=O)c1c(O)cc(C(C)CC/C=C/NC(=O)OC)oc1=O)n2C]

The compound was synthesized as in Example 9.6, using 1-methyl-5-(sec-butoxy)-1H-indole-2-carbaldehyde (Example 83.1; 13 mg, 0.06 mmol) in place of 4-hexyl-2-formylfuran to give APY122 (1.2 mg) as an off-white solid containing a mixture of E and Z isomers: LRMS (ES) m/z [M+H]+. found 537 (Exact mass=536.25).

Example 82

APY123 Prepared by Method C

Example 82.1

5-isopropoxy-1-methyl-1H-indole-2-carbaldehyde

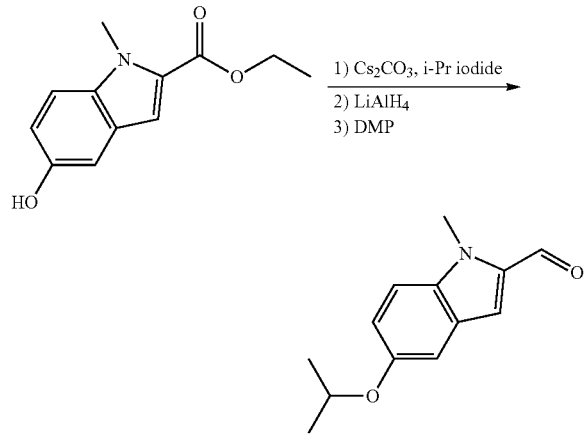

The compound was synthesized by the same sequence of alkylation, reduction and oxidation as in Example 82.1 to give 5-(isopropoxy)-1-methyl-1H-indole-2-carbaldehyde (49 mg, 60% over three steps). Used without further characterization.

Example 82.2

APY123

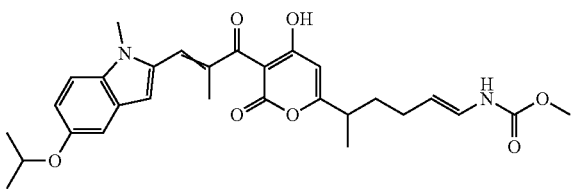

The compound was synthesized as in Example 9.6, using 1-methyl-5-(isopropoxy)-1H-indole-2-carbaldehyde (Example 84.1; 13 mg, 0.06 mmol) in place of 4-hexyl-2-formylfuran to give APY123 (2.4 mg) as an off-white solid containing a mixture of E and Z isomers: LRMS (ES+) m/z [M+H]+. found 523 (Exact mass=522.24).

Example 83

APY124 Prepared by Method C

Example 83.1

3-bromo-5-isobutylthiophene-2-carbaldehyde

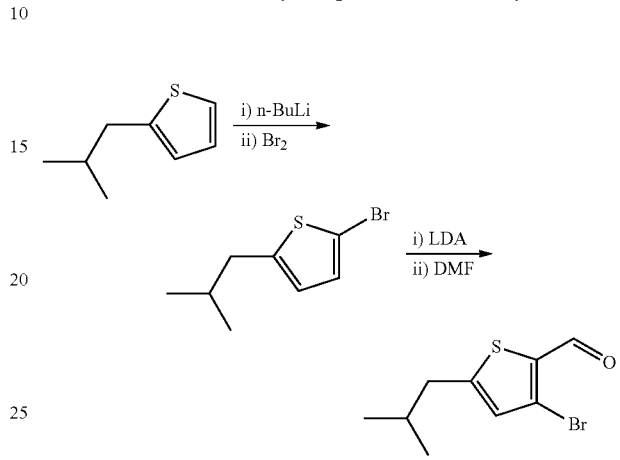

To solution of 2-isobutylthiophene (743 mg, 5.30 mmol) in 9:1 tetrahydrofuran/hexamethylphosphoramide under argon at −78° C. was added n-butyllithium (2.3 mL, 2.5 M in hexanes) dropwise. The resulting solution was stirred for 20 minutes at −78° C. Bromine (0.35 mL, 6.89 mmol) was added dropwise as a solution in 1 mL anhydrous dichloromethane. The resulting mixture was stirred at −78° C. for 30 minutes before being poured, while cold, into 50 mL of 5% sodium bisulfite solution. 1 N hydrochloric acid (50 mL) was added and organics were extracted with ether (3×75 mL), washed with 0.1 N hydrochloric acid, water and brine (50 mL each), dried over magnesium sulfate, filtered and concentrated. The crude residue was subjected to chromatography on silica gel with gradient elution (0-10% ethyl acetate in hexanes) to give 2-bromo-5-isobutylthiophene as the major component of a mixture of two compounds. Used without further purification or characterization.

To a solution of diisopropylamine (0.81 mL, 5.74 mmol) in 10 mL anhydrous tetrahydrofuran under argon at −30° C. was added n-butyllithium (1.4 mL, 2.5 M in hexanes) dropwise. The resulting solution was stirred for 20 minutes while warming to −10° C. The solution was cooled to −78° C. and semi-pure 2-bromo-5-isobutylthiophene (ca. 700 mg, 3.19 mmol) was added dropwise as a solution in 5 mL anhydrous tetrahydrofuran. The resulting mixture was stirred for 1 h while warming to −40° C. The mixture was cooled to −78° C. and dimethylformamide (1.2 mL, 16.00 mmol) was added in a single portion. The reaction mixture was removed from the cooling bath and stirred while warming to room temperature. The reaction mixture was poured into 100 mL 1 N hydrochloric acid and stirred vigorously for 5 minutes. Organics were extracted with ether (3×75 mL), washed with 0.1 N hydrochloric acid and brine (75 mL each), dried over magnesium sulfate, filtered and concentrated. The crude residue was subjected to chromatography on silica gel with gradient elution (2-10% ethyl acetate in hexanes) to give 3-bromo-5-isobutylthiophene-2-carbaldehyde (289 mg) as the major component of a mixture of three compounds. Used without further purification or characterization.

Example 83.2

APY124

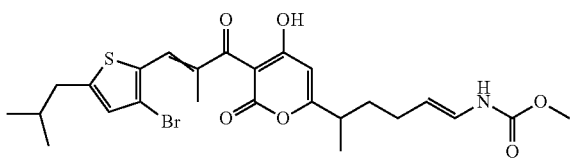

The compound was synthesized as in Example 9.6, using 3-bromo-5-isobutylthiophene-2-carbaldehyde (Example 85.1; ca. 23 mg, 0.093 mmol) in place of 4-hexyl-2-formylfuran to give APY124 (8.2 mg) as an oily solid containing a mixture of E and Z isomers: LRMS (ES) m/z [M+H]$^+$. found 552 (Exact mass=551.10).

Example 84

APY125 Prepared by Method C

Example 84.1

5-(cyclopropylmethyl)thiophene-2-carbaldehyde

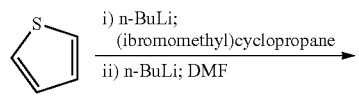

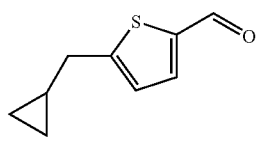

The compound was synthesized as in Example 32.1, using (bromomethyl)cyclopropane (0.25 mL, 2.53 mmol) in place of 1-chloro-3,3-dimethylbutane to give 5-(cyclopropylmethyl)thiophene-2-carbaldehyde (268 mg, 67%). Used without further characterization.

Example 84.2

APY125

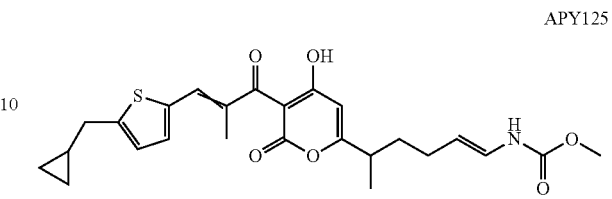

The compound was synthesized as in Example 9.6, using 5-(cyclopropylmethyl)thiophene-2-carbaldehyde (Example 86.1; 11.6 mg, 0.07 mmol) in place of 4-hexyl-2-formylfuran and isopropanol in place of methanol to give APY125 (3.8 mg) as an oily solid containing a mixture of E and Z isomers: LRMS (ES$^+$) m/z [M+H]$^+$. found 472 (Exact mass=471.17).

Example 85

APY126 Prepared by Method C

Example 85.1

4-(3,3,3-trifluoropropoxyl)benzaldehyde

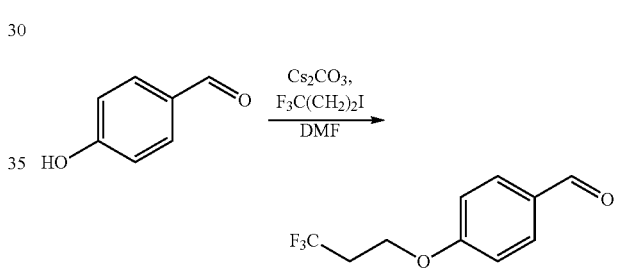

To a solution of 4-hydroxybenzaldehyde (740 mg, 6.0 mmol) and (3,3,3-trifluoro)-1-iodopropane (2.67 g, 12.0 mmol) in 10 mL dimethylformamide was added cesium carbonate (4.0 g, 12.3 mmol) and the resulting slurry stirred vigorously at 85° C. for 24 h. After cooling to room temperature the reaction mixture was poured into 100 mL water. Organics were extracted with ether (3×75 mL), dried over magnesium sulfate, filtered and concentrated. The residue was subjected to chromatography on silica gel (30% ethyl acetate in hexanes) to give 4-(3,3,3-trifluoropropoxyl)benzaldehyde (24 mg, 2%). Used without further characterization.

Example 85.2

APY126

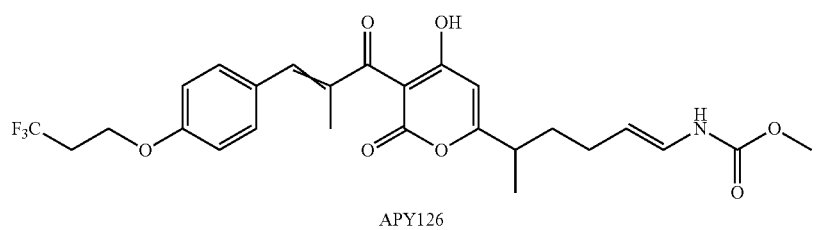 [SMILES: "APY126" ; COC(=O)N/C=C/CCC(C)c1cc(O)c(C(=O)C(C)=Cc2ccc(OCCC(F)(F)F)cc2)c(=O)o1]

The compound was synthesized as in Example 9.6, using 4-(3,3,3-trifluoropropoxyl)benzaldehyde (Example 87.1; 21.8 mg, 0.1 mmol) in place of 4-hexyl-2-formylfuran and isopropanol in place of methanol to give APY126 (4.5 mg) as a solid containing a mixture of E and Z isomers: LRMS (ES$^+$) m/z [M+H]$^+$. found 524 (Exact mass=523.18).

Example 86

APY127 Prepared by Method C

Example 86.1

2-methyl-4-(3,3,3-trifluoropropyl)benzaldehyde

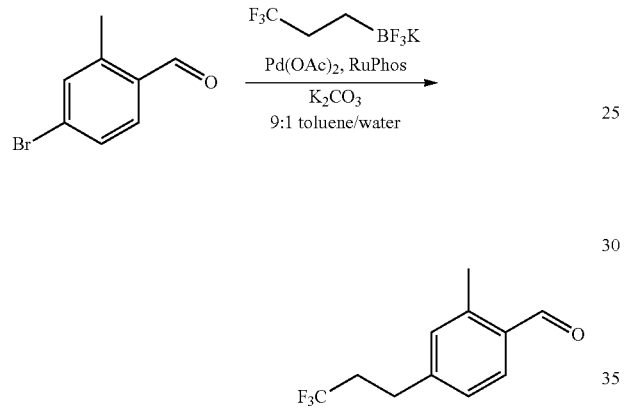

The compound was synthesized as in Example 3.1 using 4-bromo-2-methylbenzaldehyde (60 mg, 0.3 mmol) in place of 5-bromo-2-formylfuran and potassium (3,3,3-trifluoro)propyl trifluoroborate (92 mg, 0.45 mmol) in place of hexylboronic acid to give 2-methyl-4-(3,3,3-trifluoropropyl)benzaldehyde (50 mg, 77%). Used without further characterization.

Example 86.2

APY127

The compound was synthesized as in Example 9.6, using 2-methyl-4-(3,3,3-trifluoropropyl)benzaldehyde (Example 88.1; 12 mg, 0.05 mmol) in place of 4-hexyl-2-formylfuran and isopropanol in place of methanol to give APY127 (3.5 mg) as a solid containing a mixture of E and Z isomers: LRMS (ES$^+$) m/z [M+H]$^+$. found 522 (Exact mass=521.20).

Example 87

APY128 Prepared by Method C

Example 87.1

2-methyl-4-propoxybenzaldehyde

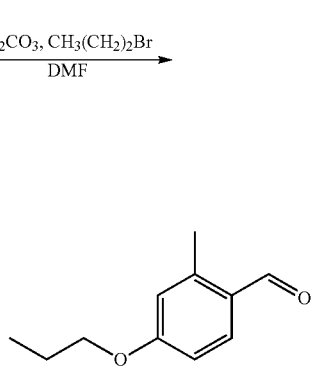

The compound was synthesized as in Example 87.1, using 4-hydroxy-2-methylbenzaldehyde (54.4 mg, 0.40 mmol) in place of 4-hydroxybenzaldehyde and 1-bromopropane (98 mg, 0.80 mmol) in place of 1-iodo-(3,3,3-trifluoro)propane to give 2-methyl-4-propoxybenzaldehyde (50 mg, 71%). Used without further characterization.

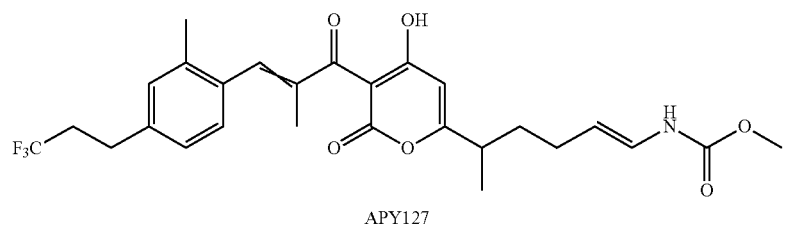 [SMILES: "APY127" ; COC(=O)N/C=C/CCC(C)c1cc(O)c(C(=O)C(C)=Cc2ccc(CCC(F)(F)F)cc2C)c(=O)o1]

APY127

Example 87.2

APY128

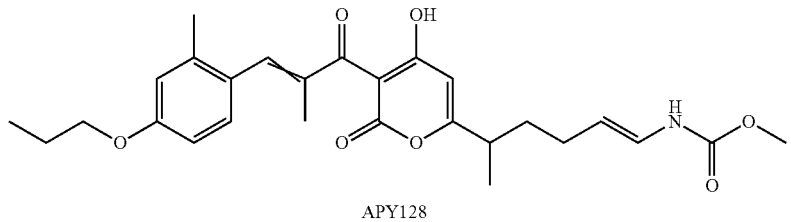 [SMILES: "APY128" ; CCCOc1ccc(C=C(C)C(=O)c2c(O)cc(C(C)CC/C=C/NC(=O)OC)oc2=O)c(C)c1]

APY128

The compound was synthesized as in Example 9.6, using 2-methyl-4-propoxybenzaldehyde (Example 89.1; 9 mg, 0.05 mmol) in place of 4-hexyl-2-formylfuran and isopropanol in place of methanol to give APY128 (3.6 mg) as a solid containing a mixture of E and Z isomers: LRMS (ES$^+$) m/z [M+H]$^+$. found 484 (Exact mass=483.23).

Example 88

APY129 Prepared by Method C

Example 88.1

2-methyl-4-butoxybenzaldehyde

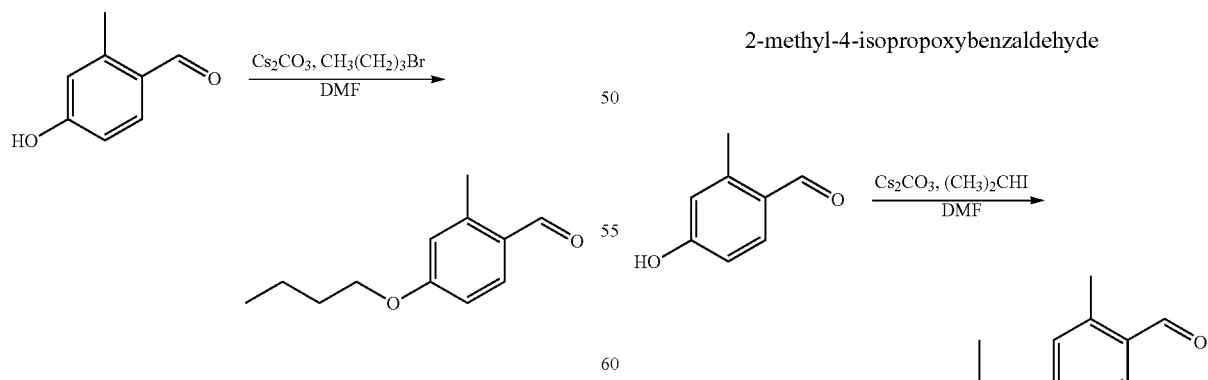

The compound was synthesized as in Example 87.1, using 4-hydroxy-2-methylbenzaldehyde (54.4 mg, 0.40 mmol) in place of 4-hydroxybenzaldehyde and 1-bromobutane (77 μL, 0.80 mmol) in place of 1-iodo-(3,3,3-trifluoro)propane to give 2-methyl-4-butoxybenzaldehyde (52 mg, 68%). Used without further characterization.

Example 88.2

APY129

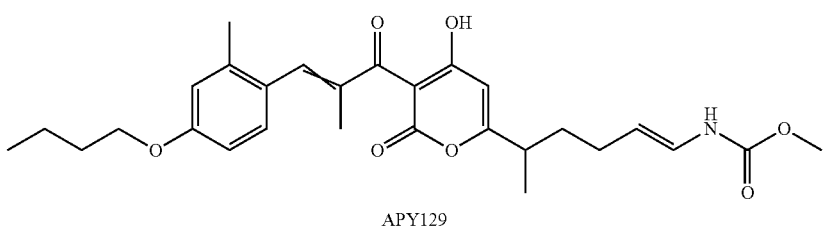 [SMILES: "APY129" ; CCCCOc1ccc(C=C(C)C(=O)c2c(O)cc(C(C)CC/C=C/NC(=O)OC)oc2=O)c(C)c1]

APY129

The compound was synthesized as in Example 9.6, using 2-methyl-4-butoxybenzaldehyde (Example 90.1; 15 mg, 0.075 mmol) in place of 4-hexyl-2-formylfuran and isopropanol in place of methanol to give APY129 (3.0 mg) as a solid containing a mixture of E and Z isomers: LRMS (ES$^+$) m/z [M+H]$^+$. found 499 (Exact mass=497.24).

Example 89

APY130 Prepared by Method C

Example 89.1

2-methyl-4-isopropoxybenzaldehyde

The compound was synthesized as in Example 87.1, using 4-hydroxy-2-methylbenzaldehyde (54.4 mg, 0.40 mmol) in place of 4-hydroxybenzaldehyde and 2-iodopropane (100 μL, 0.80 mmol) in place of 1-iodo-(3,3,3-trifluoro)propane to give 2-methyl-4-isopropoxybenzaldehyde (54 mg, 76%). Used without further characterization.

Example 89.2

APY130

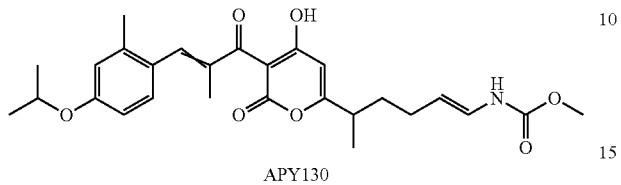

APY130

The compound was synthesized as in Example 9.6, using 2-methyl-4-isopropoxybenzaldehyde (Example 91.1; 15 mg, 0.075 mmol) in place of 4-hexyl-2-formylfuran and isopropanol in place of methanol to give APY130 (3.2 mg) as a solid containing a mixture of E and Z isomers: LRMS (ES$^+$) m/z [M+H]$^+$. found 484 (Exact mass=483.23).

Example 90

APY131 Prepared by Method C

Example 90.1

4-(2,2-difluoroethoxy)-2-methylbenzaldehyde

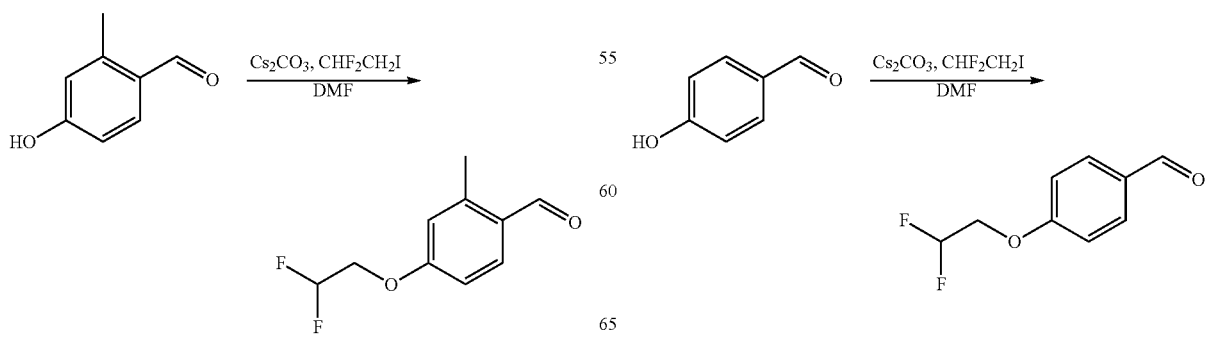

The compound was synthesized as in Example 87.1, using 4-hydroxy-2-methylbenzaldehyde (54.4 mg, 0.40 mmol) in place of 4-hydroxybenzaldehyde and 2,2-difluoro-1-iodoethane (153 mg, 0.80 mmol) in place of 1-iodo-(3,3,3-trifluoro) propane to give 4-(2,2-difluoroethoxy)-2-methylbenzaldehyde (54 mg, 68%). Used without further characterization.

Example 90.2

APY131

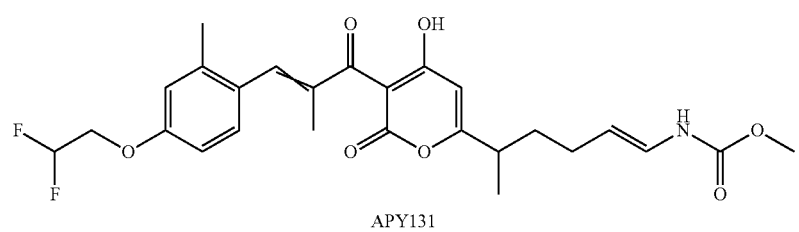 [SMILES: "APY131" ; COC(=O)N/C=C/CCC(C)c1cc(O)c(C(=O)C(C)=Cc2ccc(OCC(F)F)cc2C)c(=O)o1]

APY131

The compound was synthesized as in Example 9.6, using 4-(2,2-difluoroethoxy)-2-methylbenzaldehyde (Example 92.1; 18 mg, 0.075 mmol) in place of 4-hexyl-2-formylfuran and isopropanol in place of methanol to give APY131 (3.0 mg) as a solid containing a mixture of E and Z isomers: LRMS (ES$^+$) m/z [M+H]$^+$. found 506 (Exact mass=505.19).

Example 91

APY132 Prepared by Method C

Example 91.1

4-(2,2-difluoroethoxyl)benzaldehyde

The compound was synthesized as in Example 87.1, using 2,2-difluoro-1-iodoethane (384 mg, 2.0 mmol) in place of 1-iodo-(3,3,3-trifluoro)propane to give 4-(2,2-difluoroethoxyl)benzaldehyde (325 mg, 58%). Used without further characterization.

Example 91.2

APY132

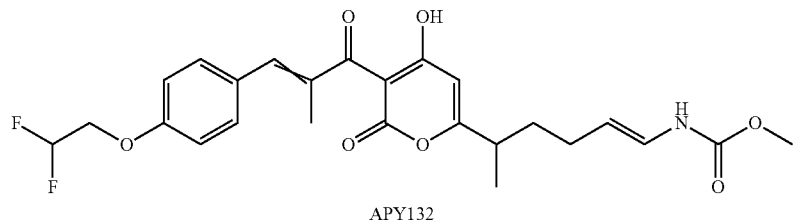 [SMILES: "APY132" ; COC(=O)N/C=C/CCC(C)c1cc(O)c(C(=O)C(C)=Cc2ccc(OCC(F)F)cc2)c(=O)o1]

APY132

The compound was synthesized as in Example 9.6, using 4-(2,2-difluoroethoxyl)benzaldehyde (Example 93.1; 15 mg, 0.075 mmol) in place of 4-hexyl-2-formylfuran and isopropanol in place of methanol to give APY132 (3.8 mg) as a solid containing a mixture of E and Z isomers: LRMS (ES$^+$) m/z [M+H]$^+$. found 492 (Exact mass=491.18).

Example 92

APY135 Prepared by Method C

Example 92.1

1-methyl-4-(3,3,3-trifluoropropyl)-1H-pyrrole-2-carbaldehyde

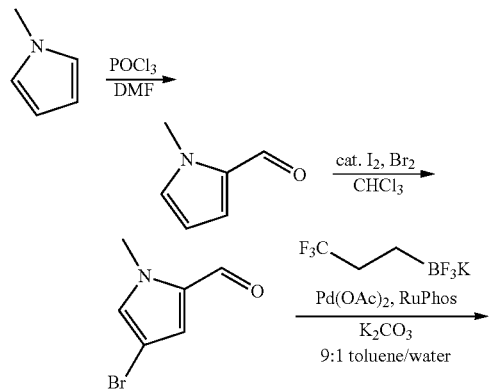

To dimethylformamide (3.9 mL, 50.40 mmol) in a 3-necked round-bottom flask fitted with an internal temperature probe at 5° C. was added phosphorous oxychloride (4.6 mL, 50.40 mmol) dropwise at a rate such that the internal temperature did not exceed 20° C. After completion of the addition, 20 mL anhydrous 1,2-dichloroethane was added and the reaction mixture stirred at room temperature until homogeneous. N-methylpyrrole (4.1 mL, 45.82 mmol) was added dropwise as a solution in 4 mL 1,2-dichloroethane at a rate such that the internal temperature did not exceed 35° C. After the addition was complete, the reaction mixture was heated to reflux for 15 minutes, then cooled to room temperature. An aqueous solution of potassium acetate (5.5 M, 46 mL) was added slowly and the mixture stirred vigorously at reflux for 5 minutes. After cooling to room temperature, organics were extracted with ether (3×75 mL), washed with saturated sodium bicarbonate (3×75 mL), brine (75 mL), dried over magnesium sulfate, filtered and concentrated to give 4.75 g of brown liquid. The crude liquid was purified by distillation with a Kügelrohr apparatus to give 1-methyl-1H-pyrrole-2-carbaldehyde (3.22 g, 64%) as a pale pink liquid. Used without further characterization.

To a solution of 1-methyl-1H-pyrrole-2-carbaldehyde (1.09 g, 10.0 mmol) in 60 mL chloroform at −20° C. was added a single crystal of iodine. The mixture was stirred until homogeneous. Bromine (0.51 mL, 10.0 mmol) was added dropwise as a solution in 10 mL chloroform. The solution was stirred while warming from −20 to 0° C. over 1.5 h. Chloroform was removed in vacuo and the residue added to 5% sodium bisulfite solution to quench excess bromine/iodine. Saturated sodium bicarbonate was added until the pH of the mixture reached 7. Organics were extracted with ether (3×75 mL), dried over magnesium sulfate, filtered and concentrated to give crude 4-bromo-1-methyl-1H-pyrrole-2-carbaldehyde (1.80 g) as the major component of a mixture of starting aldehyde and dibromopyrrole. Used without further purification.

1-Methyl-4-(3,3,3-trifluoropropyl)-1H-pyrrole-2-carbaldehyde (23 mg, ca. 13% over two steps) was synthesized as in Example 3.1 using 4-bromo-1-methyl-1H-pyrrole-2-carbaldehyde (crude mixture, ca. 92 mg, 0.49 mmol) in place of 5-bromo-2-formylfuran and potassium (3,3,3-trifluoro)propyl trifluoroborate (125 mg, 0.61 mmol) in place of hexylboronic acid. Used without further characterization.

Example 92.2

APY135

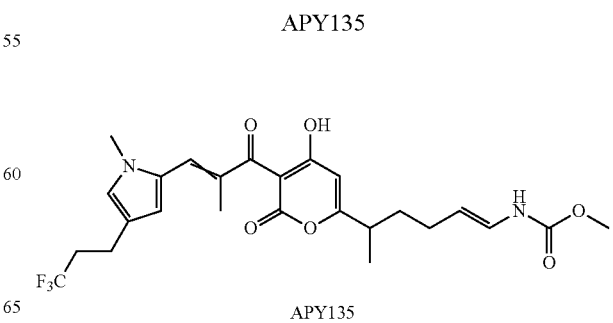

APY135

The compound was synthesized as in Example 9.6, using 1-methyl-4-(3,3,3-trifluoropropyl)-1H-pyrrole-2-carbaldehyde (Example 94.1; 23 mg, 0.112 mmol) in place of 4-hexyl-2-formylfuran and isopropanol in place of methanol to give APY135 (0.9 mg) as an oily solid containing a mixture of E and Z isomers: LRMS (ES$^+$) m/z [M+H]$^+$. found 511 (Exact mass=510.20).

Example 93

APY136 Prepared by Method C

Example 93.1

2-butylthiazole-5-carbaldehyde

The compound was synthesized as in Example 9.6, using 2-butylthiazole-5-carbaldehyde (Example 95.1; 10 mg, 0.05 mmol) in place of 4-hexyl-2-formylfuran and isopropanol in place of methanol to give APY136 (6.8 mg) as an off-white solid containing a mixture of E and Z isomers: LRMS (ES$^+$) m/z [M+H]$^+$. found 475 (Exact mass=474.18).

Example 94

APY137 Prepared by Method C

Example 94.1

2-isopentylthiazole-5-carbaldehyde

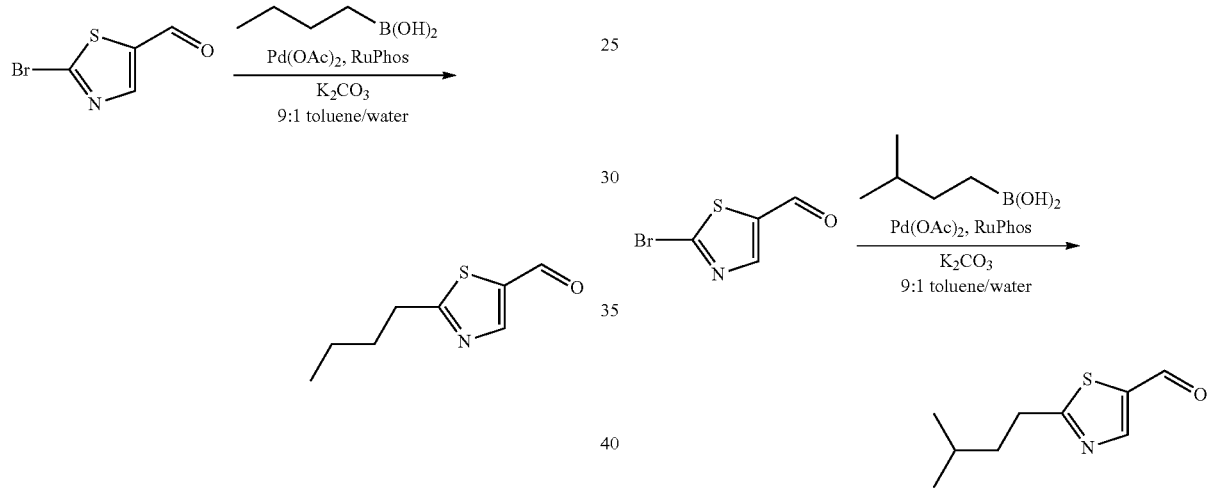

The compound was synthesized as in Example 3.1 using 2-bromothiazole-2-carbaldehyde (192 mg, 1.0 mmol) in place of 5-bromo-2-formylfuran and n-butylboronic acid (150 mg, 1.5 mmol) in place of hexylboronic acid to give 2-butylthiazole-5-carbaldehyde (13 mg, 8%). Used without further characterization.

Example 93.2

APY136

The compound was synthesized as in Example 3.1 using 2-bromothiazole-2-carbaldehyde (192 mg, 1.0 mmol) in place of 5-bromo-2-formylfuran and isopentylboronic acid (174 mg, 1.5 mmol) in place of hexylboronic acid to give 2-butylthiazole-5-carbaldehyde (16 mg, 9%). Used without further characterization.

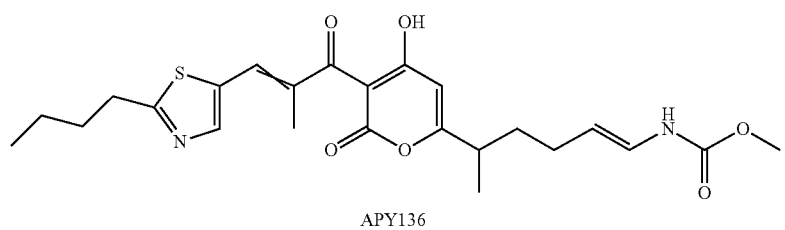 [SMILES: "APY136" ; CCCCc1ncc(C=C(C)C(=O)c2c(O)cc(C(C)CC/C=C/NC(=O)OC)oc2=O)s1]

APY136

Example 94.2

APY137

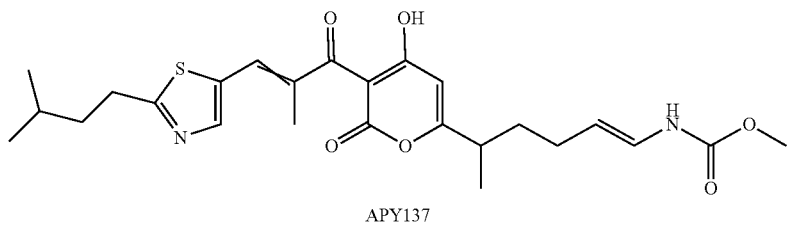 [SMILES: "APY137" ; COC(=O)N/C=C/CCC(C)c1cc(O)c(C(=O)C(C)=Cc2cnc(CCC(C)C)s2)c(=O)o1]

APY137

The compound was synthesized as in Example 9.6, using 2-isopentylthiazole-5-carbaldehyde (Example 96.1; 16 mg, 0.05 mmol) in place of 4-hexyl-2-formylfuran and isopropanol in place of methanol to give APY137 (10.6 mg) as an off-white solid containing a mixture of E and Z isomers: LRMS (ES$^+$) m/z [M+H]$^+$. found 489 (Exact mass=488.20).

Example 95

APY138 Prepared by Method C

Example 95.1

5-(2,2-difluoroethoxyl)thiophene-2-carbaldehyde

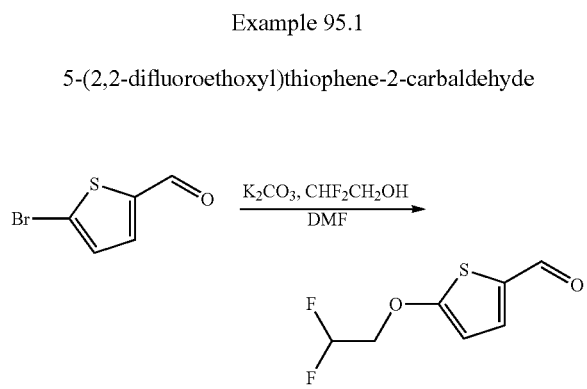

The compound was synthesized as in Example 78.1, using 2,2-difluoroethanol (250 mg, 3.0 mmol) in place of trifluoroethanol to give 5-(2,2-difluoroethoxyl)thiophene-2-carbaldehyde (94 mg, 68%). Used without further characterization.

Example 95.2

APY138

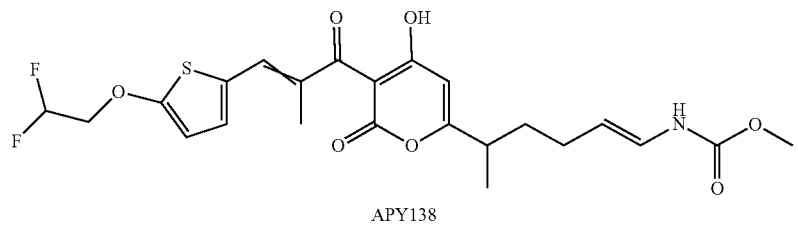 [SMILES: "APY138" ; COC(=O)N/C=C/CCC(C)c1cc(O)c(C(=O)C(C)=Cc2ccc(OCC(F)F)s2)c(=O)o1]

APY138

The compound was synthesized as in Example 9.6, using 5-(2,2-difluoroethoxyl)thiophene-2-carbaldehyde (Example 97.1; 18 mg, 0.075 mmol) in place of 4-hexyl-2-formylfuran and isopropanol in place of methanol to give APY138 (1.6 mg) as an off-white solid containing a mixture of E and Z isomers: LRMS (ES$^+$) m/z [M+H]$^+$. found 482 (Exact mass=481.14).

Example 96

APY139 Prepared by Method E

Example 96.1

5-(3,3,3-trifluoropropoxyl)thiophene-2-carbaldehyde

To a suspension of hexanes-washed sodium hydride (918 mg, 22.95 mmol) in 10 mL anhydrous tetrahydrofuran at 0° C. was added 3,3,3-trifluoropropanol (3.5 g, 30.60 mmol) dropwise. After the addition was complete, the mixture was stirred at room temperature for 30 minutes. 2-Iodothiophene (3.21 g, 15.30 mmol) and copper(I) iodide (728 mg, 3.82 mmol) were added, the reaction vessel was flushed with argon, sealed and stirred at 100° C. for 48 h. The reaction mixture was allowed to cool to room temperature and poured into 150 mL of 5% aqueous potassium cyanide solution. Organics were extracted with 1:1 ether/hexanes (3×100 mL), dried with magnesium sulfate, filtered and concentrated. The crude residue was subjected to chromatography on silica gel (100% hexanes) to give 2-(3,3,3-trifluoropropoxyl)thiophene (1.70 g, 57%).

To 8 mL dimethylformamide at room temperature was added phosphorous oxychloride (4.0 mL, 43.33 mmol) dropwise. After stirring for 10 minutes at room temperature, 2-(3,3,3-trifluoropropoxyl)thiophene (1.70 g, 8.67 mmol) as a solution in 8 mL dimethylformamide. The resulting solution was heated to 100° C. for 15 minutes. After cooling to room temperature, the reaction mixture was poured into 100 mL of ice-water and stirred vigorously for 5 minutes. Sodium bicarbonate (11 g) was added carefully and the mixture stirred until homogeneous. Organics were extracted with ether (3×100 mL), washed with water (3×50 mL), brine (50 mL), dried over magnesium sulfate, filtered and concentrated. The crude residue was subjected to chromatography on silica gel with gradient elution (0-20% ethyl acetate in hexanes) to give 5-(3,3,3-trifluoropropoxyl)thiophene-2-carbaldehyde (761 mg, 39%) as an off-white solid. Used without further characterization.

over 30 minutes. After cooling the solution to −78° C., enecarbamate 11 (25 mg, 0.077 mmol) was added dropwise as a solution in 0.5 mL anhydrous tetrahydrofuran. The resulting mixture was stirred for 1 h at −78° C. A solution of 5-(3,3,3-trifluoropropoxyl)thiophene-2-carbaldehyde (22.4 mg, 0.10 mmol) in 0.5 mL anhydrous tetrahydrofuran was added dropwise. The resulting mixture was stirred for 2 h at −78° C. The reaction mixture was removed from the cooling bath and poured into 25 mL of 0.2 N hydrochloric acid. Organics were extracted with ether (2×25 mL) dried over magnesium sulfate, filtered and concentrated. The crude residue was subjected to chromatography on silica gel with gradient elution (15-35% ethyl acetate in hexanes+1% acetic acid) to give hydroxy ketone 19a as a viscous oil (18.5 mg, 44%)

Example 96.2

Method E, Aldol Addition: Hydroxy Ketone 19a

Example 96.3

Method E, Acetate Ester Formation: Acetate 20a

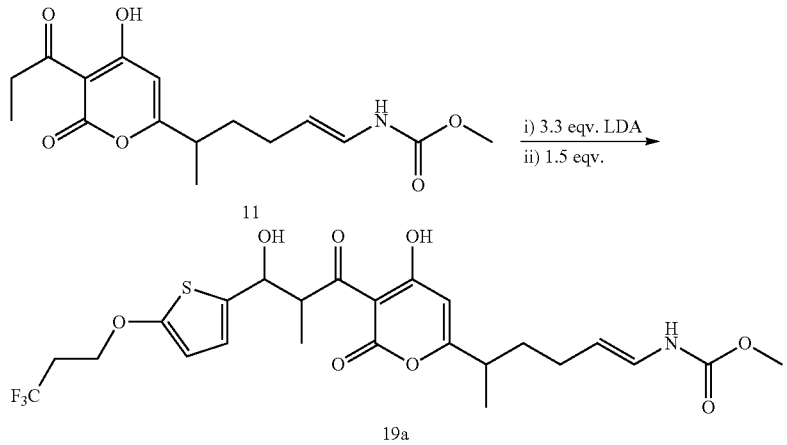

To a solution of diisopropylamine (38 μL, 0.27 mmol) in 1 mL of anhydrous tetrahydrofuran under argon at −40° C. was added n-butyllithium (0.10 mL, 2.5 M in hexanes) dropwise. The resulting solution was stirred while warming to −20° C.

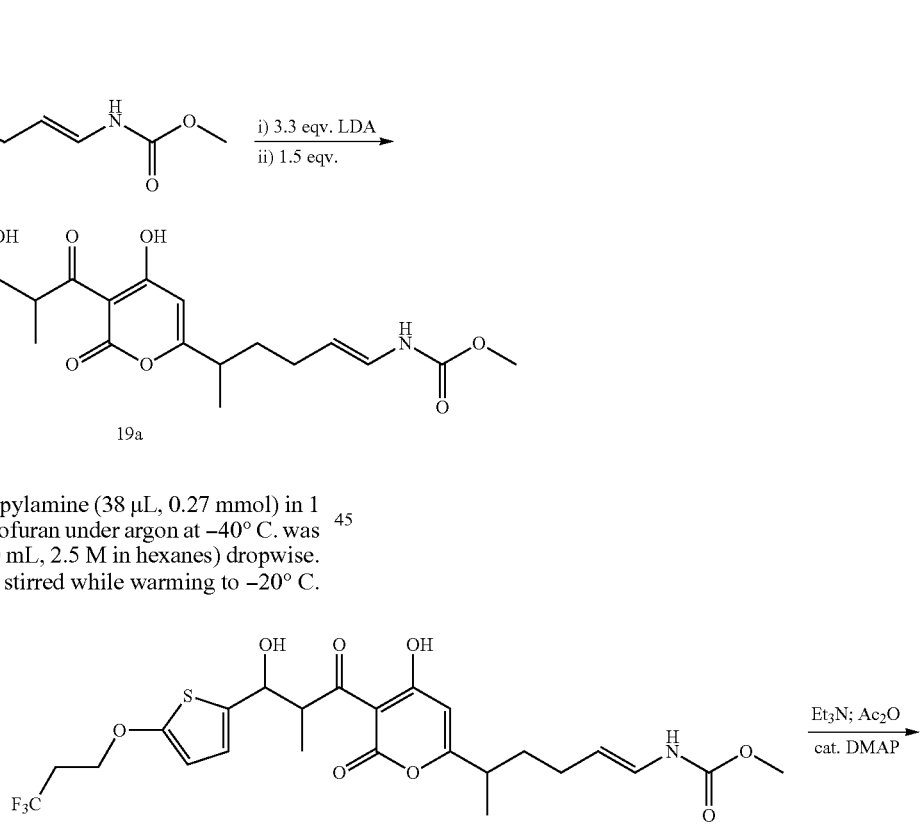

To a solution of hydroxy ketone 19a (18.5 mg, 0.033 mmol), triethylamine (14 µL, 0.099 mmol) and acetic anhydride (6.4 µL, 0.066 mmol) in 0.5 mL anhydrous dichloromethane under argon at room temperature was added N,N-dimethylaminopyridine (0.4 mg, 0.003 mmol). The resulting solution was stirred at room temperature for 15 minutes, before being diluted with 10 mL ether and washed with 0.2 N hydrochloric acid (2×10 mL). The combined acid washes were extracted with ether (15 mL). The combined ether phases were washed with brine (20 mL), dried over magnesium sulfate, filtered and concentrated to give crude acetate 20a. Used without further purification or characterization.

Example 96.4

Method E, Elimination: APY139

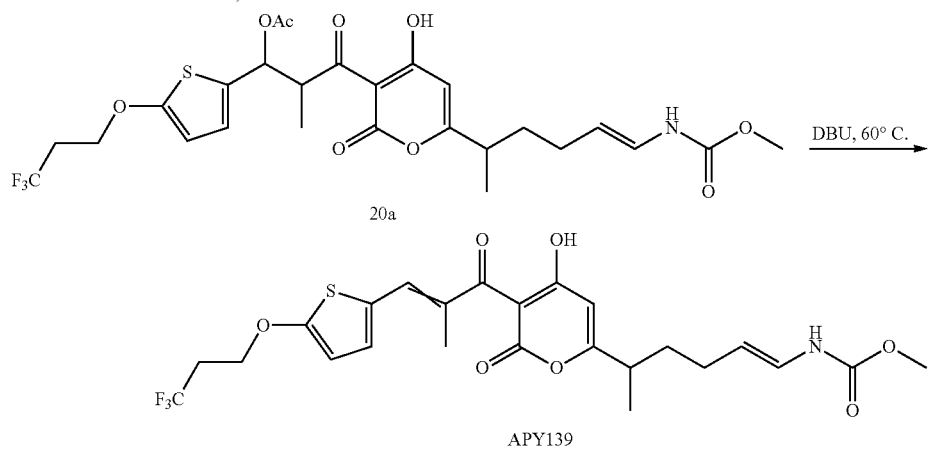

To a solution of crude acetate 20a (Example 95.3) in 0.5 mL tetrahydrofuran at room temperature was added 1,8-diazabicyclo[5.4.0]undec-7-ene (15 µL, 0.099 mmol). The resulting solution was heated to 60° C. and stirred for 6 h. After cooling to room temperature, the reaction mixture was diluted with ether (15 mL) and washed with 0.2 N hydrochloric acid (2×15 mL). The combined acid washes were extracted with ether (15 mL). The combined ether phases were washed with brine (15 mL), dried over magnesium sulfate, filtered and concentrated. The crude residue was subjected to RP-HPLC on a PrincetonSPHER-60 $C_{18}$ column (60 Å-10µ, 250×30 mm) at a flow rate of 20 mL/min with a linear gradient of 65-75% acetonitrile/water+1% acetic acid over 20 minutes to give APY139 (1.6 mg, 9% over two steps) as an off-white solid containing a mixture of E and Z isomers: LRMS (ES$^+$) m/z [M+H]$^+$. found 530 (Exact mass=529.14).

Example 97

APY142 Prepared by Method C

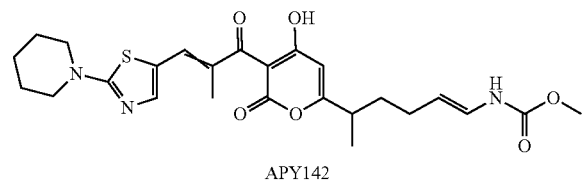 [SMILES: "APY142" ; COC(=O)N/C=C/CCC(C)c1cc(O)c(C(=O)C(C)=Cc2cnc(N3CCCCC3)s2)c(=O)o1]

The compound was synthesized as in Example 9.6, using 2-bromothiazole-5-carbaldehyde (12 mg, 0.063 mmol) in place of 4-hexyl-2-formylfuran and isopropanol in place of methanol to give APY142 (2.4 mg) as an off-white solid containing a mixture of E and Z isomers: LRMS (ES$^+$) m/z [M+H]$^+$. found 502 (Exact mass=501.19).

Example 98

APY143 Prepared by Method C

Example 98.1

1-methyl-4-propyl-1H-imidazole-2-carbaldehyde

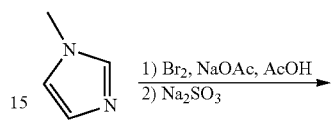

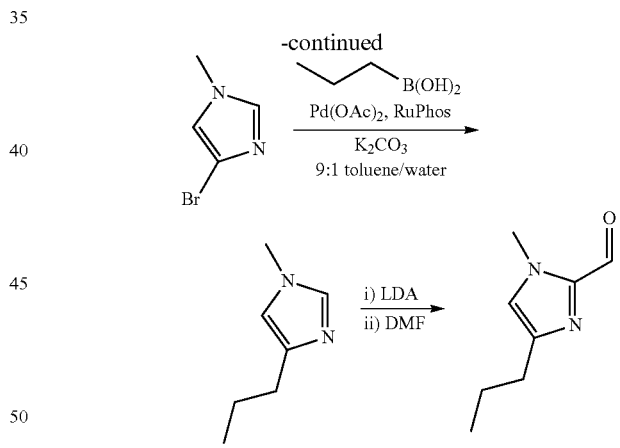

To a solution of N-methylimidazole (1.64 g, 19.97 mmol) and sodium acetate (25 g, 300 mmol) in acetic acid (180 mL) at room temperature was added bromine (9.6 g, 60.07 mmol) dropwise as a solution in 20 mL acetic acid. The resulting mixture was stirred for 2.5 h at room temperature. Acetic acid was removed in vacuo, the residue was suspended in 500 mL water and stirred at room temperature for 10 minutes. The resultant precipitate was filtered, washed with water and dried under high vacuum to give 2,4,5-tribromo-1-methyl-1H-imidazole (1.82 g, 29%—some product remained in the mother liquor) as a light yellow powder. Used without further characterization.

To a suspension of the tribromide (1.82 g, 5.71 mmol) in 45 mL water was added sodium sulfite (13 g, 103 mmol) and the resulting mixture was stirred at rapid reflux for 24 h. After cooling to room temperature, organics were extracted with ether (3×75 mL), dried over magnesium sulfate, filtered and concentrated to give 1.61 g of a mixture of tri-, di- and monobromoimidazoles. This mixture was re-subjected to the reduction conditions (same quantity of sodium sulfite) using 15 mL of 3:1 water/acetic acid as solvent and heating in a sealed vessel at 130° C. for 60 h. After cooling to room temperature, the pH of the reaction mixture was adjusted to 9-10 by addition of 2 N sodium hydroxide. Organics were extracted with ether (3×50 mL), dried over magnesium sulfate, filtered and concentrated to give crude 4-bromo-1-methyl-1H-imidazole (571 mg, ca. 62%). Used without further characterization.

4-Butyl-1-methyl-1H-imidazole (95 mg, 22%) was synthesized as in Example 3.1 using 4-bromo-1-methyl-1H-imidazole (571 mg, ca. 3.53 mmol) in place of 5-bromo-2-formylfuran and propylboronic acid (372 mg, 4.24 mmol) in place of hexylboronic acid. Used without further characterization.

To a solution of diisopropylamine (0.13 mL, 0.918 mmol) in 2 mL anhydrous tetrahydrofuran at −40° C. was added n-butyllithium (0.34 mL, 2.5 M in hexanes) dropwise. The solution was stirred while warming to −20° C. over 20 minutes. After cooling to −78° C., 4-butyl-1-methyl-1H-imidazole (95 mg, 0.765 mmol) was added dropwise as a solution in 2 mL anhydrous tetrahydrofuran. The resulting solution was stirred for 40 minutes at −78° C. Dimethylformamide (0.24 mL, 3.06 mmol) was added and the solution stirred while warming to room temperature. The reaction mixture was poured into 15 mL of 1 N hydrochloric acid and stirred for 5 minutes. The pH of the reaction mixture was adjusted to 7-8 by careful addition of saturated sodium bicarbonate solution. Organics were extracted with dichloromethane (3×20 mL), dried over magnesium sulfate, filtered and concentrated. The crude residue was subjected to chromatography on silica gel with gradient elution (5-50% ethyl acetate in hexanes) to give 1-methyl-4-propyl-1H-imidazole-2-carbaldehyde (9 mg, 8%) as an off-white solid. Used without further characterization.

Example 98.2

APY143

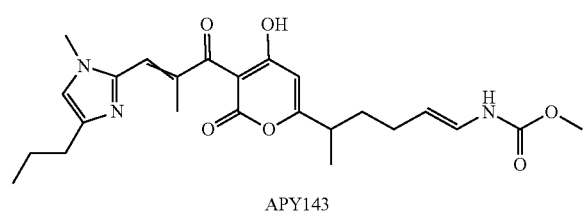 [SMILES: "APY143" ; CCCc1cn(C)c(C=C(C)C(=O)c2c(O)cc(C(C)CC/C=C/NC(=O)OC)oc2=O)n1]

APY143

The compound was synthesized as in Example 9.6, using 1-methyl-4-propyl-1H-imidazole-2-carbaldehyde (Example 99.1; 9 mg, 0.059 mmol) in place of 4-hexyl-2-formylfuran and isopropanol in place of methanol to give APY143 (1.4 mg) as an off-white solid containing a mixture of E and Z isomers: LRMS (ES+) m/z [M+H]+. found 458 (Exact mass=457.22).

Example 99

Assay of Inhibition of Bacterial RNA Polymerase

Example 99.1

Assay of Inhibition of Escherichia coli RNA Polymerase

Fluorescence-detected RNA polymerase assays with E. coli RNA polymerase were performed by a modification of the procedure of Kuhlman et al., 2004 [Kuhlman, P., Duff, H. & Galant, A. (2004) A fluorescence-based assay for multisubunit DNA-dependent RNA polymerases. Anal. Biochem. 324, 183-190]. Reaction mixtures contained (20 μl): 0-100 nM test compound, 75 nM E. coli RNA polymerase $\sigma^{70}$ holoenzyme, 20 nM 384 by DNA fragment containing the bacteriophage T4 N25 promoter, 100 μM ATP, 100 μM GTP, 100 μM UTP, 100 μM CTP, 50 mM Tris-HCl, pH 8.0, 100 mM KCl, 10 mM $MgCl_2$, 1 mM DTT, 10 μg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 μl 5 mM $CaCl_2$ and 2 U DNaseI (Ambion, Inc.), followed by incubation for 90 min at 37° C. RNA was quantified by addition of 100 μl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC50 is defined as the concentration of inhibitor resulting in 50% inhibition of RNA polymerase activity.

Example 99.2

Assay of Inhibition of Mycobacterium tuberculosis RNA Polymerase

Fluorescence-detected RNA polymerase assays with M. tuberculosis RNA polymerase were performed as in Example 99.1, using reaction mixtures containing (20 μl): 0-100 nM test compound, 75 nM M. tuberculosis RNA polymerase core enzyme, 300 nM M. tuberculosis $\sigma^A$, 20 nM 384 by DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM $MgCl_2$, 2.5 mM DTT, and 12.7% glycerol. IC50 is defined as the concentration of inhibitor resulting in 50% inhibition of RNA polymerase activity.

Example 99.3

Assay of Inhibition of Staphylococcus aureus RNA Polymerase

Fluorescence-detected RNA polymerase assays with S. aureus RNA polymerase were performed as in Example 99.1, using reaction mixtures containing (20 μl): 0-100 nM test compound, 75 nM S. aureus RNA polymerase core enzyme, 300 nM S. aureus $\sigma^A$, 20 nM 384 by DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM $MgCl_2$, 2.5 mM DTT, and 12.7% glycerol.

IC50 is defined as the concentration of inhibitor resulting in 50% inhibition of RNA polymerase activity.

Example 100

Assay of Inhibition of Bacterial Growth in Culture

Example 100.1

Assay of Inhibition of Growth of *Staphylococcus aureus*, *Acinetobacter baumannii*, and *Escherichia coli*

Minimum inhibitory concentrations (MICs) for *Staphylococcus aureus* ATCC 12600, methicillin-resistant *Staphylococcus aureus* (MRSA) strain BAA-1707 (USA-400; MW2), methicillin-resistant *Staphylococcus aureus* (MRSA) strain BAA-1717 (USA-300), rifampin-resistant *Staphylococcus aureus* (RRSA) strain ATCC 12600-Rif (H526N), linezolid-resistant *Staphylococcus aureus* (LRSA) strain NRS120, vancomycin-intermediate *Staphylococcus aureus* (VISA) strain NRS1, *Acinetobacter baumannii* ATCC 19606, and *Escherichia coli* D21f2tolC were quantified using spiral gradient endpoint assays, essentially as described [Wallace, A. and Corkill, J. (1989) Application of the spiral plating method to study antimicrobial action. *J. Microbiol. Meths.* 10, 303-310; Paton, J., Holt, A., and Bywater, M. (1990) Measurement of MICs of antibacterial agents by spiral gradient endpoint compared with conventional dilution methods. *Int. J. Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-100 µg/ml of test compound. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-compound concentration at the streak endpoint was calculated using the program SGE (Spiral Biotech, Inc.), and the MIC was defined as the calculated test-compound concentration at the streak endpoint.

Example 100.2

Assay of Inhibition of Growth of *Mycobacterium tuberculosis*

MICs for *Mycobacterium tuberculosis* H37Rv were quantified using microplate Alamar Blue assays as described [Collins, L. & Franzblau, S. (1997) Microplate Alamar Blue assay versus BACTEC 460 system for high-throughput screening of compounds against *Mycobacterium tuberculosis* and *Mycobacterium avium*. *Antimicrob. Agents Chemother.* 41, 1004-1009].

Example 100.3

Assay of Inhibition of Growth of *Bacillus anthracis*, *Francisella tularensis*, *Yersinia pestis*, *Burkholderia mallei*, *Burkholderia pseudomallei*, and *Brucella melitensis*

MICs for *Bacillus anthracis* Vollum 1b, *Francisella tularensis* SCHU4, *Yersinia pestis* C092, *Burkholderia mallei* CHN7, *Burkholderia pseudomallei* Human/Blood/OW US/1994, and *Brucella melitensis* 16M were quantified using broth microdilution assays as described [Clinical and Laboratory Standards Institute (CLSI/NCCLS) (2009) *Methods for Dilution Antimicrobial Susceptibility Tests for Bacteria That Grow Aerobically; Approved Standard, Eighth Edition. CLIS Document M07-A8* (CLIS, Wayne Pa.)].

Example 101

Assay of Antibacterial Efficacy in Mouse Model of *Staphylococcus aureus* Systemic Infection ("Peritonitis Model")

Female Swiss Webster mice were experimentally infected by intraperitoneal administration of $1 \times 10^7$ colony forming units of methicillin-resistant *Staphylococcus aureus* (MRSA) strain BAA-1707 (USA-400, MW2) in 5% hog gastric mucin. Test compounds (1.56, 3.13, and 6.25 mg/ml in vehicle [5% dimethylacetamide and 4% Cremophor EL in 100 mM sodium phosphate, pH 7.4]), positive control (1.56 mg/ml linezolid in vehicle), and negative control (vehicle only), were administered by intravenous injection into a tail vein (200 µl per injection) 0 h post-infection or oral gavage (400 µl per gavage) 1 h pre-infection. Survival was monitored for 24 h post-infection. Identities of test compounds and controls were blinded from personnel performing injections and monitoring survival. The protective dose 50 (PD50) was defined as the test-compound dose resulting in 50% survival at 48 h (calculated using the probit method).

Structures and names of representative compounds of this invention (compounds APY15-APY143) are presented in Tables 1 and 2. The E/Z ratios in Table 1 are ratios observed in particular preparations; other E/Z ratios are possible in other preparations.

TABLE 1

Representative compounds.

| Example Number | Compound Number | Structure | Prep Method | Amount Isolated | E/Z Ratio ($^1$H NMR) |
|---|---|---|---|---|---|
| 1 | APY15 | 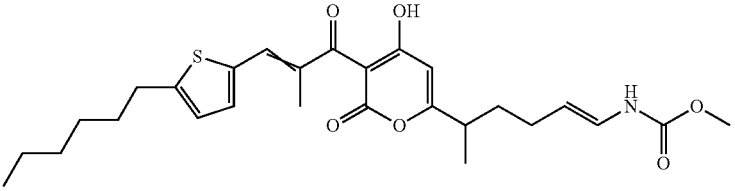 [SMILES: CCCCCCc1ccc(C=C(C)C(=O)c2c(O)cc(C(C)CC/C=C/NC(=O)OC)oc2=O)s1] | A | 9.0 mg | 8:1 |

TABLE 1-continued

Representative compounds.

| Example Number | Compound Number | Structure | Prep Method | Amount Isolated | E/Z Ratio ($^1$H NMR) |
|---|---|---|---|---|---|
| 2 | APY16 | 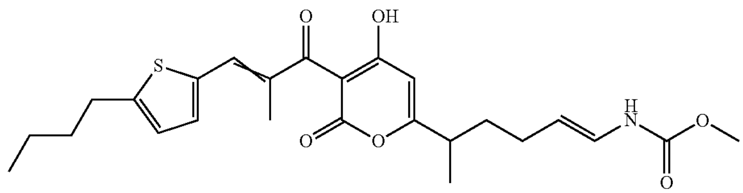 [SMILES: CCCCc1ccc(C=C(C)C(=O)c2c(O)cc(C(C)CC/C=C/NC(=O)OC)oc2=O)s1] | A | 7.0 mg | 12:1 |
| 3 | APY17 | 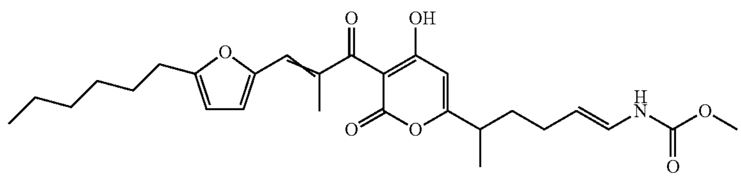 [SMILES: CCCCCCc1ccc(C=C(C)C(=O)c2c(O)cc(C(C)CC/C=C/NC(=O)OC)oc2=O)o1] | A | 18.5 mg | 5:1 |
| 4 | APY18 | 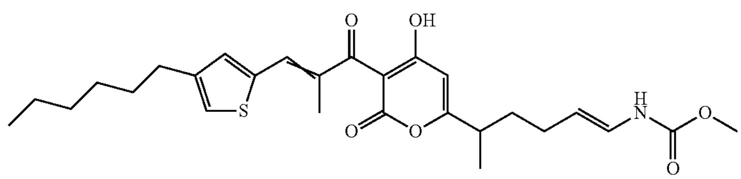 | A | 62 mg | 12:1 |
| 5 | APY20 | 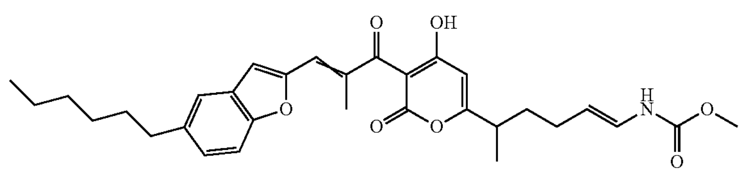 [SMILES: CCCCCCc1ccc2oc(C=C(C)C(=O)c3c(O)cc(C(C)CC/C=C/NC(=O)OC)oc3=O)cc2c1] | A | 60 mg | 3.5:1 |
| 6 | APY21 | 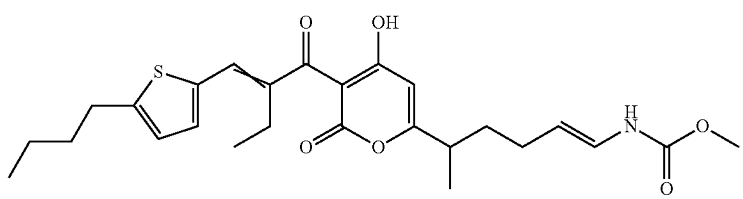 [SMILES: CCCCc1ccc(C=C(CC)C(=O)c2c(O)cc(C(C)CC/C=C/NC(=O)OC)oc2=O)s1] | B | 11.2 mg | 2.5:1 |
| 7 | APY25 | 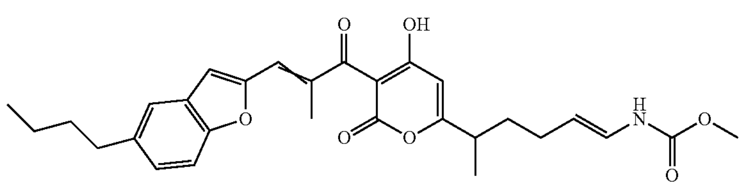 [SMILES: CCCCc1ccc2oc(C=C(C)C(=O)c3c(O)cc(C(C)CC/C=C/NC(=O)OC)oc3=O)cc2c1] | B | 51 mg | 2.7:1 |
| 8 | APY27 | 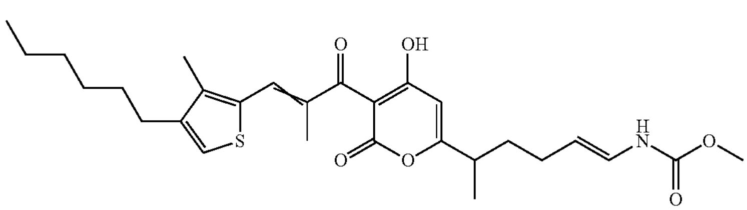 [SMILES: CCCCCCc1csc(C=C(C)C(=O)c2c(O)cc(C(C)CC/C=C/NC(=O)OC)oc2=O)c1C] | B | 6.7 mg | 10:1 |
| 9 | APY19 | 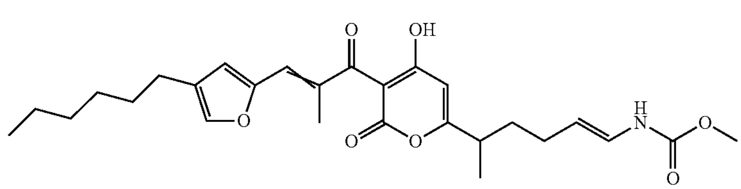 [SMILES: CCCCCCc1coc(C=C(C)C(=O)c2c(O)cc(C(C)CC/C=C/NC(=O)OC)oc2=O)c1] | C | 15.2 mg | 5:1 |

TABLE 1-continued

Representative compounds.

| Example Number | Compound Number | Structure | Prep Method | Amount Isolated | E/Z Ratio (¹H NMR) |
|---|---|---|---|---|---|
| 10 | APY26 | 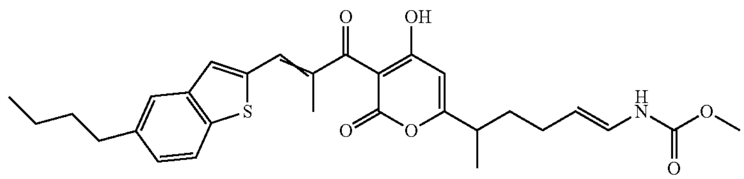 [SMILES: CCCCc1ccc2sc(C=C(C)C(=O)c3c(O)cc(C(C)CC/C=C/NC(=O)OC)oc3=O)cc2c1] | C | 32 mg | 3:1 |
| 11 | APY28 | 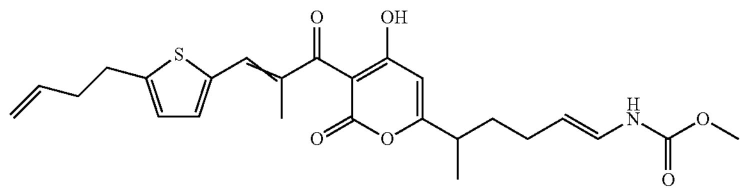 [SMILES: C=CCCc1ccc(C=C(C)C(=O)c2c(O)cc(C(C)CC/C=C/NC(=O)OC)oc2=O)s1] | C | 1.1 mg | 4:1 |
| 12 | APY29 | 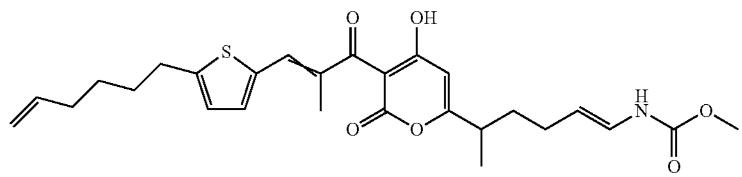 [SMILES: C=CCCCCc1ccc(C=C(C)C(=O)c2c(O)cc(C(C)CC/C=C/NC(=O)OC)oc2=O)s1] | C | 1.8 mg | 10:1 |
| 13 | APY31 | 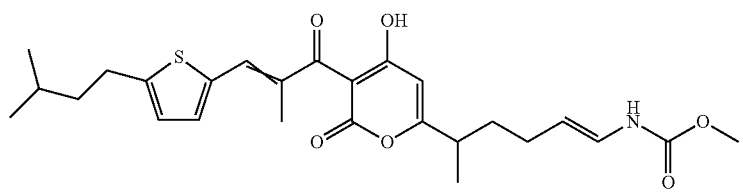 | C | 1.7 mg | 8:1 |
| 14 | APY32 | 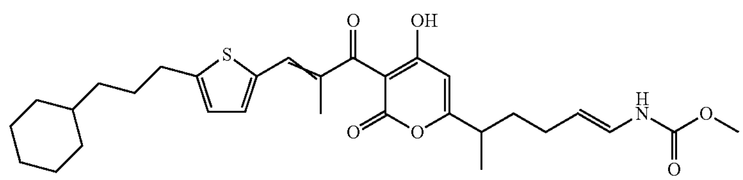 [SMILES: COC(=O)N/C=C/CCC(C)c1cc(O)c(C(=O)C(C)=Cc2ccc(CCCC3CCCCC3)s2)c(=O)o1] | C | 1.7 mg | 12:1 |
| 15 | APY33 | 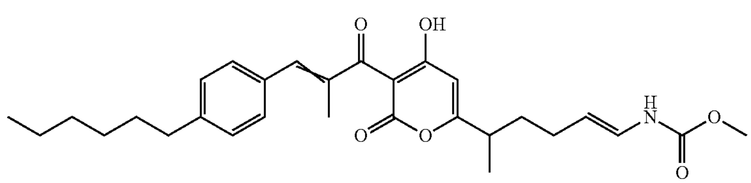 [SMILES: CCCCCCc1ccc(C=C(C)C(=O)c2c(O)cc(C(C)CC/C=C/NC(=O)OC)oc2=O)cc1] | C | 3.0 mg | 2.3:1 |
| 16 | APY34 | 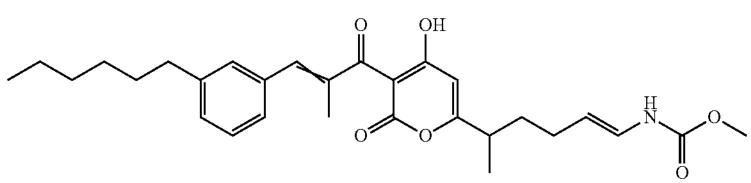 [SMILES: CCCCCCc1cccc(C=C(C)C(=O)c2c(O)cc(C(C)CC/C=C/NC(=O)OC)oc2=O)c1] | C | 6.5 mg | 2.3:1 |
| 17 | APY36 | 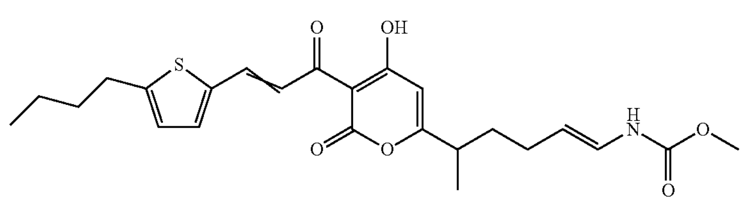 [SMILES: CCCCc1ccc(C=CC(=O)c2c(O)cc(C(C)CC/C=C/NC(=O)OC)oc2=O)s1] | C | 15.4 mg | 3.7:1 |

TABLE 1-continued

Representative compounds.

| Example Number | Compound Number | Structure | Prep Method | Amount Isolated | E/Z Ratio ($^1$H NMR) |
|---|---|---|---|---|---|
| 18 | APY37 | 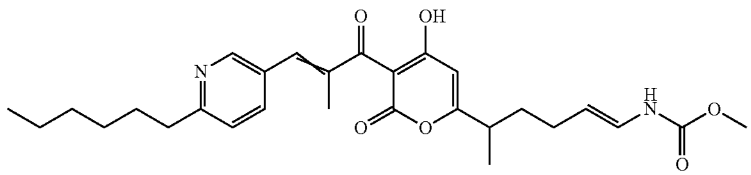 [SMILES: CCCCCCc1ccc(C=C(C)C(=O)c2c(O)cc(C(C)CC/C=C/NC(=O)OC)oc2=O)cn1] | C | 0.8 mg | 2:1 |
| 19 | APY39 | 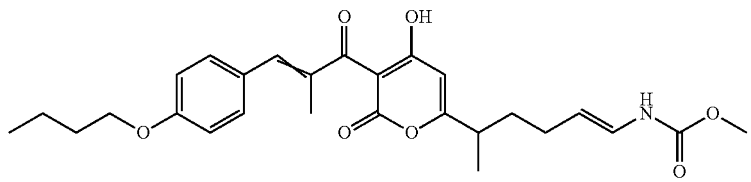 [SMILES: CCCCOc1ccc(C=C(C)C(=O)c2c(O)cc(C(C)CC/C=C/NC(=O)OC)oc2=O)cc1] | C | 9.1 mg | 4:1 |
| 20 | APY40 | 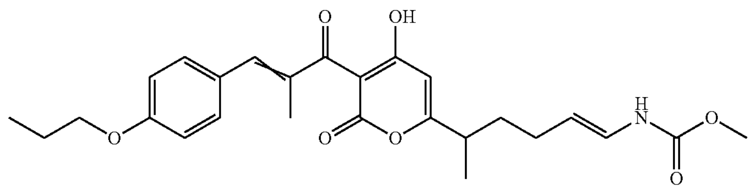 [SMILES: CCCOc1ccc(C=C(C)C(=O)c2c(O)cc(C(C)CC/C=C/NC(=O)OC)oc2=O)cc1] | C | 6.3 mg | 4:1 |
| 21 | APY41 | 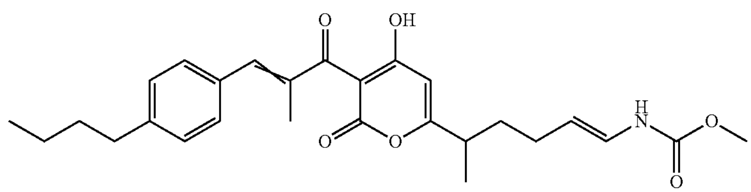 [SMILES: CCCCc1ccc(C=C(C)C(=O)c2c(O)cc(C(C)CC/C=C/NC(=O)OC)oc2=O)cc1] | C | 10.5 mg | 4:1 |
| 22 | APY42 | 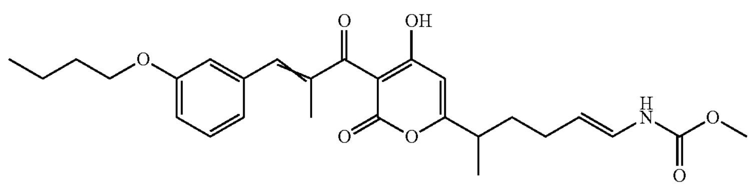 [SMILES: CCCCOc1cccc(C=C(C)C(=O)c2c(O)cc(C(C)CC/C=C/NC(=O)OC)oc2=O)c1] | C | 5.5 mg | 3:1 |
| 23 | APY43 | 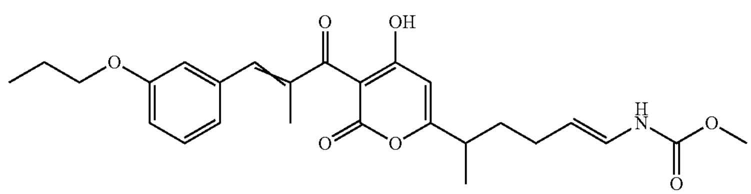 [SMILES: CCCOc1cccc(C=C(C)C(=O)c2c(O)cc(C(C)CC/C=C/NC(=O)OC)oc2=O)c1] | C | 6.6 mg | 3:1 |
| 24 | APY48 | 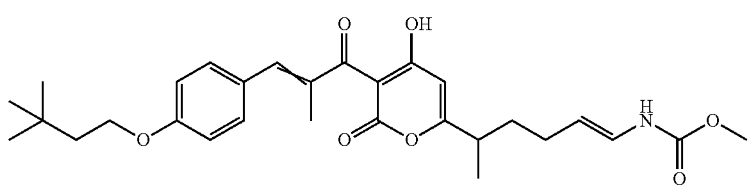 [SMILES: COC(=O)N/C=C/CCC(C)c1cc(O)c(C(=O)C(C)=Cc2ccc(OCCC(C)(C)C)cc2)c(=O)o1] | C | 1.7 mg | 5:1 |
| 25 | APY49 | 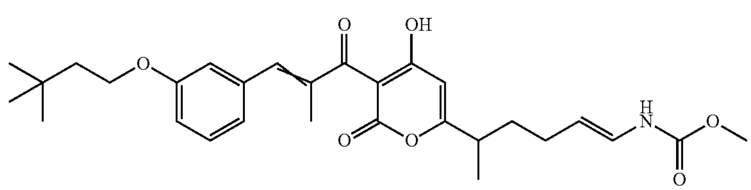 [SMILES: COC(=O)N/C=C/CCC(C)c1cc(O)c(C(=O)C(C)=Cc2cccc(OCCC(C)(C)C)c2)c(=O)o1] | C | 8.8 mg | 2.7:1 |

TABLE 1-continued

Representative compounds.

| Example Number | Compound Number | Structure | Prep Method | Amount Isolated | E/Z Ratio ($^1$H NMR) |
|---|---|---|---|---|---|
| 26 | APY50 | 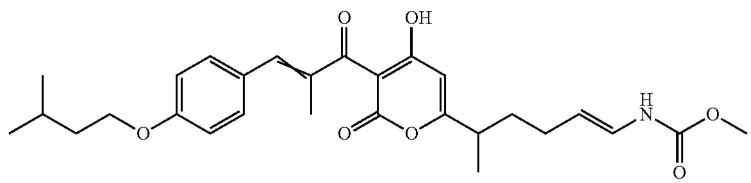 [SMILES: COC(=O)N/C=C/CCC(C)c1cc(O)c(C(=O)C(C)=Cc2ccc(OCCC(C)C)cc2)c(=O)o1] | C | 3.9 mg | 4.5:1 |
| 27 | APY51 | 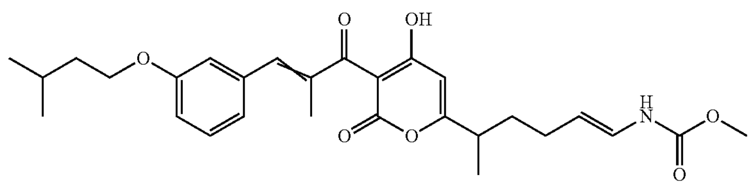 [SMILES: COC(=O)N/C=C/CCC(C)c1cc(O)c(C(=O)C(C)=Cc2cccc(OCCC(C)C)c2)c(=O)o1] | C | 4.8 mg | 2.6:1 |
| 28 | APY52 | 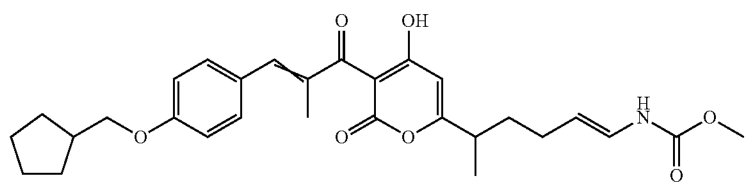 [SMILES: COC(=O)N/C=C/CCC(C)c1cc(O)c(C(=O)C(C)=Cc2ccc(OCC3CCCC3)cc2)c(=O)o1] | C | 3.6 mg | 4:1 |
| 29 | APY53 | 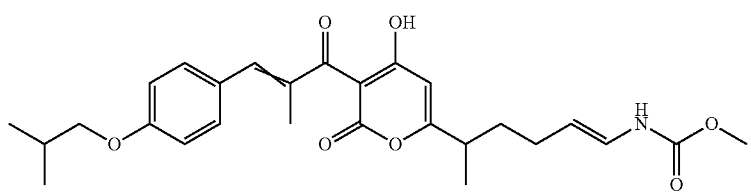 [SMILES: COC(=O)N/C=C/CCC(C)c1cc(O)c(C(=O)C(C)=Cc2ccc(OCC(C)C)cc2)c(=O)o1] | C | 6.9 mg | 5:1 |
| 30 | APY54 | 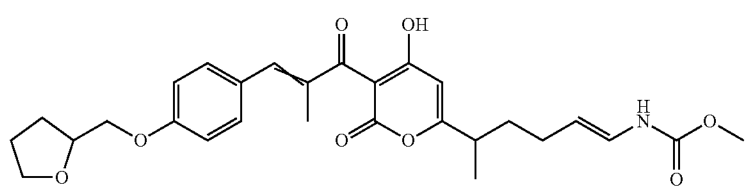 [SMILES: COC(=O)N/C=C/CCC(C)c1cc(O)c(C(=O)C(C)=Cc2ccc(OCC3CCCO3)cc2)c(=O)o1] | C | 6.6 mg | 3:1 |
| 31 | APY55 | 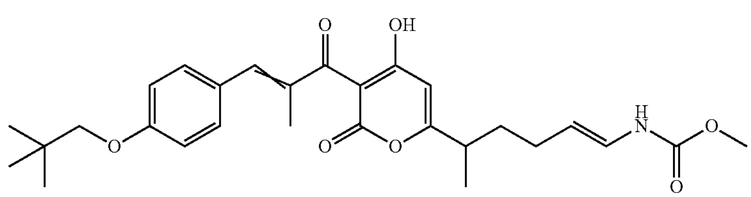 [SMILES: COC(=O)N/C=C/CCC(C)c1cc(O)c(C(=O)C(C)=Cc2ccc(OCC(C)(C)C)cc2)c(=O)o1] | C | 6.8 mg | 4:1 |
| 32 | APY56 | 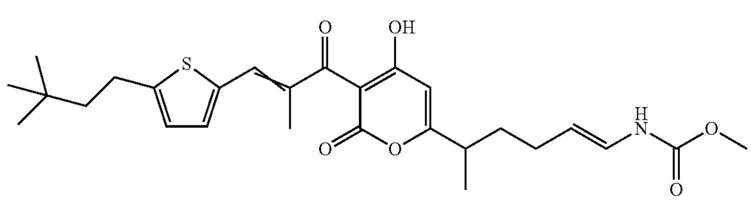 [SMILES: COC(=O)N/C=C/CCC(C)c1cc(O)c(C(=O)C(C)=Cc2ccc(CCC(C)(C)C)s2)c(=O)o1] | C | 5.6 mg | >10:1 |

TABLE 1-continued
Representative compounds.
| Example Number | Compound Number | Structure | Prep Method | Amount Isolated | E/Z Ratio ($^1$H NMR) |
|---|---|---|---|---|---|
| 33 | APY57 | 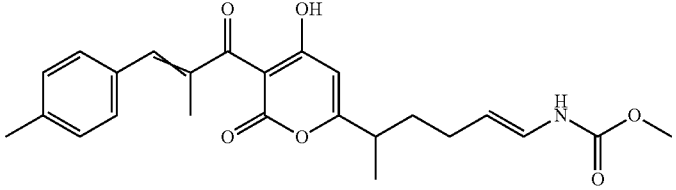 | C | 2.9 mg | 3.5:1 |
| 34 | APY58 | 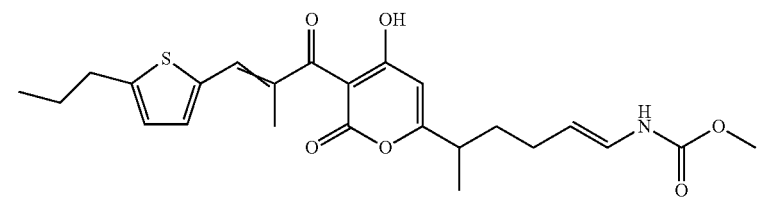 | C | 3.6 mg | 3:1 |
| 35 | APY59 | 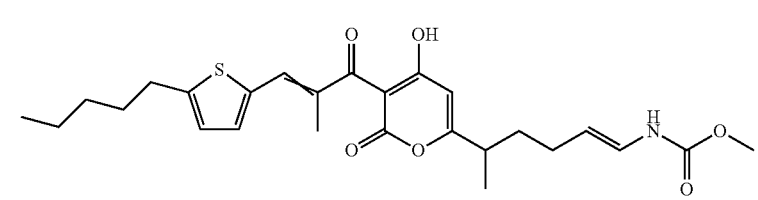 | C | 3.1 mg | 2:1 |
| 36 | APY60 | 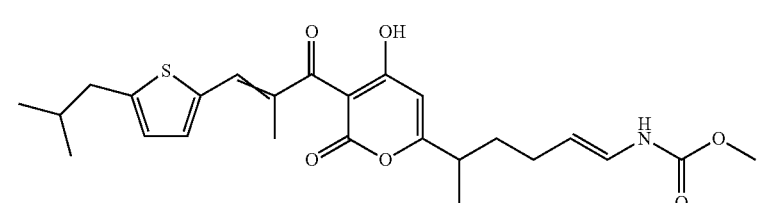 | C | 2.8 mg | >10:1 |
| 37 | APY61 | 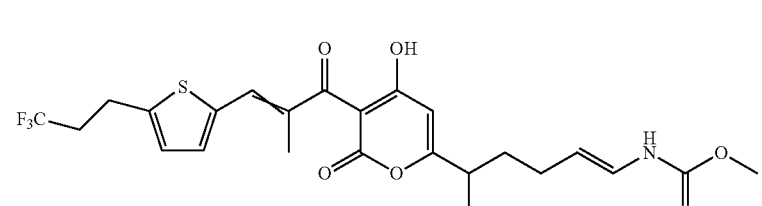 | C | 2.7 mg | >10:1 |
| 38 | APY62 | 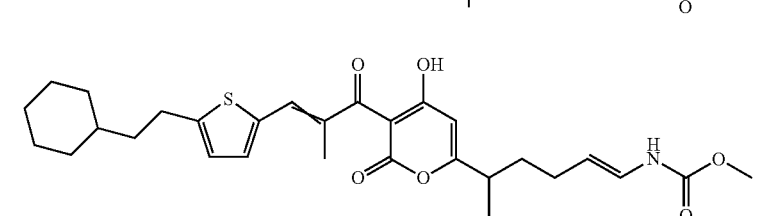 | C | 7.0 mg | 3.5:1 |
| 39 | APY64 | 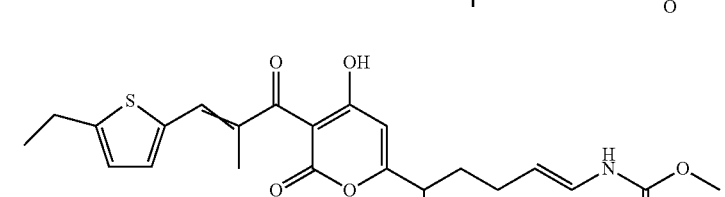 | C | 7.0 mg | >10:1 |

TABLE 1-continued

Representative compounds.

| Example Number | Compound Number | Structure | Prep Method | Amount Isolated | E/Z Ratio ($^1$H NMR) |
|---|---|---|---|---|---|
| 40 | APY66 | 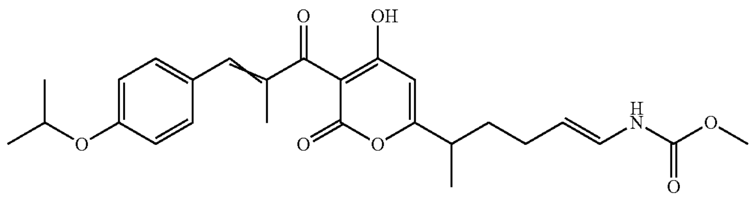 [SMILES: COC(=O)N/C=C/CCC(C)c1cc(O)c(C(=O)C(C)=Cc2ccc(OC(C)C)cc2)c(=O)o1] | C | 7.4 mg | 4.5:1 |
| 41 | APY67 | 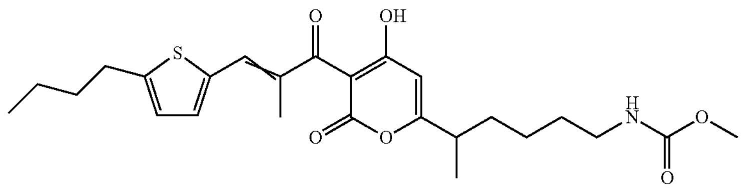 [SMILES: CCCCc1ccc(C=C(C)C(=O)c2c(O)cc(C(C)CCCCNC(=O)OC)oc2=O)s1] | C | 6.9 mg | >10:1 |
| 42 | APY69 | 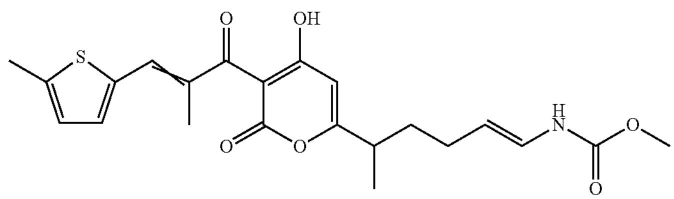 | C | 4.0 mg | >10:1 |
| 43 | APY70 | 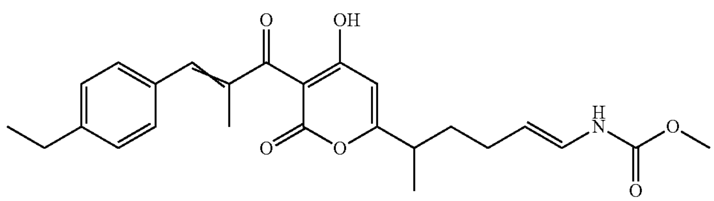 [SMILES: CCc1ccc(C=C(C)C(=O)c2c(O)cc(C(C)CC/C=C/NC(=O)OC)oc2=O)cc1] | C | 3.0 mg | 4:1 |
| 44 | APY71 | 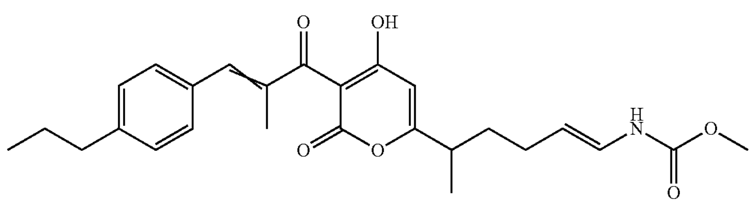 [SMILES: CCCc1ccc(C=C(C)C(=O)c2c(O)cc(C(C)CC/C=C/NC(=O)OC)oc2=O)cc1] | C | 3.0 mg | 4:1 |
| 45 | APY72 | 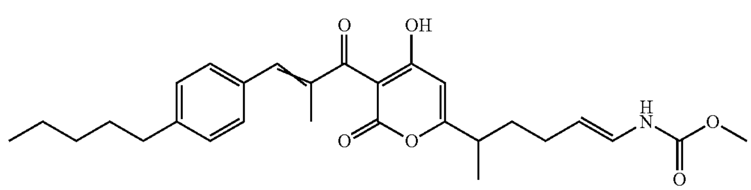 [SMILES: CCCCCc1ccc(C=C(C)C(=O)c2c(O)cc(C(C)CC/C=C/NC(=O)OC)oc2=O)cc1] | C | 5.0 mg | 2:1 |
| 46 | APY73 | 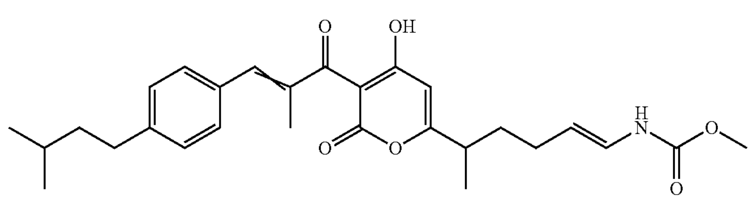 [SMILES: COC(=O)N/C=C/CCC(C)c1cc(O)c(C(=O)C(C)=Cc2ccc(CCC(C)C)cc2)c(=O)o1] | C | 4.0 mg | 2:1 |

TABLE 1-continued

Representative compounds.

| Example Number | Compound Number | Structure | Prep Method | Amount Isolated | E/Z Ratio ($^1$H NMR) |
|---|---|---|---|---|---|
| 47 | APY74 | 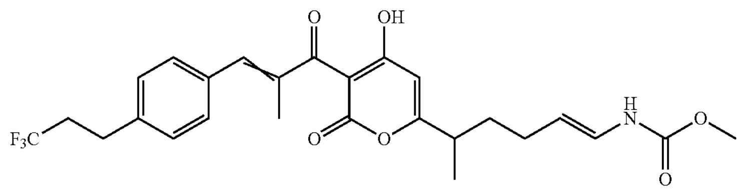 [SMILES: COC(=O)N/C=C/CCC(C)c1cc(O)c(C(=O)C(C)=Cc2ccc(CCC(F)(F)F)cc2)c(=O)o1] | C | 4.0 mg | 2:1 |
| 48 | APY75 | 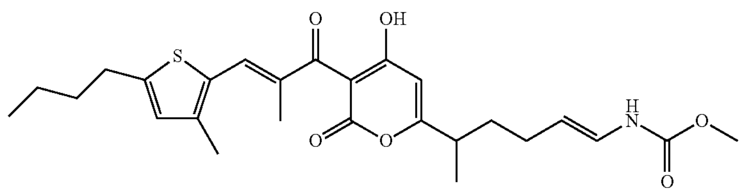 [SMILES: CCCCc1cc(C)c(/C=C(\C)C(=O)c2c(O)cc(C(C)CC/C=C/NC(=O)OC)oc2=O)s1] | C | 4.2 mg | >19:1 |
| 49 | APY76 | 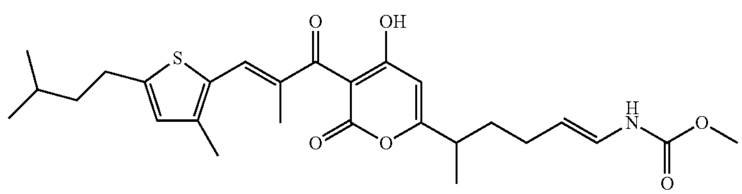 [SMILES: COC(=O)N/C=C/CCC(C)c1cc(O)c(C(=O)/C(C)=C/c2sc(CCC(C)C)cc2C)c(=O)o1] | C | 3.4 mg | >19:1 |
| 50 | APY81 | 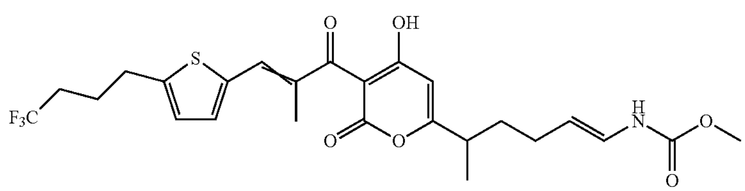 [SMILES: COC(=O)N/C=C/CCC(C)c1cc(O)c(C(=O)C(C)=Cc2ccc(CCCC(F)(F)F)s2)c(=O)o1] | C | 8.9 mg | |
| 51 | APY82 | 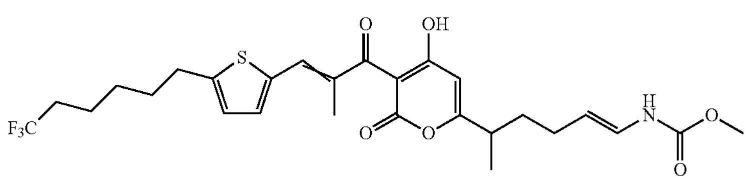 [SMILES: COC(=O)N/C=C/CCC(C)c1cc(O)c(C(=O)C(C)=Cc2ccc(CCCCCC(F)(F)F)s2)c(=O)o1] | C | 4.2 mg | |
| 52 | APY84 | 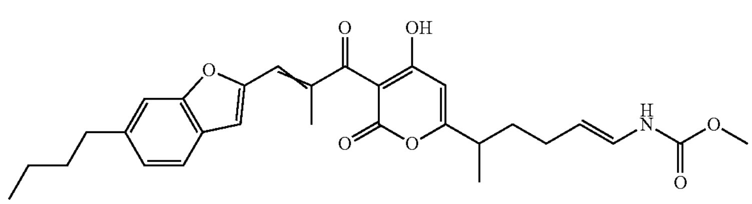 [SMILES: CCCCc1ccc2cc(C=C(C)C(=O)c3c(O)cc(C(C)CC/C=C/NC(=O)OC)oc3=O)oc2c1] | C | 8.5 mg | |
| 53 | APY86 | 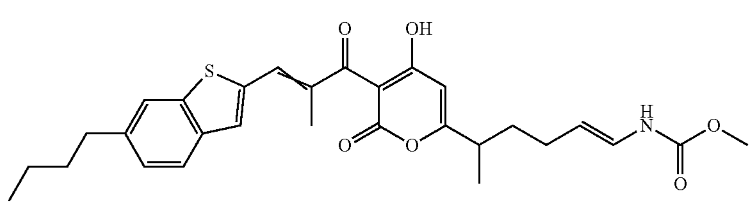 [SMILES: CCCCc1ccc2cc(C=C(C)C(=O)c3c(O)cc(C(C)CC/C=C/NC(=O)OC)oc3=O)sc2c1] | C | 6.0 mg | |

TABLE 1-continued
Representative compounds.
| Example Number | Compound Number | Structure | Prep Method | Amount Isolated | E/Z Ratio ($^1$H NMR) |
|---|---|---|---|---|---|
| 54 | APY87 | 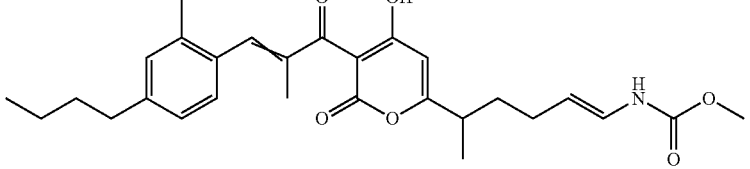 | C | 2.9 mg | |
| 55 | APY90 | 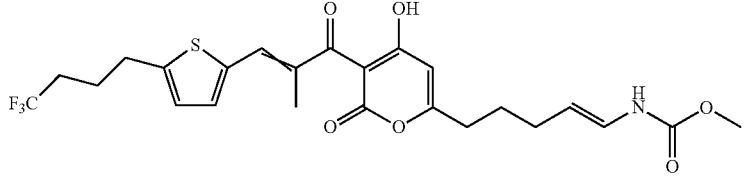 [SMILES: COC(=O)N/C=C/CCC(C)c1cc(O)c(C(=O)C(C)=Cc2ccc(CCCO)s2)c(=O)o1] | C | 4.0 mg | |
| 56 | APY91 | 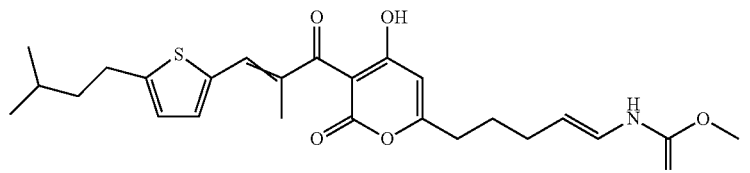 | C | 3.0 mg | |
| 57 | APY94 | 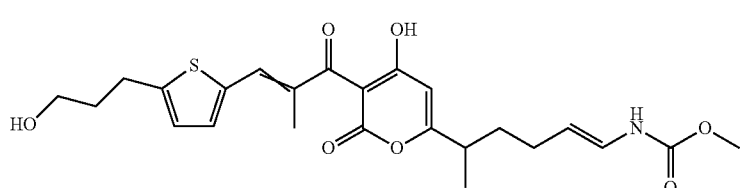 | C | 6.6 mg | |
| 58 | APY95 | 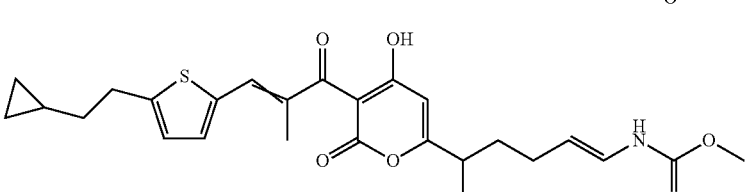 | C | 7.7 mg | |
| 59 | APY96 | 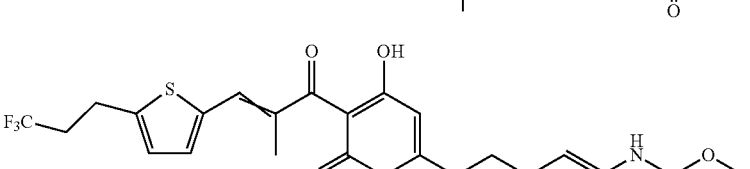 | C | 5.0 mg | |
| 60 | APY97 | 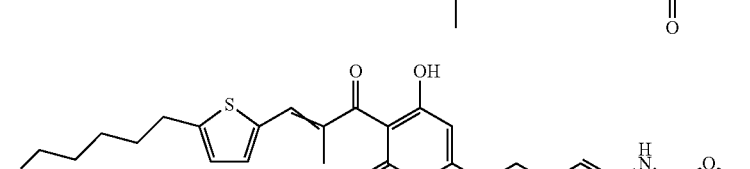 | C | 8.0 mg | |
| 61 | APY98 | 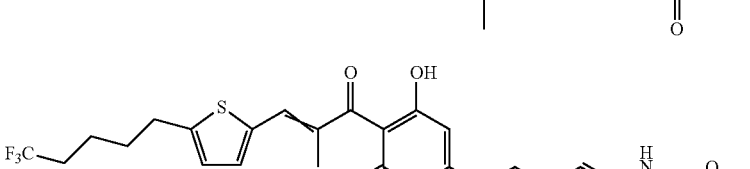 | C | 7.0 mg | |

TABLE 1-continued

Representative compounds.

| Example Number | Compound Number | Structure | Prep Method | Amount Isolated | E/Z Ratio ($^1$H NMR) |
|---|---|---|---|---|---|
| 62 | APY100 | 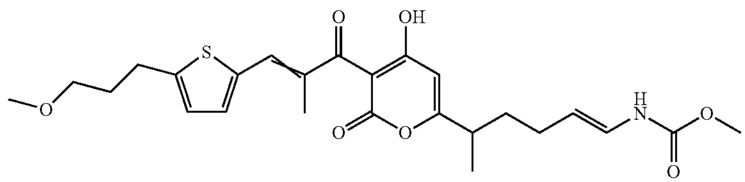 | C | 7.6 mg | |
| 63 | APY101 | 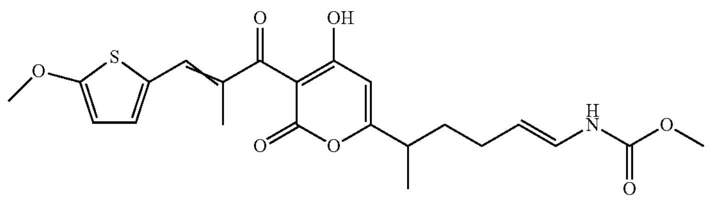 | C | 2.6 mg | |
| 64 | APY102 | 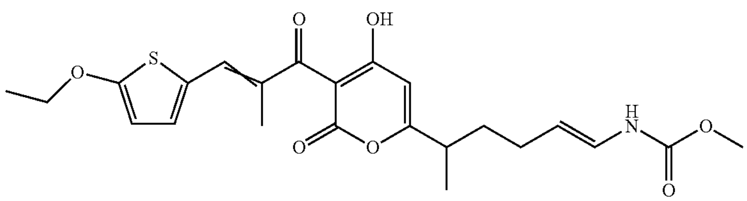 [SMILES: CCOc1ccc(C=C(C)C(=O)c2c(O)cc(C(C)CC/C=C/NC(=O)OC)oc2=O)s1] | C | 7.3 mg | |
| 65 | APY103 | 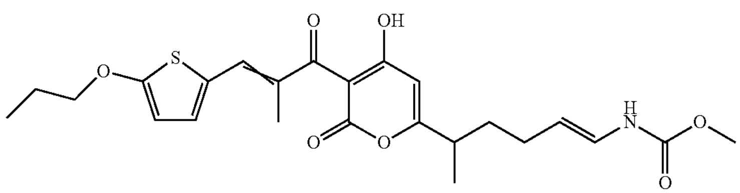 [SMILES: CCCOc1ccc(C=C(C)C(=O)c2c(O)cc(C(C)CC/C=C/NC(=O)OC)oc2=O)s1] | C | 6.6 mg | |
| 66 | APY104 | 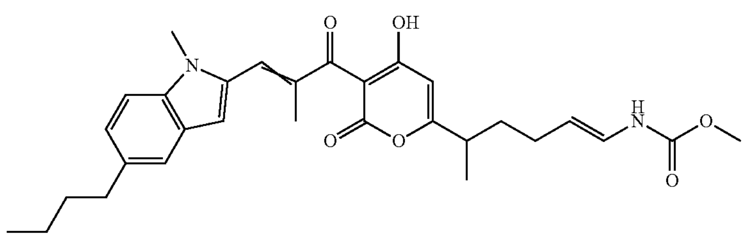 | C | 3.0 mg | |
| 67 | APY105 | 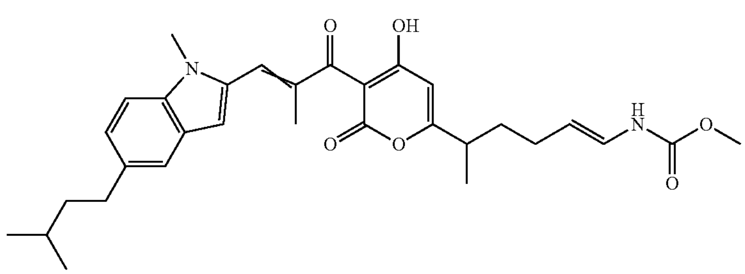 [SMILES: COC(=O)N/C=C/CCC(C)c1cc(O)c(C(=O)C(C)=Cc2cc3cc(CCC(C)C)ccc3n2C)c(=O)o1] | C | 2.0 mg | |
| 68 | APY106 | 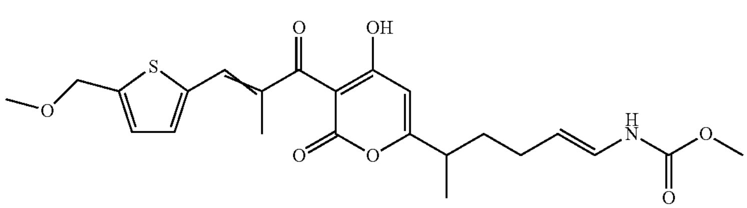 | C | 8.6 mg | |

TABLE 1-continued

Representative compounds.

| Example Number | Compound Number | Structure | Prep Method | Amount Isolated | E/Z Ratio (¹H NMR) |
|---|---|---|---|---|---|
| 69 | APY107 | 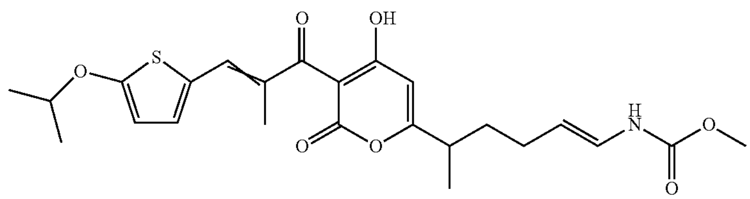 [SMILES: COC(=O)N/C=C/CCC(C)c1cc(O)c(C(=O)C(C)=Cc2ccc(OC(C)C)s2)c(=O)o1] | C | 5.8 mg | |
| 70 | APY108 | 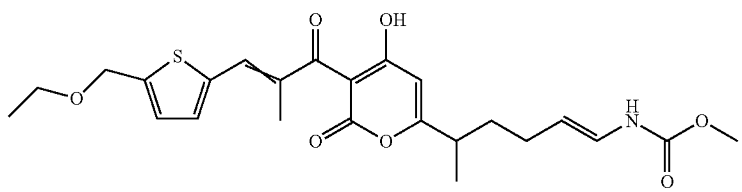 | C | 12.4 mg | |
| 71 | APY109 | 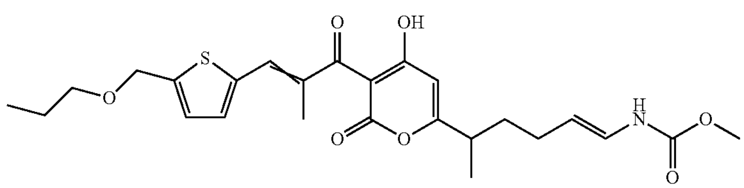 [SMILES: CCCOCc1ccc(C=C(C)C(=O)c2c(O)cc(C(C)CC/C=C/NC(=O)OC)oc2=O)s1] | C | 11.1 mg | |
| 72 | APY110 | 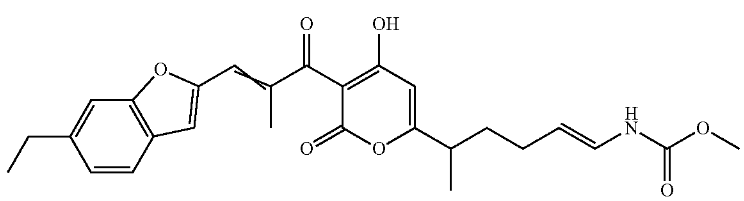 [SMILES: CCc1ccc2cc(C=C(C)C(=O)c3c(O)cc(C(C)CC/C=C/NC(=O)OC)oc3=O)oc2c1] | C | 9.0 mg | |
| 73 | APY111 | 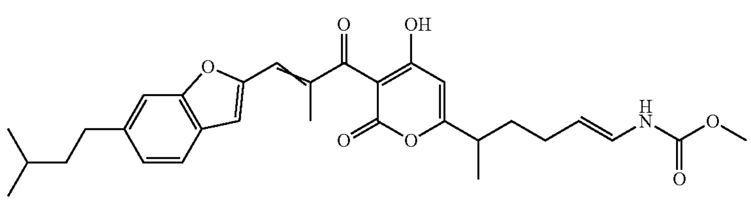 [SMILES: COC(=O)N/C=C/CCC(C)c1cc(O)c(C(=O)C(C)=Cc2cc3ccc(CCC(C)C)cc3o2)c(=O)o1] | C | 8.0 mg | |
| 74 | APY112 | 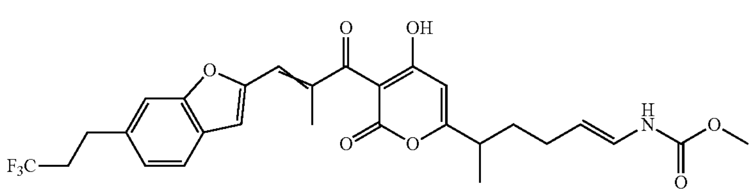 [SMILES: COC(=O)N/C=C/CCC(C)c1cc(O)c(C(=O)C(C)=Cc2cc3ccc(CCC(F)(F)F)cc3o2)c(=O)o1] | C | 4.0 mg | |
| 75 | APY114 | 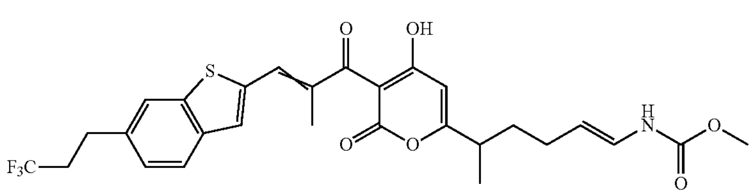 [SMILES: COC(=O)N/C=C/CCC(C)c1cc(O)c(C(=O)C(C)=Cc2cc3ccc(CCC(F)(F)F)cc3s2)c(=O)o1] | C | 5.0 mg | |

TABLE 1-continued

Representative compounds.

| Example Number | Compound Number | Structure | Prep Method | Amount Isolated | E/Z Ratio (¹H NMR) |
|---|---|---|---|---|---|
| 76 | APY116 | 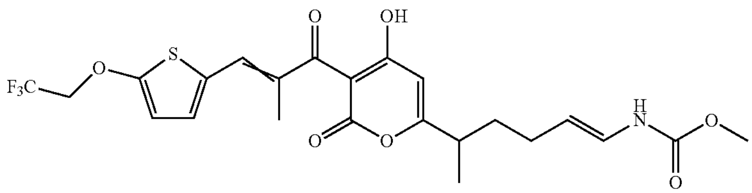 [SMILES: COC(=O)N/C=C/CCC(C)c1cc(O)c(C(=O)C(C)=Cc2ccc(OCC(F)(F)F)s2)c(=O)o1] | C | 5.8 mg | |
| 77 | APY117 | 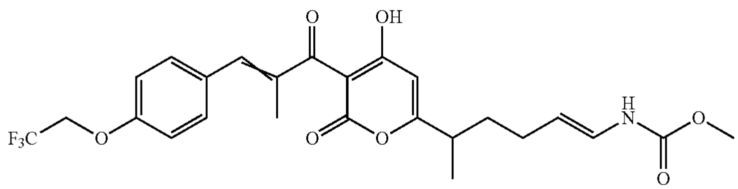 [SMILES: COC(=O)N/C=C/CCC(C)c1cc(O)c(C(=O)C(C)=Cc2ccc(OCC(F)(F)F)cc2)c(=O)o1] | C | 7.0 mg | |
| 78 | APY119 | 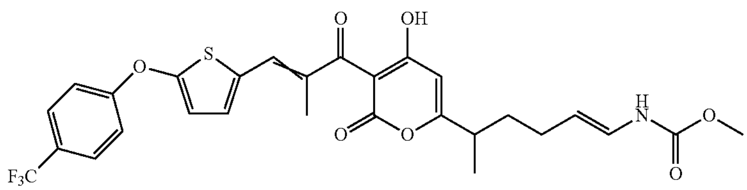 [SMILES: COC(=O)N/C=C/CCC(C)c1cc(O)c(C(=O)C(C)=Cc2ccc(Oc3ccc(C(F)(F)F)cc3)s2)c(=O)o1] | C | 10.1 mg | |
| 79 | APY120 | 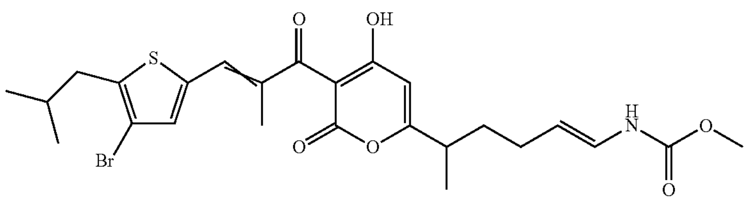 [SMILES: COC(=O)N/C=C/CCC(C)c1cc(O)c(C(=O)C(C)=Cc2cc(Br)c(CC(C)C)s2)c(=O)o1] | C | 6.7 mg | |
| 80 | APY121 | 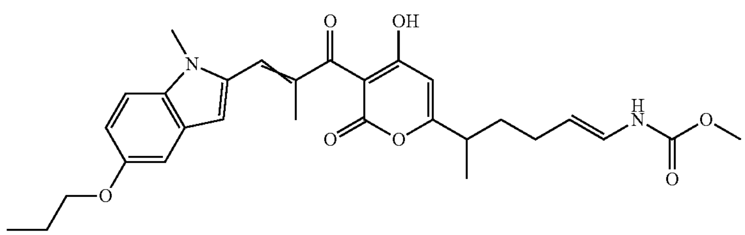 [SMILES: CCCOc1ccc2c(c1)cc(C=C(C)C(=O)c1c(O)cc(C(C)CC/C=C/NC(=O)OC)oc1=O)n2C] | C | 1.5 mg | |
| 81 | APY122 | 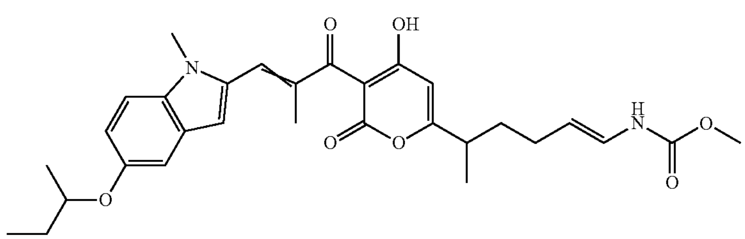 [SMILES: CCC(C)Oc1ccc2c(c1)cc(C=C(C)C(=O)c1c(O)cc(C(C)CC/C=C/NC(=O)OC)oc1=O)n2C] | C | 1.2 mg | |
| 82 | APY123 | 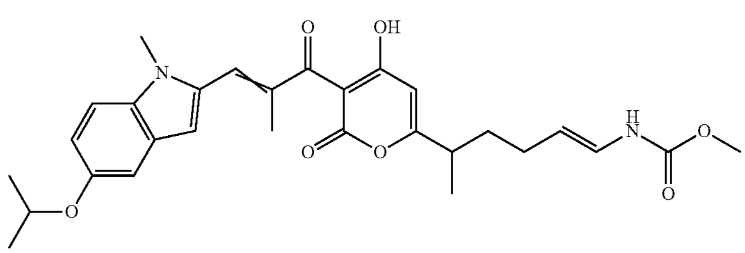 [SMILES: COC(=O)N/C=C/CCC(C)c1cc(O)c(C(=O)C(C)=Cc2cc3cc(OC(C)C)ccc3n2C)c(=O)o1] | C | 2.4 mg | |

TABLE 1-continued

Representative compounds.

| Example Number | Compound Number | Structure | Prep Method | Amount Isolated | E/Z Ratio (¹H NMR) |
|---|---|---|---|---|---|
| 83 | APY124 | 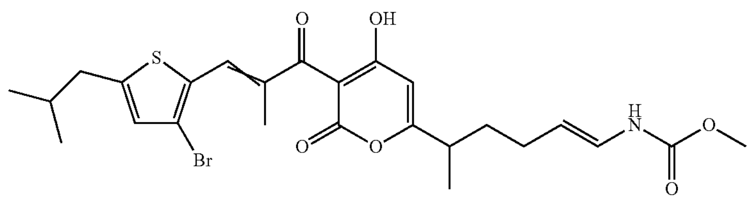 [SMILES: COC(=O)N/C=C/CCC(C)c1cc(O)c(C(=O)C(C)=Cc2sc(CC(C)C)cc2Br)c(=O)o1] | C | 8.2 mg | |
| 84 | APY125 | 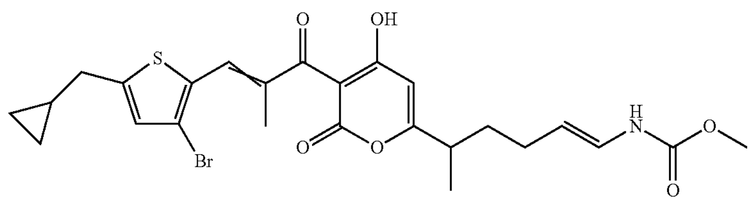 [SMILES: COC(=O)N/C=C/CCC(C)c1cc(O)c(C(=O)C(C)=Cc2sc(CC3CC3)cc2Br)c(=O)o1] | C | 3.8 mg | |
| 85 | APY126 | 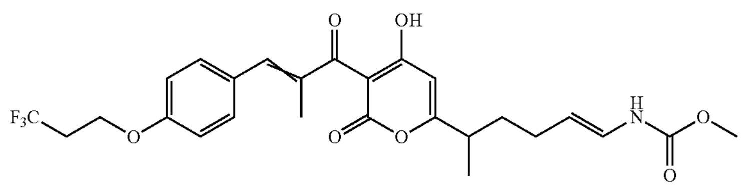 [SMILES: COC(=O)N/C=C/CCC(C)c1cc(O)c(C(=O)C(C)=Cc2ccc(OCCC(F)(F)F)cc2)c(=O)o1] | C | 4.5 mg | |
| 86 | APY127 | 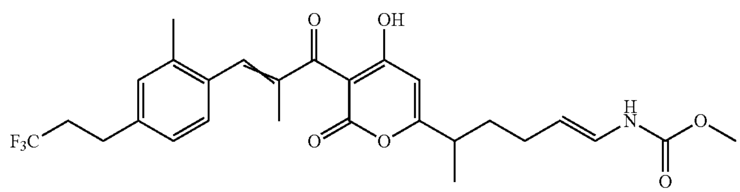 [SMILES: COC(=O)N/C=C/CCC(C)c1cc(O)c(C(=O)C(C)=Cc2ccc(CCC(F)(F)F)cc2C)c(=O)o1] | C | 3.5 mg | |
| 87 | APY128 | 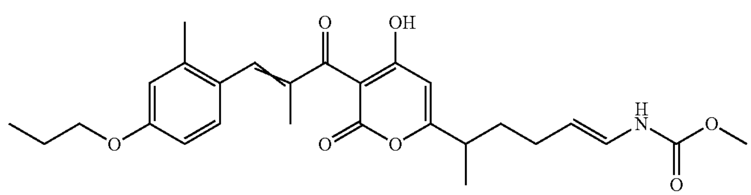 [SMILES: CCCOc1ccc(C=C(C)C(=O)c2c(O)cc(C(C)CC/C=C/NC(=O)OC)oc2=O)c(C)c1] | C | 3.6 mg | |
| 88 | APY129 | 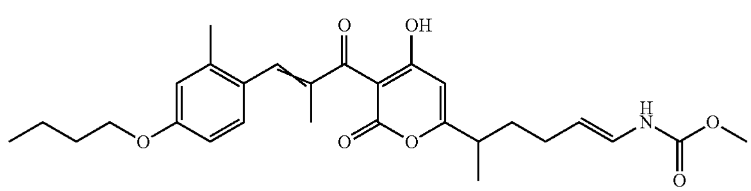 [SMILES: CCCCOc1ccc(C=C(C)C(=O)c2c(O)cc(C(C)CC/C=C/NC(=O)OC)oc2=O)c(C)c1] | C | 3.0 mg | |
| 89 | APY130 | 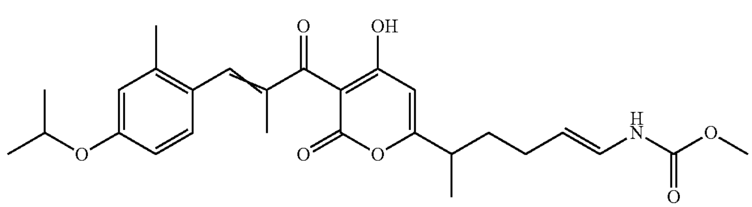 [SMILES: COC(=O)N/C=C/CCC(C)c1cc(O)c(C(=O)C(C)=Cc2ccc(OC(C)C)cc2C)c(=O)o1] | C | 3.2 mg | |

TABLE 1-continued
Representative compounds.
| Example Number | Compound Number | Structure | Prep Method | Amount Isolated | E/Z Ratio ($^1$H NMR) |
|---|---|---|---|---|---|
| 90 | APY131 | 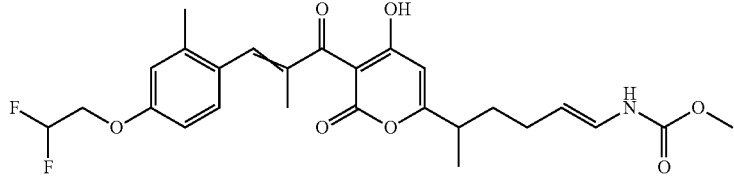 | C | 3.0 mg | |
| 91 | APY132 | 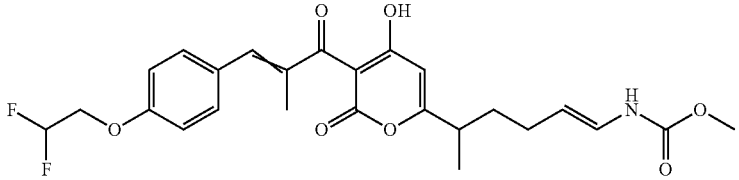 [SMILES: COC(=O)N/C=C/CCC(C)c1cc(O)c(C(=O)C(C)=Cc2ccc(OCC(F)F)cc2)c(=O)o1] | C | 3.8 mg | |
| 92 | APY135 | 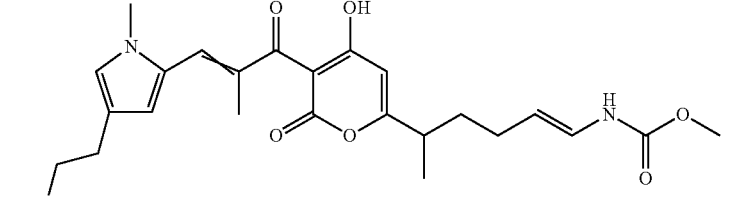 | C | 0.9 mg | |
| 93 | APY136 | 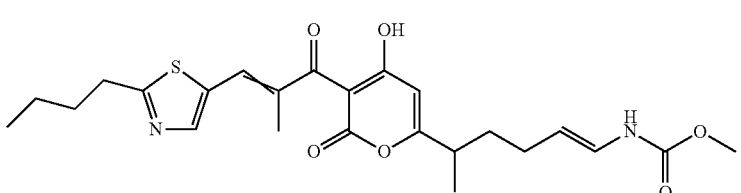 | C | 6.8 mg | |
| 94 | APY137 | 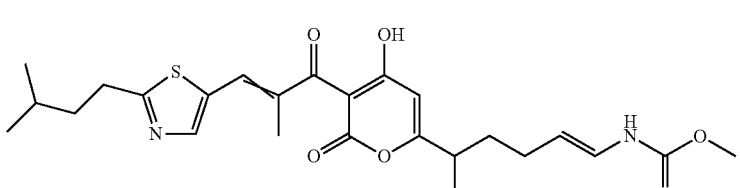 | C | 10.6 mg | |
| 95 | APY138 | 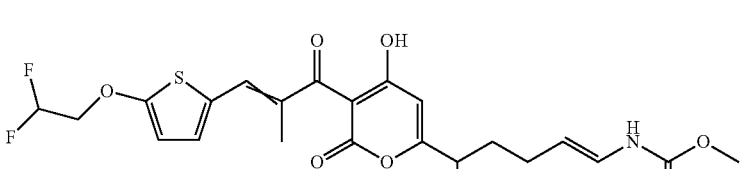 | C | 1.6 mg | |
| 96 | APY139 | 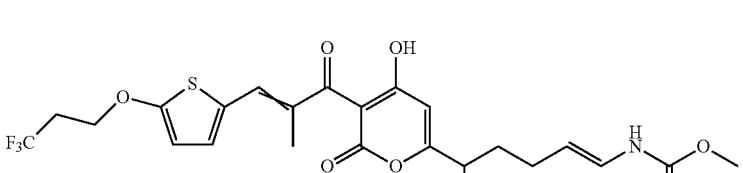 | C | 1.6 mg | |

TABLE 1-continued

Representative compounds.

| Example Number | Compound Number | Structure | Prep Method | Amount Isolated | E/Z Ratio ($^1$H NMR) |
|---|---|---|---|---|---|
| 97 | APY142 | 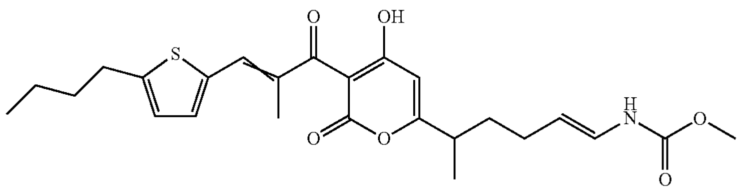 | C | 2.4 mg | |
| 98 | APY143 | 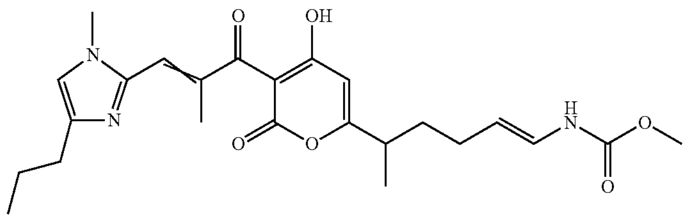 [SMILES: CCCc1cn(C)c(C=C(C)C(=O)c2c(O)cc(C(C)CC/C=C/NC(=O)OC)oc2=O)n1] | C | 1.4 mg | |

TABLE 2

Representative compound names.

| Example Number | Compound Number | Name |
|---|---|---|
| 1 | APY15 | methyl (E)-5-(3-((E/Z)-3-(5-hexylthiophen-2-yl)-2-methylacryloyl)-4-hydroxy-2-oxo-2H-pyran-6-yl)hex-1-enylcarbamate |
| 2 | APY16 | methyl (E)-5-(3-((E/Z)-3-(5-butylthiophen-2-yl)-2-methylacryloyl)-4-hydroxy-2-oxo-2H-pyran-6-yl)hex-1-enylcarbamate |
| 3 | APY17 | methyl (E)-5-(3-((E/Z)-3-(5-hexylfuran-2-yl)-2-methylacryloyl)-4-hydroxy-2-oxo-2H-pyran-6-yl)hex-1-enylcarbamate |
| 4 | APY18 | methyl (E)-5-(3-((E/Z)-3-(4-hexylthiophen-2-yl)-2-methylacryloyl)-4-hydroxy-2-oxo-2H-pyran-6-yl)hex-1-enylcarbamate |
| 5 | APY20 | methyl (E)-5-(3-((E/Z)-3-(5-hexylbenzofuran-2-yl)-2-methylacryloyl)-4-hydroxy-2-oxo-2H-pyran-6-yl)hex-1-enylcarbamate |
| 6 | APY21 | methyl (E)-5-(3-((E/Z)-2-((5-butylthiophen-2-yl)methylene)butanoyl)-4-hydroxy-2-oxo-2H-pyran-6-yl)hex-1-enylcarbamate |
| 7 | APY25 | methyl (E)-5-(3-((E/Z)-3-(5-butylbenzofuran-2-yl)-2-methylacryloyl)-4-hydroxy-2-oxo-2H-pyran-6-yl)hex-1-enylcarbamate |
| 8 | APY27 | methyl (E)-5-(3-((E/Z)-3-(4-hexyl-3-methylthiophen-2-yl)-2-methylacryloyl)-4-hydroxy-2-oxo-2H-pyran-6-yl)hex-1-enylcarbamate |
| 9 | APY19 | methyl (E)-5-(3-((E/Z)-3-(4-hexylfuran-2-yl)-2-methylacryloyl)-4-hydroxy-2-oxo-2H-pyran-6-yl)hex-1-enylcarbamate |
| 10 | APY26 | methyl (E)-5-(3-((E/Z)-3-(5-butylbenzo[b]thiophen-2-yl)-2-methylacryloyl)-4-hydroxy-2-oxo-2H-pyran-6-yl)hex-1-enylcarbamate |
| 11 | APY28 | methyl (E)-5-(3-((E/Z)-3-(5-(but-3-enyl)thiophen-2-yl)-2-methylacryloyl)-4-hydroxy-2-oxo-2H-pyran-6-yl)hex-1-enylcarbamate |
| 12 | APY29 | methyl (E)-5-(3-((E/Z)-3-(5-(hex-5-enyl)thiophen-2-yl)-2-methylacryloyl)-4-hydroxy-2-oxo-2H-pyran-6-yl)hex-1-enylcarbamate |
| 13 | APY31 | methyl (E)-5-(4-hydroxy-3-((E/Z)-3-(5-isopentylthiophen-2-yl)-2-methylacryloyl)-2-oxo-2H-pyran-6-yl)hex-1-enylcarbamate |
| 14 | APY32 | methyl (E)-5-(3-((E/Z)-3-(5-(3-cyclohexylpropyl)thiophen-2-yl)-2-methylacryloyl)-4-hydroxy-2-oxo-2H-pyran-6-yl)hex-1-enylcarbamate |
| 15 | APY33 | methyl (E)-5-(3-((E/Z)-3-(4-hexylphenyl)-2-methylacryloyl)-4-hydroxy-2-oxo-2H-pyran-6-yl)hex-1-enylcarbamate |
| 16 | APY34 | methyl (E)-5-(3-((E/Z)-3-(3-hexylphenyl)-2-methylacryloyl)-4-hydroxy-2-oxo-2H-pyran-6-yl)hex-1-enylcarbamate |
| 17 | APY36 | methyl (E)-5-(3-((E/Z)-3-(5-butylthiophen-2-yl)acryloyl)-4-hydroxy-2-oxo-2H-pyran-6-yl)hex-1-enylcarbamate |
| 18 | APY37 | methyl (E)-5-(3-((E/Z)-3-(6-hexylpyridin-3-yl)-2-methylacryloyl)-4-hydroxy-2-oxo-2H-pyran-6-yl)hex-1-enylcarbamate |
| 19 | APY39 | methyl (E)-5-(3-((E/Z)-3-(4-butoxyphenyl)-2-methylacryloyl)-4-hydroxy-2-oxo-2H-pyran-6-yl)hex-1-enylcarbamate |
| 20 | APY40 | methyl (E)-5-(4-hydroxy-3-((E/Z)-2-methyl-3-(4-propoxyphenyl)acryloyl)-2-oxo-2H-pyran-6-yl)hex-1-enylcarbamate |
| 21 | APY41 | methyl (E)-5-(3-((E/Z)-3-(4-butylphenyl)-2-methylacryloyl)-4-hydroxy-2-oxo-2H-pyran-6-yl)hex-1-enylcarbamate |
| 22 | APY42 | methyl (E)-5-(3-((E/Z)-3-(3-butoxyphenyl)-2-methylacryloyl)-4-hydroxy-2-oxo-2H-pyran-6-yl)hex-1-enylcarbamate |

TABLE 2-continued

Representative compound names.

| Example Number | Compound Number | Name |
|---|---|---|
| 23 | APY43 | methyl (E)-5-(4-hydroxy-3-((E/Z)-2-methyl-3-(3-propoxyphenyl)acryloyl)-2-oxo-2H-pyran-6-yl)hex-1-enylcarbamate |
| 24 | APY48 | methyl (E)-5-(3-((E/Z)-3-(4-(3,3-dimethylbutoxy)phenyl)-2-methylacryloyl)-4-hydroxy-2-oxo-2H-pyran-6-yl)hex-1-enylcarbamate |
| 25 | APY49 | methyl (E)-5-(3-((E/Z)-3-(3-(3,3-dimethylbutoxy)phenyl)-2-methylacryloyl)-4-hydroxy-2-oxo-2H-pyran-6-yl)hex-1-enylcarbamate |
| 26 | APY50 | methyl (E)-5-(4-hydroxy-3-((E/Z)-3-(4-isopentyloxy)phenyl)-2-methacryloyl-2-oxo-2H-pyran-6-yl)hex-1-enylcarbamate |
| 27 | APY51 | methyl (E)-5-(4-hydroxy-3-((E/Z)-3-(3-isopentyloxy)phenyl)-2-methacryloyl-2-oxo-2H-pyran-6-yl)hex-1-enylcarbamate |
| 28 | APY52 | methyl (E)-5-(3-((E/Z)-3-(4-cyclopentylmethoxy)phenyl)-2-methacryloyl)-4-hydroxy-2-oxo-2H-pyran-6-yl)hex-1-enylcarbamate |
| 29 | APY53 | methyl (E)-5-(4-hydroxy-3-((E/Z)-3-(4-isobutoxyphenyl)-2-methacryloyl)-4-hydroxy-2-oxo-2H-pyran-6-yl)hex-1-enylcarbamate |
| 30 | APY54 | methyl (E)-5-(4-hydroxy-3-((E/Z)-2-methyl-3-(4-((tetrahydrofuran-2-yl)methoxy)phenyl)acryloyl)-2-oxo-2H-pyran-6-y)hex-1-enylcarbamate |
| 31 | APY55 | methyl (E)-5-(4-hydroxy-3-((E/Z)-2-methyl-3-(4-(neopentyloxy)phenyl)acryloyl)-2-oxo-2H-pyran-6-yl)hex-1-enylcarbamate |
| 32 | APY56 | methyl (E)-5-(4-hydroxy-5-((E/Z)-2-methyl-3-(5-(3,3-dimethylbutyl)thiophen-2-yl)acryloyl)-6-oxo-6H-pyran-2-yl)hex-1-enylcarbamate |
| 33 | APY57 | methyl (E)-5-(4-hydroxy-5-((E/Z)-2-methyl-3-p-tolylacryloyl)-6-oxo-6H-pyran-2-yl)hex-1-enylcarbamate |
| 34 | APY58 | methyl (E)-5-(4-hydroxy-5-((E/Z)-2-methyl-3-(5-propylthiophen-2-yl)acryloyl)-6-oxo-6H-pyran-2-yl)hex-1-enylcarbamate |
| 35 | APY59 | methyl (E)-5-(4-hydroxy-5-((E/Z)-2-methyl-3-(5-pentylthiophen-2-yl)acryloyl)-6-oxo-6H-pyran-2-yl)hex-1-enylcarbamate |
| 36 | APY60 | methyl (E)-5-(4-hydroxy-5-((E/Z)-3-(5-isobutylthiophen-2-yl)-2-methylacryloyl)-6-oxo-6H-pyran-2-yl)hex-1-enylcarbamate |
| 37 | APY61 | methyl (E)-5-(5-((E/Z)-3-(5-(3,3,3-trifluoropropyl)thiophen-2-yl)-2-methylacryloyl)-4-hydroxy-6-oxo-6H-pyran-2-yl)hex-1-enylcarbamate |
| 38 | APY62 | methyl (E)-5-(5-((E/Z)-3-(5-(2-cyclohexylethyl)thiophen-2-yl)-2-methylacryloyl)-4-hydroxy-6-oxo-6H-pyran-2-yl)hex-1-enylcarbamate |
| 39 | APY64 | methyl (E)-5-(5-((E/Z)-3-(5-ethylthiophen-2-yl)-2-methylacryloyl)-4-hydroxy-6-oxo-6H-pyran-2-yl)hex-1-enylcarbamate |
| 40 | APY66 | methyl (E)-5-(4-hydroxy-5-((E/Z)-3-(4-isopropoxyphenyl)-2-methylacryloyl)-6-oxo-6H-pyran-2-yl)hex-1-enylcarbamate |
| 41 | APY67 | methyl 5-(5-((E/Z)-3-(5-butylthiophen-2-yl)-2-methylacryloyl)-4-hydroxy-6-oxo-6H-pyran-2-yl)hexylcarbamate |
| 42 | APY69 | methyl (E)-5-(4-hydroxy-5-((E/Z)-2-methyl-3-(5-methylthiophen-2-yl)acryloyl)-6-oxo-6H-pyran-2-yl)hex-1-enylcarbamate |
| 43 | APY70 | methyl (E)-5-(5-((E/Z)-3-(4-ethylphenyl)-2-methylacryloyl)-4-hydroxy-6-oxo-6H-pyran-2-yl)hex-1-enylcarbamate |
| 44 | APY71 | methyl (E)-5-(4-hydroxy-5-((E/Z)-2-methyl-3-(4-propylphenyl)acryloyl)-6-oxo-6H-pyran-2-yl)hex-1-enylcarbamate |
| 45 | APY72 | methyl (E)-5-(4-hydroxy-5-((E/Z)-2-methyl-3-(4-pentylphenyl)acryloyl)-6-oxo-6H-pyran-2-yl)hex-1-enylcarbamate |
| 46 | APY73 | methyl (E)-5-(4-hydroxy-5-((E/Z)-3-(4-isopentylphenyl)-2-methylacryloyl)-6-oxo-6H-pyran-2-yl)hex-1-enylcarbamate |
| 47 | APY74 | methyl (E)-5-(5-((E/Z)-3-(4-(3,3,3-trifluoropropyl)phenyl)-2-methylacryloyl)-4-hydroxy-6-oxo-6H-pyran-2-yl)hex-1-enylcarbamate |
| 48 | APY75 | methyl (E)-5-(3-((E/Z)-3-(5-butyl-3-methylthiophen-2-yl)-2-methylacryloyl)-4-hydroxy-2-oxo-2H-pyran-6-yl)hex-1-enylcarbamate |
| 49 | APY76 | methyl (E)-5-(3-((E/Z)-3-(5-isopentyl-3-methylthiophen-2-yl)-2-methylacryloyl)-4-hydroxy-2-oxo-2H-pyran-6-yl)hex-1-enylcarbamate |
| 50 | APY81 | methyl ((1E)-5-(4-hydroxy-3-(2-methyl-3-(5-(4,4,4-trifluorobutyl)thiophen-2-yl)acryloyl)-2-oxo-2H-pyran-6-yl)hex-1-en-1-yl)carbamate |
| 51 | APY82 | methyl ((1E)-5-(4-hydroxy-3-(2-methyl-3-(5-(6,6,6-trifluorohexyl)thiophen-2-yl)acryloyl)-2-oxo-2H-pyran-6-yl)hex-1-en-1-yl)carbamate |
| 52 | APY84 | methyl ((1E)-5-(3-(3-(6-butylbenzofuran-2-yl)-2-methylacryloyl)-4-hydroxy-2-oxo-2H-pyran-6-yl)hex-1-en-1-yl)carbamate |
| 53 | APY86 | methyl ((1E)-5-(3-(3-(6-butylbenzo[b]thiophen-2-yl)-2-methylacryloyl)-4-hydroxy-2-oxo-2H-pyran-6-yl)hex-1-en-1-yl)carbamate |
| 54 | APY87 | methyl ((1E)-5-(3-(3-(4-butyl-2-methylphenyl)-2-methylacryloyl)-4-hydroxy-2-oxo-2H-pyran-6-yl)hex-1-en-1-yl)carbamate |
| 55 | APY90 | methyl ((1E)-5-(4-hydroxy-3-(2-methyl-3-(5-(4,4,4-trifluorobutyl)thiophen-2-yl)acryloyl)-2-oxo-2H-pyran-6-yl)pent-1-en-1-yl)carbamate |
| 56 | APY91 | methyl ((1E)-5-(4-hydroxy-3-(3-(5-isopentylthiophen-2-yl)-2-methylacryloyl)-2-oxo-2H-pyran-6-yl)pent-1-en-1-yl)carbamate |
| 57 | APY94 | methyl ((1E)-5-(4-hydroxy-3-(3-(5-(3-hydroxypropyl)thiophen-2-yl)-2-methylacryloyl)-2-oxo-2H-pyran-6-yl)hex-1-en-1-yl)carbamate |
| 58 | APY95 | methyl ((1E)-5-(3-(3-(5-(2-cyclopropylethyl)thiophen-2-yl)-2-methylacryloyl)-4-hydroxy-2-oxo-2H-pyran-6-yl)hex-1-en-1-yl)carbamate |
| 59 | APY96 | methyl ((1E)-5-(4-hydroxy-3-(2-methyl-3-(5-(3,3,3-trifluoropropyl)thiophen-2-yl)acryloyl)-2-oxo-2H-pyran-6-yl)hex-1-en-1-yl)carbamate |

TABLE 2-continued

Representative compound names.

| Example Number | Compound Number | Name |
|---|---|---|
| 60 | APY97 | methyl ((1E)-5-(3-(3-(5-(5-fluoropentyl)thiophen-2-yl)-2-methylacryloyl)-4-hydroxy-2-oxo-2H-pyran-6-yl)hex-1-en-1-yl)carbamate |
| 61 | APY98 | methyl ((1E)-5-(4-hydroxy-3-(2-methyl-3-(5-(5,5,5-trifluoropentyl)thiophen-2-yl)acryloyl)-2-oxo-2H-pyran-6-yl)hex-1-en-1-yl)carbamate |
| 62 | APY100 | methyl ((1E)-5-(4-hydroxy-3-(3-(5-(3-methoxypropyl)thiophen-2-yl)-2-methylacryloyl)-2-oxo-2H-pyran-6-yl)hex-1-en-1-yl)carbamate |
| 63 | APY101 | methyl ((1E)-5-(4-hydroxy-3-(3-(5-methoxythiophen-2-yl)-2-methylacryloyl)-2-oxo-2H-pyran-6-yl)hex-1-en-1-yl)carbamate |
| 64 | APY102 | methyl ((1E)-5-(3-(3-(5-ethoxythiophen-2-yl)-2-methylacryloyl)-4-hydroxy-2-oxo-2H-pyran-6-yl)hex-1-en-1-yl)carbamate |
| 65 | APY103 | methyl ((1E)-5-(4-hydroxy-3-(2-methyl-3-(5-propoxythiophen-2-yl)acryloyl)-2-oxo-2H-pyran-6-yl)hex-1-en-1-yl)carbamate |
| 66 | APY104 | methyl ((1E)-5-(3-(3-(5-butyl-1-methyl-1H-indol-2-yl)-2-methylacryloyl)-4-hydroxy-2-oxo-2H-pyran-6-yl)hex-1-en-1-yl)carbamate |
| 67 | APY105 | methyl ((1E)-5-(4-hydroxy-3-(3-(5-isopentyl-1-methyl-1H-indol-2-yl)-2-methylacryloyl)-2-oxo-2H-pyran-6-yl)hex-1-en-1-yl)carbamate |
| 68 | APY106 | methyl ((1E)-5-(4-hydroxy-3-(3-(5-(methoxymethyl)thiophen-2-yl)-2-methylacryloyl)-2-oxo-2H-pyran-6-yl)hex-1-en-1-yl)carbamate |
| 69 | APY107 | methyl ((1E)-5-(4-hydroxy-3-(3-(5-isopropoxythiophen-2-yl)-2-methylacryloyl)-2-oxo-2H-pyran-6-yl)hex-1-en-1-yl)carbamate |
| 70 | APY108 | methyl ((1E)-5-(3-(3-(5-(ethoxymethyl)thiophen-2-yl)-2-methylacryloyl)-4-hydroxy-2-oxo-2H-pyran-6-yl)hex-1-en-1-yl)carbamate |
| 71 | APY109 | methyl ((1E)-5-(4-hydroxy-3-(2-methyl-3-(5-(propoxymethyl)thiophen-2-yl)acryloyl)-2-oxo-2H-pyran-6-yl)hex-1-en-1-yl)carbamate |
| 72 | APY110 | methyl ((1E)-5-(3-(3-(6-ethylbenzofuran-2-yl)-2-methylacryloyl)-4-hydroxy-2-oxo-2H-pyran-6-yl)hex-1-en-1-yl)carbamate |
| 73 | APY111 | methyl ((1E)-5-(4-hydroxy-3-(3-(6-isopentylbenzofuran-2-yl)-2-methylacryloyl)-2-oxo-2H-pyran-6-yl)hex-1-en-1-yl)carbamate |
| 74 | APY112 | methyl ((1E)-5-(4-hydroxy-3-(2-methyl-3-(6-(3,3,3-trifluoropropyl)benzofuran-2-yl)acryloyl)-2-oxo-2H-pyran-6-yl)hex-1-en-1-yl)carbamate |
| 75 | APY114 | methyl ((1E)-5-(4-hydroxy-3-(2-methyl-3-(6-(3,3,3-trifluoropropyl)benzo[b]thiophen-2-yl)acryloyl)-2-oxo-2H-pyran-6-yl)hex-1-en-1-yl)carbamate |
| 76 | APY116 | methyl ((1E)-5-(4-hydroxy-3-(2-methyl-3-(5-(2,2,2-trifluoroethoxy)thiophen-2-yl)acryloyl)-2-oxo-2H-pyran-6-yl)hex-1-en-1-yl)carbamate |
| 77 | APY117 | methyl ((1E)-5-(4-hydroxy-3-(2-methyl-3-(4-(2,2,2-trifluoroethoxy)phenyl)acryloyl)-2-oxo-2H-pyran-6-yl)hex-1-en-1-yl)carbamate |
| 78 | APY119 | methyl ((1E)-5-(4-hydroxy-3-(2-methyl-3-(5-(4-(trifluoromethyl)phenoxy)thiophen-2-yl)acryloyl)-2-oxo-2H-pyran-6-yl)hex-1-en-1-yl)carbamate |
| 79 | APY120 | methyl ((1E)-5-(3-(3-(4-bromo-5-isobutylthiophen-2-yl)-2-methylacryloyl)-4-hydroxy-2-oxo-2H-pyran-6-yl)hex-1-en-1-yl)carbamate |
| 80 | APY121 | methyl ((1E)-5-(4-hydroxy-3-(2-methyl-3-(1-methyl-5-propoxy-1H-indol-2-yl)acryloyl)-2-oxo-2H-pyran-6-yl)hex-1-en-1-yl)carbamate |
| 81 | APY122 | methyl ((1E)-5-(3-(3-(5-(sec-butoxy)-1-methyl-1H-indol-2-yl)-2-methylacryloyl)-4-hydroxy-2-oxo-2H-pyran-6-yl)hex-1-en-1-yl)carbamate |
| 82 | APY123 | methyl ((1E)-5-(3-(3-(5-(sec-butoxy)-1-methyl-1H-indol-2-yl)-2-methylacryloyl)-4-hydroxy-2-oxo-2H-pyran-6-yl)hex-1-en-1-yl)carbamate |
| 83 | APY124 | methyl ((1E)-5-(3-(3-(3-bromo-5-isobutylthiophen-2-yl)-2-methylacryloyl)-4-hydroxy-2-oxo-2H-pyran-6-yl)hex-1-en-1-yl)carbamate |
| 84 | APY125 | methyl ((1E)-5-(3-(3-(5-(cyclopropylmethyl)thiophen-2-yl)-2-methylacryloyl)-4-hydroxy-2-oxo-2H-pyran-6-yl)hex-1-en-1-yl)carbamate |
| 85 | APY126 | methyl ((1E)-5-(4-hydroxy-3-(2-methyl-3-(4-(3,3,3-trifluoropropoxy)phenyl)acryloyl)-2-oxo-2H-pyran-6-yl)hex-1-en-1-yl)carbamate |
| 86 | APY127 | methyl ((1E)-5-(4-hydroxy-3-(2-methyl-3-(2-methyl-4-(3,3,3-trifluoropropyl)phenyl)acryloyl)-2-oxo-2H-pyran-6-yl)hex-1-en-1-yl)carbamate |
| 87 | APY128 | methyl ((1E)-5-(4-hydroxy-3-(2-methyl-3-(2-methyl-4-propoxyphenyl)acryloyl)-2-oxo-2H-pyran-6-yl)hex-1-en-1-yl)carbamate |
| 88 | APY129 | methyl ((1E)-5-(3-(3-(4-butoxy-2-methylphenyl)-2-methylacryloyl)-4-hydroxy-2-oxo-2H-pyran-6-yl)hex-1-en-1-yl)carbamate |
| 89 | APY130 | methyl ((1E)-5-(4-hydroxy-3-(3-(4-isopropoxy-2-methylphenyl)-2-methylacryloyl)-2-oxo-2H-pyran-6-yl)hex-1-en-1-yl)carbamate |
| 90 | APY131 | methyl ((1E)-5-(3-(3-(4-(2,2-difluoroethoxy)-2-methylphenyl)-2-methylacryloyl)-4-hydroxy-2-oxo-2H-pyran-6-yl)hex-1-en-1-yl)carbamate |
| 91 | APY132 | methyl ((1E)-5-(3-(3-(4-(2,2-difluoroethoxy)phenyl)-2-methylacryloyl)-4-hydroxy-2-oxo-2H-pyran-6-yl)hex-1-en-1-yl)carbamate |
| 92 | APY135 | methyl ((1E)-5-(4-hydroxy-3-(2-methyl-3-(1-methyl-4-(3,3,3-trifluoropropyl)-1H-pyrrol-2-yl)acryloyl)-2-oxo-2H-pyran-6-yl)hex-1-en-1-yl)carbamate |
| 93 | APY136 | methyl ((1E)-5-(3-(3-(2-butylthiazol-5-yl)-2-methylacryloyl)-4-hydroxy-2-oxo-2H-pyran-6-yl)hex-1-en-1-yl)carbamate |
| 94 | APY137 | methyl ((1E)-5-(4-hydroxy-3-(3-(2-isopentylthiazol-5-yl)-2-methylacryloyl)-2-oxo-2H-pyran-6-yl)hex-1-en-1-yl)carbamate |
| 95 | APY138 | methyl ((1E)-5-(3-(3-(5-(2,2-difluoroethoxy)thiophen-2-yl)-2-methylacryloyl)-4-hydroxy-2-oxo-2H-pyran-6-yl)hex-1-en-1-yl)carbamate |

TABLE 2-continued

Representative compound names.

| Example Number | Compound Number | Name |
|---|---|---|
| 96 | APY139 | methyl ((1E)-5-(4-hydroxy-3-(2-methyl-3-(5-(3,3,3-trifluoropropoxy)thiophen-2-yl)acryloyl)-2-oxo-2H-pyran-6-yl)hex-1-en-1-yl)carbamate |
| 97 | APY142 | methyl ((1E)-5-(hydroxy-3-((E)-2-methyl-3-(2-piperidin-1-yl)thiazol-5-yl)acryloyl)-2-oxo-2H-pyran-6-yl)hex-1-en-1-yl)carbamate |
| 98 | APY143 | methyl ((1E)-5-(4-hydroxy-3-(2-methyl-3-(1-methyl-4-propyl-1H-imidazol-2-yl)acryloyl)-2-oxo-2H-pyran-6-yl)hex-1-en-1-yl)carbamate |

Screening data for representative compounds of this invention (compounds APY15-APY143) and for the compound E/E-(±)myxopyronin B (Myx B) are presented in Tables 3-8:

TABLE 3

Inhibition of bacterial RNAP.

| name | IC50 E. coli RNAP (nM) | IC50 S. aureus RNAP (nM) | IC50 M. tuberculosis RNAP (nM) |
|---|---|---|---|
| Myx B | 10 | 70 | 100 |
| APY15 | 5 | 20 | 200 |
| APY16 | 30 | 100 | 300 |
| APY17 | 20 | 100 | 900 |
| APY18 | 7 | 70 | 600 |
| APY19 | 7 | 30 | 400 |
| APY20 | 4 | 20 | 300 |
| APY21 | 40 | 500 | 300 |
| APY25 | 10 | 70 | 600 |
| APY26 | 20 | 200 | 1000 |
| APY27 | 10 | 100 | 1000 |
| APY28 | 40 | 60 | 200 |
| APY29 | 40 | 90 | 500 |
| APY31 | 10 | 50 | 20 |
| APY32 | 6 | 6 | 2000 |
| APY33 | 8 | 10 | 400 |
| APY34 | 10 | 50 | 3000 |
| APY36 | 300 | | |
| APY37 | 90 | | |
| APY39 | 80 | | |
| APY40 | 10 | | |
| APY41 | 8 | | |
| APY42 | 30 | | |
| APY43 | 200 | | |
| APY48 | 900 | | |
| APY49 | 10 | | |
| APY50 | >6000 | | |
| APY51 | 1000 | | |
| APY52 | 2000 | | |
| APY53 | 2000 | | |
| APY54 | >6000 | | |
| APY55 | 40 | | |
| APY56 | 7 | | |
| APY57 | >6000 | | |
| APY58 | 80 | | |
| APY59 | 10 | | |
| APY60 | 10 | | |
| APY61 | 20 | | |
| APY62 | 10 | | |
| APY64 | 200 | | |
| APY66 | 1000 | | |
| APY67 | 1000 | | |
| APY69 | 1000 | | |
| APY70 | >6000 | | |
| APY71 | 400 | | |
| APY72 | 200 | | |
| APY73 | 40 | | |
| APY74 | 40 | | |
| APY75 | 9 | 80 | 60 |
| APY76 | 3 | 80 | 50 |
| APY81 | 10 | 30 | 50 |
| APY82 | 5 | | |
| APY84 | 2 | 60 | 20 |
| APY86 | 20 | 300 | 1000 |
| APY87 | 10 | 70 | 30 |
| APY90 | 30 | 800 | 300 |
| APY91 | 20 | 600 | 400 |
| APY94 | >6000 | | >6000 |
| APY95 | 5 | | 50 |
| APY96 | 30 | | 100 |
| APY97 | 20 | 400 | |
| APY98 | 6 | | 40 |
| APY100 | 60 | | 1000 |
| APY101 | >6000 | | >6000 |
| APY102 | 200 | | 500 |
| APY103 | 20 | | 20 |
| APY104 | 8 | | 200 |
| APY105 | 40 | | 5000 |
| APY106 | 500 | | 4000 |
| APY107 | 20 | | 400 |
| APY108 | 300 | | 700 |
| APY109 | 80 | | 800 |
| APY110 | 200 | | |
| APY111 | 50 | | |
| APY112 | 300 | | |
| APY114 | 300 | | |
| APY116 | 30 | | |
| APY117 | 100 | | |
| APY119 | 6 | | |
| APY120 | 20 | | |
| APY121 | 500 | | |
| APY122 | 100 | | |
| APY123 | 500 | | |
| APY124 | 4 | | |
| APY125 | 40 | | |
| APY126 | 80 | | |
| APY127 | 70 | | |
| APY128 | 500 | | |
| APY129 | 50 | | |
| APY130 | 200 | | |
| APY131 | 200 | | |
| APY132 | 200 | | |
| APY135 | 100 | | |
| APY136 | 20 | | |
| APY137 | 10 | | |
| APY138 | 300 | | |
| APY139 | 30 | | |
| APY142 | 600 | | |
| APY143 | 1000 | | |

TABLE 4

Inhibition of bacterial growth: Staphylococcus aureus, Mycobacterium, tuberculosis, Acinetobacter baumannii, and Escherichia coli.

| name | MIC S. aureus 12600 (µg/ml) | MIC M. tuberculosis H37Rv (µg/ml) | MIC A. baumannii 19606 (µg/ml) | MIC E. coli D21f2tolC (µg/ml) |
|---|---|---|---|---|
| Myx B | 0.8 | 2 | >40 | 0.1 |
| APY15 | 0.9 | >50 | 6 | 0.08 |
| APY16 | 0.6 | 30 | 20 | 0.1 |
| APY17 | 8 | 10 | 10 | 0.1 |
| APY18 | 4 | 10 | 4 | 0.07 |
| APY19 | 2 | 6 | 10 | 0.1 |
| APY20 | >40 | 6 | >40 | 0.3 |
| APY21 | 2 | 10 | 20 | 0.3 |
| APY25 | 3 | 6 | >40 | 0.3 |
| APY26 | >40 | 6 | >40 | 0.3 |
| APY27 | 6 | 10 | 20 | 0.3 |
| APY28 | 2 | 6 | 30 | 0.3 |
| APY29 | 4 | 30 | 30 | 0.3 |
| APY31 | 0.4 | 3 | 6 | <0.3 |
| APY32 | >40 | 6 | >40 | 0.4 |
| APY33 | 2 | 6 | 20 | 0.3 |
| APY34 | >40 | 30 | 10 | 0.3 |
| APY36 | >40 | 30 | >40 | 0.7 |
| APY37 | >40 | >50 | >40 | 0.6 |
| APY39 | 1 | 3 | >40 | 0.2 |
| APY40 | 1 | 6 | 9 | 0.4 |
| APY41 | 0.8 | 3 | >40 | <0.2 |
| APY42 | >40 | 30 | >40 | 0.4 |
| APY43 | >40 | 6 | >40 | 0.4 |
| APY48 | 10 | 10 | | |
| APY49 | >40 | 50 | >40 | 0.3 |
| APY50 | >40 | | >40 | 2 |
| APY51 | >40 | | >40 | 0.5 |
| APY52 | 4 | 30 | >40 | 0.4 |
| APY53 | 2 | 6 | >40 | 0.4 |
| APY54 | >40 | | >40 | 7 |
| APY55 | 10 | 10 | >40 | 0.7 |
| APY56 | 0.7 | 10 | 10 | 0.2 |
| APY57 | >40 | | >40 | 1 |
| APY58 | 1 | 10 | >40 | 0.2 |
| APY59 | 0.3 | 30 | 7 | 0.2 |
| APY60 | 0.4 | 10 | 9 | 0.2 |
| APY61 | 0.7 | 10 | 10 | 0.2 |
| APY62 | 2 | | >40 | 10 |
| APY64 | 9 | 30 | >40 | 0.8 |
| APY66 | 2 | 6 | >40 | 0.8 |
| APY67 | 5 | 50 | >40 | 0.5 |
| APY69 | >40 | | >40 | 7 |
| APY70 | 20 | 30 | >40 | 1 |
| APY71 | 4 | | >40 | 0.5 |
| APY72 | 2 | | >40 | 0.2 |
| APY73 | 0.6 | | >40 | 0.3 |
| APY74 | 2 | 10 | >40 | 0.2 |
| APY75 | 0.3 | 30 | 4 | 0.1 |
| APY76 | 0.2 | 30 | 4 | 0.09 |
| APY81 | 0.4 | 10 | 20 | 0.08 |
| APY82 | 10 | >50 | 20 | 0.07 |
| APY84 | 3 | 30 | >40 | 0.1 |
| APY86 | >40 | >50 | >40 | 0.2 |
| APY87 | 1 | >50 | >40 | 0.2 |
| APY90 | 0.9 | 10 | 10 | 0.07 |
| APY91 | 0.7 | 50 | 9 | 0.08 |
| APY94 | >40 | | >40 | 3 |
| APY95 | 0.8 | 10 | 10 | 0.1 |
| APY96 | 2 | 6 | 10 | 0.1 |
| APY97 | 2 | >50 | >40 | 0.1 |
| APY98 | 1 | 50 | 20 | 0.1 |
| APY100 | >40 | | >40 | 1 |
| APY101 | >40 | | >40 | 3 |
| APY102 | 10 | 30 | >40 | 1 |
| APY103 | 2 | 30 | >40 | 0.4 |
| APY104 | 5 | >50 | 9 | 0.1 |
| APY105 | >40 | | >40 | 2 |
| APY106 | >40 | | >40 | 3 |
| APY107 | 2 | 10 | >40 | 0.1 |
| APY108 | 10 | 30 | >40 | 0.4 |
| APY109 | 3 | 30 | >40 | 0.2 |
| APY110 | 8 | 30 | >40 | 0.3 |
| APY111 | >40 | | >40 | 0.3 |
| APY112 | >40 | | >40 | 0.2 |
| APY114 | >40 | | >40 | 0.2 |
| APY116 | 1 | 6 | >40 | 0.2 |
| APY117 | 2 | 10 | >40 | 0.4 |
| APY119 | 2 | >50 | >40 | 0.1 |
| APY120 | 1 | >50 | 30 | 0.2 |
| APY121 | >40 | >50 | >40 | 0.8 |
| APY122 | >40 | >50 | >40 | 0.5 |
| APY123 | >40 | >50 | >40 | 2 |
| APY124 | 0.9 | 50 | 6 | 0.3 |
| APY125 | 1 | 10 | 20 | 0.6 |
| APY126 | 1 | 6 | >40 | 0.3 |
| APY127 | 2 | 50 | >40 | 0.4 |
| APY128 | 4 | 30 | >40 | 0.6 |
| APY129 | 2 | 30 | 40 | 0.3 |
| APY130 | 3 | 30 | >40 | 2 |
| APY131 | 8 | 30 | >40 | 0.7 |
| APY132 | 5 | 10 | >40 | 0.7 |
| APY135 | 10 | | >40 | 2 |
| APY136 | 1 | 6 | >40 | 0.2 |
| APY137 | 1 | 6 | >40 | 0.08 |
| APY138 | 10 | 10 | >40 | 0.5 |
| APY139 | 2 | 6 | >40 | 0.2 |
| APY142 | 20 | | >40 | 1 |
| APY143 | >40 | | >40 | 10 |

TABLE 5

Inhibition of bacterial growth: Bacillus anthracis, Francisella tularensis, Yersinai pestis, Burkholderia mallei, Burkholderia pseudomallei, and Brucella melitensis.

| name | MIC B. anthracis Vollum-1b (µg/ml) | MIC F. tularensis SCHU4 (µg/ml) | MIC Y. pestis C092 (µg/ml) | MIC B. mallei CHN7 (µg/ml) | MIC B. pseudo-mallei Human/Blood/OH (µg/ml) | MIC B. melitensis 16M (µg/ml) |
|---|---|---|---|---|---|---|
| Myx B | 6 | 2 | 50 | 6 | 30 | 2 |
| APY15 | 0.4 | 0.4 | 3 | 0.8 | 3 | 0.4 |
| APY16 | 2 | 0.8 | 10 | 2 | 6 | 0.8 |
| APY17 | 2 | 0.8 | 10 | 3 | 30 | 2 |
| APY18 | 2 | 3 | 6 | 2 | 6 | 0.8 |
| APY19 | 2 | 6 | 6 | 0.8 | 3 | 0.4 |

TABLE 5-continued

Inhibition of bacterial growth: *Bacillus anthracis*, *Francisella tularensis*, *Yersinai pestis*, *Burkholderia mallei*, *Burkholderia pseudomallei*, and *Brucella melitensis*.

| name | MIC B. anthracis Vollum-1b (µg/ml) | MIC F. tularensis SCHU4 (µg/ml) | MIC Y. pestis C092 (µg/ml) | MIC B. mallei CHN7 (µg/ml) | MIC B. pseudo-mallei Human/Blood/OH (µg/ml) | MIC B. melitensis 16M (µg/ml) |
|---|---|---|---|---|---|---|
| APY20 | 2 | 0.8 | >50 | 2 | >50 | 0.8 |
| APY21 | 3 | 3 | >50 | 6 | 10 | 2 |
| APY25 | 0.2 | 3 | 30 | 2 | 6 | 0.8 |
| APY26 | 2 | 2 | >50 | 6 | >50 | 2 |
| APY27 | 3 | 3 | >50 | 6 | 50 | 2 |
| APY28 | 6 | 30 | 30 | 10 | 30 | 0.4 |
| APY29 | 3 | 10 | 10 | 3 | 10 | 0.8 |
| APY31 | 0.4 | 6 | 10 | 2 | 6 | 0.8 |
| APY32 | 2 | 0.8 | >50 | 2 | 6 | 2 |
| APY33 | 2 | 3 | 6 | 2 | 6 | 0.4 |
| APY34 | 3 | 6 | >50 | 3 | 30 | 3 |
| APY36 | 6 | 6 | >50 | >50 | >50 | >50 |
| APY37 | 50 | 50 | >50 | 50 | >50 | 10 |
| APY39 | 3 | 30 | 30 | 10 | 50 | 0.4 |
| APY40 | 10 | >50 | >50 | >50 | >50 | 3 |
| APY41 | 2 | 6 | 30 | 6 | 10 | 0.8 |
| APY42 | 10 | 50 | >50 | 50 | 50 | 6 |
| APY43 | 10 | 30 | >50 | 50 | 50 | 3 |
| APY48 | 6 | 10 | >50 | 50 | >50 | 6 |
| APY49 | 10 | 30 | >50 | 50 | >50 | 10 |
| APY50 | | | | | | |
| APY51 | | | | | | |
| APY52 | 2 | 30 | | 50 | >50 | 3 |
| APY53 | 3 | 50 | | >50 | >50 | 10 |
| APY54 | | | | | | |
| APY55 | 2 | 30 | | 50 | >50 | 30 |
| APY56 | 0.2 | 6 | | 3 | 6 | 3 |
| APY57 | | | | | | |
| APY58 | 10 | 50 | | 50 | 50 | >50 |
| APY59 | 2 | 10 | | 6 | 10 | 6 |
| APY60 | 3 | 10 | | 30 | 30 | 6 |
| APY61 | 6 | 30 | | 30 | 30 | >50 |
| APY62 | | | | | | |
| APY64 | 50 | 50 | | >50 | >50 | 10 |
| APY66 | 10 | >50 | | >50 | >50 | 10 |
| APY67 | 30 | 50 | | >50 | >50 | 10 |
| APY69 | | | | | | |
| APY70 | 50 | >50 | | >50 | >50 | 30 |
| APY71 | 30 | >50 | | >50 | >50 | 10 |
| APY72 | 3 | 10 | | 10 | 50 | 2 |
| APY73 | 2 | 10 | | 50 | 50 | 3 |
| APY74 | 10 | 50 | | >50 | >50 | 10 |
| APY75 | 0.8 | 10 | | 6 | 6 | 3 |
| APY76 | 0.4 | 10 | | 6 | 6 | 3 |
| APY81 | 2 | 30 | | 10 | 10 | 2 |
| APY82 | 3 | 10 | | 6 | 6 | 2 |
| APY117 | 10 | >50 | 50 | 50 | >50 | 10 |
| APY119 | 0.8 | 50 | 3 | 3 | 6 | 3 |
| APY120 | 2 | 50 | 6 | 6 | 10 | 3 |
| APY121 | >50 | >50 | >50 | >50 | >50 | >50 |
| APY122 | 50 | 50 | >50 | >50 | >50 | >50 |
| APY123 | >50 | >50 | >50 | >50 | >50 | >50 |
| APY124 | 0.2 | 6 | 6 | 10 | 30 | 10 |
| APY125 | 6 | >50 | 6 | 10 | 50 | 6 |
| APY126 | 3 | >50 | 30 | 50 | >50 | 10 |
| APY127 | 6 | >50 | 50 | 50 | 50 | 50 |
| APY128 | 10 | >50 | >50 | >50 | >50 | >50 |
| APY129 | 3 | >50 | 30 | 50 | >50 | 10 |
| APY130 | 10 | >50 | >50 | >50 | >50 | >50 |
| APY131 | 30 | >50 | >50 | >50 | >50 | >50 |
| APY132 | 30 | >50 | >50 | >50 | >50 | 30 |
| APY136 | 10 | >50 | 10 | 30 | 50 | 6 |
| APY137 | 3 | 50 | 10 | 10 | 30 | 6 |
| APY138 | 50 | >50 | 50 | >50 | >50 | 50 |
| APY139 | 6 | >50 | 10 | 50 | >50 | 10 |

TABLE 6

Inhibition of bacterial growth; drug-resistant *Staphylococcus aureus* (methicillin resistant *Staphylococcus aureus*, MRSA; rifampin-resistant *Staphylococcus aureus*, RRSA; linezolid-resistant *Stayhylococcus aureus*, LRSA; and vancomycin intermediate *Staphylococcus aureus*, VISA).

| name | MIC S. aureus MRSA BAA-1707 (µg/ml) | MIC S. aureus MRSA BAA-1717 (µg/ml) | MIC S. aureus RRSA 12600-Rif (µg/ml) | MIC S. aureus LRSA NRS120 (µg/ml) | MIC S. aureus VISA NRS1 (µg/ml) |
|---|---|---|---|---|---|
| Myx B | 0.9 | 0.8 | 1 | 0.5 | 0.5 |
| APY41 | 0.6 | 0.6 | 0.9 | | |
| APY60 | 0.4 | 0.5 | 0.7 | | |
| APY61 | 0.9 | 0.9 | 1 | 0.4 | 0.4 |
| APY66 | 2 | 2 | 3 | | |
| APY73 | 1 | 1 | 2 | | |
| APY81 | 0.5 | 0.9 | 0.8 | | |
| APY90 | 2 | 2 | 2 | | |
| APY91 | 2 | 2 | 2 | | |
| APY95 | 0.3 | 0.4 | 0.5 | | |
| APY96 | 2 | 2 | 2 | | |
| APY107 | 2 | 2 | 2 | | |
| APY108 | 20 | 20 | 20 | | |
| APY109 | 7 | 7 | 7 | | |
| APY116 | 2 | 2 | 2 | 0.8 | 0.7 |

TABLE 7

Antibacterial efficacy in mice: methicillin-resistant *Staphylococcus aureus* (MRSA) peritonitis: intravenous administration of test compounds.

| name | PD50 (mg/kg) |
|---|---|
| Myx B | 20 |
| APY60 | 20 |
| APY61 | 20 |
| APY116 | 20 |

TABLE 8

Antibacterial efficacy in mice: methicillin-resistant *Staphylococcus aureus* (MRSA) peritonitis: oral administration of test compounds.

| name | PD50 (mg/kg) |
|---|---|
| Myx B | 50 |
| APY116 | 50 |

The data in Table 3 show that certain compounds according to general structural formula (Ia), (Ib), and (Ic) potently inhibit bacterial RNA polymerases.

The data in Table 3 show that certain compounds according to general structural formula (Ia), (Ib), and (Ic) are at least approximately 5 times more potent than Myx B in inhibiting *Escherichia coli* RNA polymerase, at least 10 times more potent than Myx B in inhibiting *Staphylococcus aureus* RNA polymerase, or at least approximately 5 times more potent than Myx B in inhibiting *Mycobacterium tuberculosis* RNA polymerase.

The data in Tables 4-6 show that certain compounds according to general structural formula (Ia), (Ib), and (Ic) potently inhibit the Gram-positive bacterial pathogens *Staphylococcus aureus* (including both drug-sensitive and drug-resistant strains), *Mycobacterium tuberculosis*, and *Bacillus anthracis*, and the Gram-negative pathogens *Acinetobacter baumannii*, *Francisella tularensis*, *Yersinia pestis*, *Burkholderia mallei*, *Burkholderia pseudomallei*, and *Brucella melitensis*.

The data in Tables 4-6 further show that certain compounds according to general structural formula (Ia), (Ib), and (Ic) are at least approximately 4 times more potent than Myx B in inhibiting *Staphylococcus aureus*, at least approximately 30 times more potent than Myx B in inhibiting *Bacillus anthracis*, at least approximately 10 times more potent than Myx B in inhibiting *Acinetobacter baumannii*, at least approximately 5 times more potent than Myx B in inhibiting *Francisella tularensis*, at least approximately 15 times more potent than Myx B in inhibiting *Yersinia pestis*, at least approximately 10 times more potent than Myx B in inhibiting *Burkholderia mallei*, at least approximately 8 times more potent than Myx B in inhibiting *Burkholderia pseudomallei*, or at least approximately 5 times more potent than Myx B in inhibiting *Brucella melitensis*.

The data in Tables 4-5 further show that certain compounds according to general structural formula (Ia), (Ib), and (Ic) potently inhibit a bacterial pathogen that Myx B does not inhibit, *Acinetobacter baumannii*, indicating that certain compounds according to general structural formula (Ia), (Ib), and (Ic) exhibit a broader spectrum of antibacterial activity than Myx B.

The data in Tables 7-8 indicate that certain compounds of this invention clear infection and prevent death in a mammal. Table 7 presents data from experiments with mice systemically infected with methicillin-resistant *Staphylococcus aureus* (MRSA) and compounds administered intravenously. Table 8 presents data from experiments with mice systemically infected with methicillin-resistant *Staphylococcus aureus* (MRSA) and test compounds administered orally.

The data in Tables 7-8 further indicate that certain compounds of this invention are at least as potent as Myx B in clearing infection and preventing death in a mammal.

The data in Tables 7-8 further indicate that certain compounds of this invention are able to clear infection and prevent death in a mammal when administered intravenously or when administered orally.

What is claimed is:

1. A compound of formula Ia, Ib or Ic:

-continued

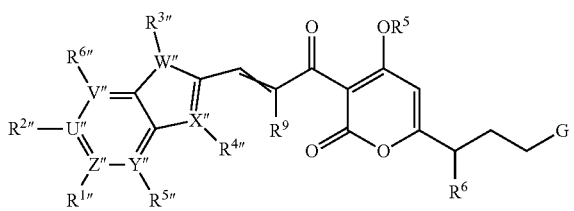

Ic or a salt thereof, wherein:
W is sulfur, oxygen, or nitrogen;
X, Y, and Z are individually carbon, sulfur, oxygen, or nitrogen, wherein at least two of X, Y, and Z are carbon;
one of $R^1$ and $R^2$ is $C_1$-$C_{10}$ alkyl, $C_2$-$C_{10}$ alkenyl, $C_1$-$C_{10}$ alkoxy, aryloxy, heteroaryloxy, or $NR^aN^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or
one of $R^1$ and $R^2$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^1$ and $R^2$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;
$R^3$ is absent, or is one of H, $C_1$-$C_2$ alkyl, or halogen-substituted $C_1$-$C_2$ alkyl;
$R^4$ is absent, or is one of H, halogen, $C_1$-$C_2$ alkyl, or halogen-substituted $C_1$-$C_2$ alkyl;
V', W', X', Y', and Z' are individually carbon or nitrogen; wherein at least three of V', W', X', Y', and Z' are carbon;
one of $R^{1'}$ and $R^{2'}$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or
one of $R^{1'}$ and $R^{2'}$ is a 5-6-membered saturated, partially unsaturated, or aromatic heterocycle that is optionally substituted by at least one of halogen, hydroxy, $C_1$-$C_{10}$ alkyl, $C_2$-$C_{10}$ alkenyl, or $C_1$-$C_{10}$ alkoxy; and the other of $R^{1'}$ and $R^{2'}$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;
$R^{3'}$, $R^{4'}$, and $R^{5'}$ are each independently absent, H, halogen, $C_1$-$C_2$ alkyl, or halogen-substituted $C_1$-$C_2$ alkyl;
W" is sulfur, oxygen, or nitrogen;
U", V", X", Y", and Z" are individually carbon, sulfur, oxygen, or nitrogen, wherein at least three of U", V", X", Y", and Z" are carbon;

one of $R^{1''}$ and $R^{2''}$ is $C_1$-$C_{10}$ alkyl, $C_2$-$C_{10}$ alkenyl, $C_1$-$C_{10}$ alkoxy, aryloxy, heteroaryloxy, or $NR^aR^b$, wherein any $C_1$-$C_{10}$ alkyl, $C_2$-$C_{10}$ alkenyl, or $C_1$-$C_{10}$ alkoxy, is optionally substituted by at least one of halogen, hydroxy, $C_1$-$C_5$ alkoxy, tetrahydrofuranyl, or furanyl, and wherein any aryloxy or heteroaryloxy is optionally substituted by at least one of halogen, hydroxy, $C_1$-$C_5$ alkyl, or $C_1$-$C_5$ alkoxy, wherein any $C_1$-$C_5$ alkyl and $C_1$-$C_5$ alkoxy is optionally substituted by at least one of halogen, hydroxy, or $C_1$-$C_5$ alkoxy; or
one of $R^{1''}$ and $R^{2''}$ is a 5-6-membered saturated, partially unsaturated, or aromatic heterocycle that is optionally substituted by at least one of halogen, hydroxy, alkyl, $C_2$-$C_{10}$ alkenyl, or $C_1$-$C_{10}$ alkoxy; and the other of $R^{1''}$ and $R^{2''}$ is absent or is one of H, halogen, $C_1$-$C_{10}$ alkyl, $C_2$-$C_{10}$ alkenyl, or $C_1$-$C_{10}$ alkoxy, wherein any $C_1$-$C_{10}$ alkyl, $C_2$-$C_{10}$ alkenyl, or $C_1$-$C_{10}$ alkoxy is optionally substituted by at least one of halogen, hydroxy, or $C_1$-$C_5$ alkoxy;
$R^{3'}$ is absent or is one of H, $C_1$-$C_2$ alkyl, or halogen-substituted $C_1$-$C_2$ alkyl;
$R^{4''}$, $R^{5''}$, and $R^{6''}$ are each independently absent, H, halogen, $C_1$-$C_2$ alkyl, or halogen-substituted $C_1$-$C_2$ alkyl;
$R^5$ and $R^6$ are individually H or methyl;
G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$;
$R^7$ is one of $C_1$-$C_6$ alkyl, —O($C_1$-$C_6$ alkyl), —S($C_1$-$C_6$ alkyl), or —N($R^8$)$_2$;
each $R^8$ is independently one of hydrogen or —$C_1$-$C_6$ alkyl;
$R^9$ is $C_1$-$C_{10}$ alkyl or $C_2$-$C_{10}$ alkenyl, wherein any $C_1$-$C_{10}$ alkyl or $C_2$-$C_{10}$ alkenyl is optionally substituted by at least one of halogen, hydroxy, alkoxy, or $NR^aR^b$;
each $R^a$ is $C_1$-$C_{10}$ alkyl that is optionally substituted by at least one of halogen, hydroxy, or $C_1$-$C_5$ alkoxy; and
each $R^b$ is H or $C_1$-$C_{10}$ alkyl that is optionally substituted by at least one of halogen, hydroxy, or $C_1$-$C_5$ alkoxy.

2. The compound of formula Ia', Ib' or Ic':

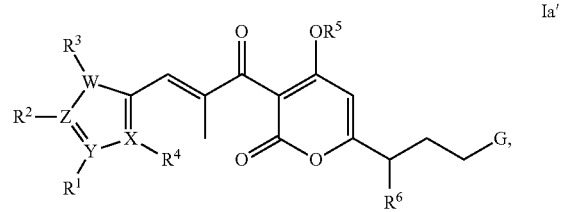

Ia'

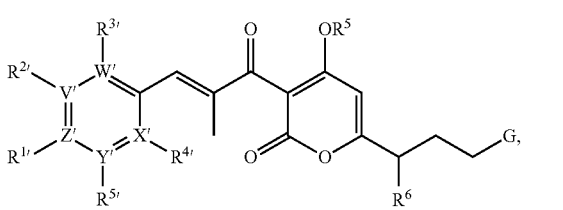

Ib'

-continued

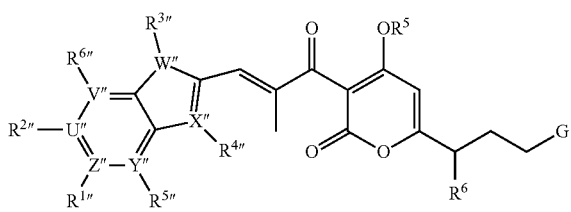

or a salt thereof, wherein:

W is sulfur, oxygen, or nitrogen;

X, Y, and Z are individually carbon, sulfur, oxygen, or nitrogen, wherein at least two of X, Y, and Z are carbon;

one of $R^1$ and $R^2$ is $C_1$-$C_8$ alkyl or $C_1$-$C_8$ alkoxy optionally substituted by at least one of halogen, hydroxy, alkoxy, or furanyl; and the other of $R^1$ and $R^2$ is absent or is one of H, halogen, or $C_1$-$C_8$ alkyl or $C_1$-$C_8$ alkoxy optionally substituted by at least one of halogen, hydroxy, or alkoxy;

$R^3$ is absent, or is one of H, $C_1$-$C_2$ alkyl, or halogen-substituted $C_1$-$C_2$ alkyl;

$R^4$ is absent, or is one of H, halogen, $C_1$-$C_2$ alkyl, or halogen-substituted $C_1$-$C_2$ alkyl;

V', W, X', Y', and Z' are individually carbon or nitrogen; wherein at least four of V', W, X', Y', and Z' are carbon;

one of $R^{1'}$ and $R^{2'}$ is $C_1$-$C_5$ alkyl or $C_1$-$C_8$ alkoxy optionally substituted by at least one of halogen, hydroxy, or alkoxy, or furanyl; and the other of $R^{1'}$ and $R^{2'}$ is absent, or is one of H, halogen, or $C_1$-$C_8$ alkyl or $C_1$-$C_8$ alkoxy optionally substituted by at least one of halogen, hydroxy, or alkoxy;

$R^{3'}$, $R^{4'}$, and $R^{5'}$ each is absent, or each of $R^{3'}$, $R^{4'}$, and $R^{5'}$ is one of is H, halogen, $C_1$-$C_2$ alkyl, or halogen-substituted $C_1$-$C_2$ alkyl;

W" is sulfur, oxygen, or nitrogen;

U", V", X", Y", and Z" are individually carbon, sulfur, oxygen, or nitrogen, wherein at least three of U", V", X", Y", and Z" are carbon;

one of $R^{1''}$ and $R^{2''}$ is $C_1$-$C_8$ alkyl or $C_1$-$C_5$ alkoxy optionally substituted by at least one of halogen, hydroxy, or alkoxy, or furanyl; and the other of $R^{1''}$ and $R^{2''}$ is absent, or is one of H, halogen, or $C_1$-$C_8$ alkyl or $C_1$-$C_8$ alkoxy optionally substituted by at least one of halogen, hydroxy, or alkoxy;

$R^{3''}$ is absent or is one of H, $C_1$-$C_2$ alkyl, or halogen-substituted $C_1$-$C_2$ alkyl;

$R^{4''}$, $R^{5''}$, and $R^{6''}$ each is absent, or each of $R^{4''}$, $R^{5''}$, and $R^{6''}$ is H, halogen, $C_1$-$C_2$ alkyl, or halogen-substituted $C_1$-$C_2$ alkyl; and $R^5$ and $R^6$ are individually H or methyl;

G is one of —CH=CH—NHC(O)—$R^7$, —CH=CH—NHC(S)—$R^7$, —CH$_2$CH$_2$NHC(O)—$R^7$, —CH$_2$CH$_2$NHC(S)—$R^7$, —CH$_2$NHNHC(O)—$R^7$, or —CH$_2$NHNHC(S)—$R^7$, $R^7$ is one of $C_1$-$C_6$ alkyl, —O($C_1$-$C_6$ alkyl), —S($C_1$-$C_6$ alkyl), or —N($R^8$)$_2$; and each $R^8$ is independently one of hydrogen or —$C_1$-$C_6$ alkyl.

3. The compound of claim 1, which is a compound of formula Ia, or a salt thereof.

4. The compound of claim 1, which is a compound of formula Ib, or a salt thereof.

5. The compound of claim 1, which is a compound of formula Ic, or a salt thereof.

6. The compound of claim 1, or a salt thereof, wherein $R^6$ is H.

7. The compound of claim 1, or a salt thereof, wherein $R^6$ is methyl.

8. A compound selected from

Structure

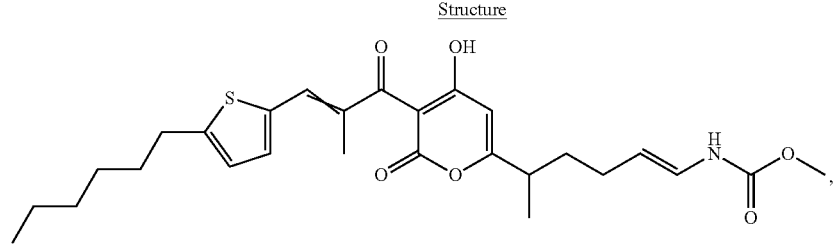

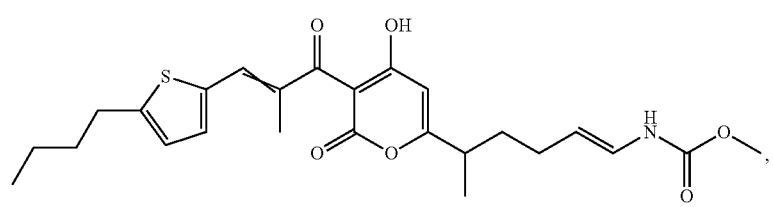

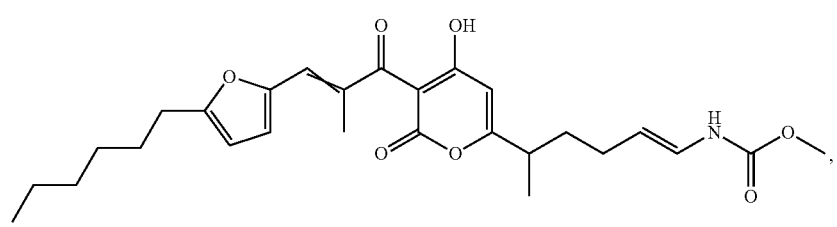

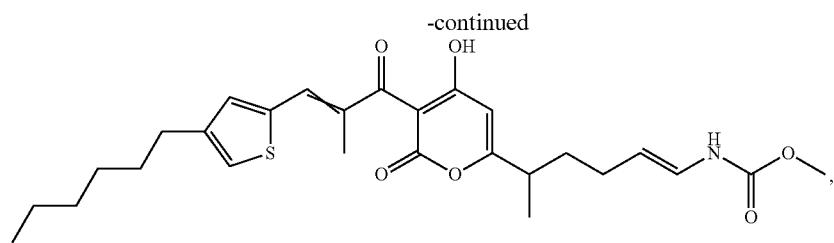
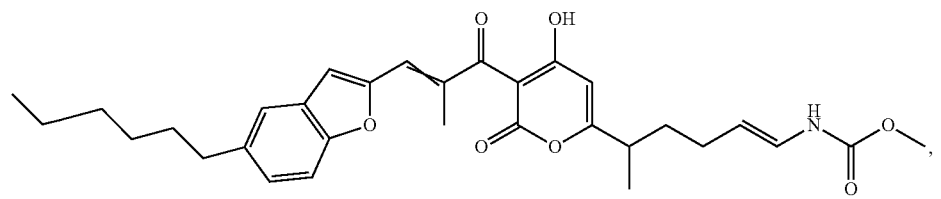
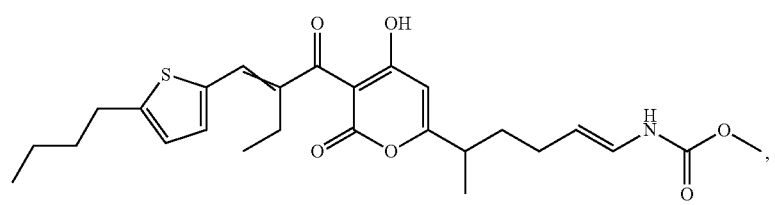
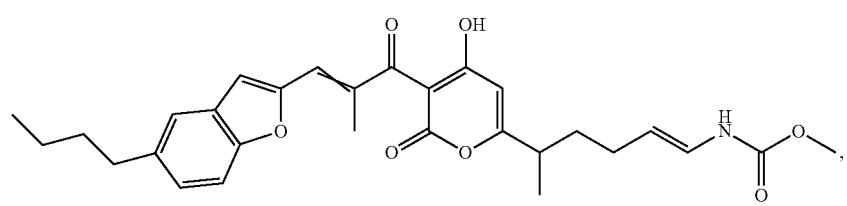
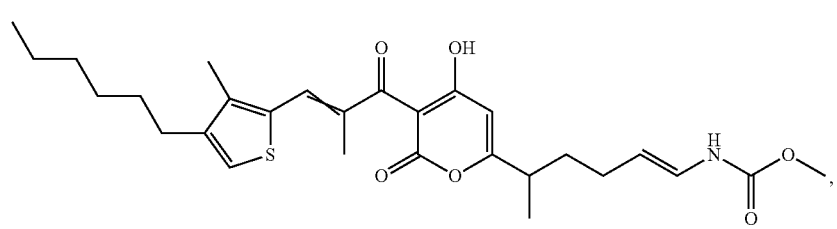
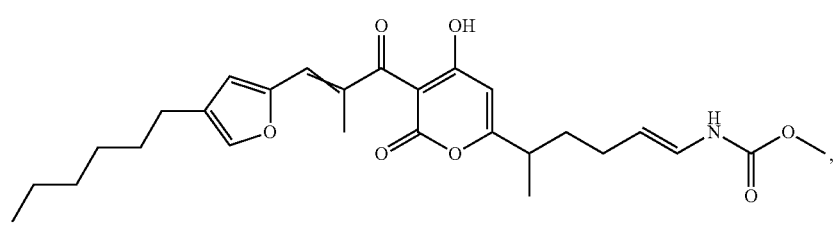
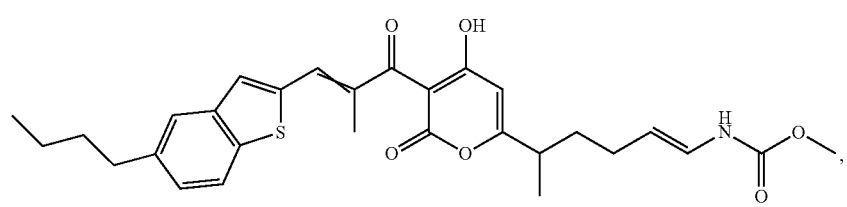
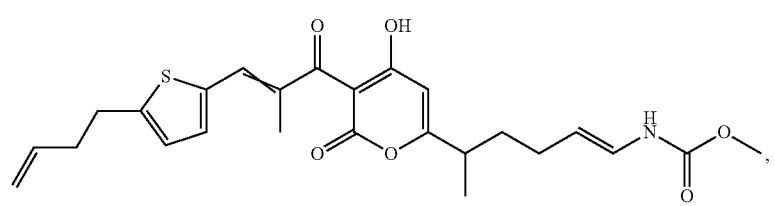

-continued
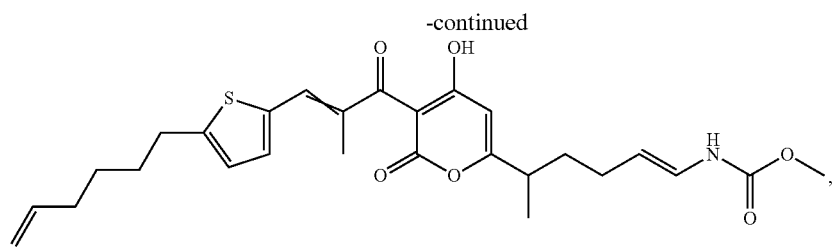
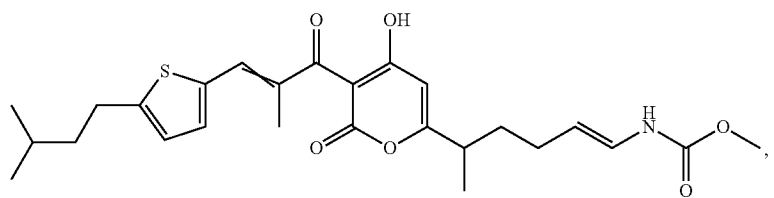
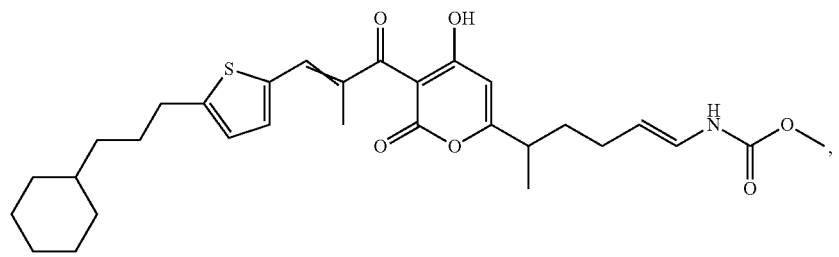
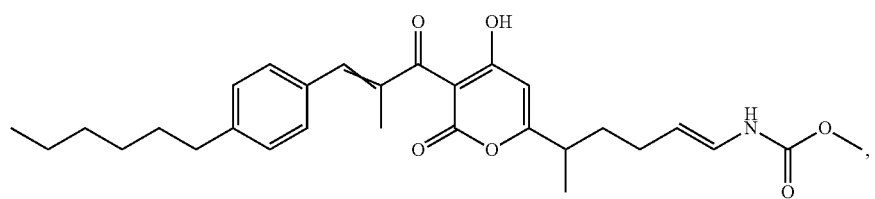
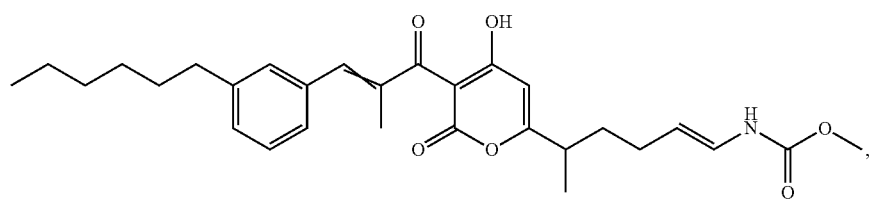
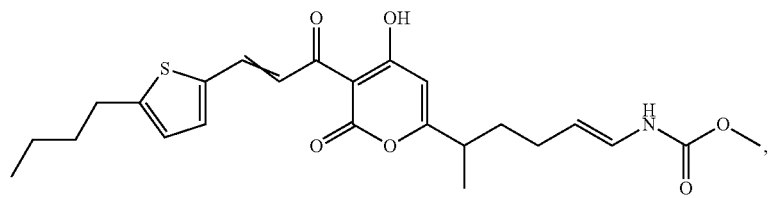
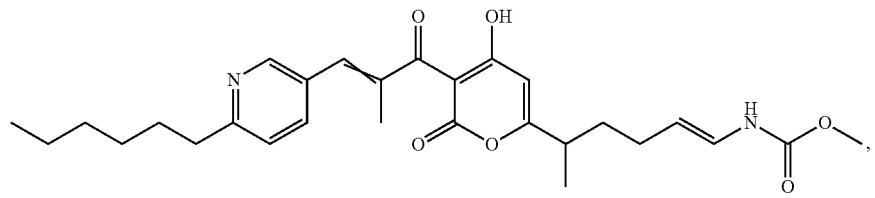
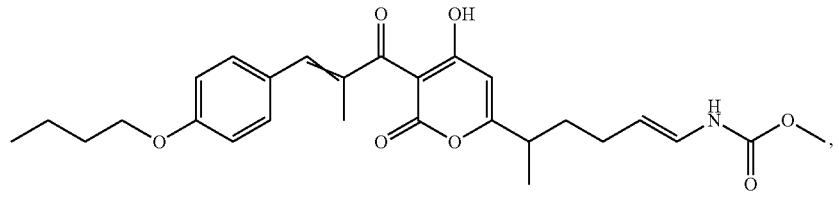

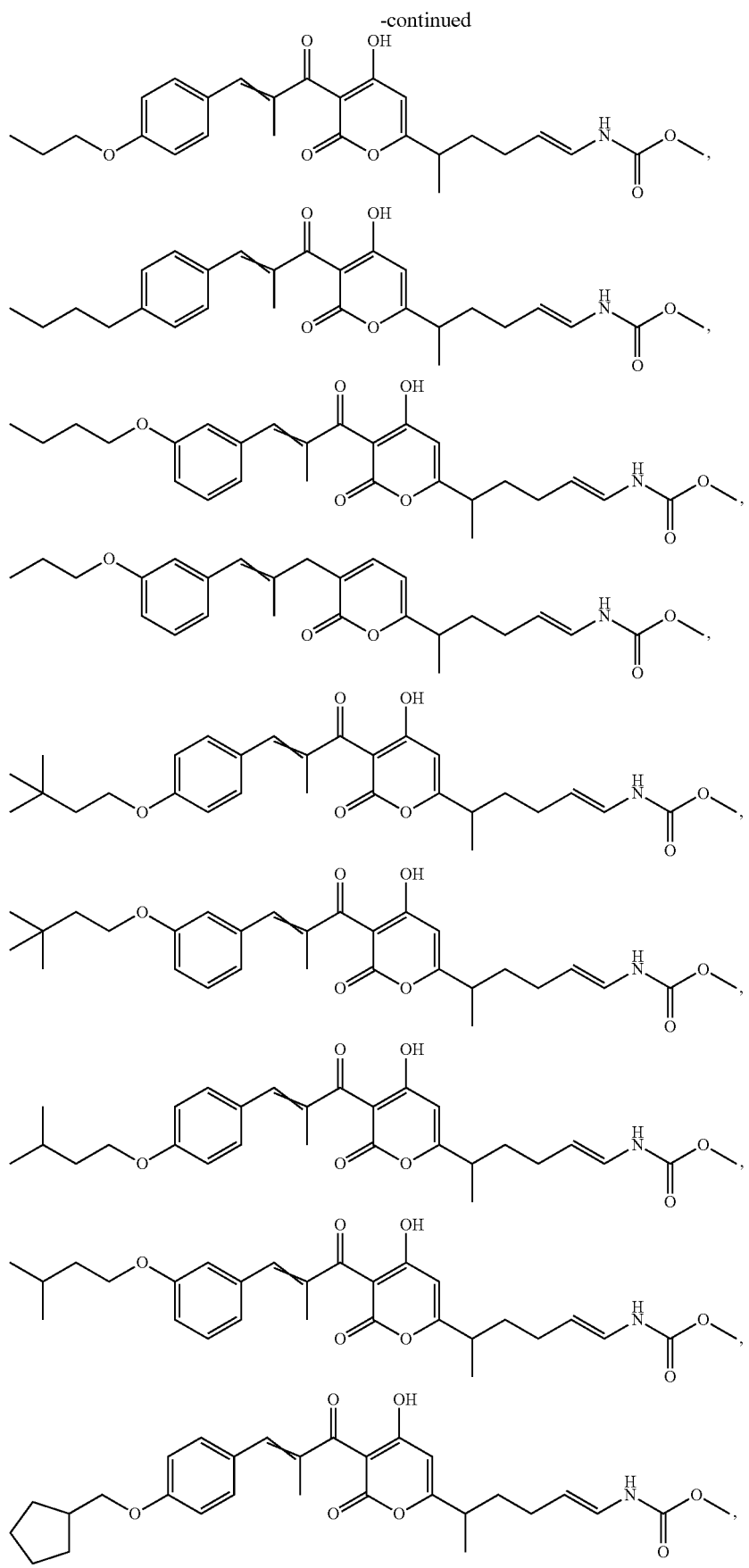

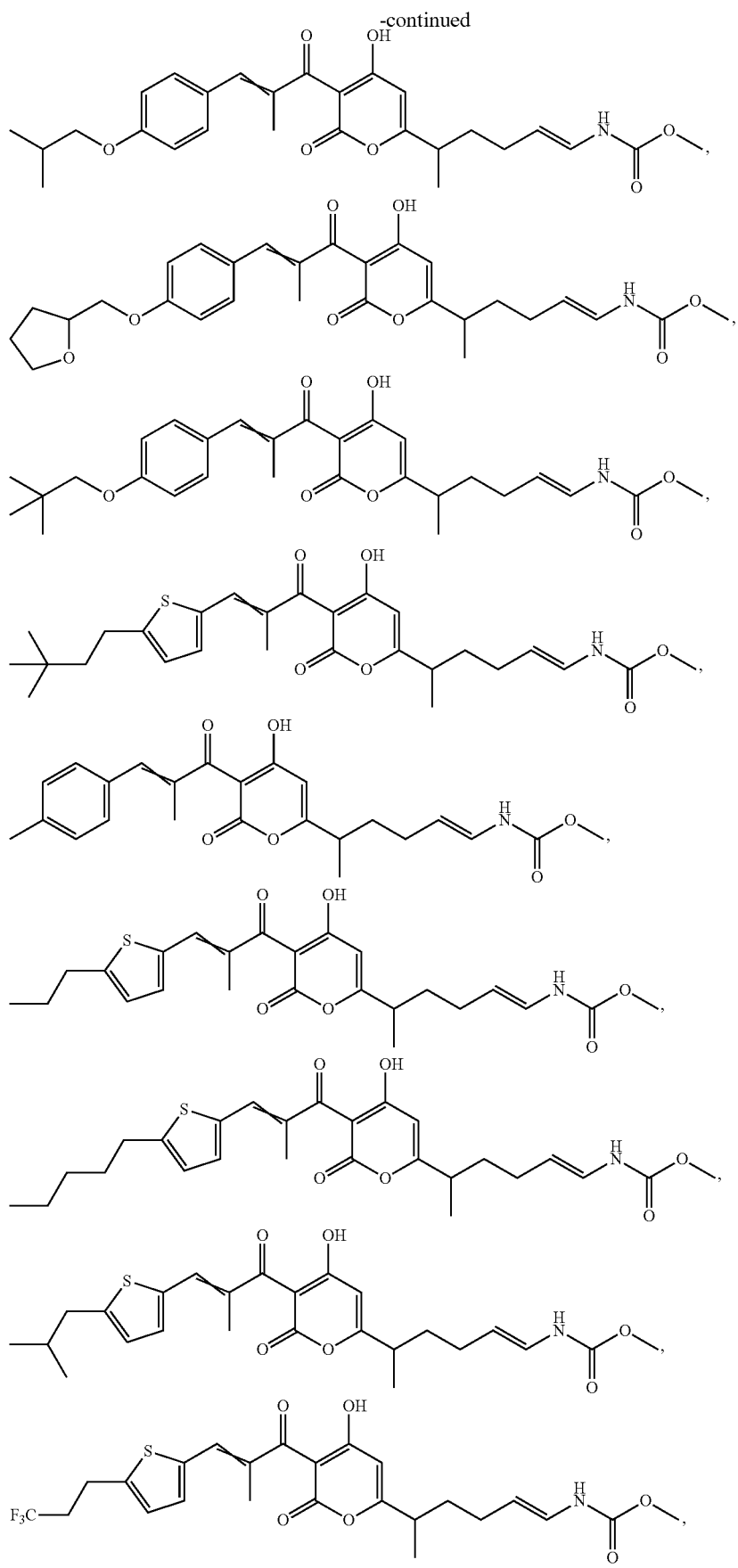

-continued
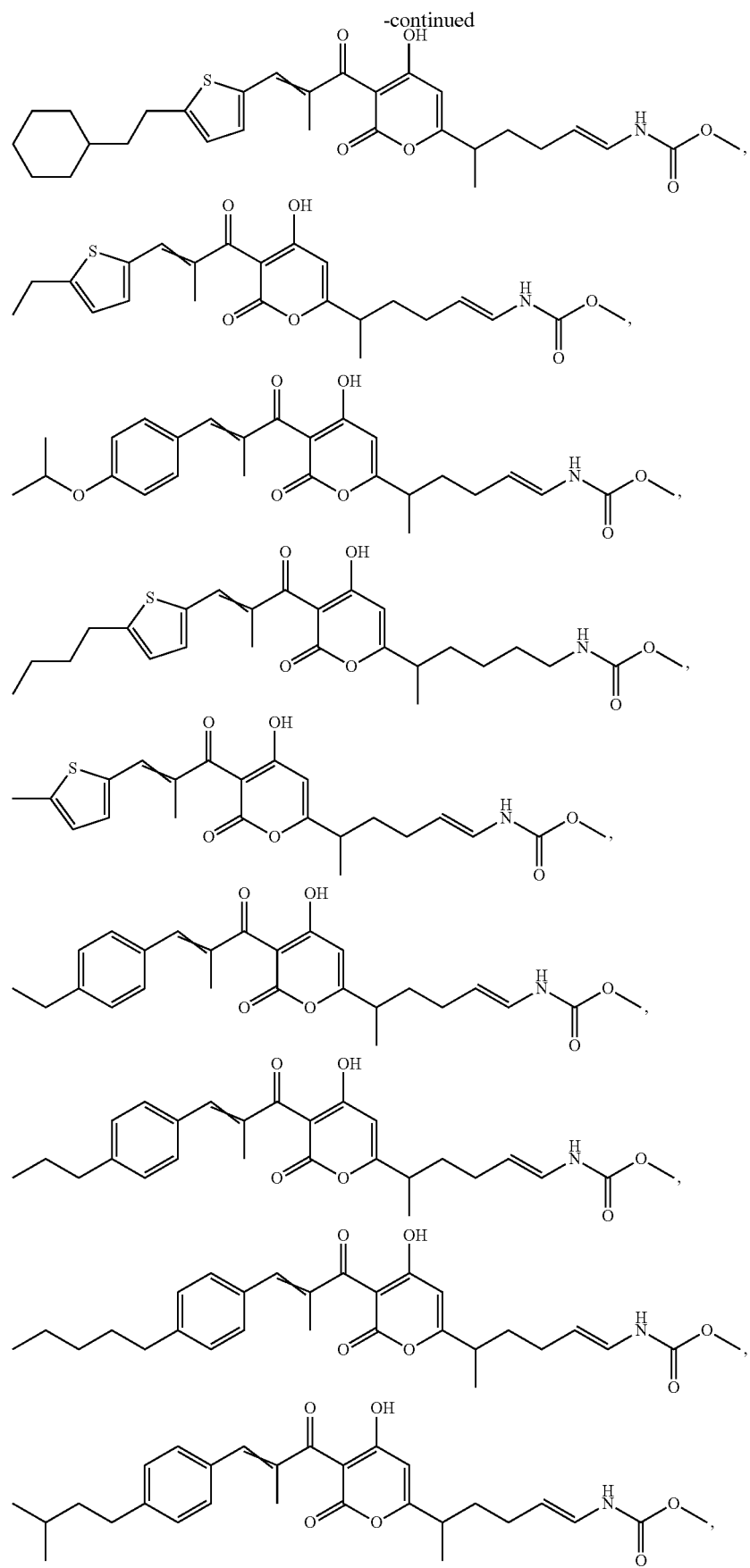

-continued
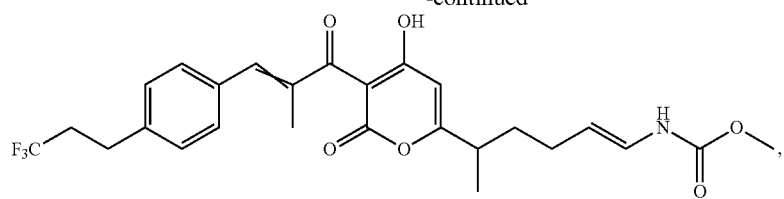
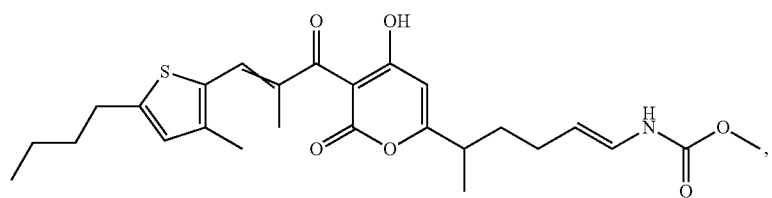
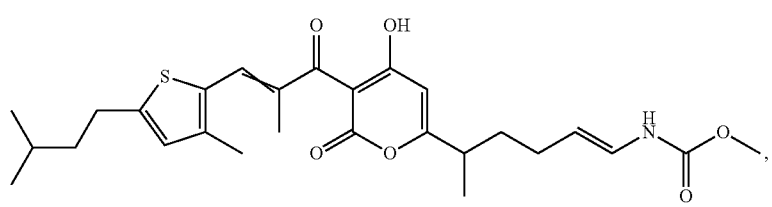
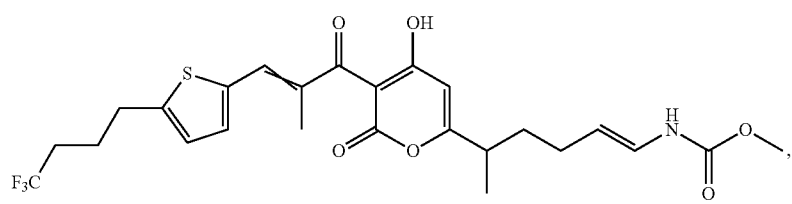
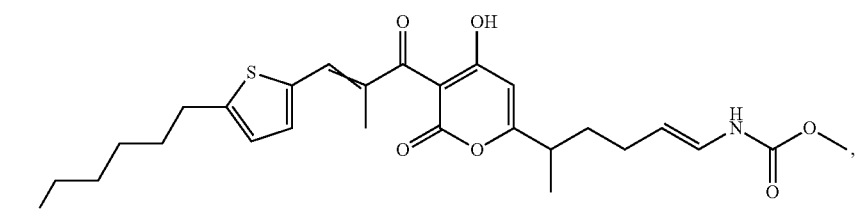
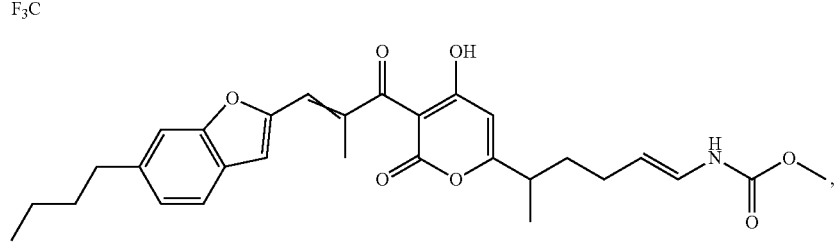
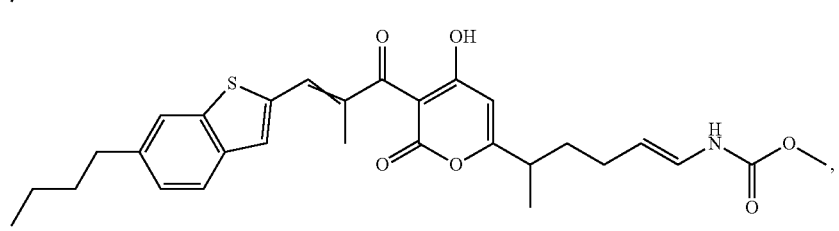
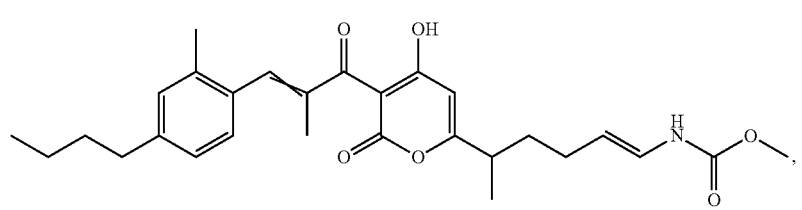

-continued
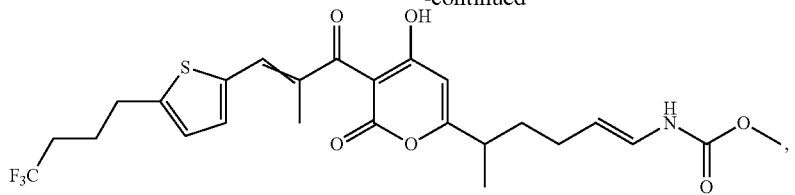
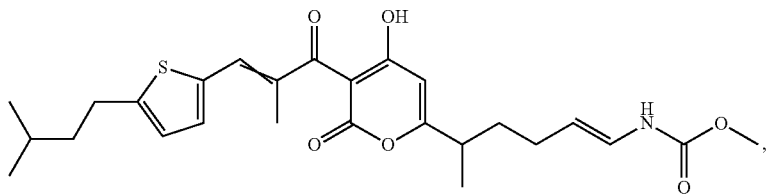
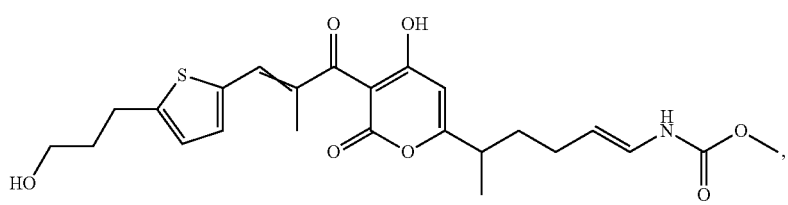
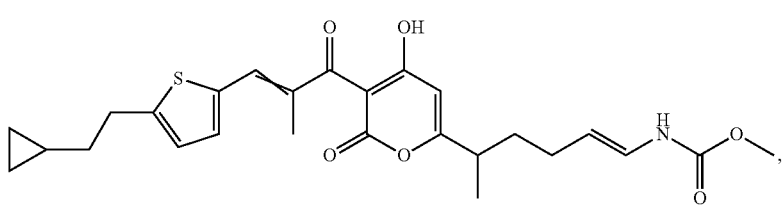
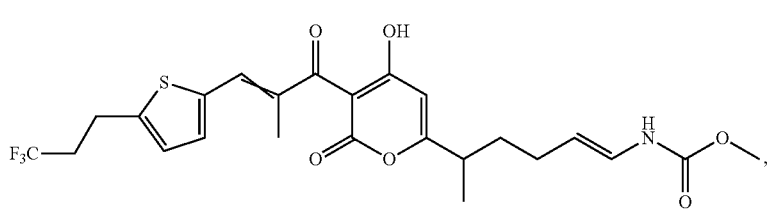
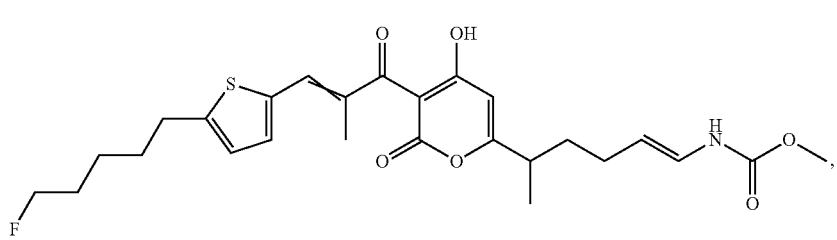
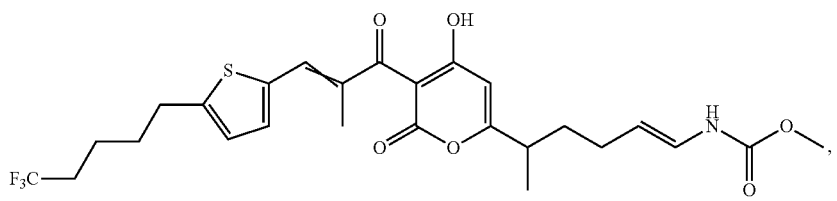
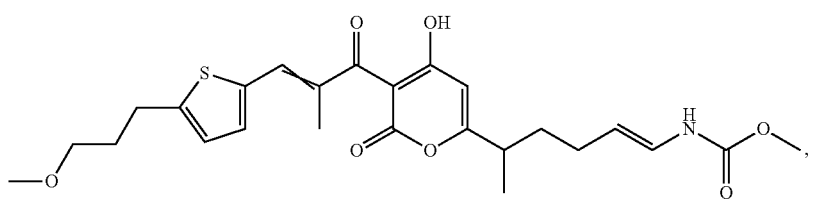

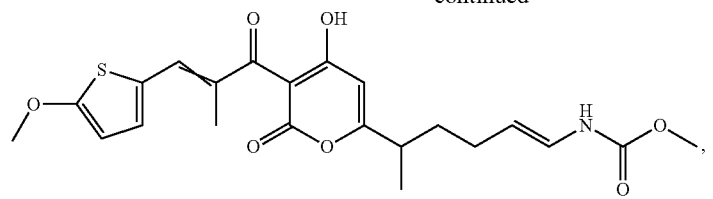
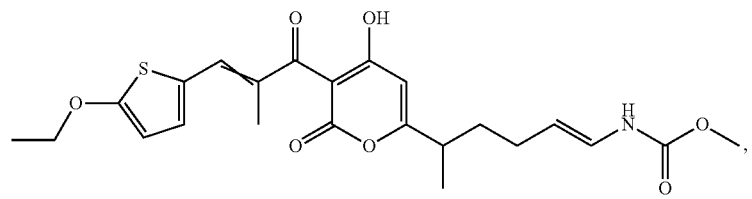
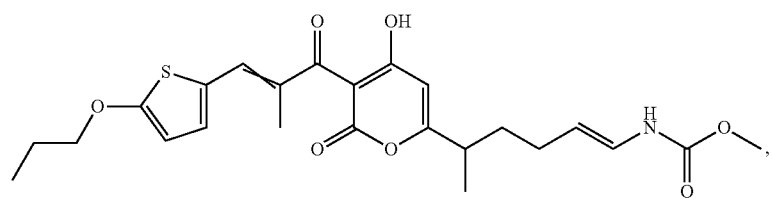
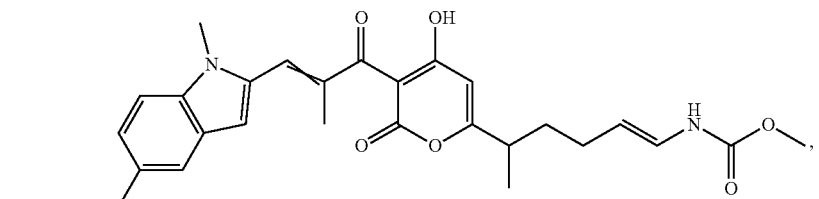
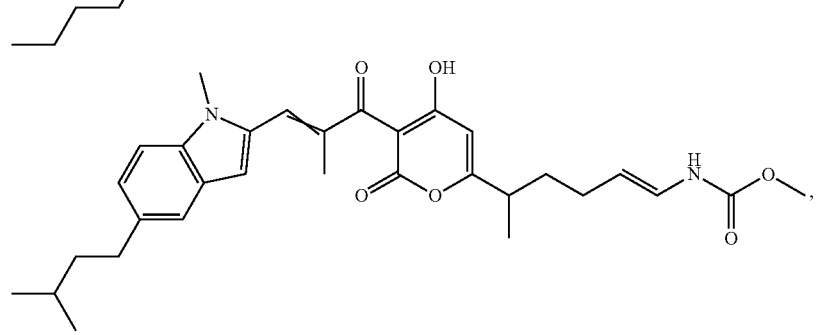
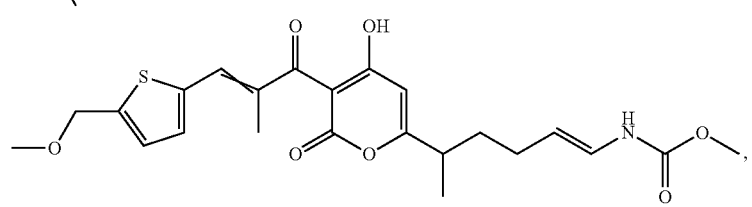
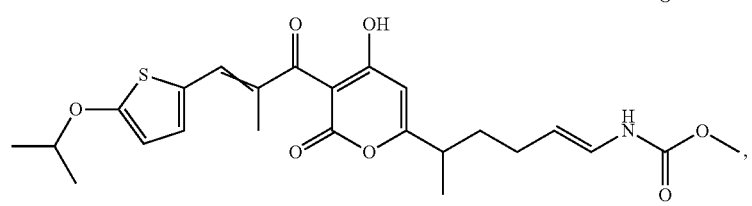
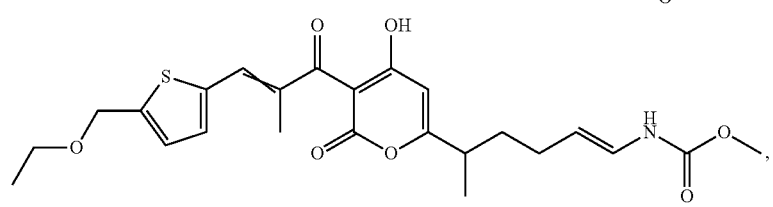

-continued
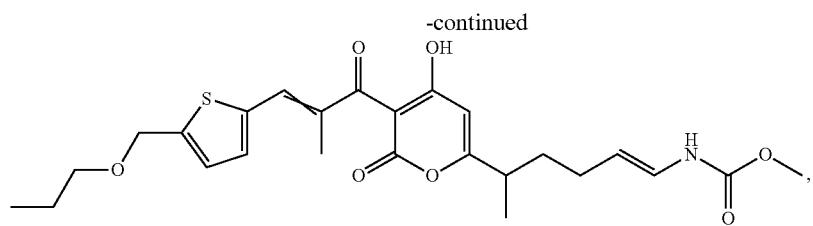
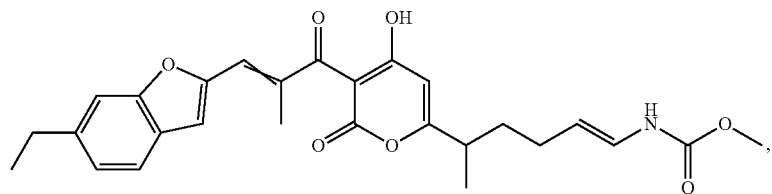
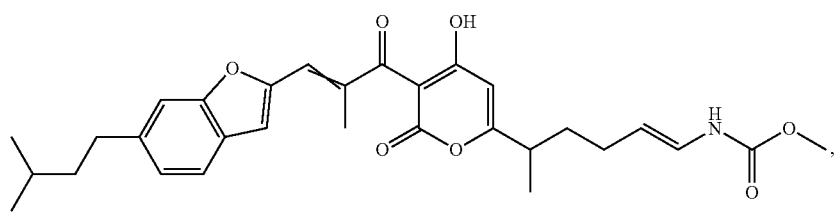
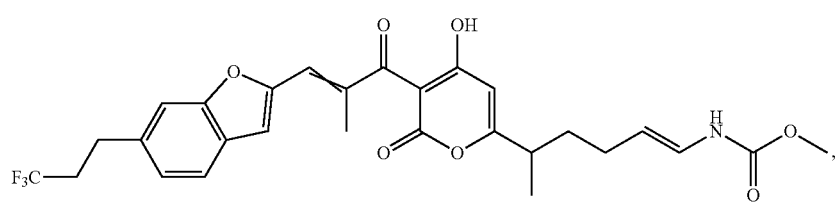
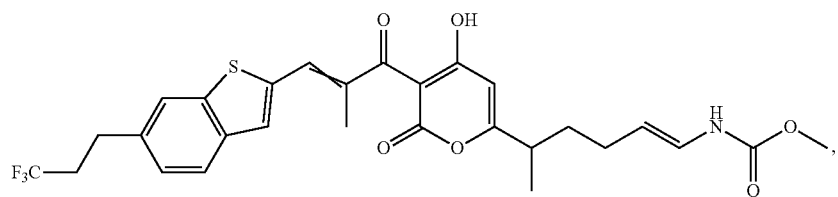
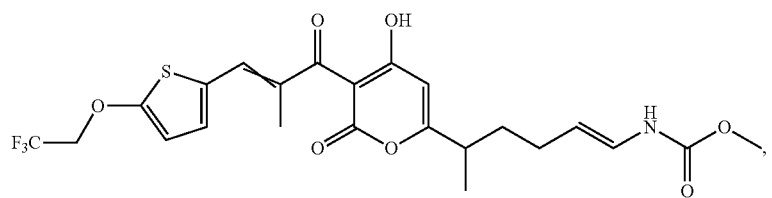
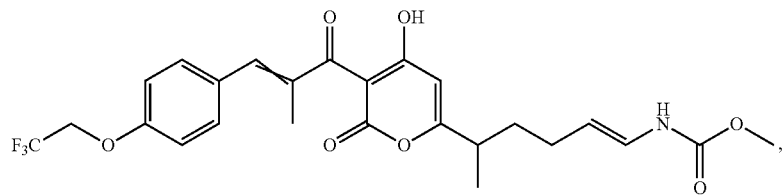
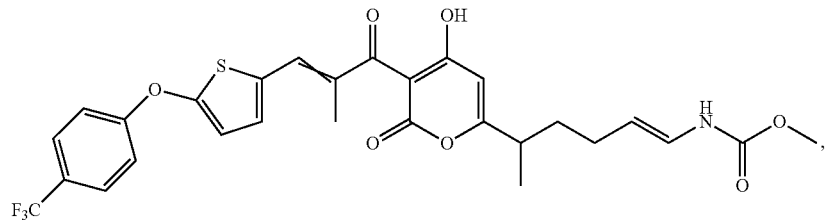

-continued
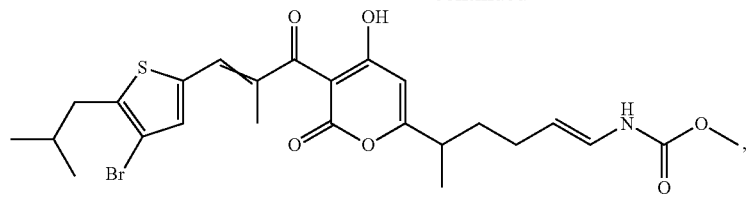
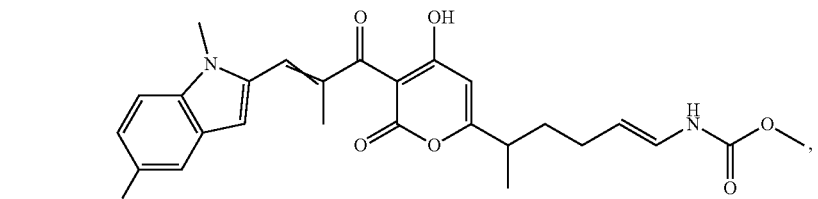
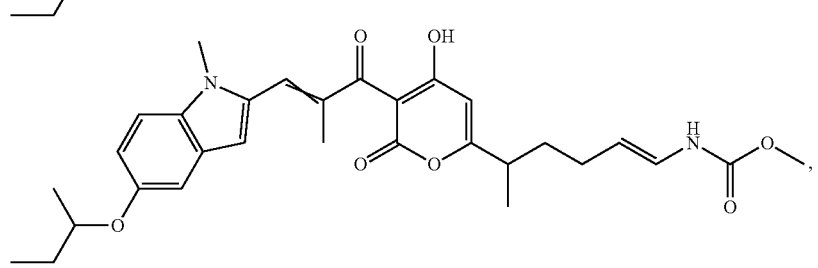
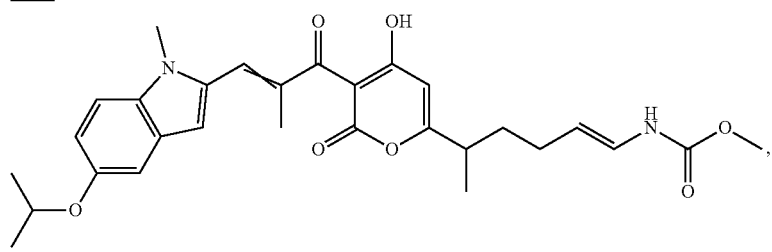
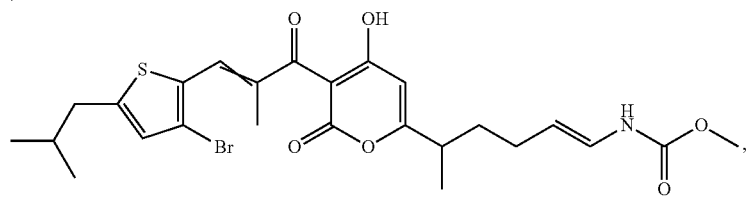
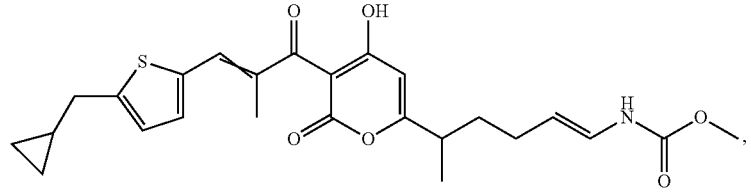
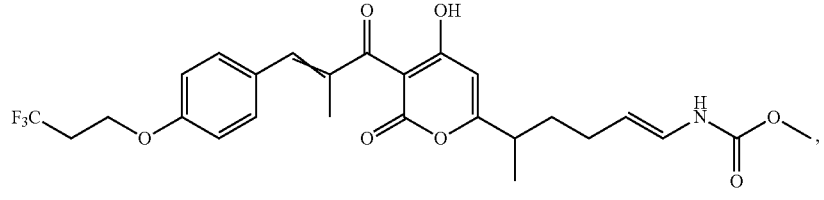
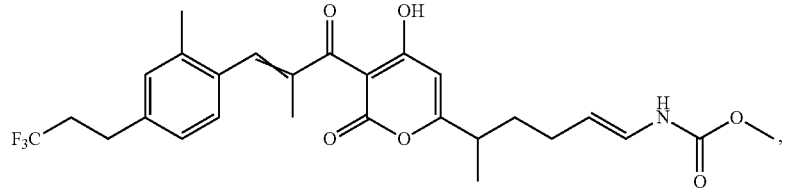

-continued
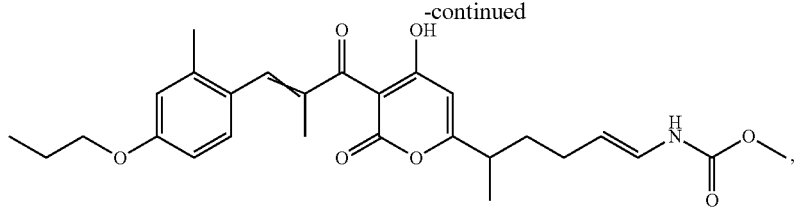
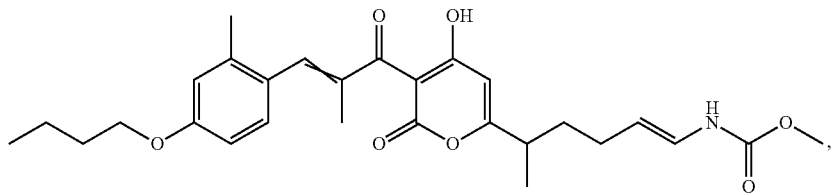
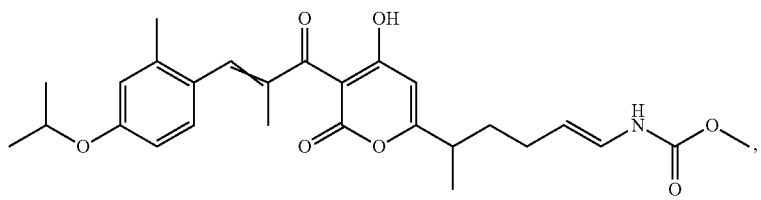
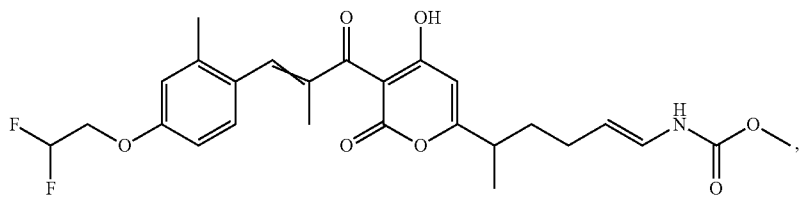
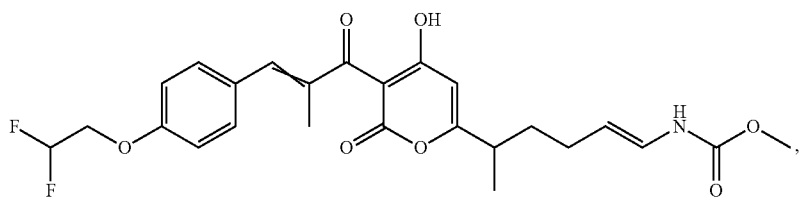
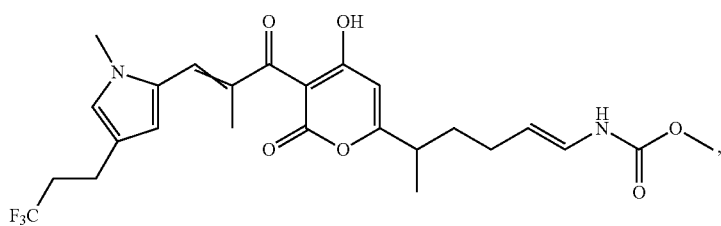
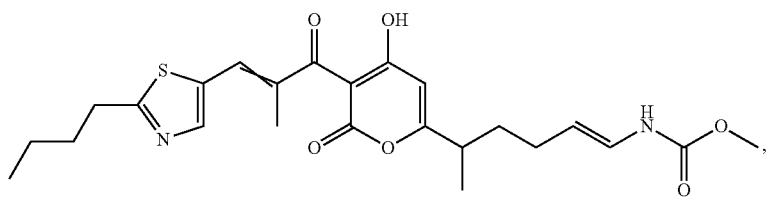
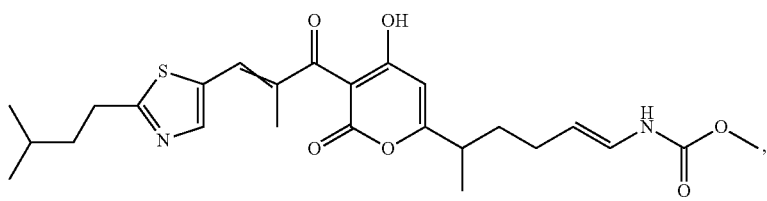

-continued
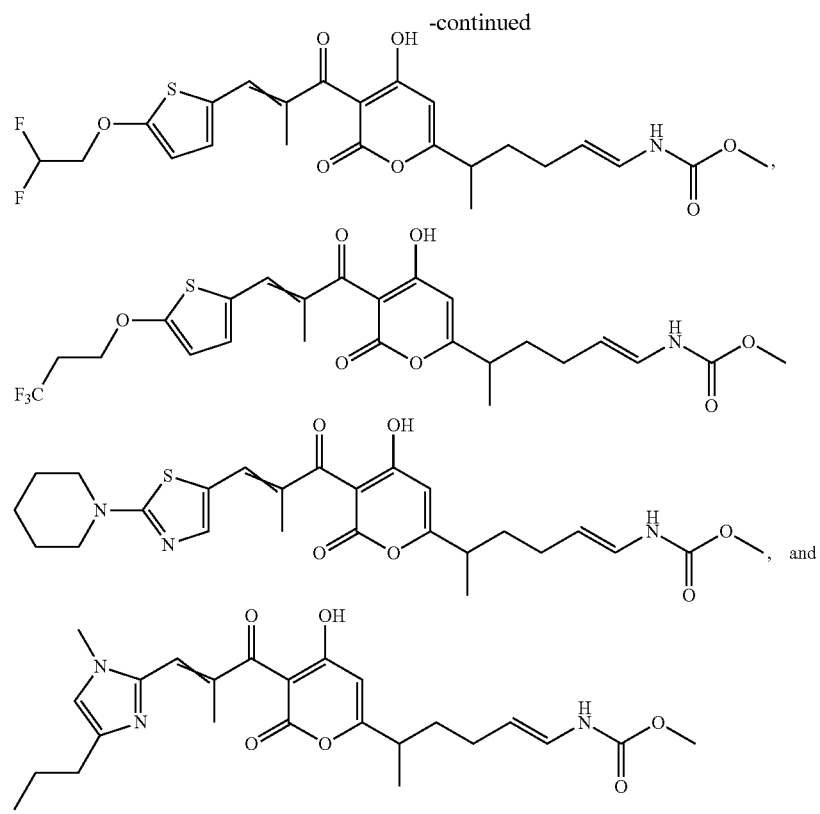
and salts thereof.
9. The compound of claim 1, or a salt thereof, wherein the salt is a pharmaceutically acceptable salt.
10. A composition comprising the compound of claim 1, or a pharmaceutically acceptable salt thereof, and a pharmaceutically acceptable carrier.
* * * * *